United States Patent
Kim et al.

(10) Patent No.: US 10,033,001 B2
(45) Date of Patent: *Jul. 24, 2018

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Cheonan (KR)

(72) Inventors: Hyun Kim, Suwon (KR); So-Young Jung, Hwaseong (KR); Sung-Woo Jang, Suwon (KR); Ga-Won Lee, Hwaseong (KR)

(73) Assignee: ROHM AND HAAS ELECTRONIC MATERIALS KOREA LTD., Cheonan (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/521,904

(22) PCT Filed: Nov. 6, 2015

(86) PCT No.: PCT/KR2015/011888
§ 371 (c)(1),
(2) Date: Apr. 26, 2017

(87) PCT Pub. No.: WO2016/072780
PCT Pub. Date: May 12, 2016

(65) Prior Publication Data
US 2017/0317297 A1    Nov. 2, 2017

(30) Foreign Application Priority Data

Nov. 6, 2014 (KR) .................. 10-2014-0153821
Jan. 2, 2015 (KR) .................. 10-2015-0000088
Aug. 7, 2015 (KR) .................. 10-2015-0111327

(51) Int. Cl.
*C07F 15/00* (2006.01)
*H01L 51/50* (2006.01)
*H01L 51/00* (2006.01)
*C09K 11/06* (2006.01)

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1029* (2013.01); *C09K 2211/185* (2013.01); *H01L 51/5016* (2013.01)

(58) Field of Classification Search
CPC .............................. C07F 15/00; H01L 51/50
USPC ............................................. 546/10; 313/504
See application file for complete search history.

(56) References Cited

U.S. PATENT DOCUMENTS

| | | |
|---|---|---|
| 6,458,475 B1 | 10/2002 | Adachi et al. |
| 2009/0026929 A1 | 1/2009 | Song et al. |
| 2010/0133524 A1 | 6/2010 | Kim et al. |
| 2012/0292608 A1 | 11/2012 | Ise et al. |
| 2013/0328019 A1 | 12/2013 | Xia et al. |
| 2014/0070204 A1 | 3/2014 | Nagao et al. |
| 2014/0158992 A1 | 6/2014 | Xia et al. |
| 2014/0374728 A1 | 12/2014 | Adamovich et al. |

FOREIGN PATENT DOCUMENTS

| | | | |
|---|---|---|---|
| JP | 2009130141 A | 6/2009 | |
| KR | 100662381 B1 | 12/2006 | |
| KR | 2011-0086021 A | 7/2011 | |
| TW | I378986 B | 12/2012 | |
| WO | 2008/109824 A2 | 9/2008 | |
| WO | 2010/033550 A1 | 3/2010 | |
| WO | WO 2016/072743 A1 * | 5/2016 | ............. H01L 51/50 |

* cited by examiner

*Primary Examiner* — Charanjit Aulakh
(74) *Attorney, Agent, or Firm* — S. Matthew Cairns

(57) ABSTRACT

The present disclosure relates to an organic electroluminescent compound and an organic electroluminescent device comprising the same. The organic electroluminescent compound of the present disclosure can provide an organic electroluminescent device showing excellence in color purity, solubility, heat stability, driving voltage, current efficiency, and power efficiency, as well as remarkably improved lifespan.

6 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time.

An organic EL device was first developed by Eastman Kodak, by using small aromatic diamine molecules and aluminum complexes as materials to form a light-emitting layer [Appl. Phys. Lett. 51, 913, 1987].

Generally, the organic EL device has a structure comprising an anode, a cathode, and an organic layer disposed between the anode and the cathode. The organic layer of the organic EL device comprises a hole injection layer, a hole transport layer, an electron blocking layer, a light-emitting layer, a hole blocking layer, an electron transport layer, an electron injection layer, etc. When a voltage is applied to the organic EL device, holes and electrons are injected from an anode and a cathode, respectively, to the light-emitting layer. Excitons having high energy are formed by recombinations between the holes and the electrons. The energy of excitons puts the light-emitting organic compound in an excited state, and the decay of the excited state results in a relaxation of the energy level into a ground state, accompanied by light-emission. Therefore, the most important factor determining luminous efficiency in the organic EL device is light-emitting materials.

Depending on its function, the light-emitting materials can be classified as a host material and a dopant material. Generally, devices showing good electroluminescent characteristics comprise a light-emitting layer in which a dopant is doped into a host. The dopant/host system is provided to enhance luminous efficiency through energy transfer from a host to a dopant. In the dopant/host material system, the dopant and host materials highly affect efficiencies and lifespan of the device.

Iridium(III) complexes have been widely known as phosphorescent materials, including bis(2-(2'-benzothienyl)-pyridinato-N,C-3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green-, and blue-emitting materials, respectively.

However, considering EL characteristic requirements for a middle or large-sized panel of OLED, Iridium(III) complex-based dopant compounds showing better characteristics, i.e., long lifespan, high efficiency, and high color purity must be urgently developed.

Particularly, for a full-color display, pixels which show particular colors called as a "saturated" color are required, and especially, saturated red, green, and blue pixels are required, which can be measured by a CIE coordinate known in this field. In order to display more various colors, each of red, green, and blue should have high color purity. In the case of red, color purity becomes higher, as it approaches a deep-red coordinate around 0.680 of x-axis of CIE. A dopant compound which meets such requirements is desired.

Korean Patent No. 0662381, Korean Patent Application Laying-Open No. 2011-0086021, WO 2008/109824, and WO 2010/033550 disclose iridium complexes having 2-phenylquinoline-based ligand, as a dopant compound of an organic electroluminescent device. However, said prior arts fail to specifically disclose an iridium complex having a ligand in which quinoline of 2-phenylquinoline is substituted with alkyl at 4-position and is substituted with phenyl at 6-position.

DISCLOSURE OF THE INVENTION

Problems to be Solved

The object of the present disclosure is to provide a compound which can be used to prepare an organic electroluminescent device showing good color purity and long lifespan, and to provide an organic electroluminescent device comprising the compound.

Solution to Problems

The present inventors found that the above object can be achieved by a compound represented by the following formula 1.

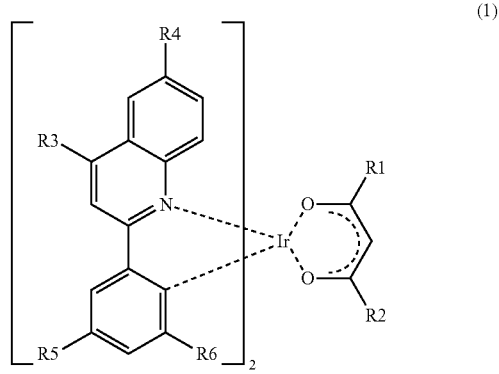

wherein $R_1$ and $R_2$, each independently, represent a (C1-C5)alkyl, $R_3$ represents a (C3-C5)alkyl unsubstituted or substituted with deuterium, $R_4$ represents phenyl unsubstituted or substituted with a (C1-C5)alkyl unsubstituted or substituted with deuterium, and $R_5$ and $R_6$, each independently, represent methyl unsubstituted or substituted with deuterium.

Effects of the Invention

The compound of the present disclosure can provide an organic electroluminescent device showing remarkably improved color purity and lifespan.

An electron-donating property and an electron-withdrawing property between two materials exchanging electrons are not absolutely determined, but relatively determined depending on relation between the materials. Phenyl is generally an electron-donating group, but in the present disclosure, is used as an electron-withdrawing group. In formula 1, phenyl is introduced as an electron-withdrawing group at $R_4$ position of quinoline which affects LUMO energy level of the molecule, thereby reducing electron density and lowering LUMO energy level. Due to the lowered LUMO energy level, an energy gap between HOMO energy level and LUMO energy level becomes smaller. As a result, color purity of a red-emitting organic electroluminescent device is improved.

EMBODIMENTS OF THE INVENTION

Hereinafter, the present disclosure will be described in detail. However, the following description is intended to explain the invention, and is not meant in any way to restrict the scope of the invention.

The present disclosure provides the compound of formula 1 above, an organic electroluminescent material comprising the compound, and an organic electroluminescent device comprising the compound.

The details of the compound of formula 1 are as follows.

Herein, a "(C1-C5)alkyl" indicates a linear or branched alkyl having 1 to 5 carbon atoms. Specifically, a (C1-C5) alkyl includes methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, and 1-ethylpropyl.

In formula 1, $R_1$ and $R_2$, each independently, represent a (C1-C5)alkyl. Specifically, $R_1$ and $R_2$, each independently, may be selected from methyl, ethyl, and a branched (C3-C5)alkyl. Preferably, $R_1$ and $R_2$ may be the same.

In formula 1, $R_3$ represents a (C3-C5)alkyl unsubstituted or substituted with deuterium. Specifically, $R_3$ may be selected from isopropyl, isobutyl, sec-butyl, tert-butyl, 1-methylbutyl, 2-methylbutyl, 3-methylbutyl, 1,1-dimethylpropyl, 1,2-dimethylpropyl, 2,2-dimethylpropyl, and 1-ethylpropyl. More specifically, $R_3$ may be selected from isopropyl, isobutyl, sec-butyl, tert-butyl, 1-methylbutyl, 2-methylbutyl, 3-methylbutyl, 1,1-dimethylpropyl, 1,2-dimethylpropyl, 2,2-dimethylpropyl, and 1-ethylpropyl.

In formula 1, $R_4$ represents phenyl unsubstituted or substituted with a (C1-C5)alkyl unsubstituted or substituted with deuterium. Specifically, $R_4$ may be phenyl unsubstituted or substituted with a (C1-C3)alkyl. More specifically, $R_4$ may be selected from phenyl, phenyl substituted with methyl, phenyl substituted with deuterium-substituted methyl, phenyl substituted with isopropyl, phenyl substituted with isobutyl, phenyl substituted with tert-butyl, and phenyl substituted with 2,2-dimethylpropyl.

According to one embodiment of the present disclosure, in formula 1, $R_4$ may be phenyl unsubstituted or substituted with a (C1-C4)alkyl.

According to another embodiment of the present disclosure, in formula 1, $R_3$ may be selected from a branched (C3-C5)alkyl unsubstituted or substituted with deuterium, and $R_4$ may be phenyl unsubstituted or substituted with methyl unsubstituted or substituted with deuterium.

More specifically, the compound of formula 1 includes the following, but is not limited thereto.

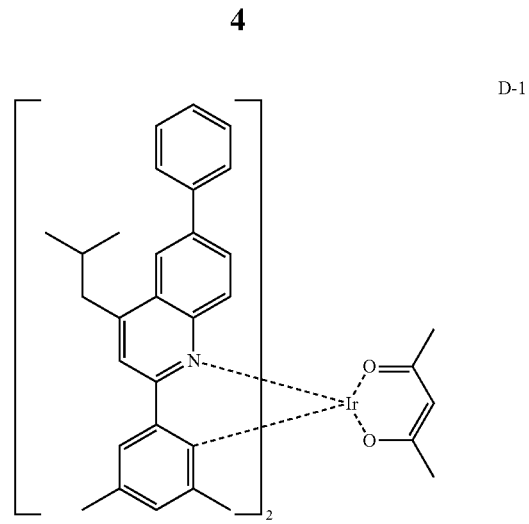

D-1

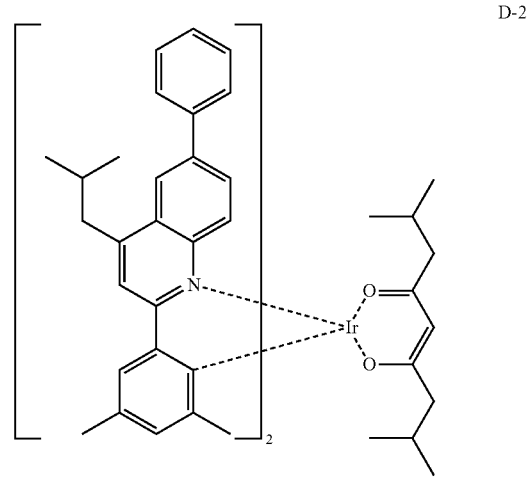

D-2

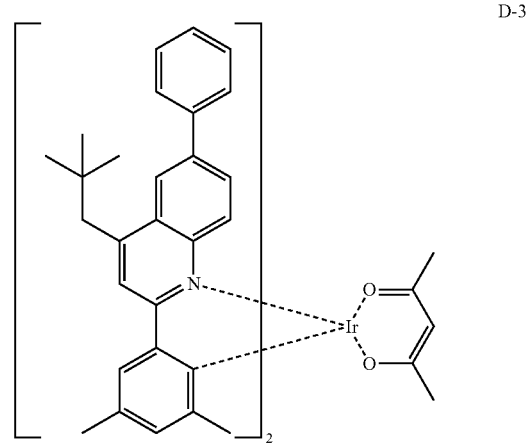

D-3

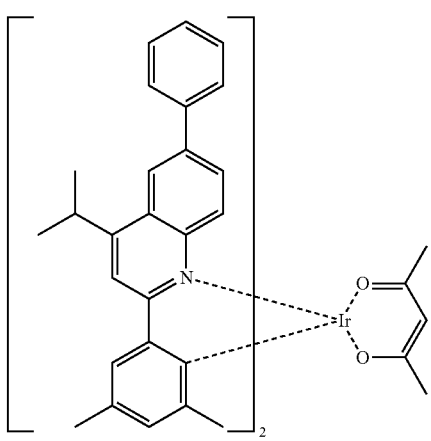
D-4
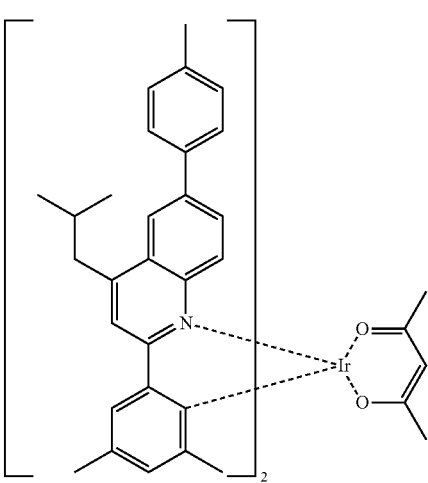
D-7
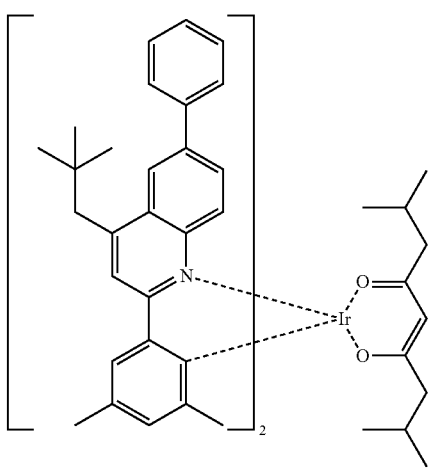
D-5
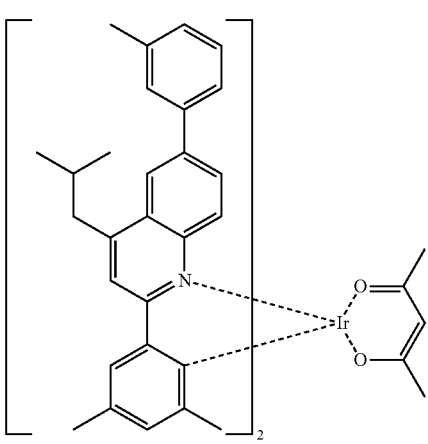
D-8
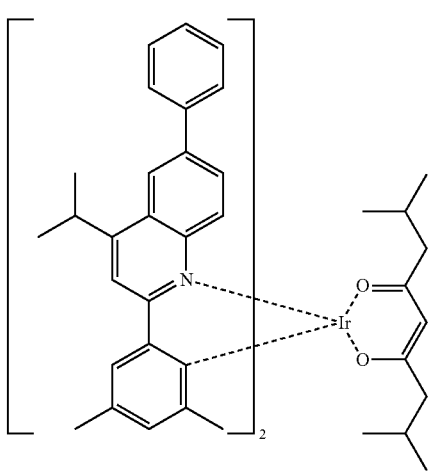
D-6
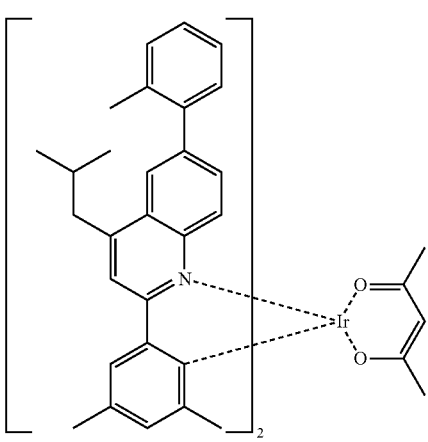
D-9

D-10
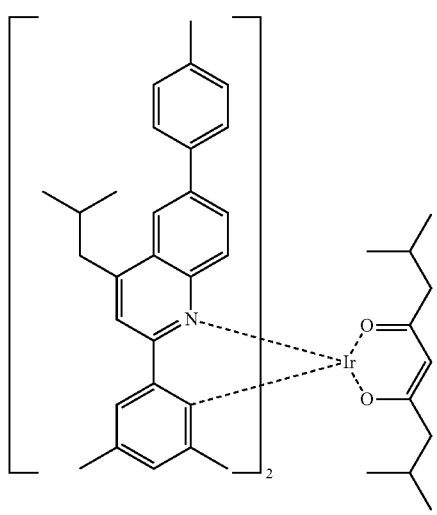
D-11
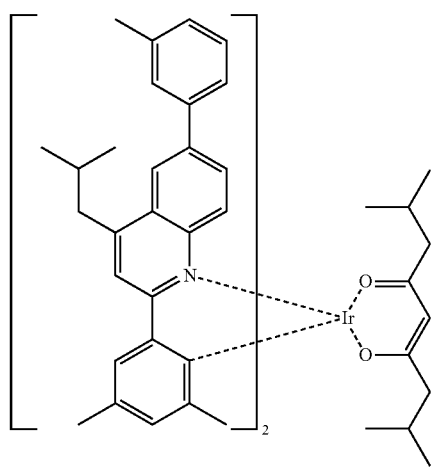
D-12
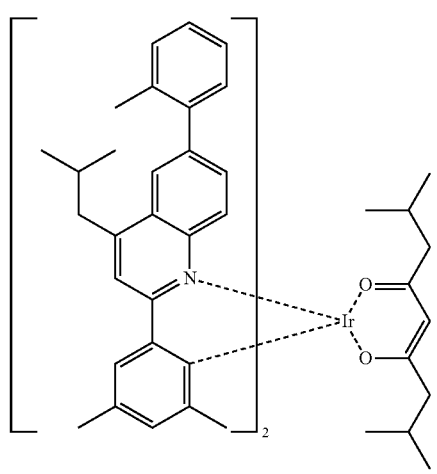
D-13
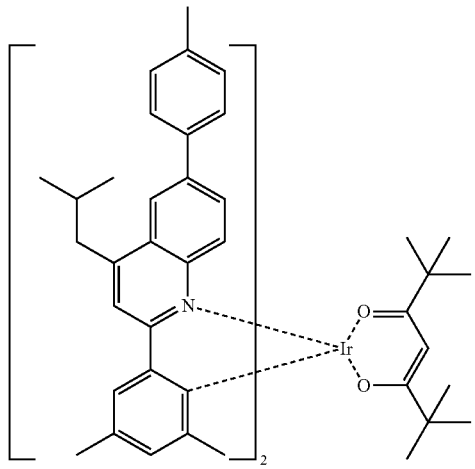
D-15
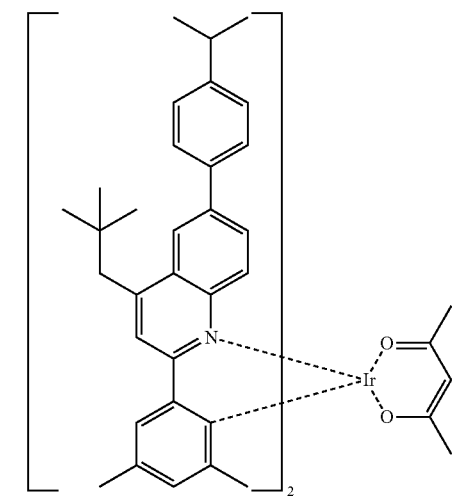
D-16
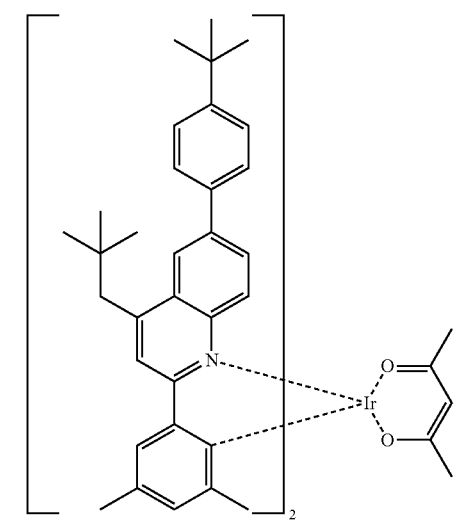

D-17
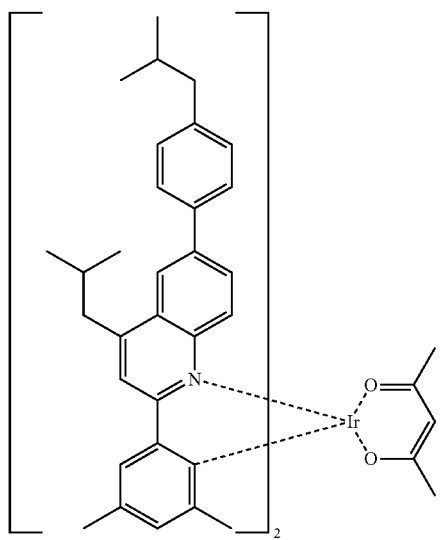
D-18
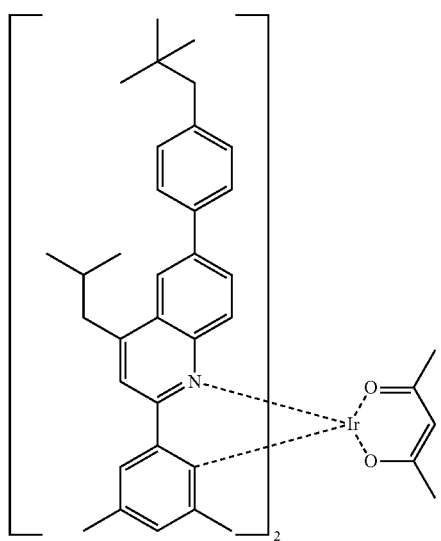
D-19
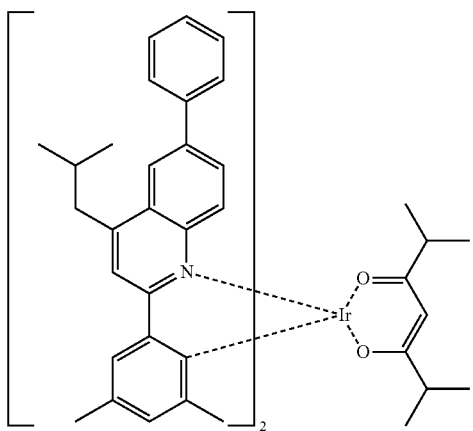
D-20
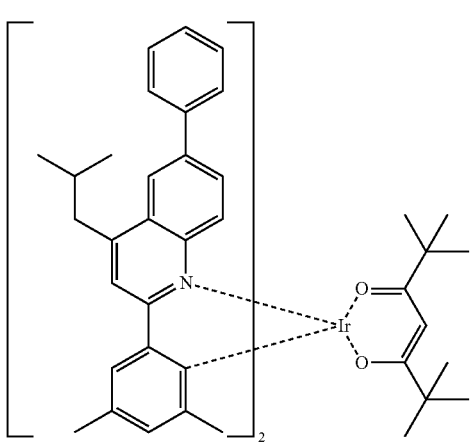
D-21
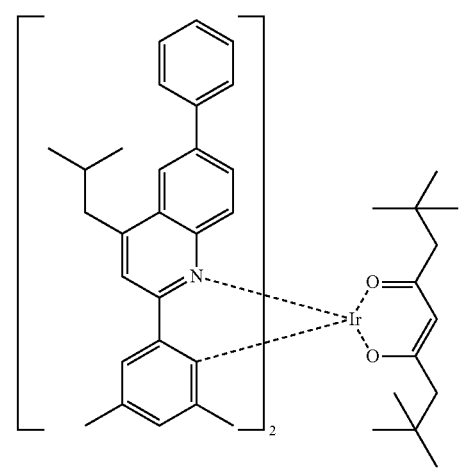
D-22
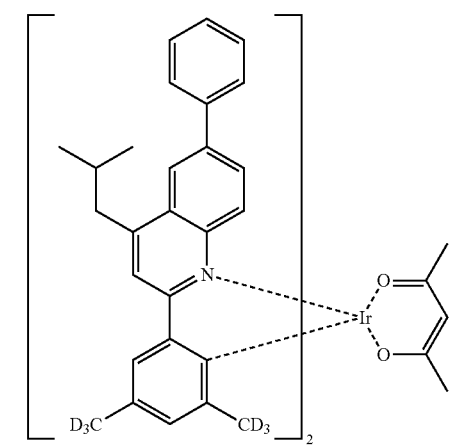

D-23
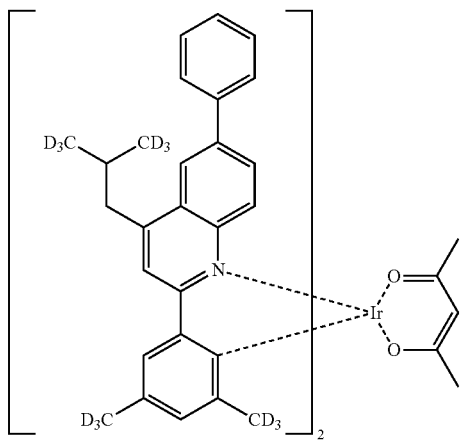
D-24
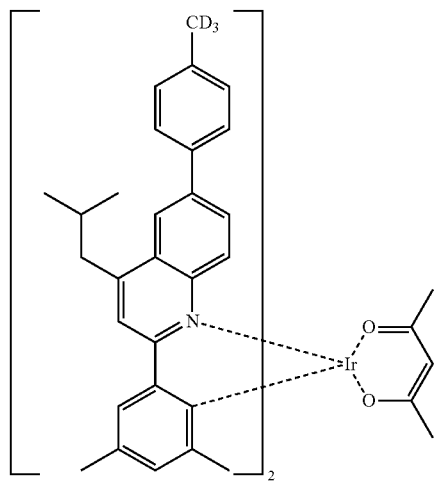
The compound of the present disclosure can be prepared by a synthetic method known to one skilled in the art. For example, it can be prepared according to the following reaction scheme 1.
[Reaction Scheme 1]
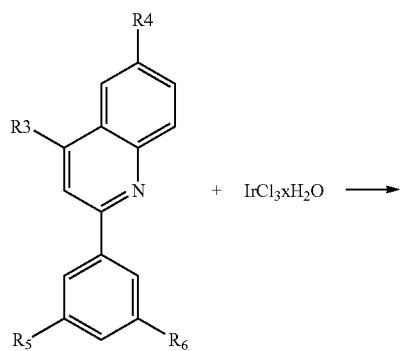
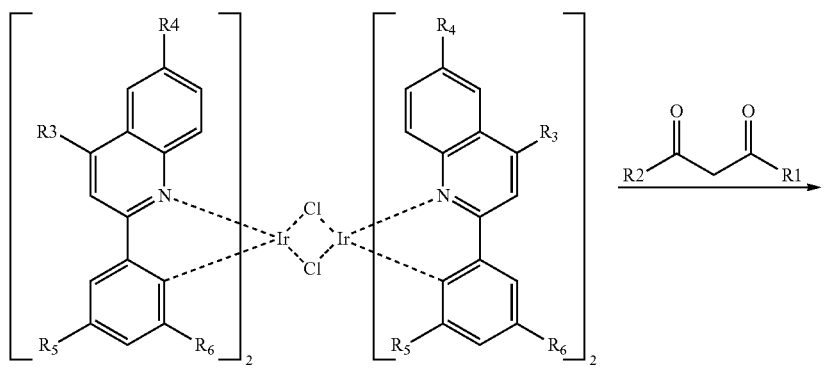

-continued

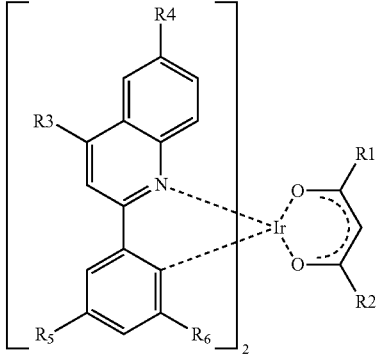

In reaction scheme 1, $R_1$ to $R_6$ are as defined in formula 1.

In addition, the present disclosure provides an organic electroluminescent material comprising the compound of formula 1, and an organic electroluminescent device comprising the material.

The material may consist of the compound of the present disclosure. Otherwise, the material may further comprise a conventional compound(s) which has been comprised for an organic electroluminescent material.

The organic electroluminescent device of the present disclosure may comprise a first electrode, a second electrode, and at least one organic layer disposed between the first and second electrodes. The organic layer may comprise at least one compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron injection layer, an interlayer, a hole blocking layer, an electron blocking layer, and an electron buffer layer.

The compound of formula 1 of the present disclosure may be comprised as a dopant material in the light-emitting layer. The light-emitting layer may further comprise at least one host material.

A host material which may be used to be comprised with the compound of the present disclosure includes the compound of formula 2:

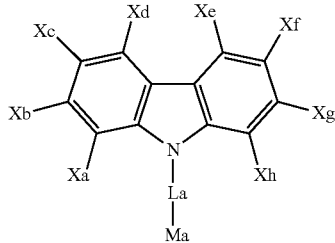

(2)

wherein

Ma represents a substituted or unsubstituted nitrogen-containing 5- to 11-membered heteroaryl;

La represents a single bond, or a substituted or unsubstituted (C6-C30)arylene;

Xa to Xh, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted (C1-C30)alkyl(C6-C30)arylamino, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring whose carbon atom(s) may be replaced with at least one hetero atom selected from nitrogen, oxygen, and sulfur; and the heteroaryl contains at least one hetero atom selected from B, N, O, S, Si, and P.

In formula 2, the substituent for the substituted alkyl, the substituted alkenyl, the substituted alkynyl, the substituted cycloalkyl, the substituted aryl, the substituted heteroaryl, the substituted trialkylsilyl, the substituted triarylsilyl, the substituted dialkylarylsilyl, the substituted alkyldiarylsilyl, the substituted alkylarylamino, the substituted monoarylamino, the substituted diarylamino, or the substituted mono- or polycyclic, alicyclic or aromatic ring, each independently, may be at least one selected from the group consisting of deuterium; a halogen; a cyano; a carboxyl; a nitro; a hydroxy; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a 3- to 7-membered heterocycloalkyl; a (C6-C30)aryloxy; a (C6-C30)arylthio; a 3- to 30-membered heteroaryl unsubstituted or substituted with a tri(C6-C30)arylsilyl, a (C6-C30)aryl, a (C1-C30)alkyl(C6-C30)aryl, or a tri(C6-C30)arylsilyl(C6-C30)aryl; a (C6-C30)aryl unsubstituted or substituted with a (C1-C30)alkyl, a halogen, a (C6-C30)aryl, or a 3- to 30-membered heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

In formula 2, preferably, La may be a single bond, or a substituted or unsubstituted (C6-C12)arylene. More preferably, La may be a single bond, or a (C6-C12)arylene unsubstituted or substituted with a tri(C6-C10)arylsilyl. Specifically, La may be a single bond, a substituted or unsubstituted phenylene, a substituted or unsubstituted naphthylene, or a substituted or unsubstituted biphenylene.

In formula 2, preferably, Ma may be a substituted or unsubstituted nitrogen-containing 5- to 11-membered heteroaryl. More preferably, Ma may be a nitrogen-containing 6- to 11-membered heteroaryl unsubstituted or substituted with a cyano, a (C1-C6)alkyl, a tri(C6-C12)arylsilyl, a (C6-C18)aryl, or a 5- to 15-membered heteroaryl.

Specifically, Ma may be a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, a substituted or unsubstituted pyridazinyl, a substituted or unsubstituted benzimidazolyl, a substituted or unsubstituted isoindolyl, a substituted or unsubstituted indolyl, a substituted or unsubstituted indazolyl, a substituted or unsubstituted benzothiadiazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthylidinyl, or a substituted or unsubstituted quinoxalinyl. More specifically, Ma may be a substituted or unsubstituted triazinyl, a substituted or unsubstituted pyrimidinyl, a substituted or unsubstituted pyridyl, a substituted or unsubstituted quinolyl, a substituted or unsubstituted isoquinolyl, a substituted or unsubstituted quinazolinyl, a substituted or unsubstituted naphthylidinyl, or a substituted or unsubstituted quinoxalinyl.

In formula 2, preferably, Xa to Xh, each independently, may be hydrogen, a cyano, a substituted or unsubstituted (C6-C15)aryl, a substituted or unsubstituted 6- to 20-membered heteroaryl, or a substituted or unsubstituted tri(C6-C15)arylsilyl; or may be linked to an adjacent substituent(s) to form a substituted or unsubstitued 6- to 20-membered, mono- or polycyclic aromatic ring whose carbon atom(s) may be replaced with at least one hetero atom selected from nitrogen, oxygen, and sulfur. More preferably, Xa to Xh, each independently, may be hydrogen; a cyano; a (C6-C15) aryl unsubstitued or substituted with a tri(C6-C10)arylsilyl; or a 10- to 20-membered heteroaryl unsubstituted or substituted with a (C6-C12)aryl; or may be linked to an adjacent substituent(s) to form a substituted or unsubstituted benzene, a substituted or unsubstituted indole, a substituted or unsubstituted benzindole, a substituted or unsubstituted indene, a substituted or unsubstituted benzofuran, or a substituted or unsubstituted benzothiophene. Specifically, at least one of Xa to Xh, for example, Xb, Xc, Xf, or Xg, may be a substituted or unsubstituted dibenzothiophene; a substituted or unsubstituted dibenzofuran; a substituted or unsubstituted carbazole; a substituted or unsubstituted benzocarbazole; or may be linked to an adjacent substituent(s) to form a substituted or unsubstituted benzene, a substituted or unsubstituted indole, a substituted or unsubstituted benzindole, a substituted or unsubstituted indene, a substituted or unsubstituted benzofuran, or a substituted or unsubstituted benzothiophene.

More specifically, the compound of formula 2 includes the following, but is not limited thereto:

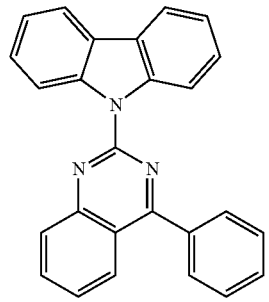

H2-1

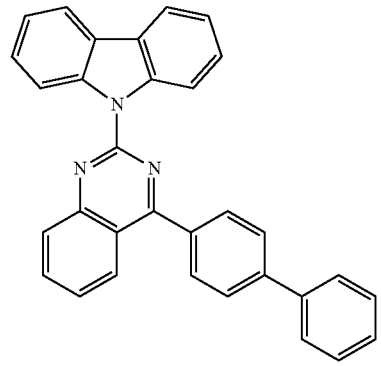

H2-2

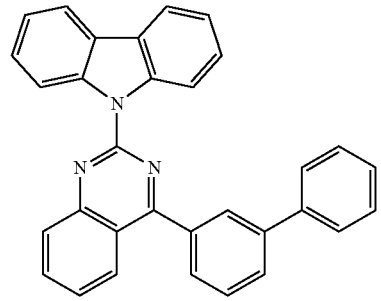

H2-3

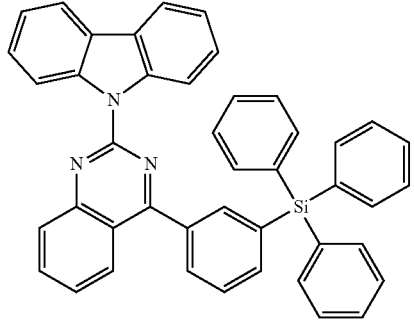

H2-4

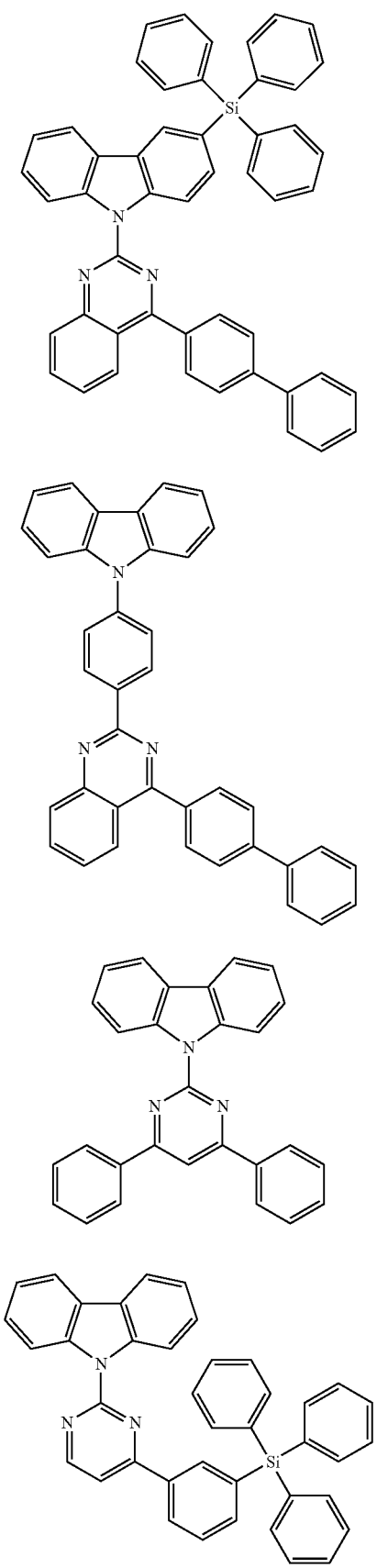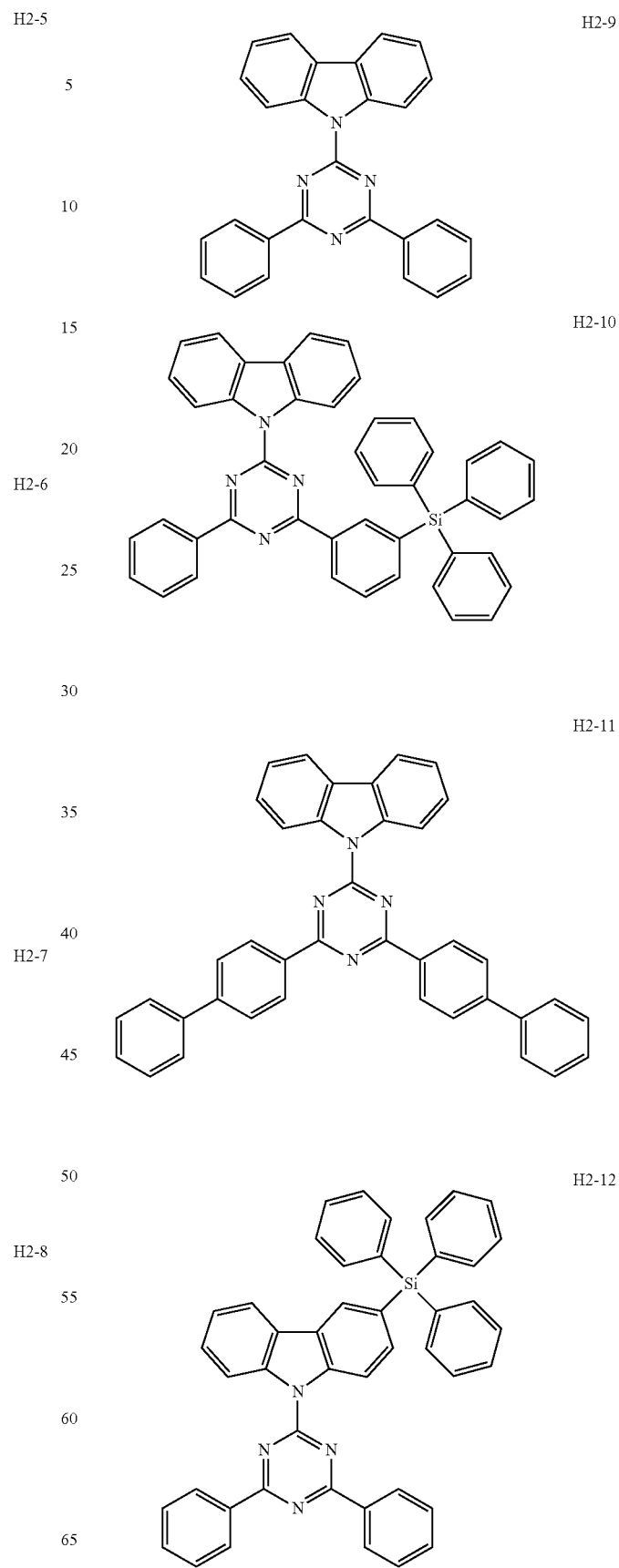

H2-13
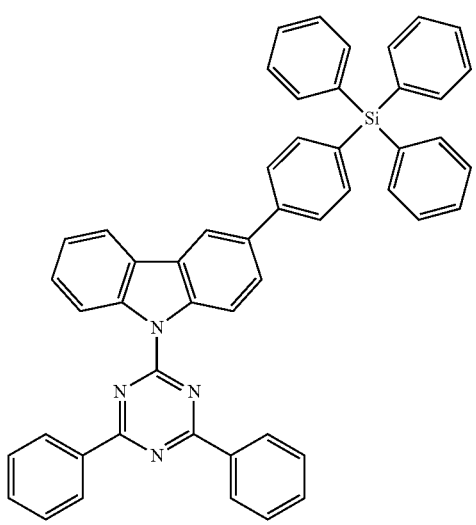
H2-14
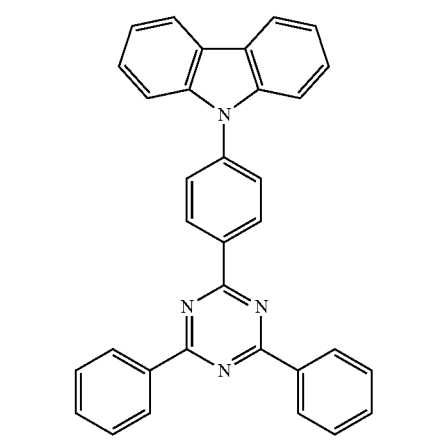
H2-15
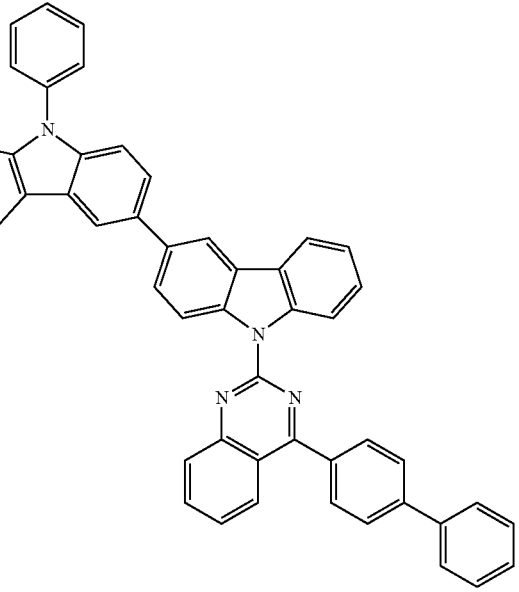
H2-16
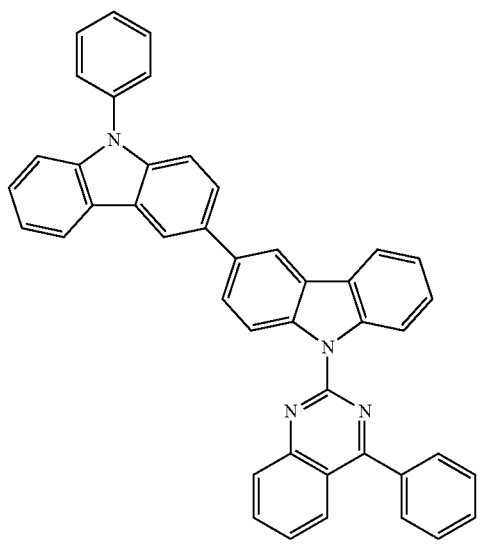
H2-17

H2-18
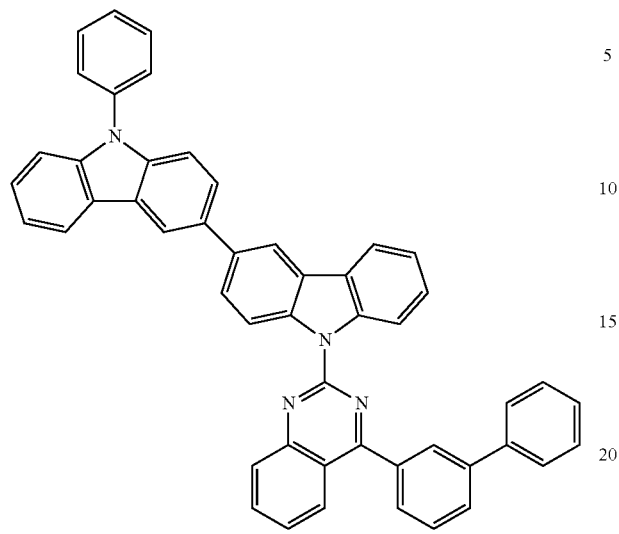
H2-21
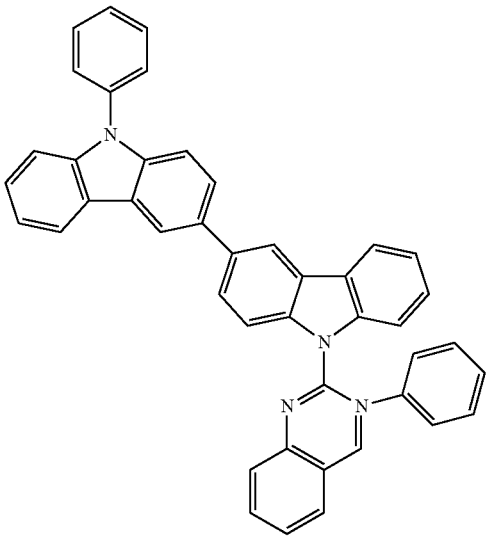
H2-19
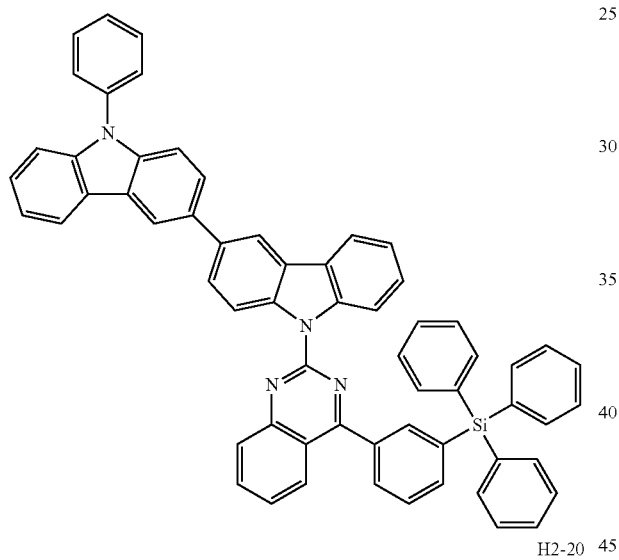
H2-22
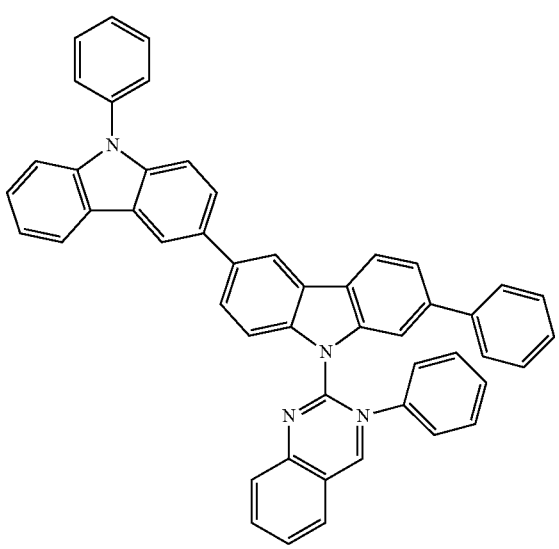
H2-20
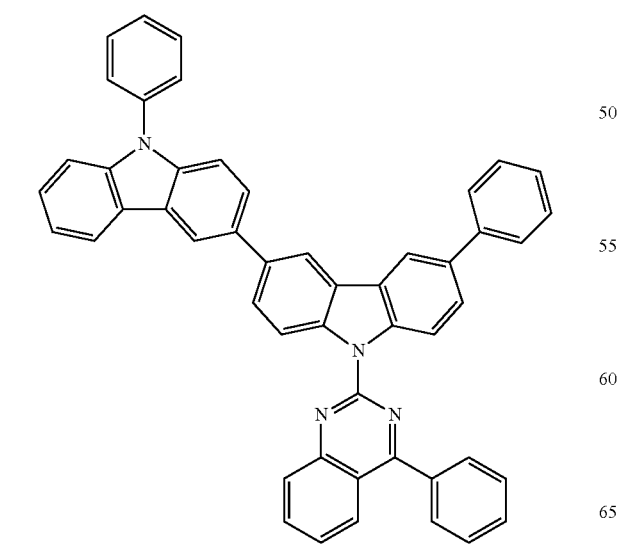
H2-23
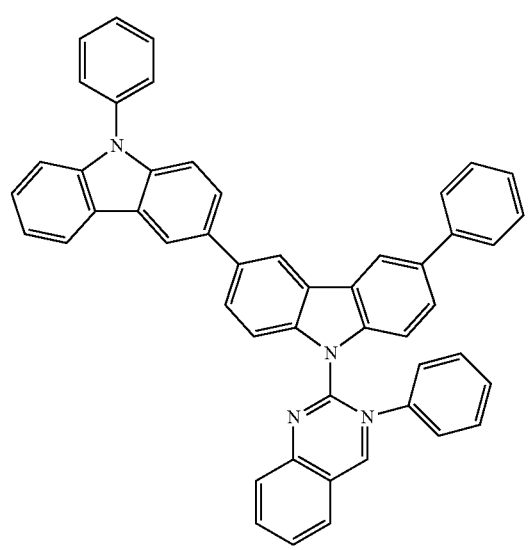

H2-24
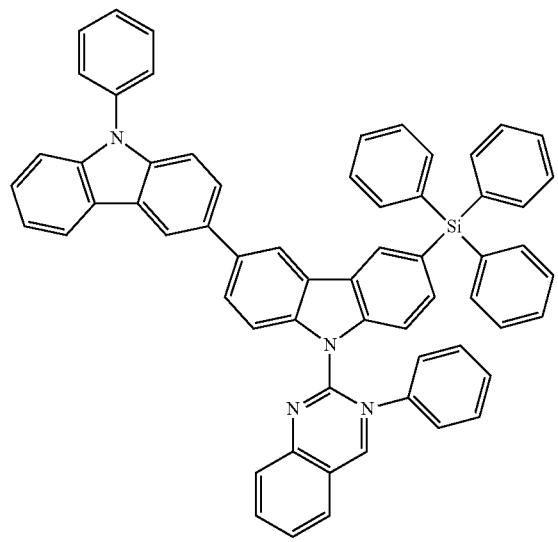
H2-25
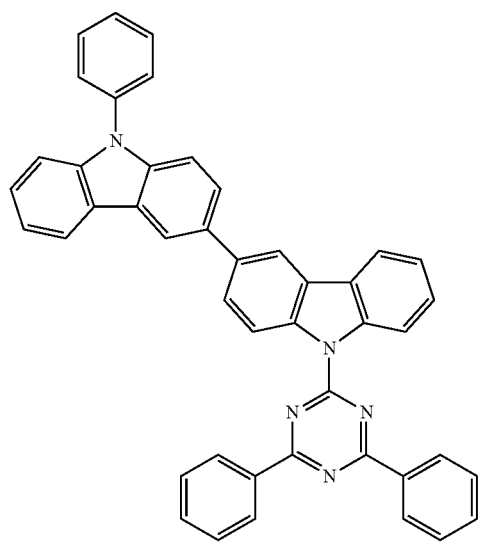
H2-26
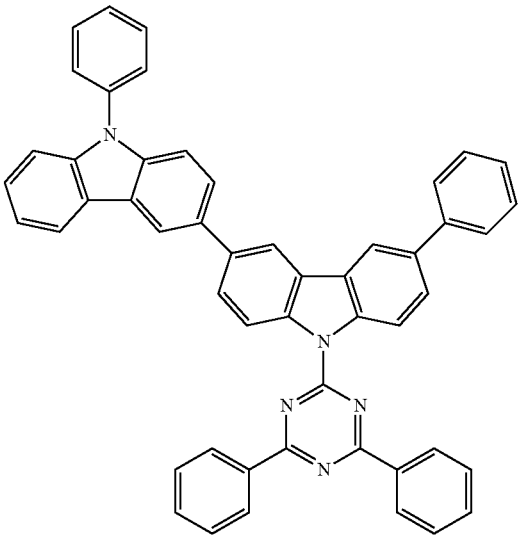
H2-27
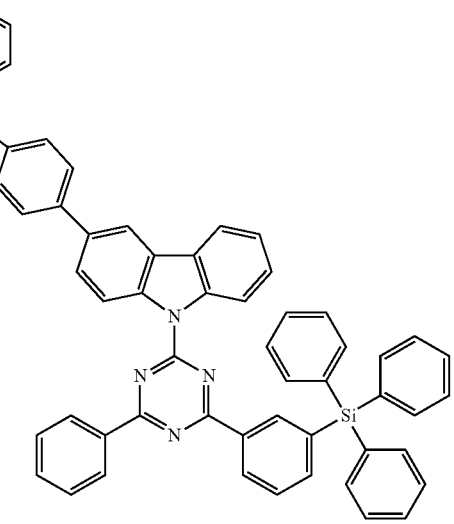
H2-28

H2-29
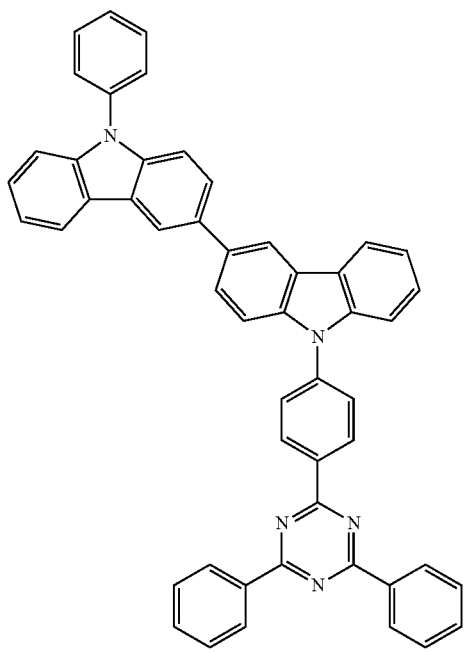
H2-30
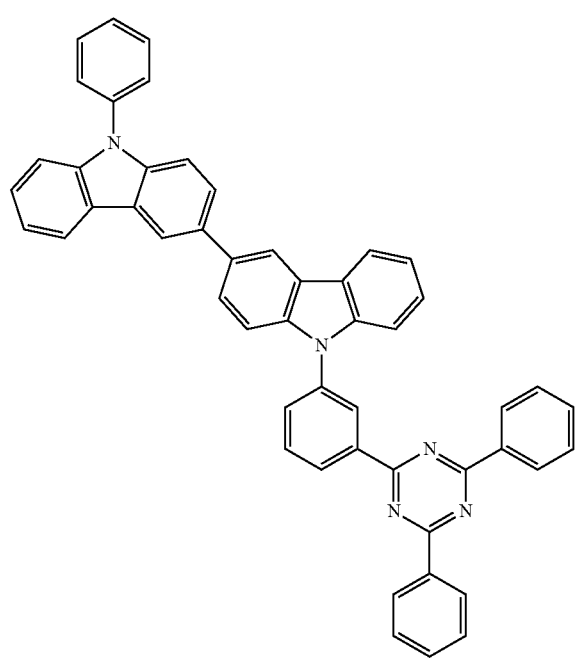
H2-31
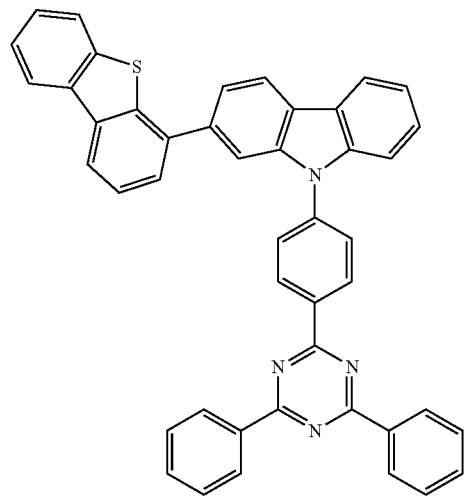
H2-32
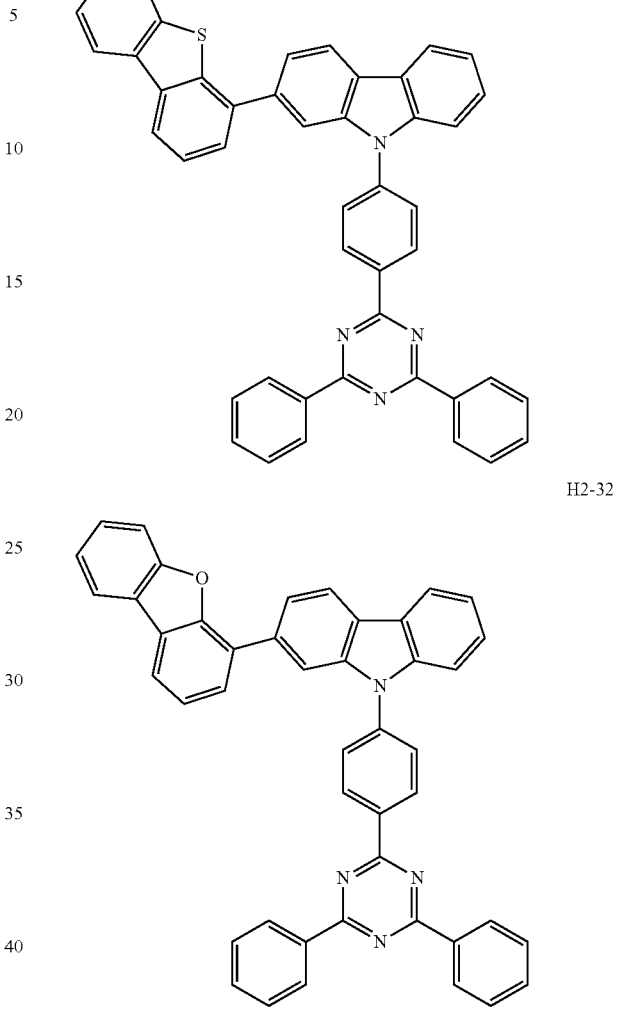
H2-33
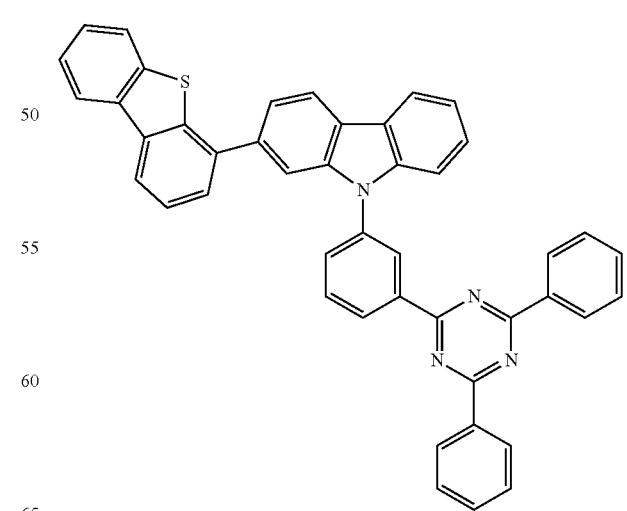

H2-34
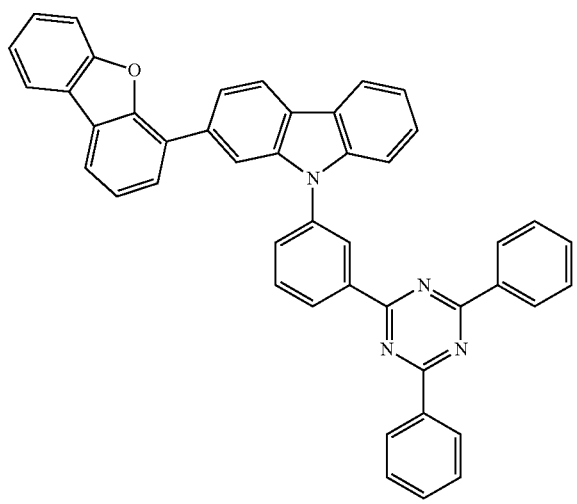
H2-35
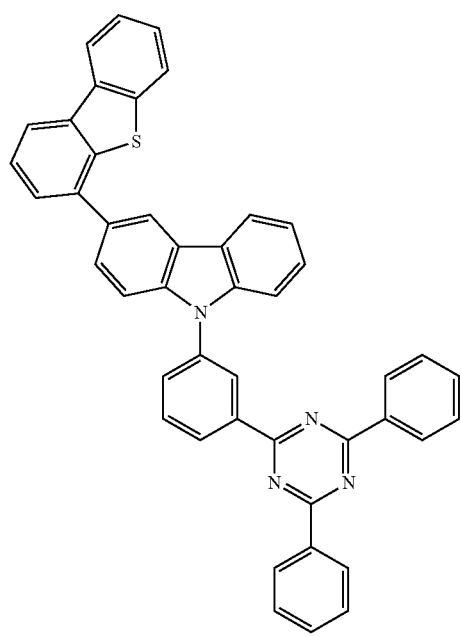
H2-36
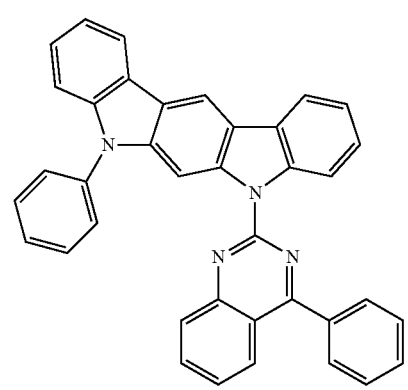
H2-37
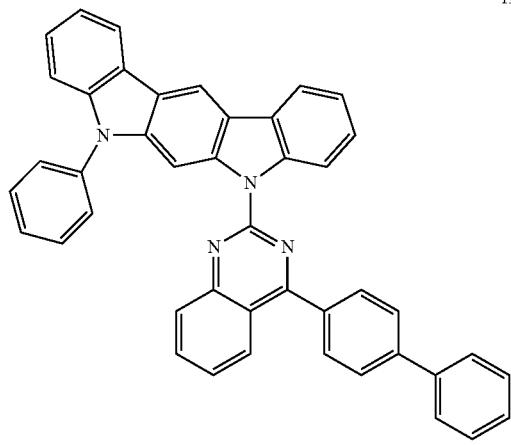
H2-38
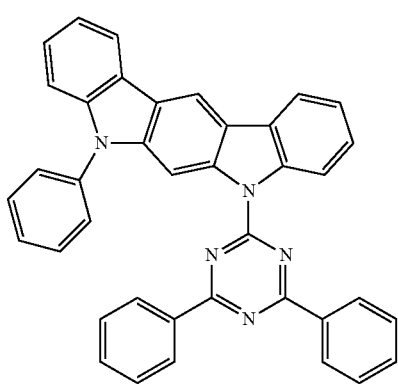
H2-39
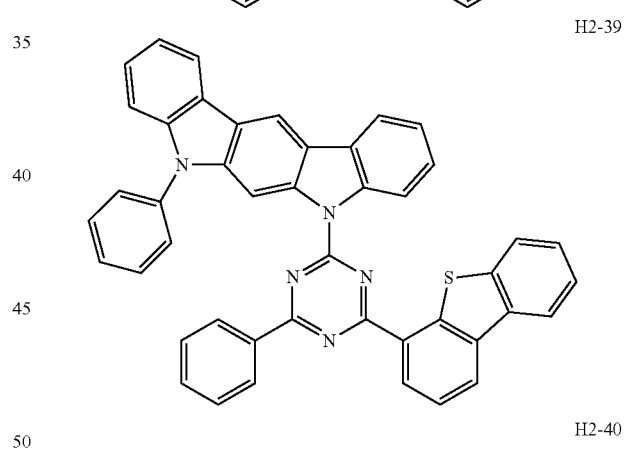
H2-40
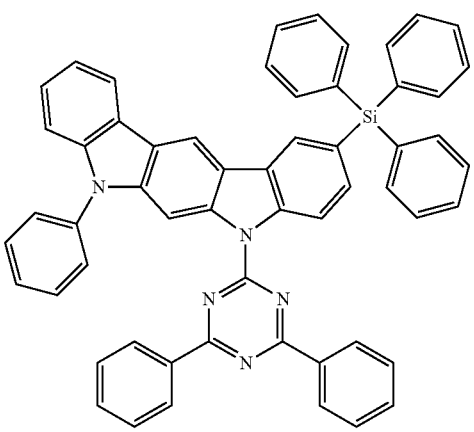

H2-41
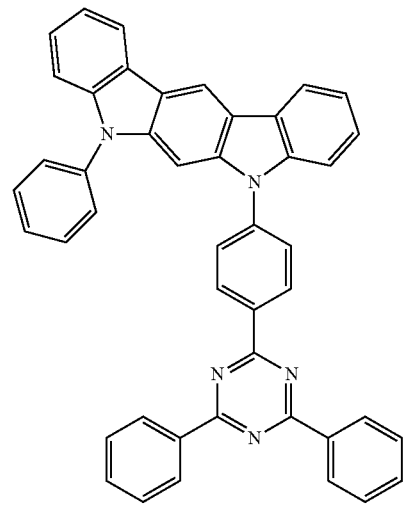
H2-42
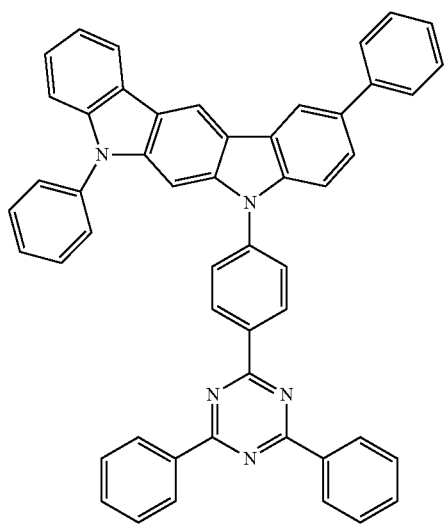
H2-43
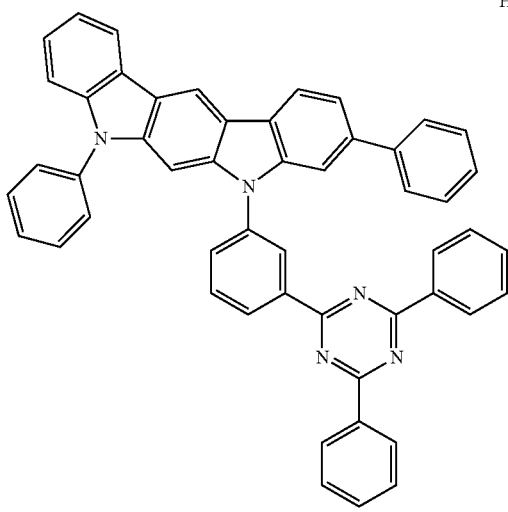
H2-44
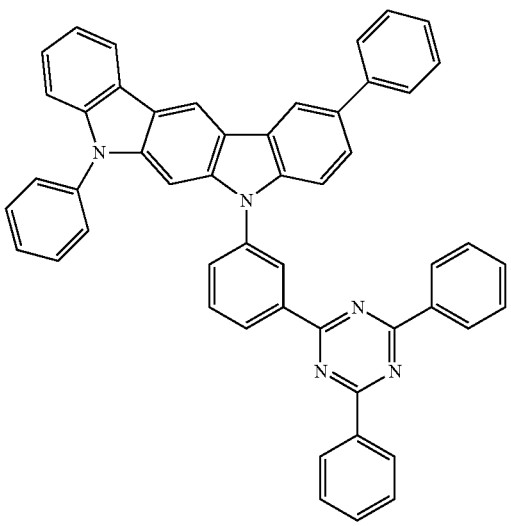
H2-45
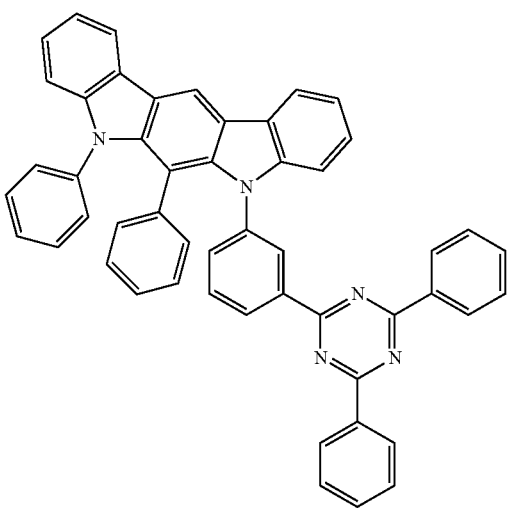
H2-46
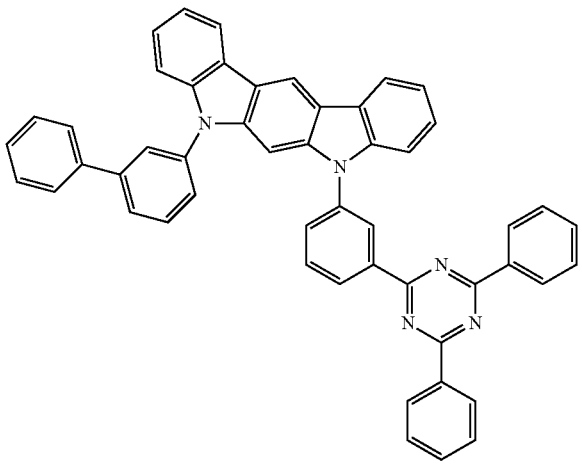

-continued
H2-47
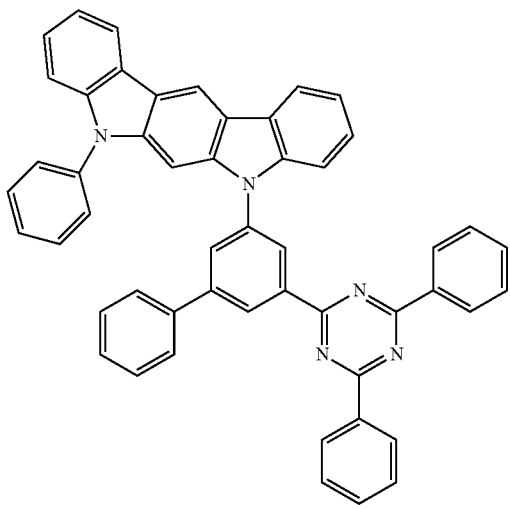
H2-48
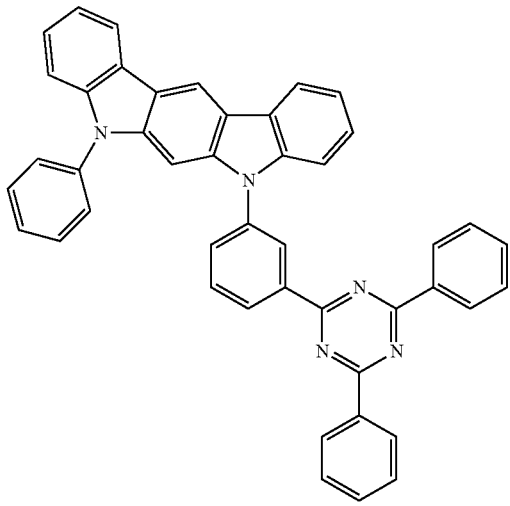
-continued
H2-49
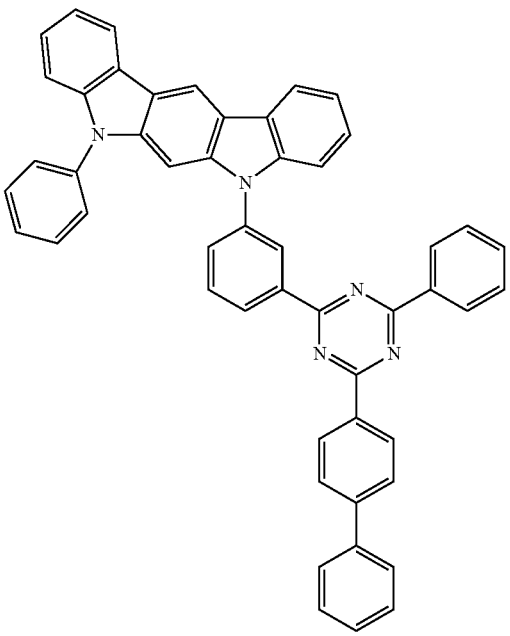
H2-50
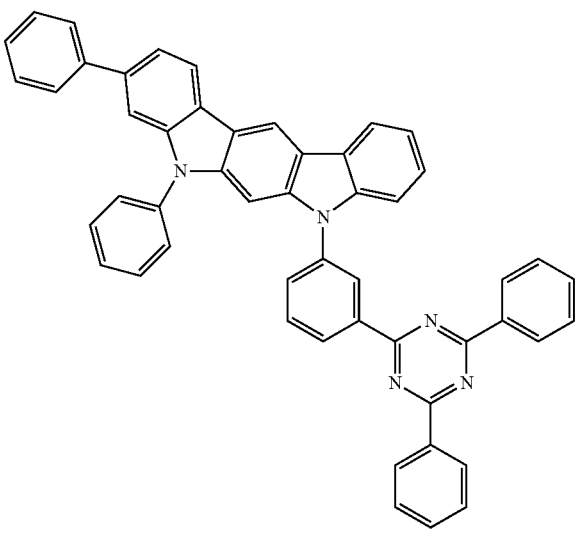

H2-51
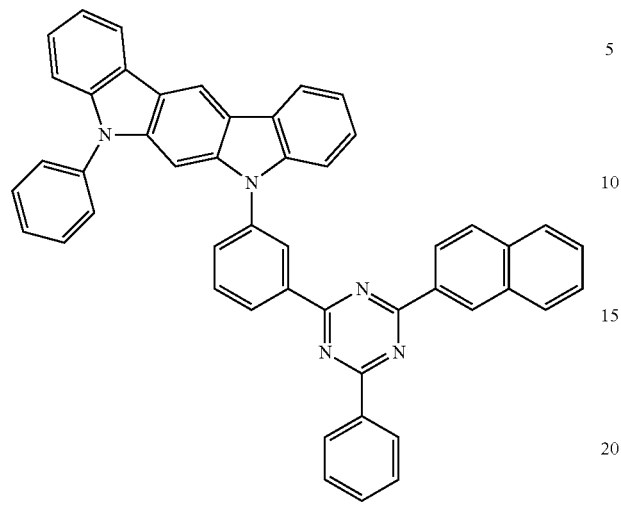
H2-52
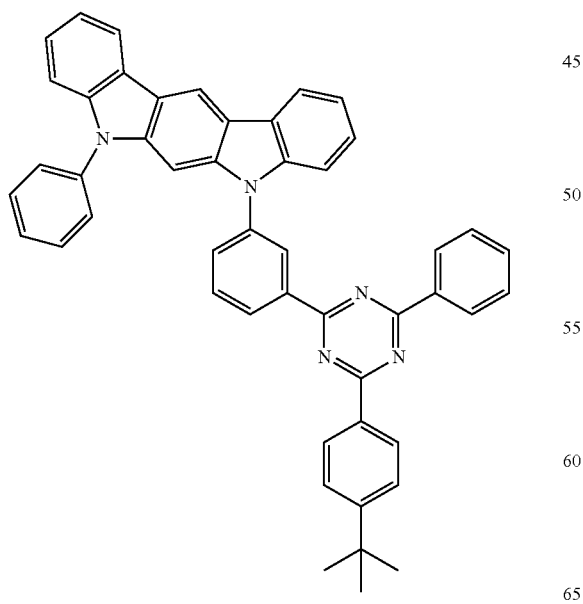
H2-53
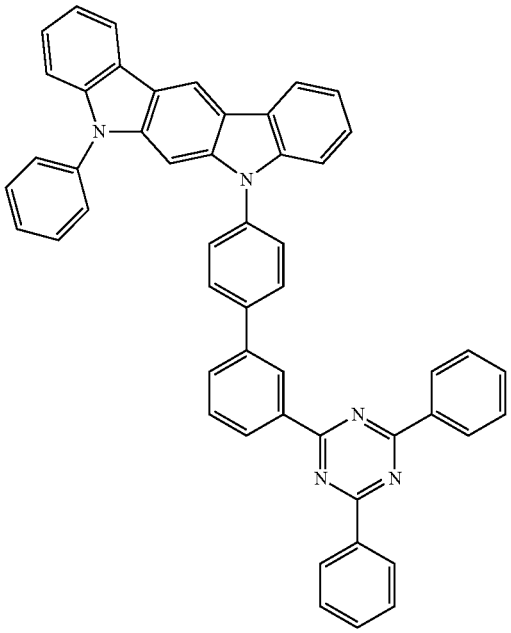
H2-54
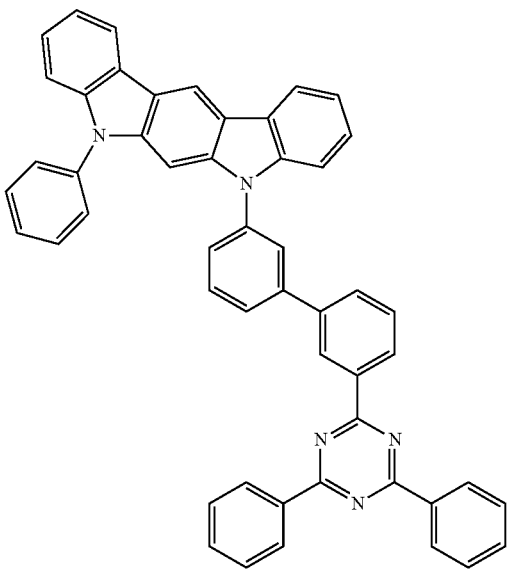

H2-55
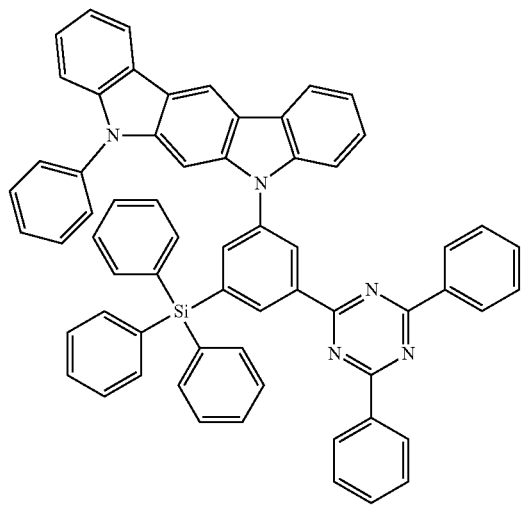
H2-56
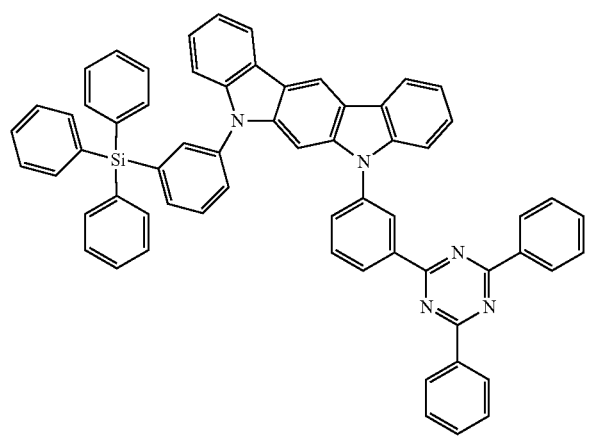
H2-57
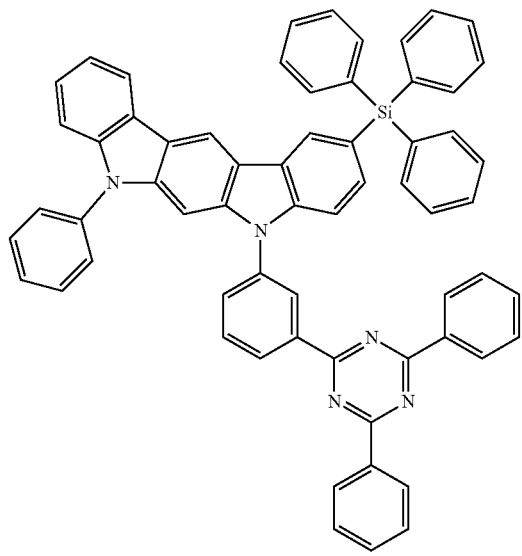
H2-58
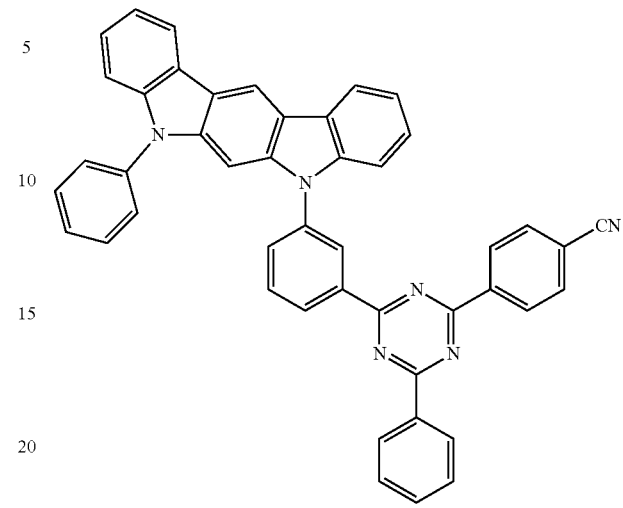
H2-59
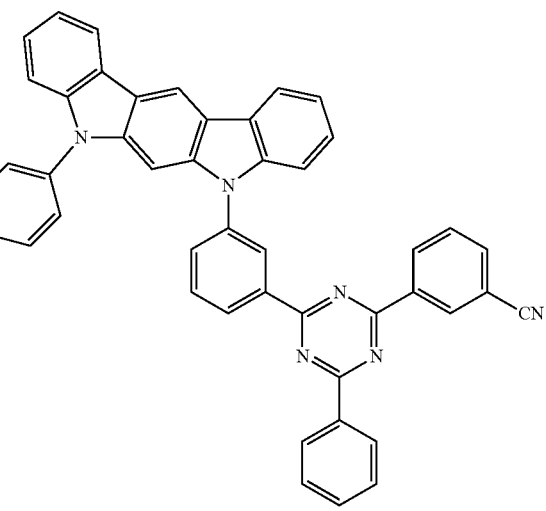
H2-60

H2-61
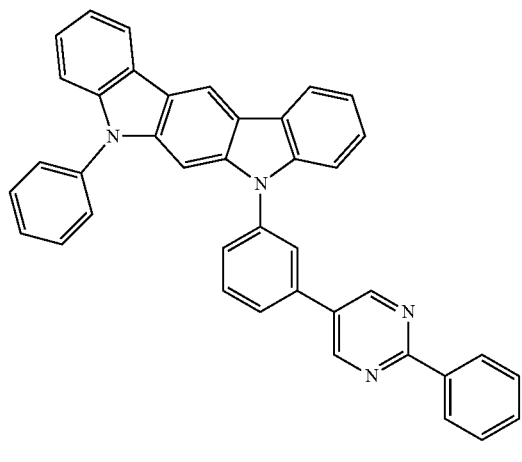
H2-64
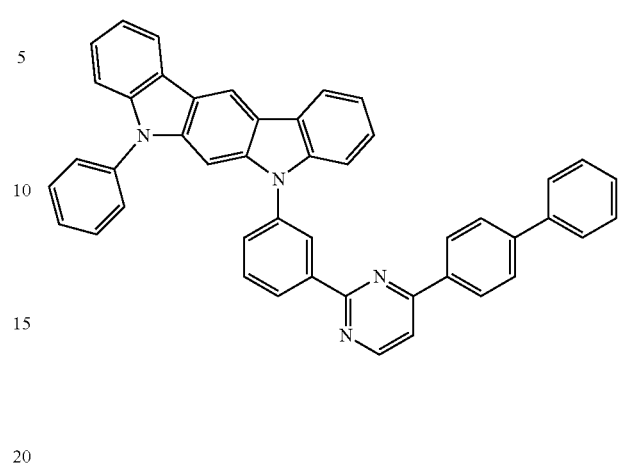
H2-62
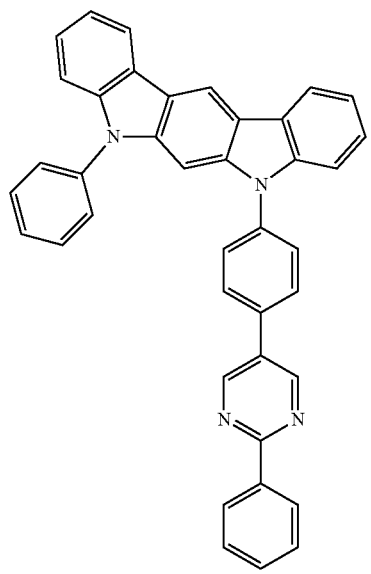
H2-65
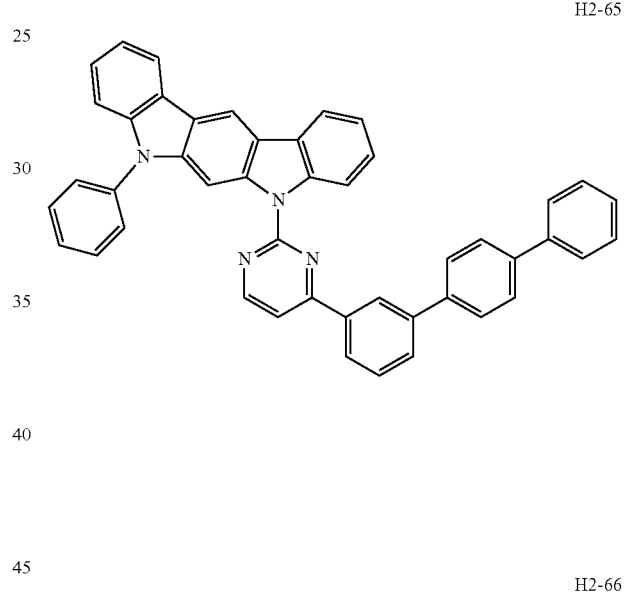
H2-63
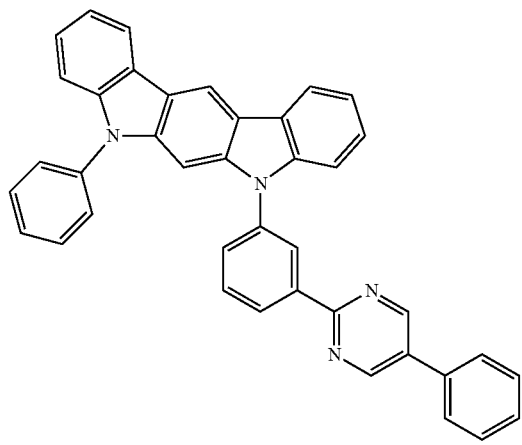
H2-66
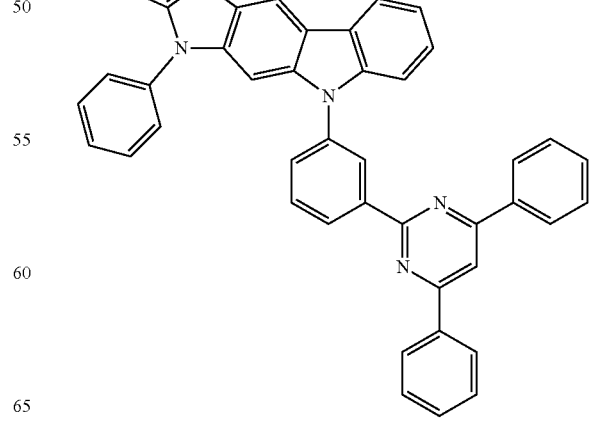

H2-67
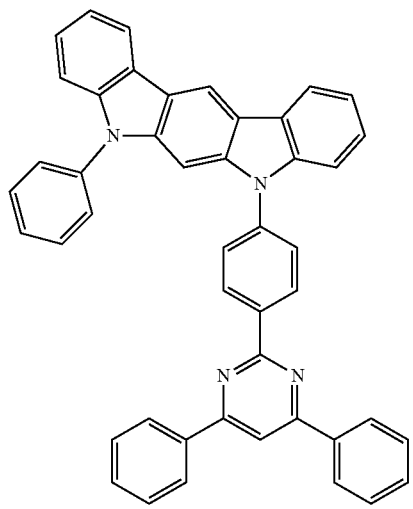
H2-68
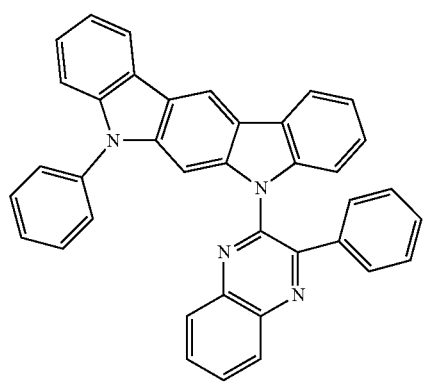
H2-69
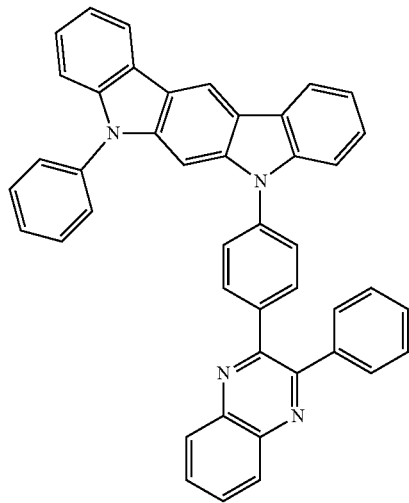
H2-70
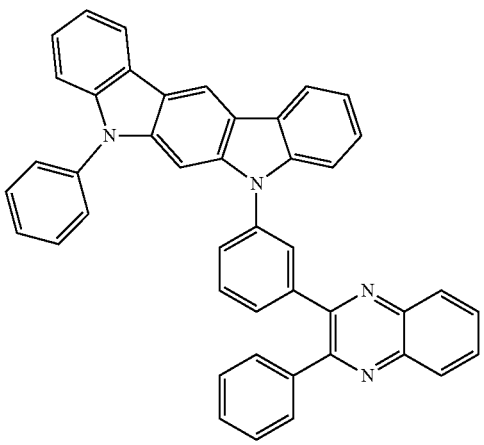
H2-71
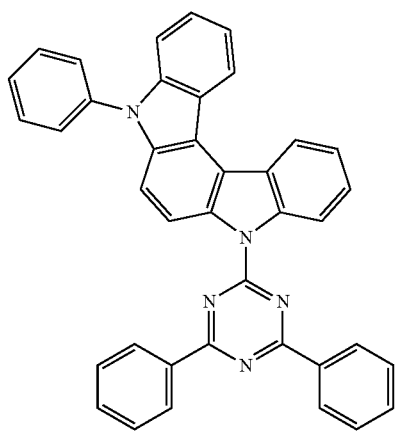
H2-72
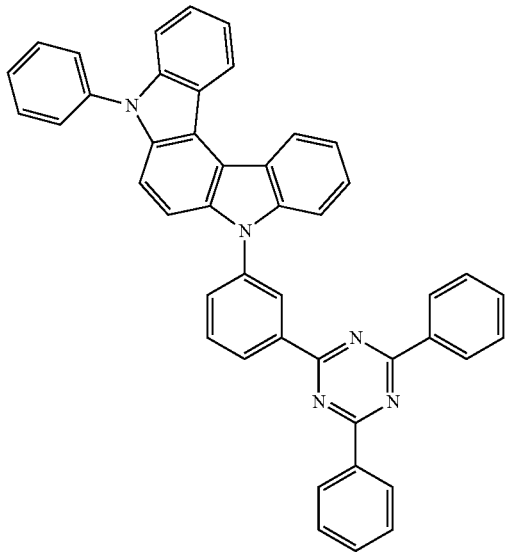

H2-73
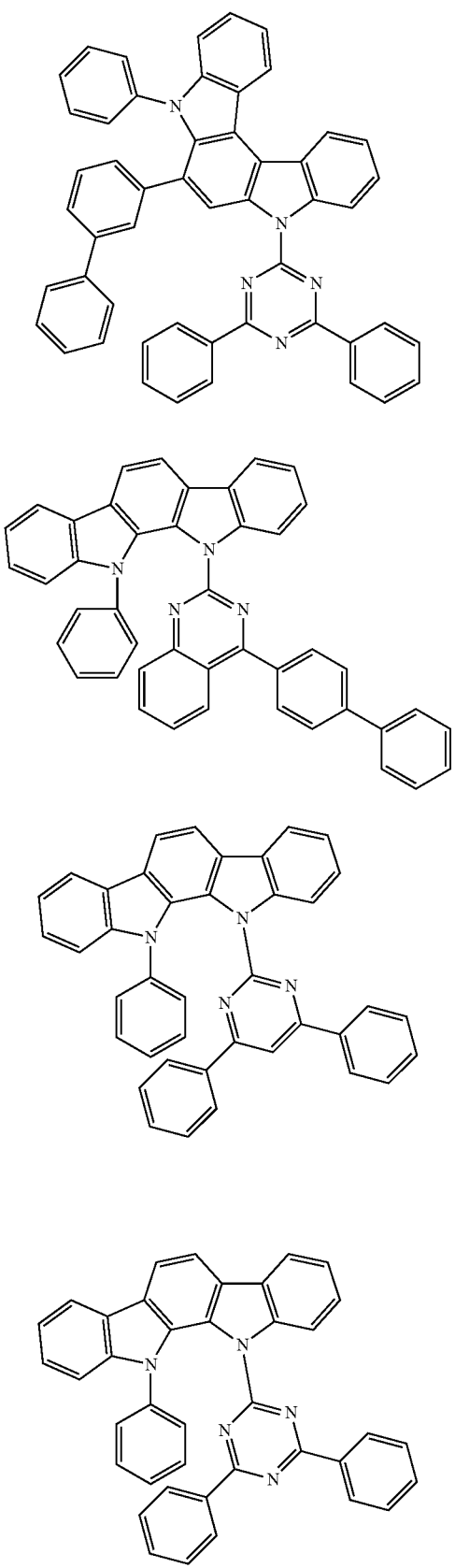
H2-74
H2-75
H2-76
H2-77
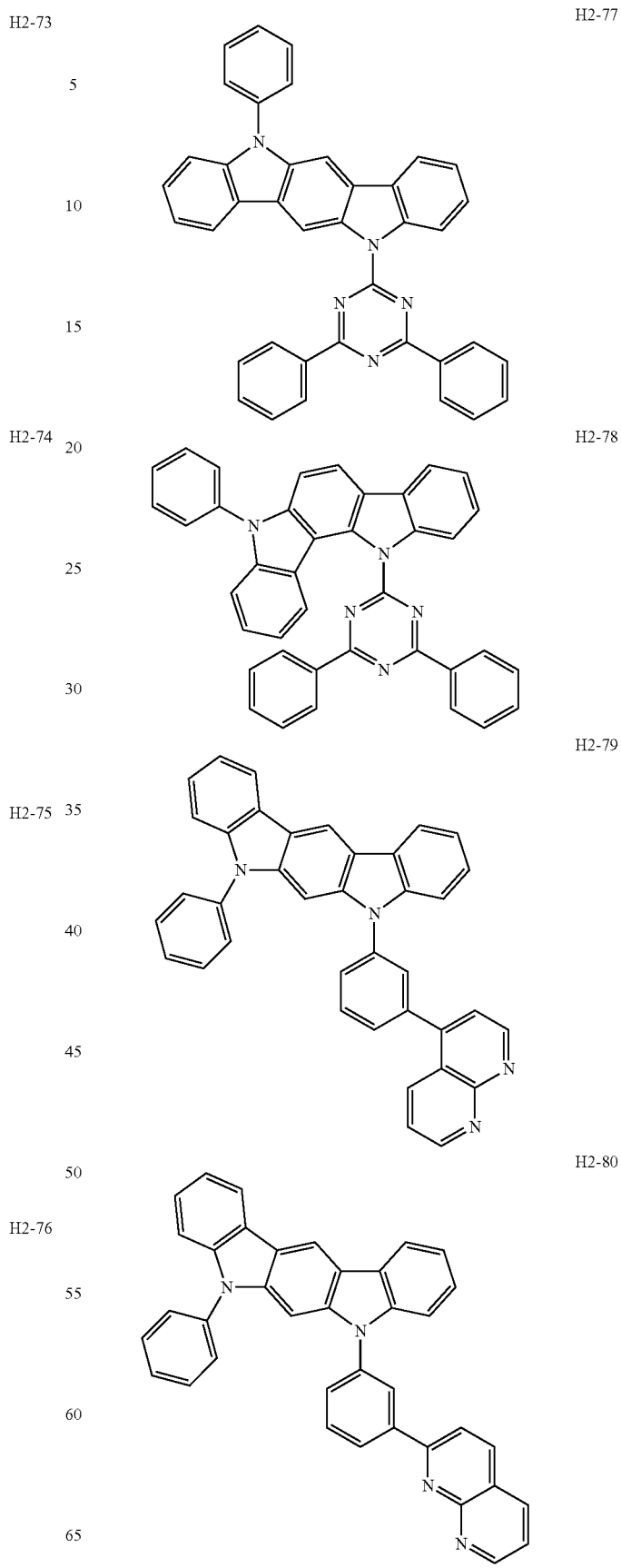
H2-78
H2-79
H2-80

H2-81
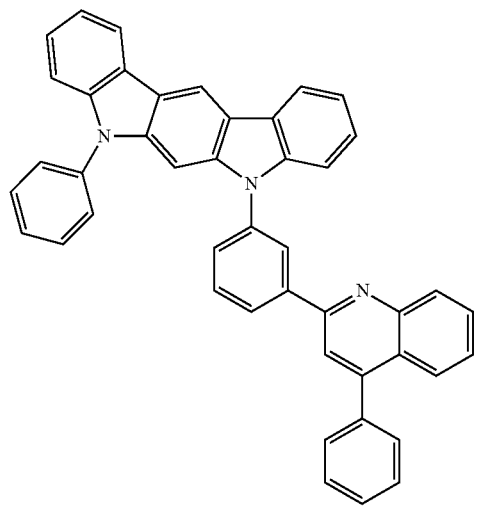
H2-82
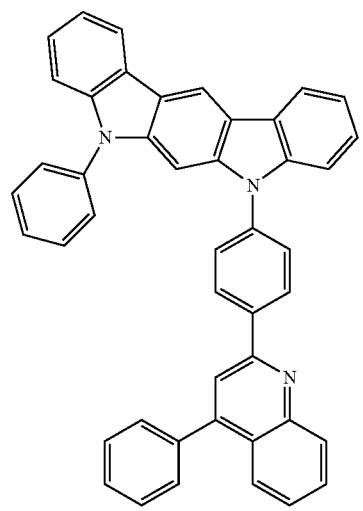
H2-83
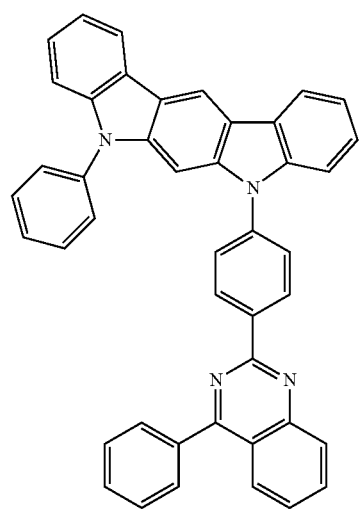
H2-84
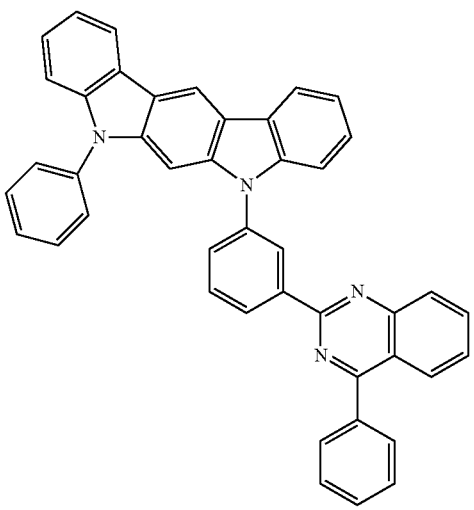
H2-85
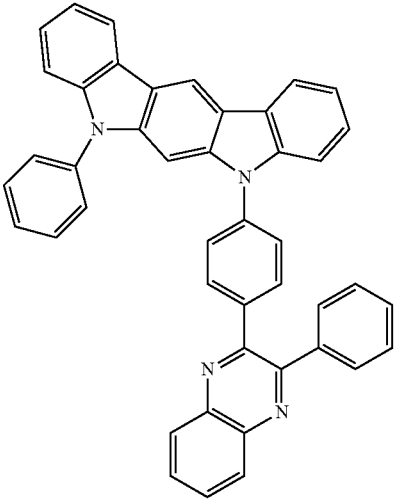
H2-86
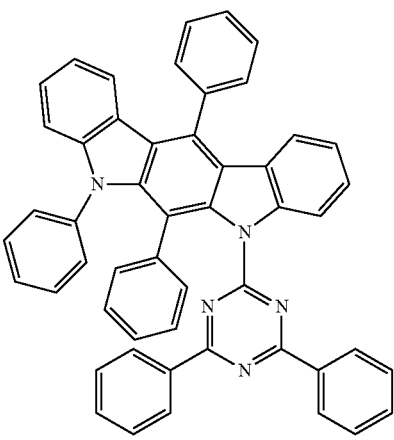

H2-87
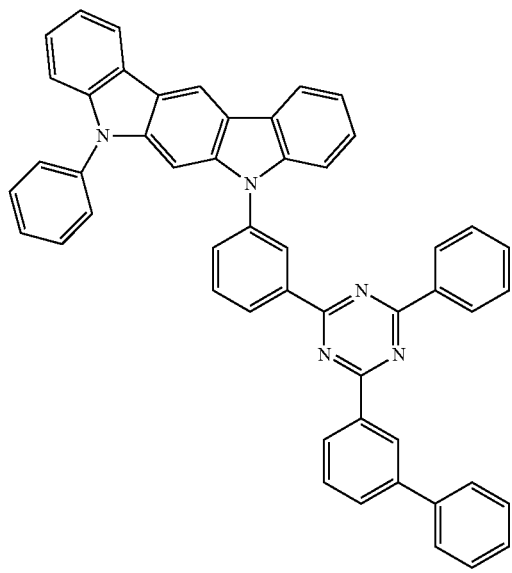
H2-89
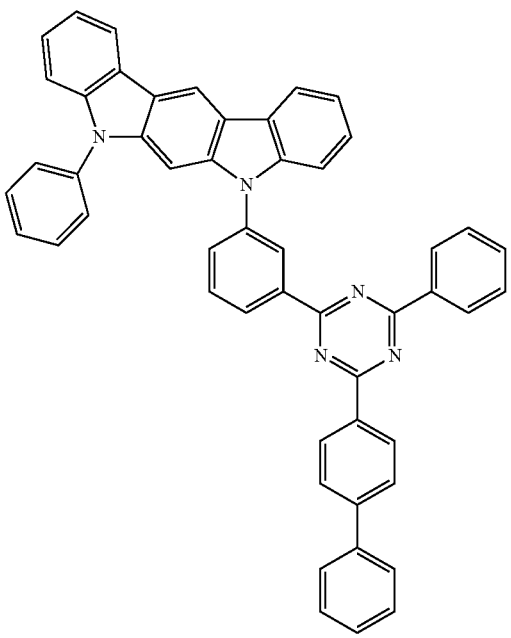
H2-88
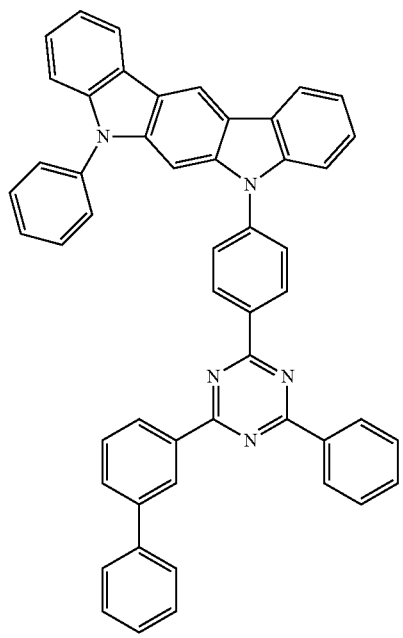
H2-90
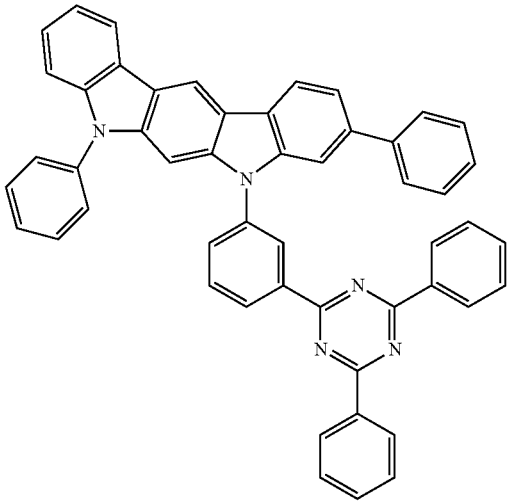

H2-91
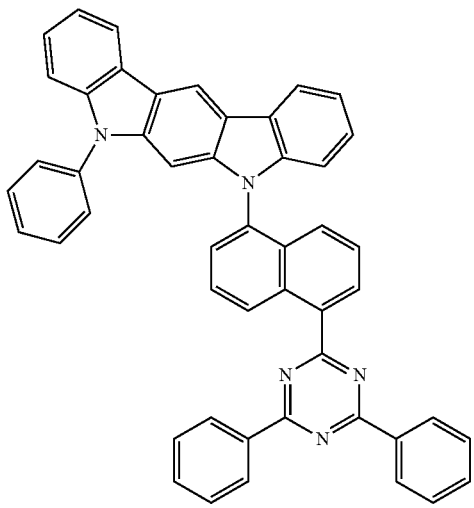
H2-92
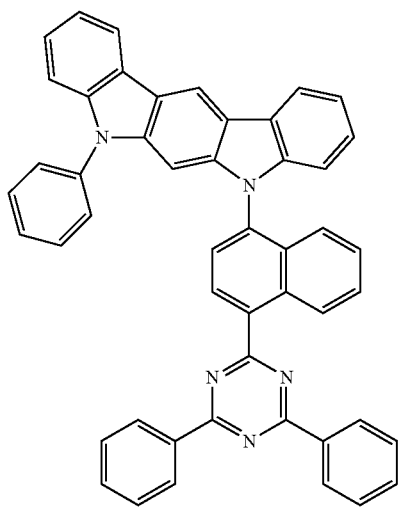
H2-93
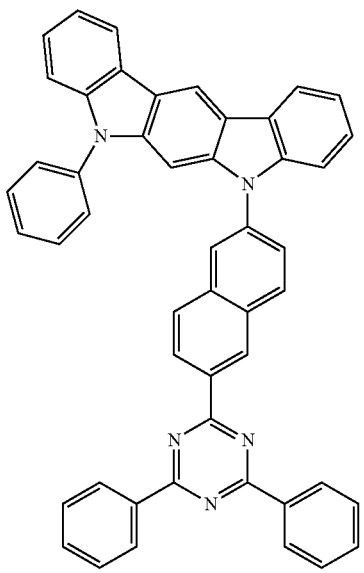
H2-94
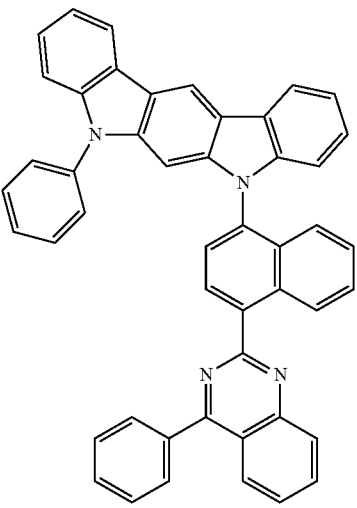
H2-95
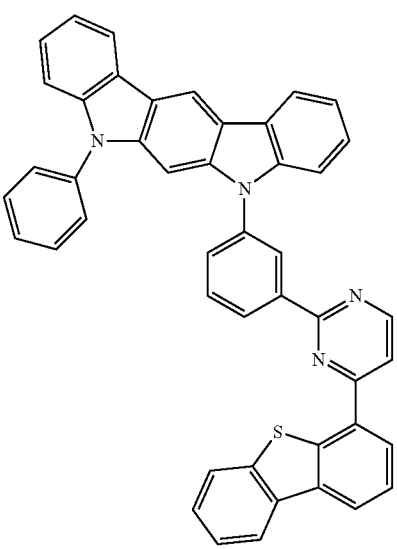
H2-96
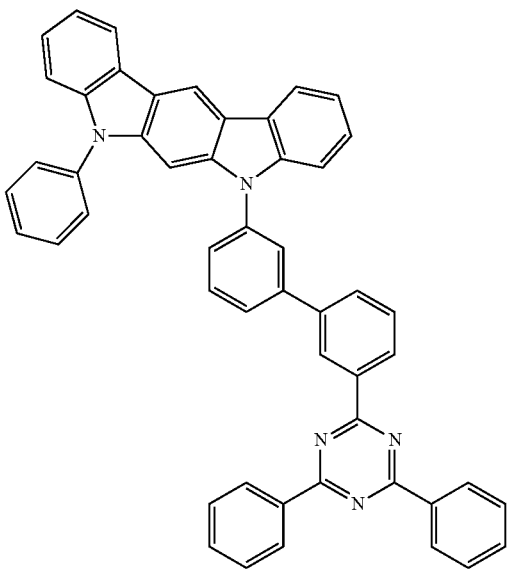

H2-97
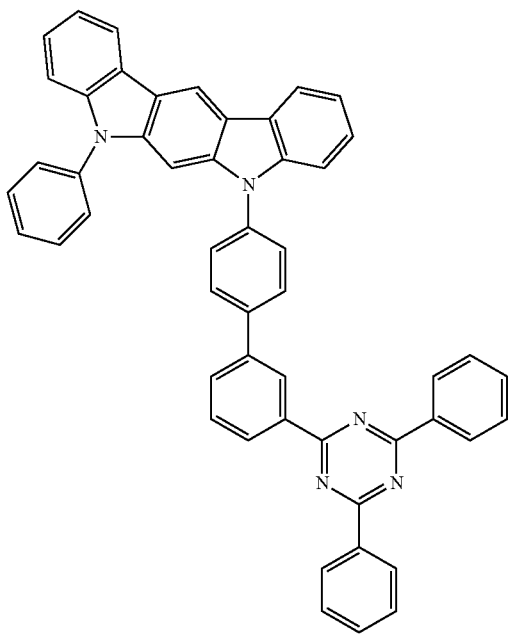
H2-98
H2-99
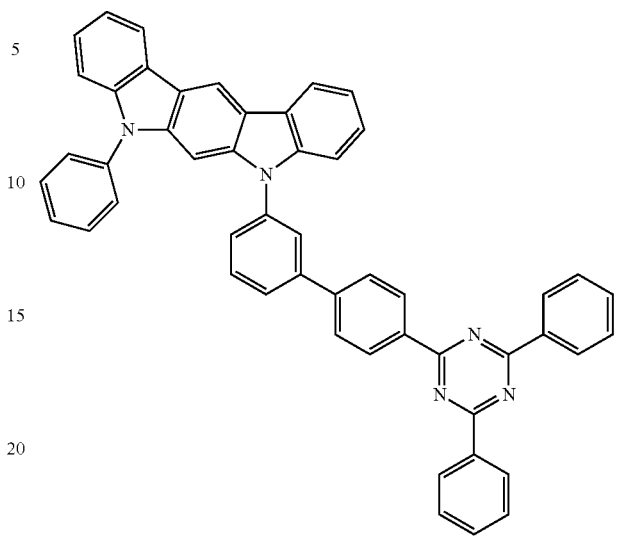
H2-100
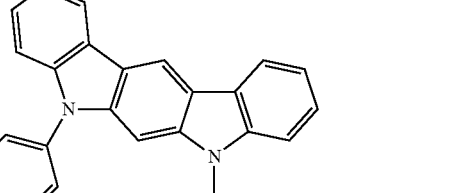
H2-101

-continued
H2-102
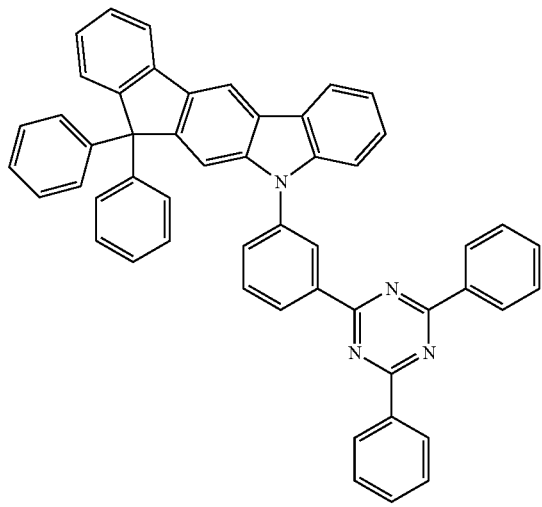
H2-103
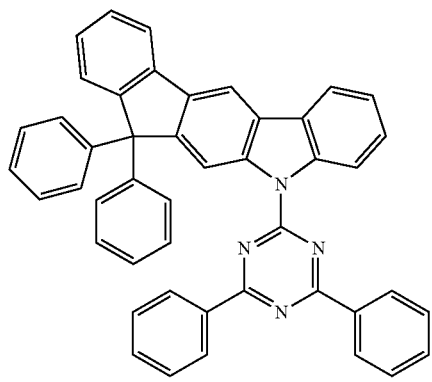
H2-104
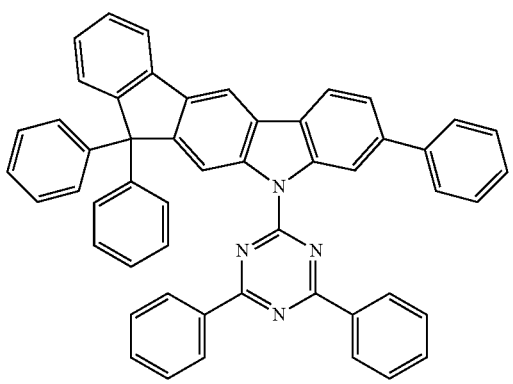
-continued
H2-105
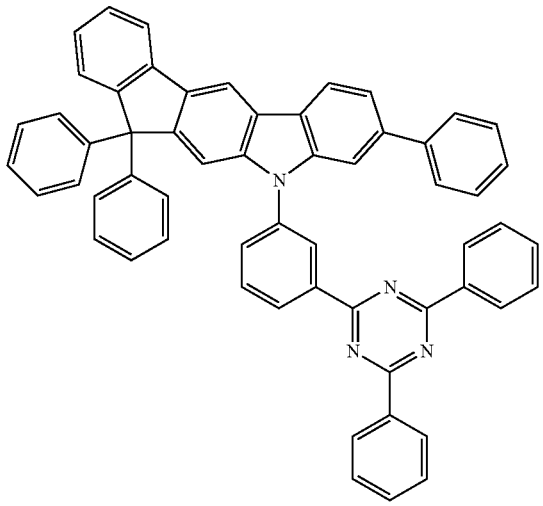
H2-106
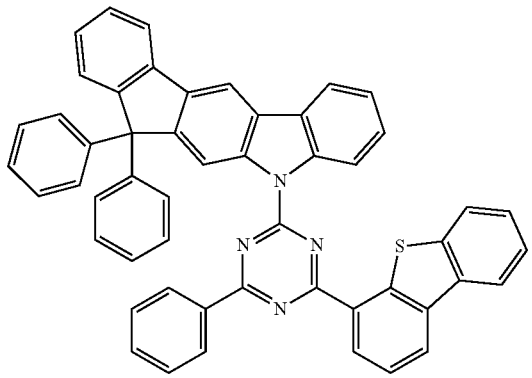
H2-107
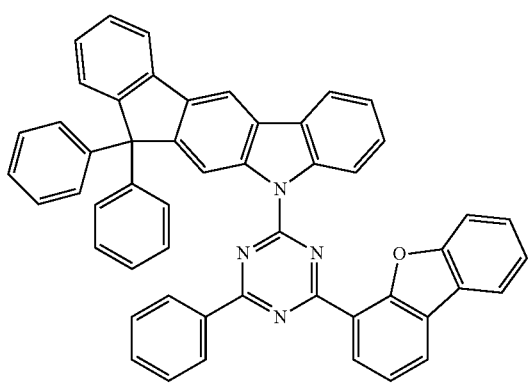

H2-108
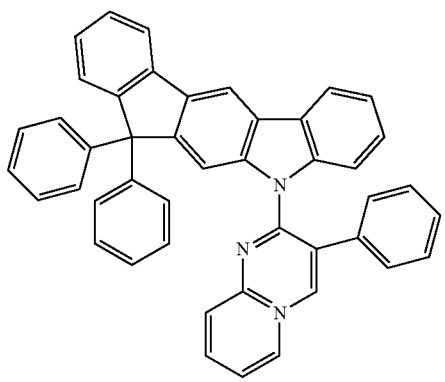
H2-109
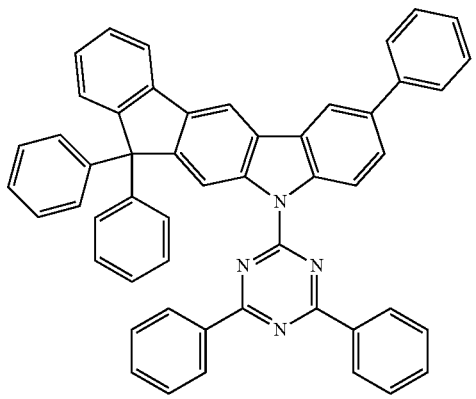
H2-110
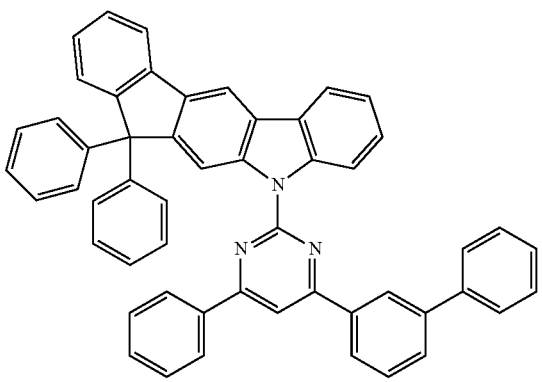
H2-111
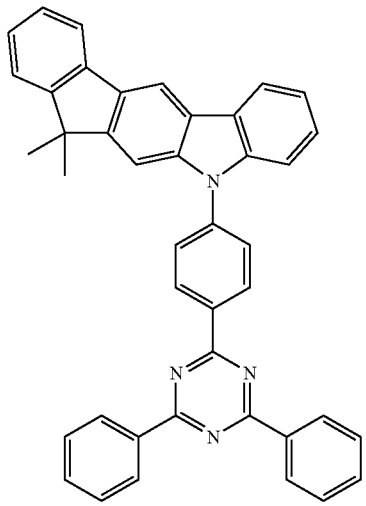
H2-112
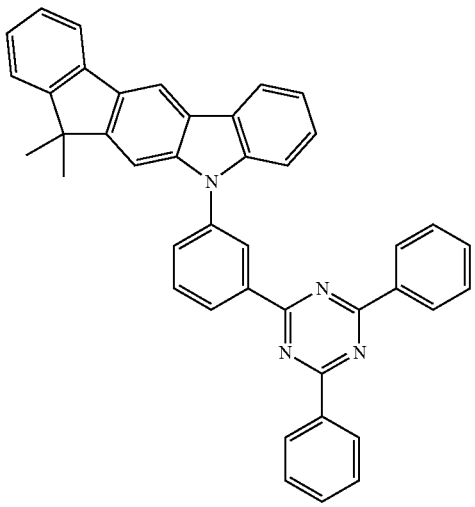
H2-113
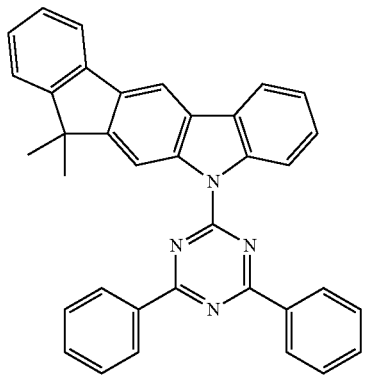

H2-114
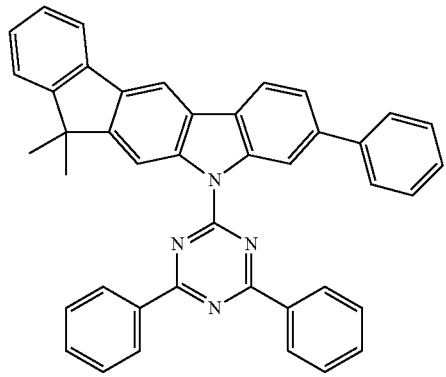
H2-115
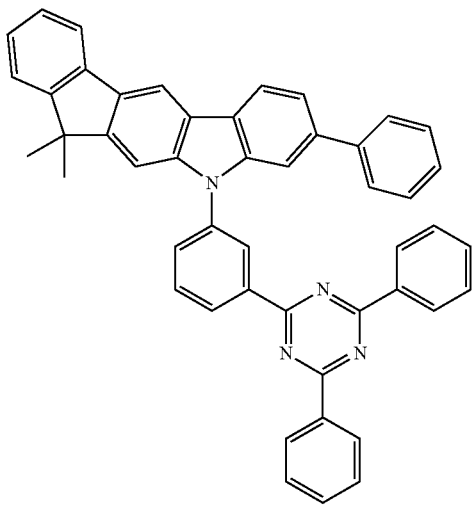
H2-116
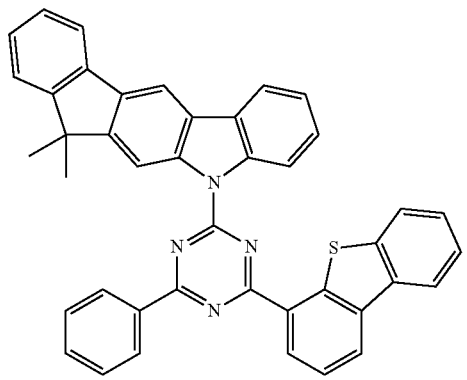
H2-117
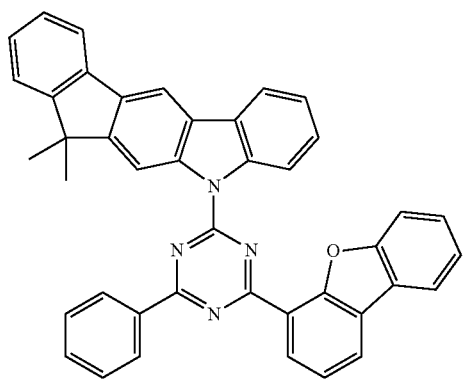
H2-118
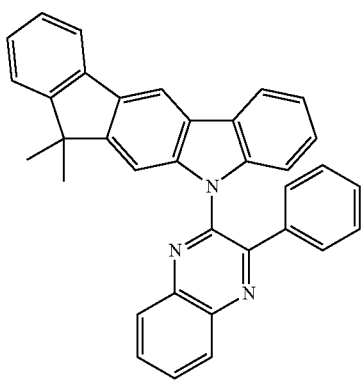
H2-119
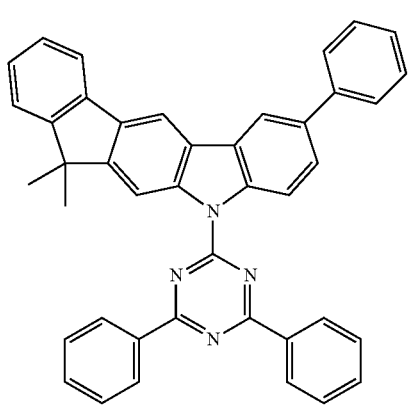
H2-120
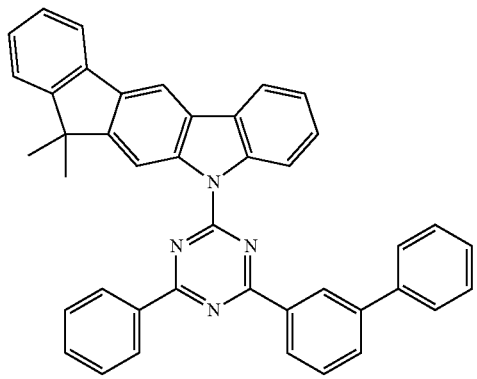
H2-121
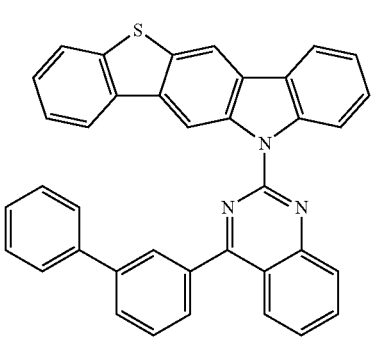

-continued
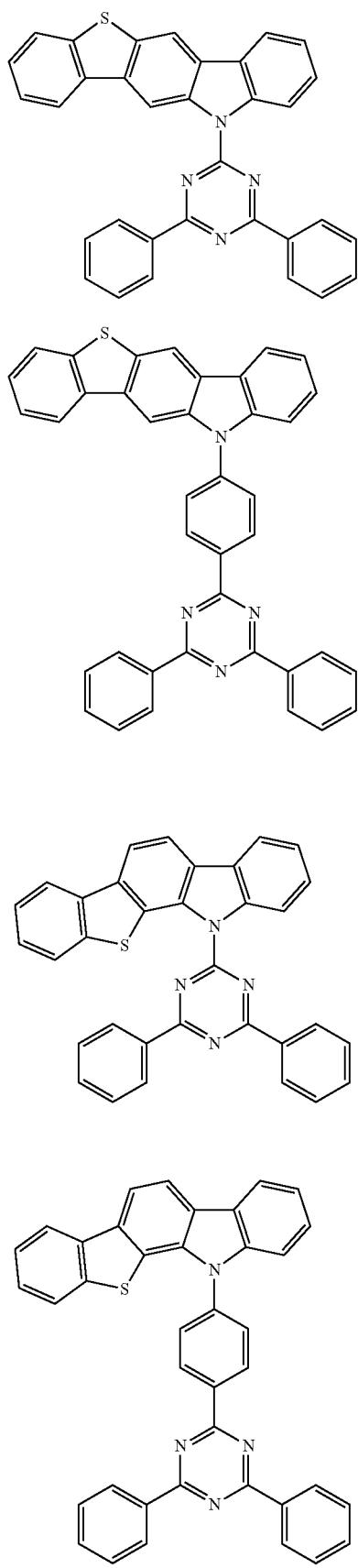
H2-122
H2-123
H2-124
H2-125
-continued
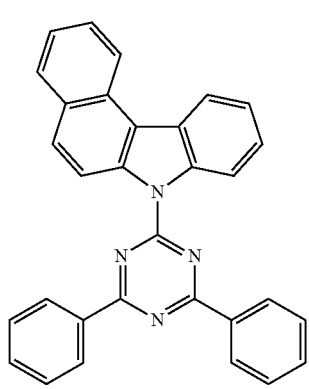
H2-126
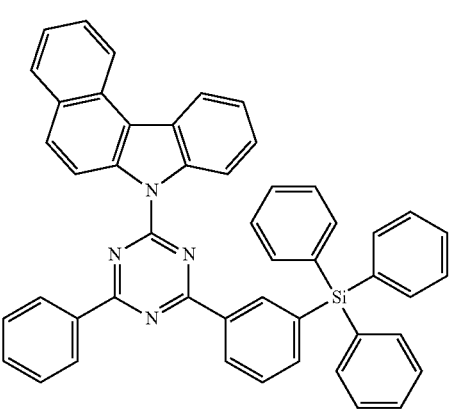
H2-127
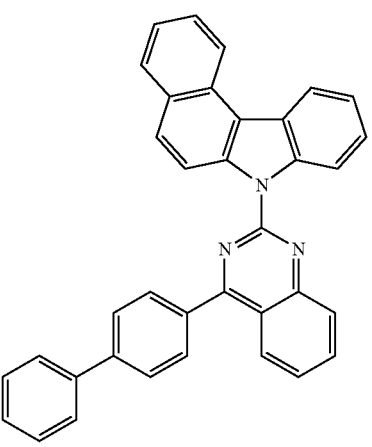
H2-128

H2-129
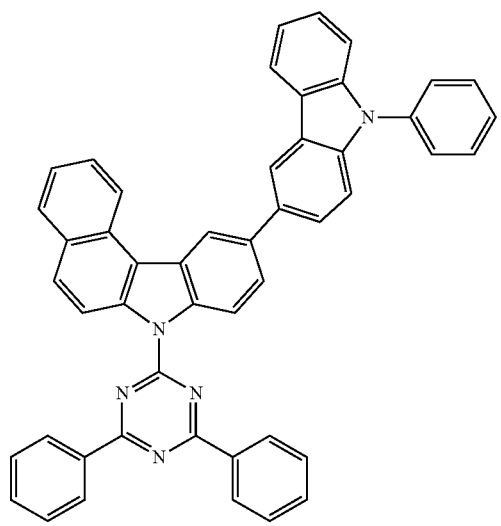
H2-130
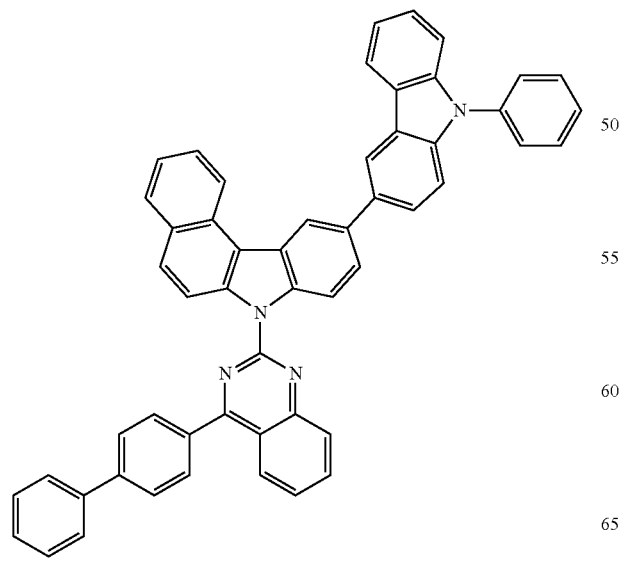
H2-131
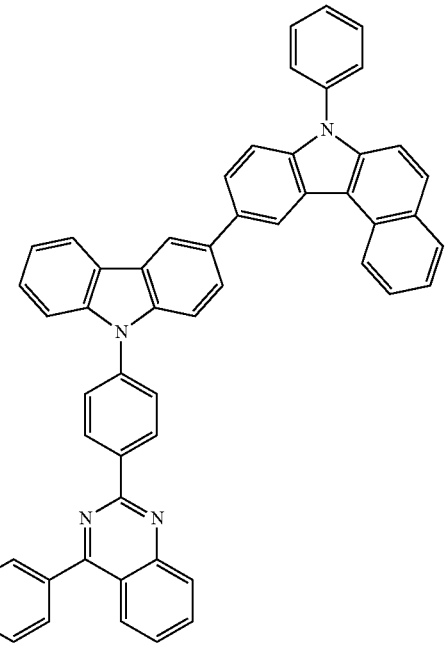
H2-132
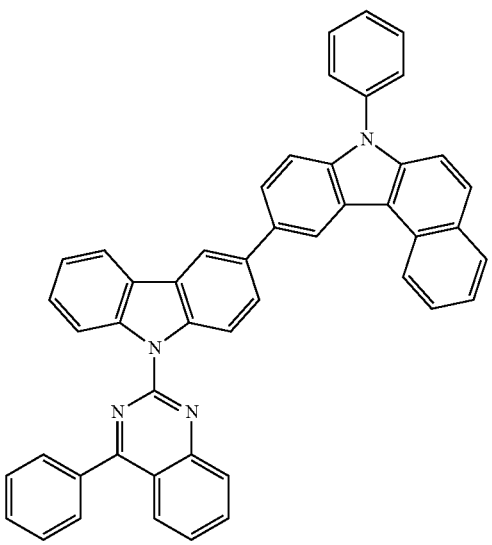

H2-133
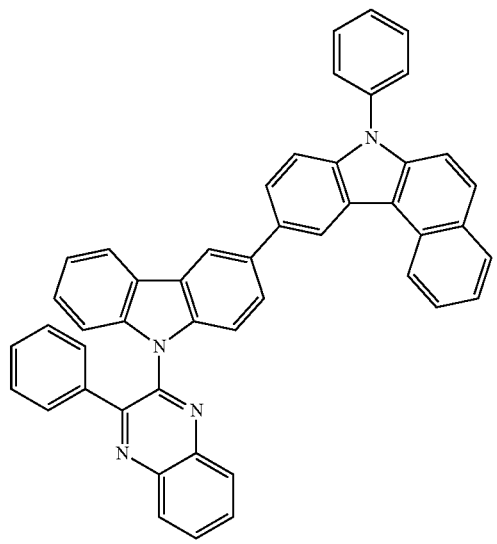
H2-134
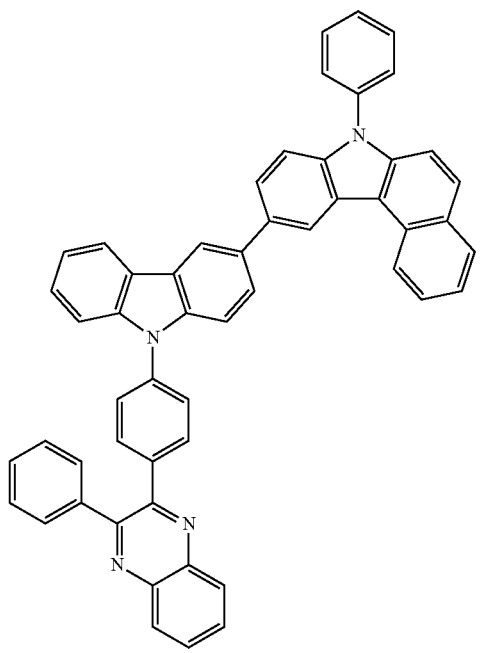
H2-135
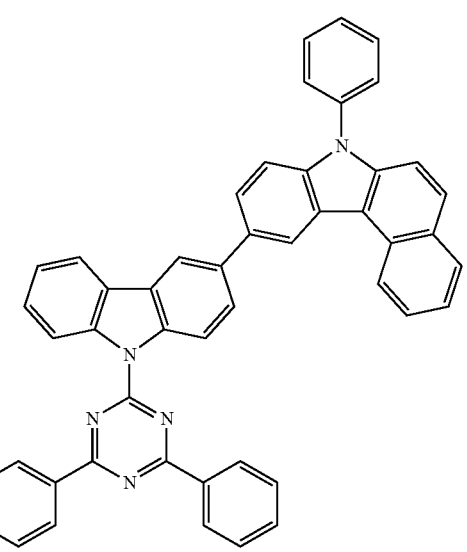
H2-136
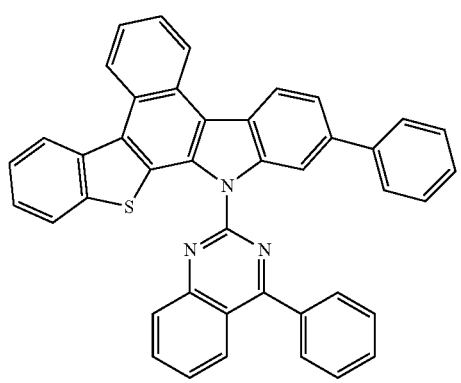
H2-137
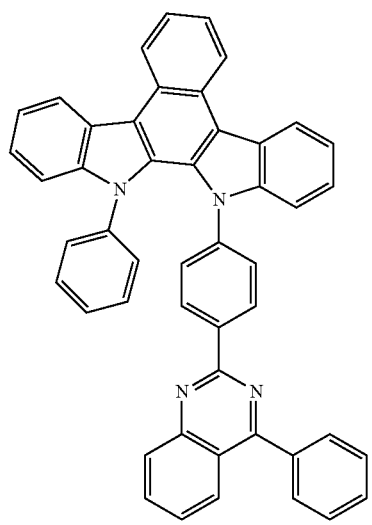

H2-138
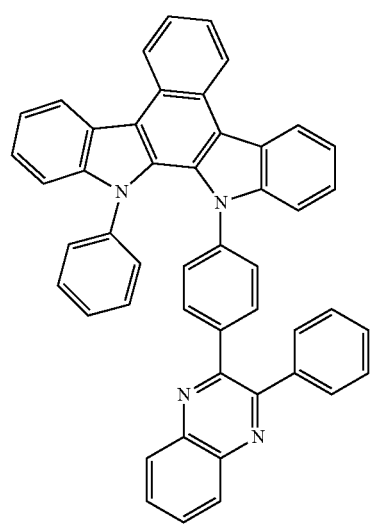
H2-139
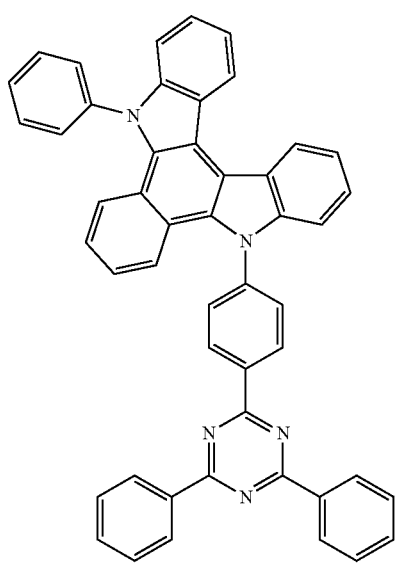
H2-140
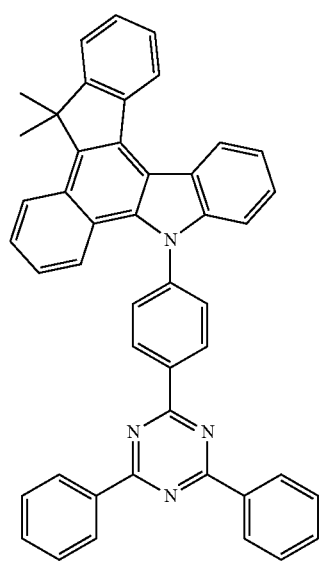
H2-141
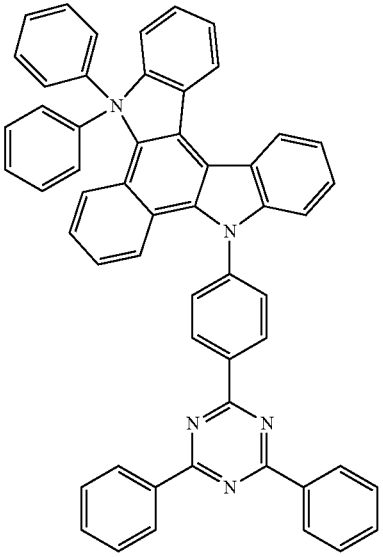
H2-142
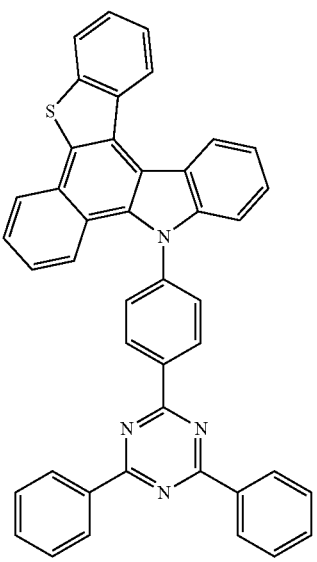
H2-143
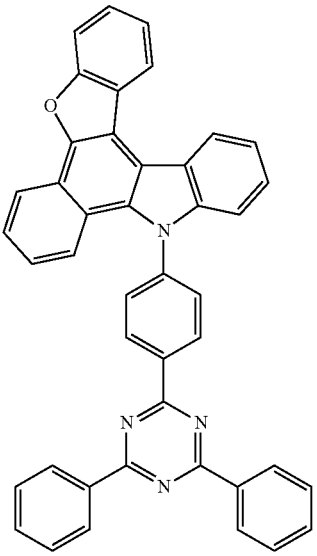

-continued
H2-144
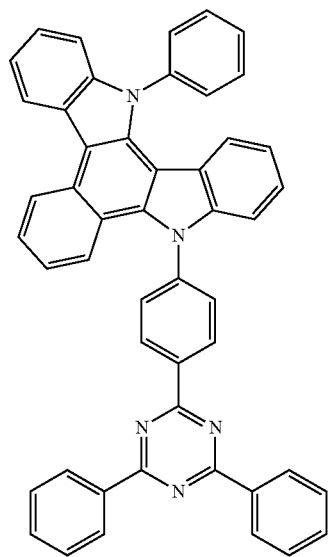
H2-146
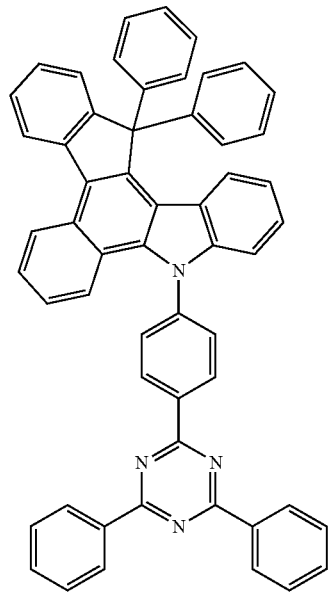
H2-147
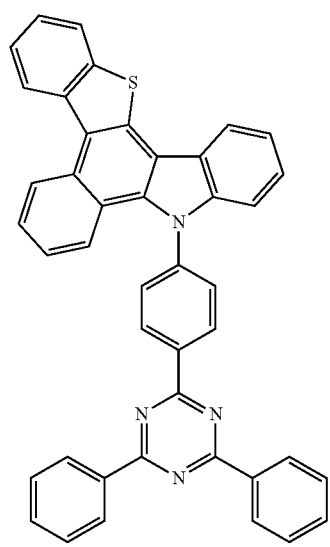
H2-145
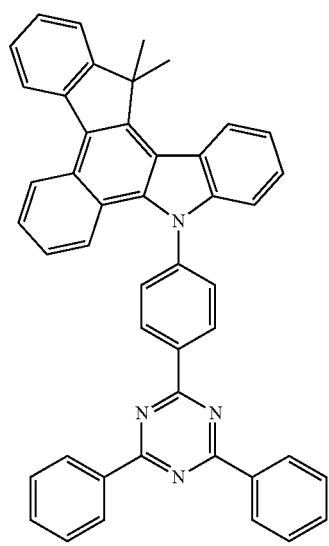
H2-148
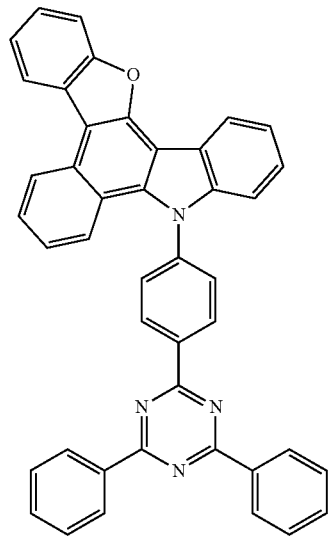

-continued
H2-149
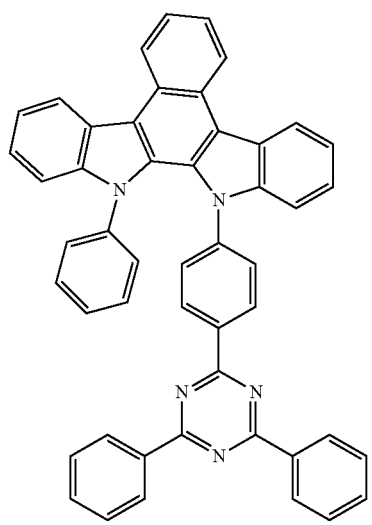
H2-150
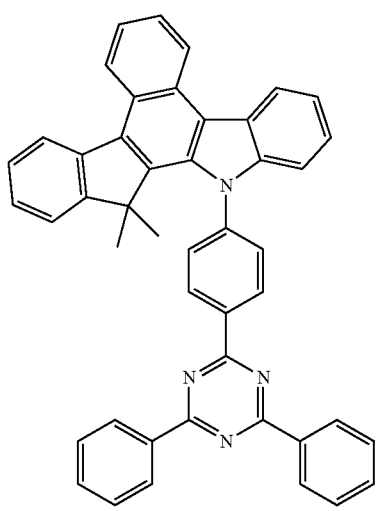
H2-151
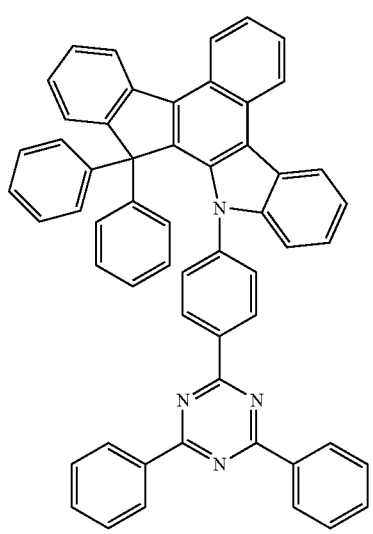
-continued
H2-152
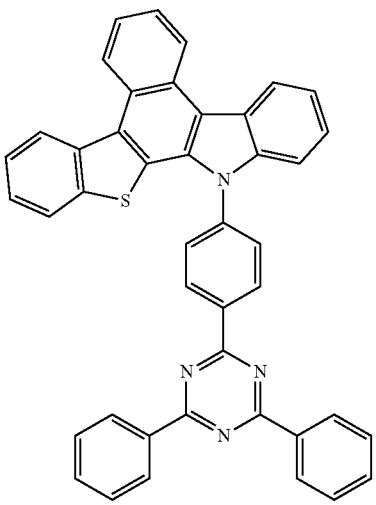
H2-153
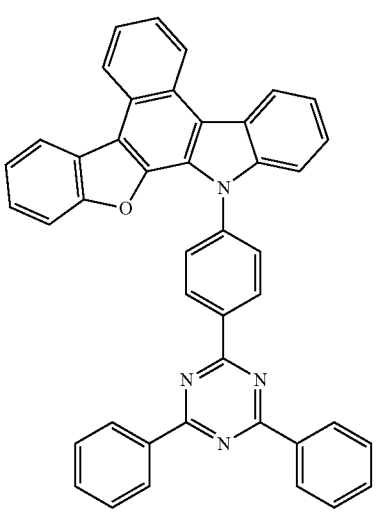
H2-154
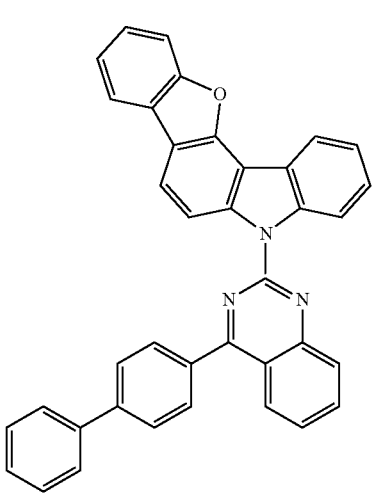

-continued
H2-155
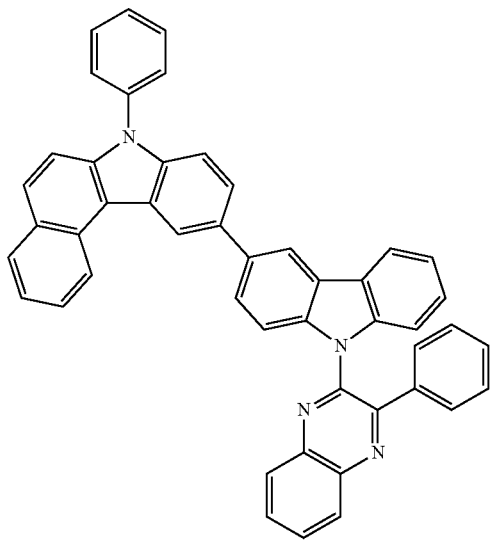
H2-158
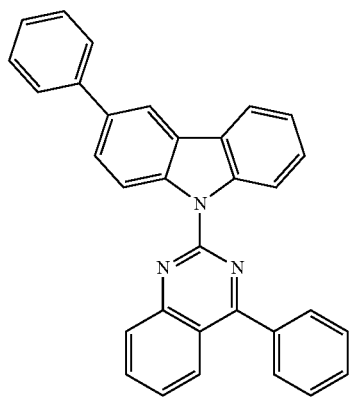
H2-156
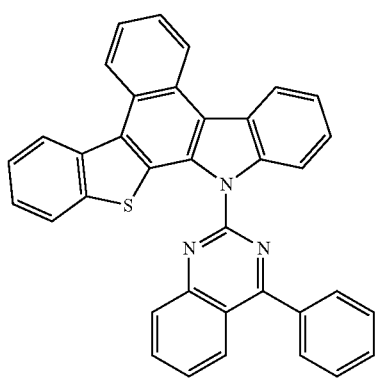
H2-159
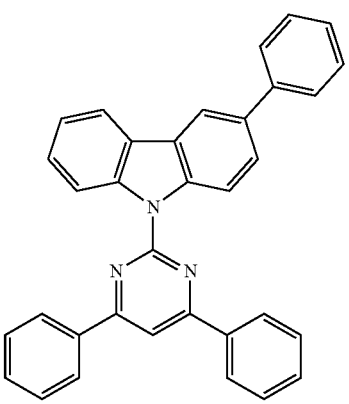
H2-157
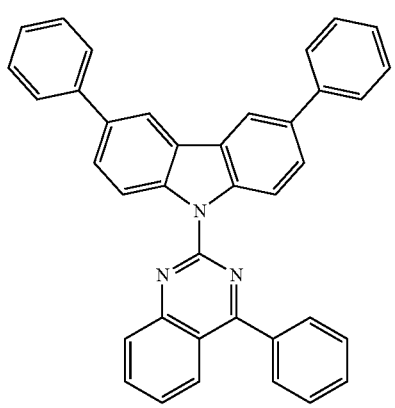
H2-160
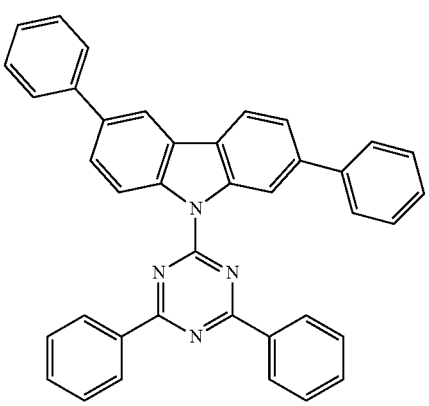

-continued
H2-161
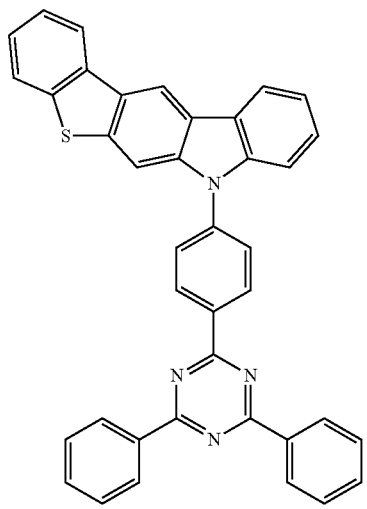
H2-162
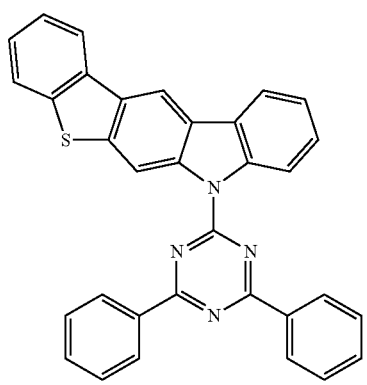
H2-163
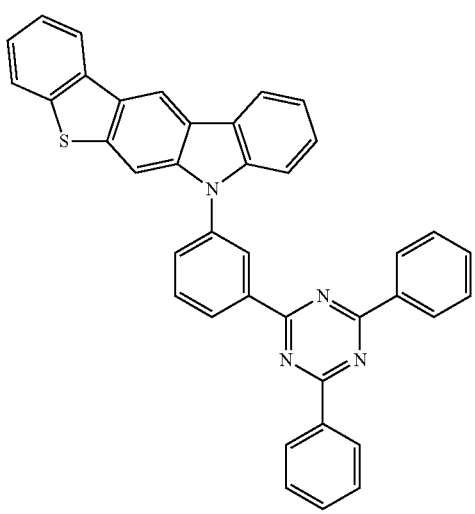
-continued
H2-164
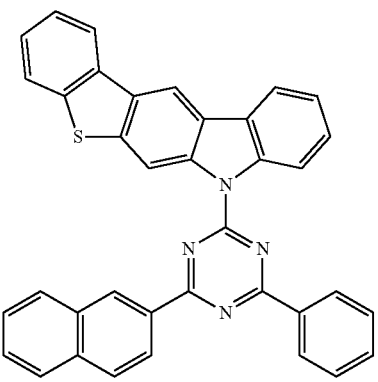
H2-165
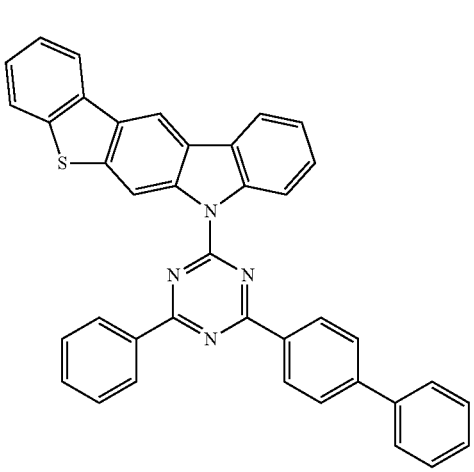
H2-166
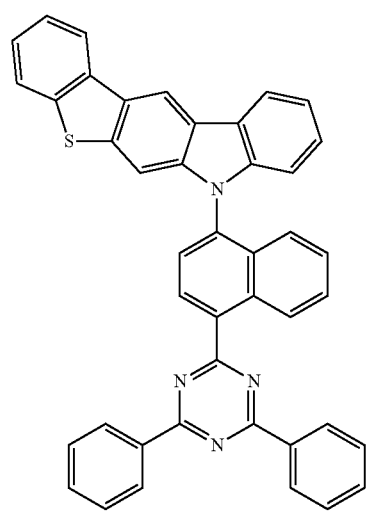

H2-167
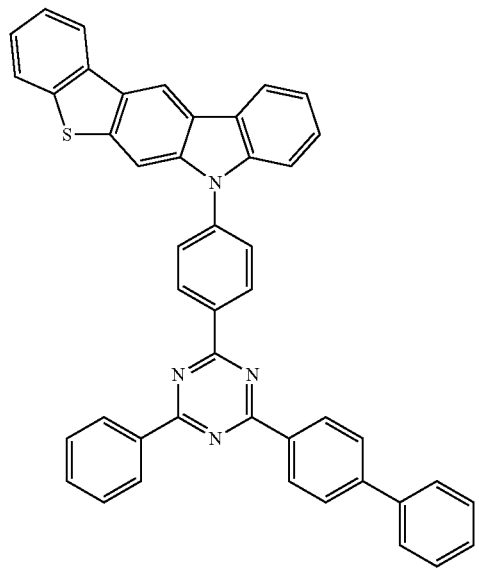
H2-168
H2-169
H2-170
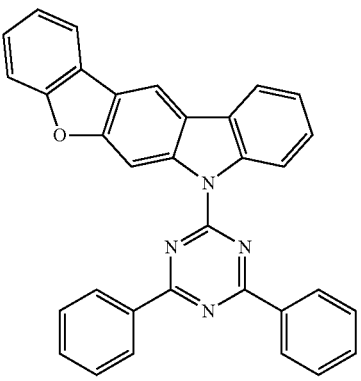
H2-171
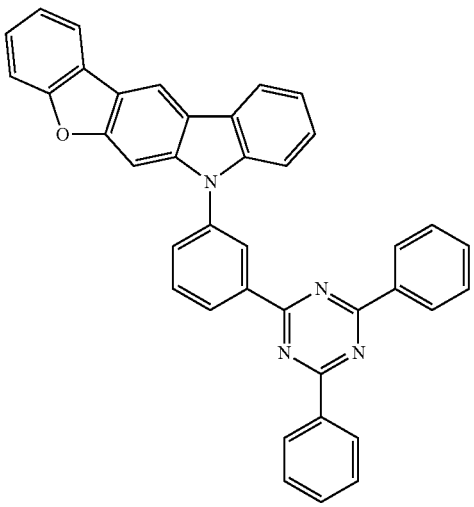
H2-172
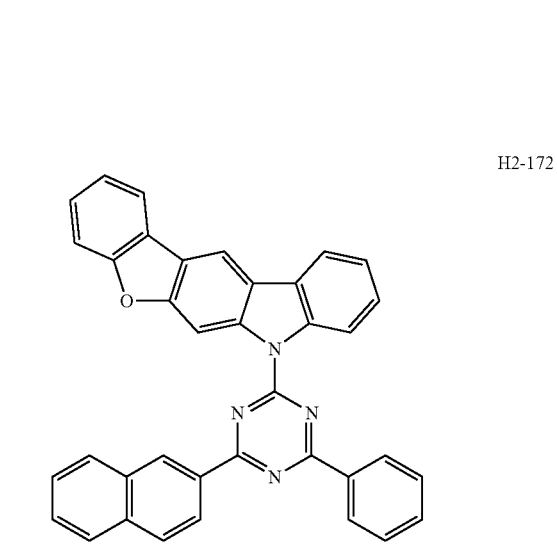

H2-173
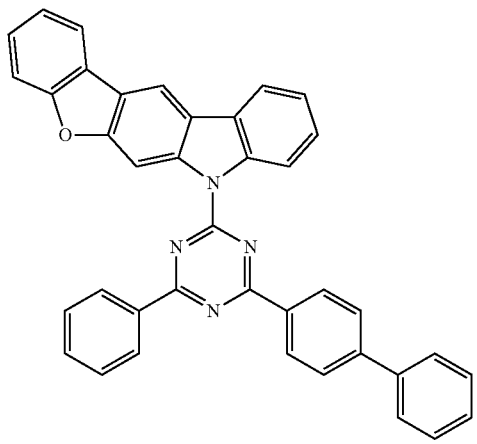
H2-174
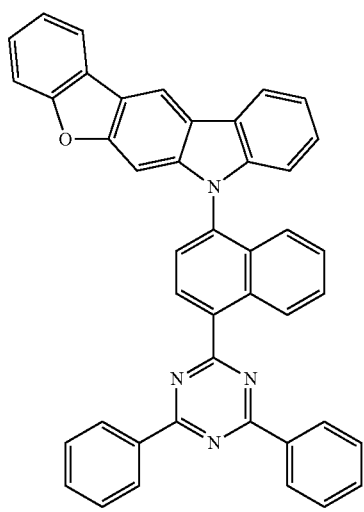
H2-175
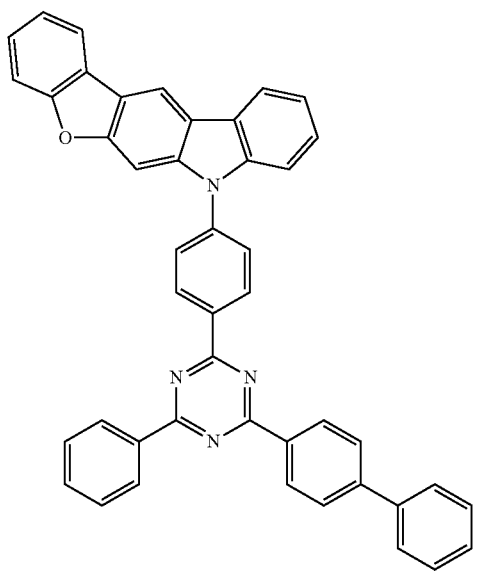
H2-176
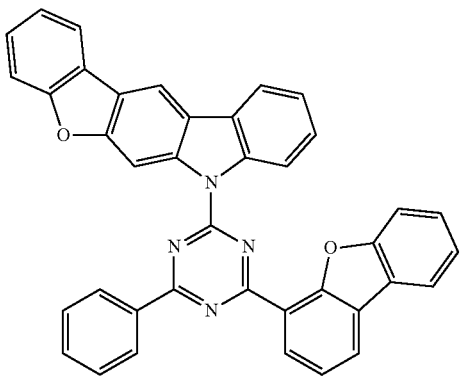
H2-177
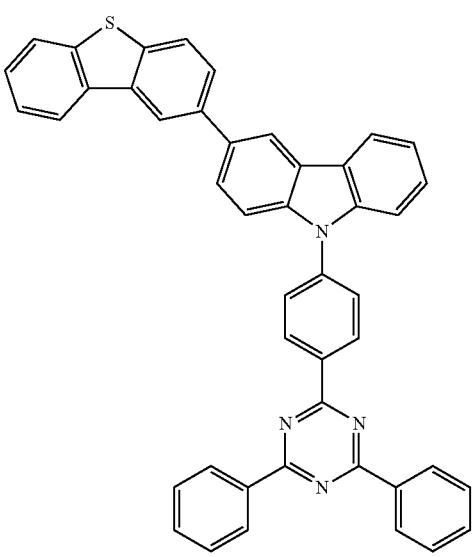
H2-178
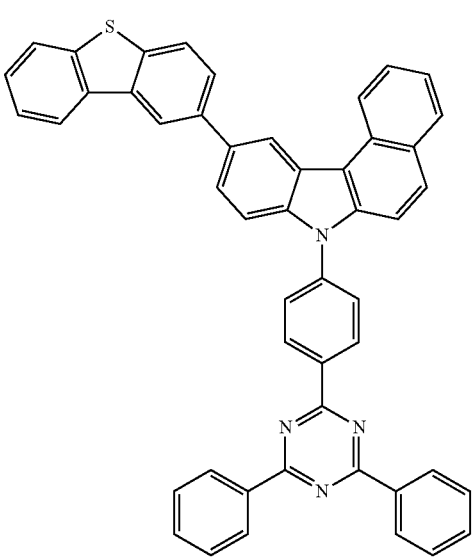

H2-179
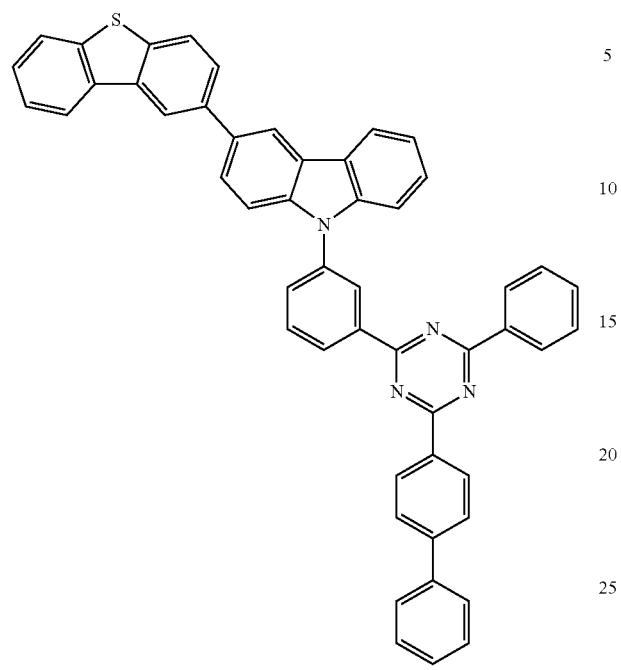
H2-180
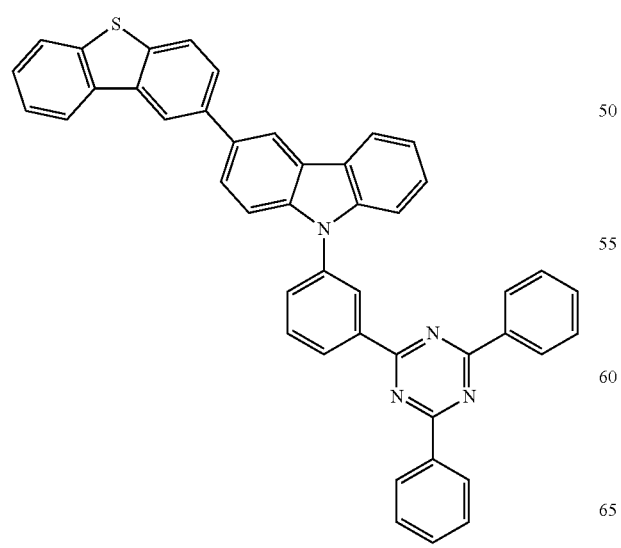
H2-181
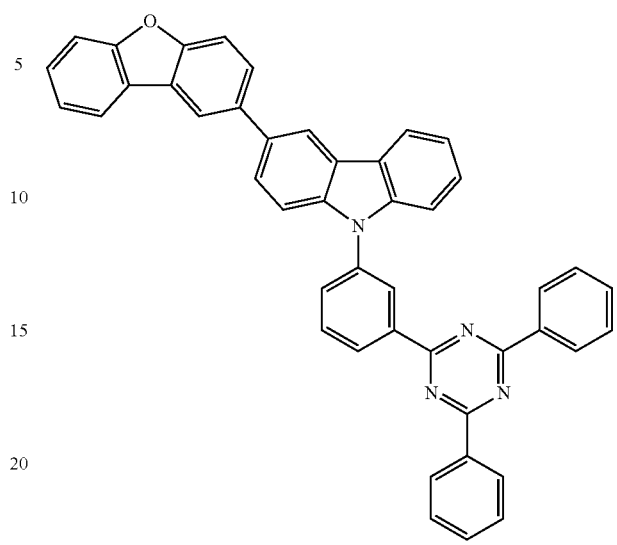
H2-182
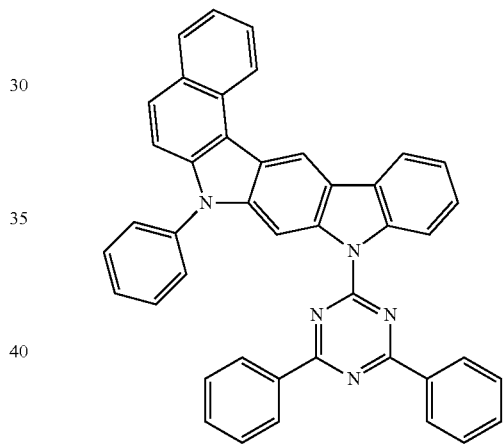
H2-183
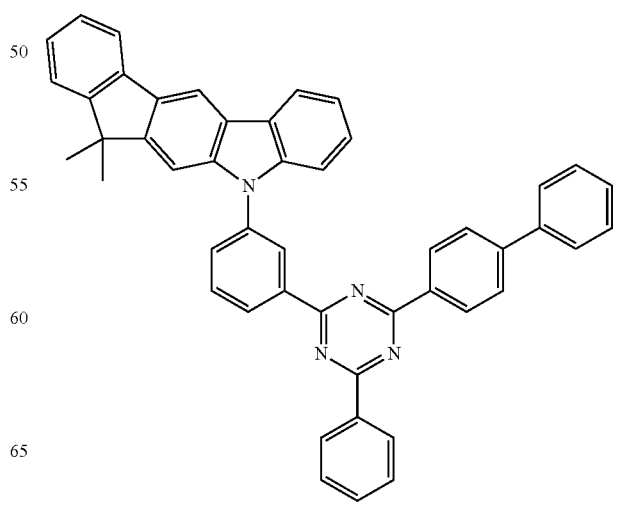

H2-184
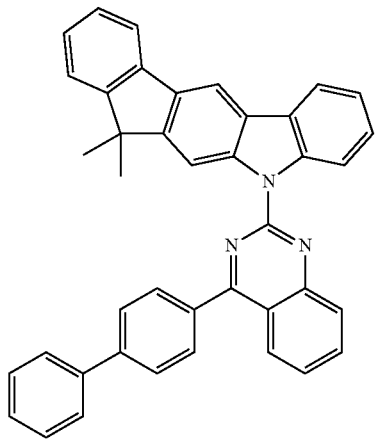
H2-185
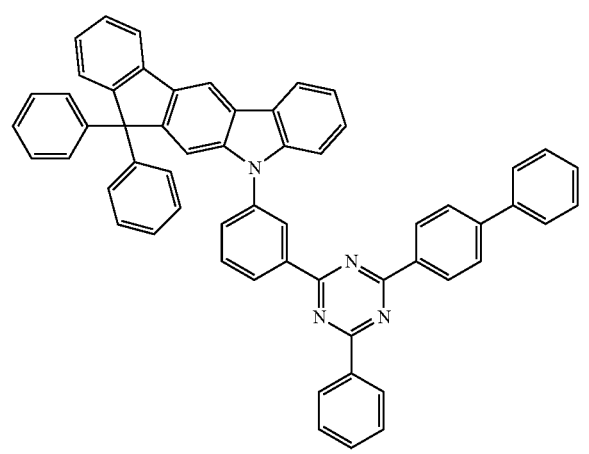
H2-186
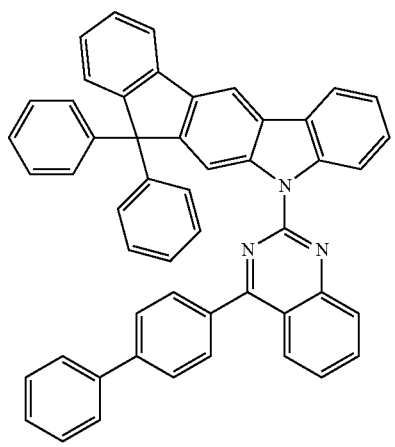
H2-187
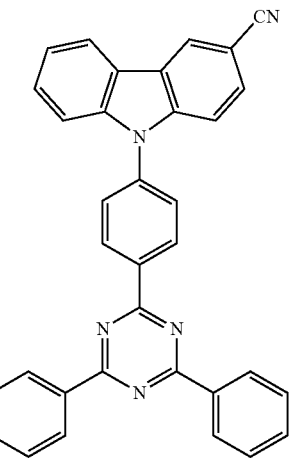
H2-188
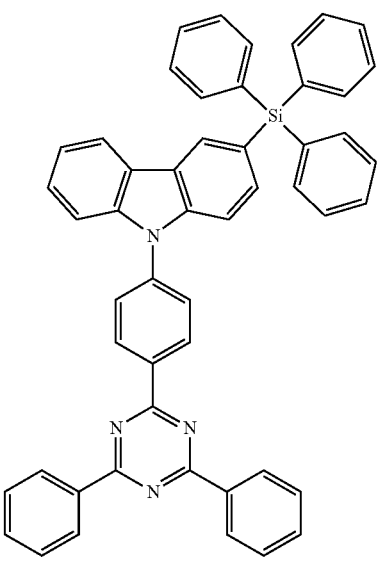
H2-189
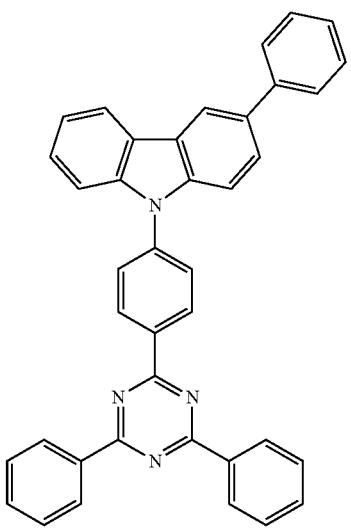

H2-190
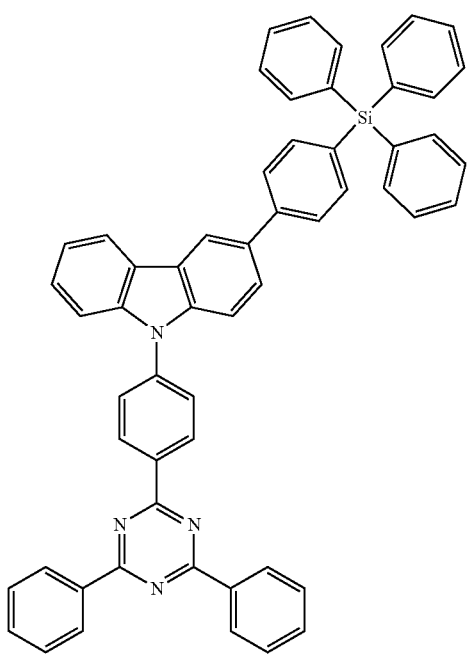
H2-191
H2-192
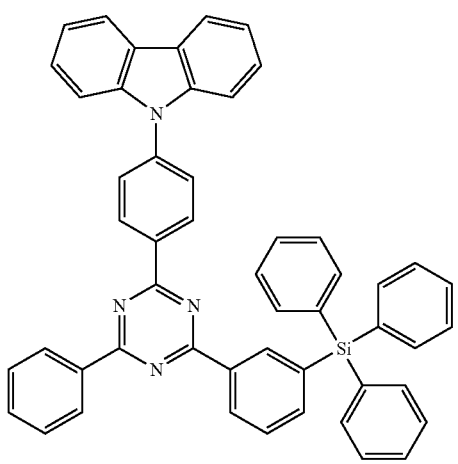
H2-193
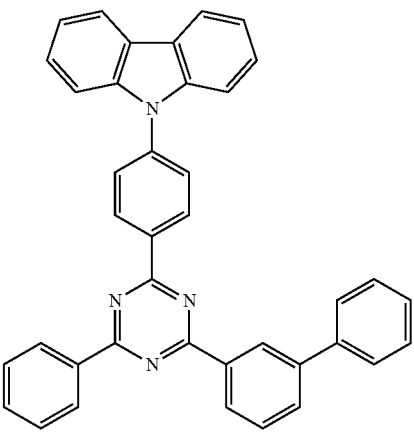
H2-194
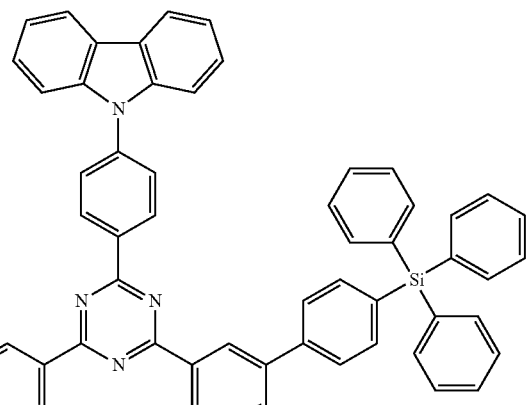
H2-195
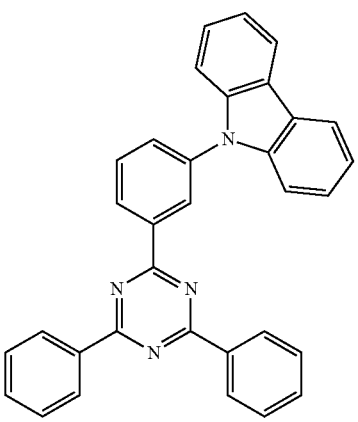

H2-196
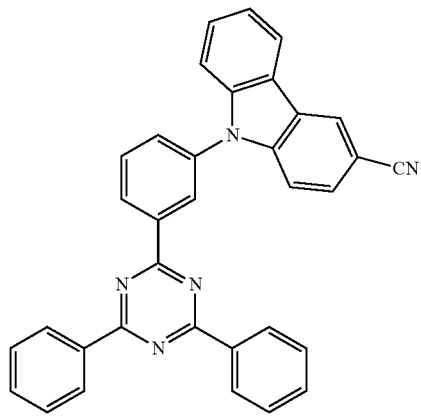
H2-197
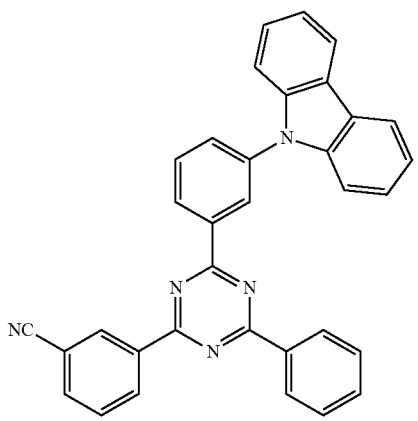
H2-198
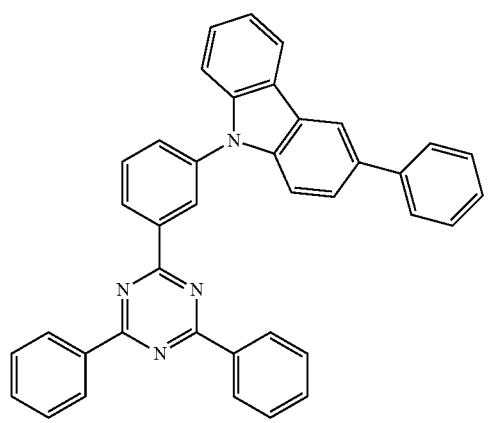
H2-199
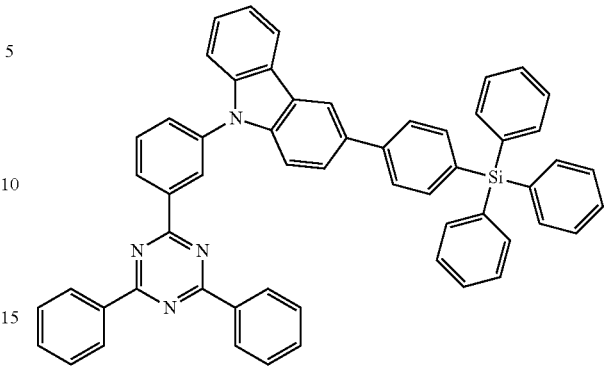
H2-200
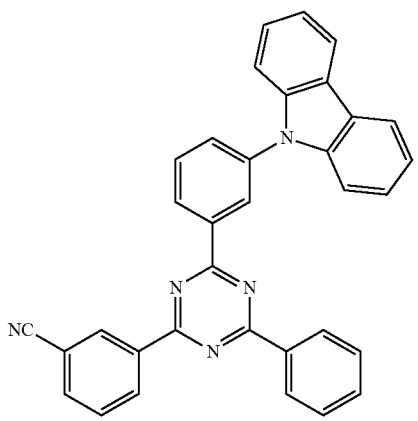
H2-201
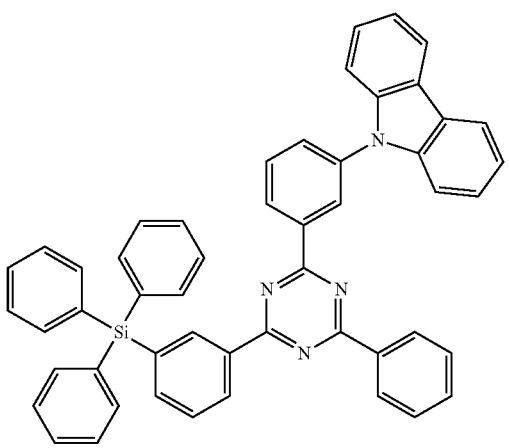

-continued
H2-202
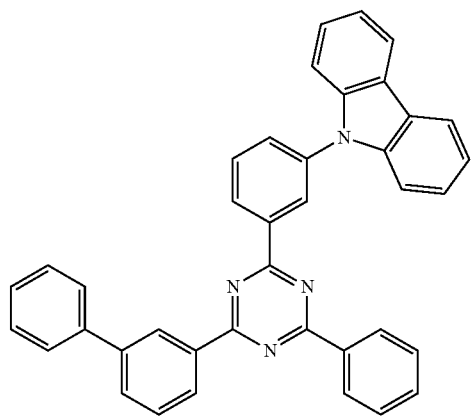
H2-203
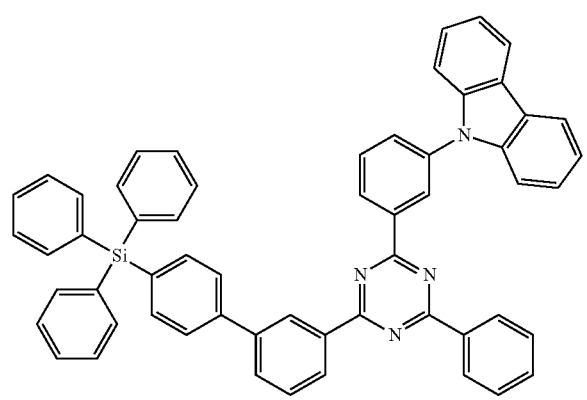
H2-204
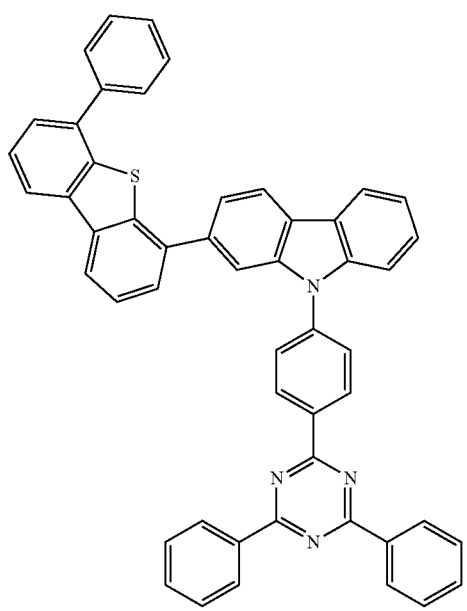
-continued
H2-205
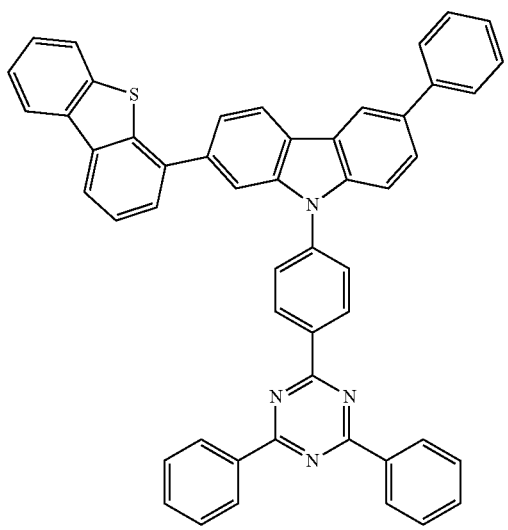
H2-206
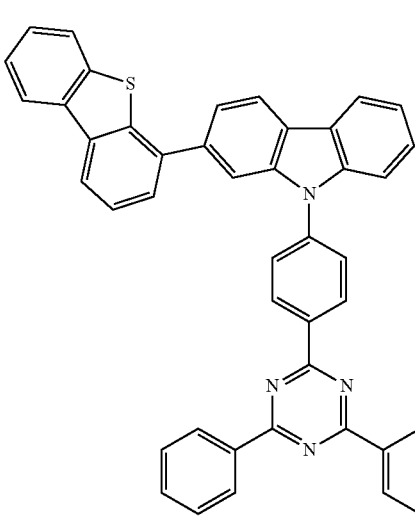
H2-207
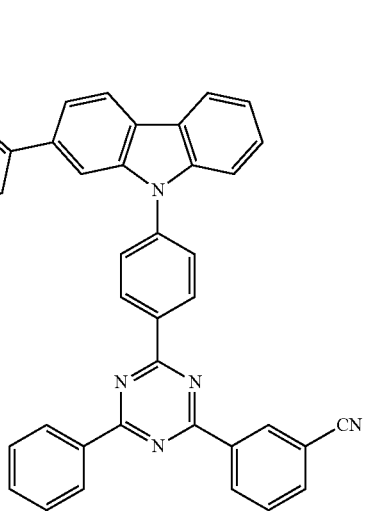

H2-208
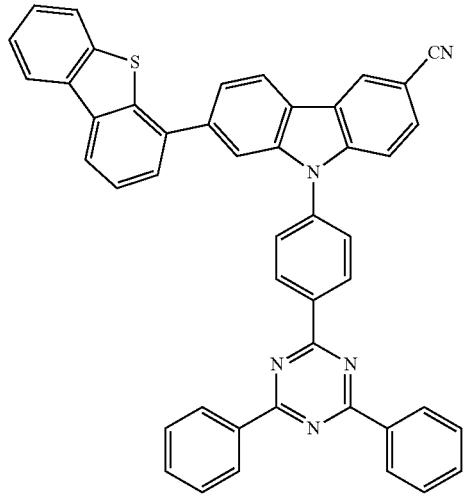
H2-209
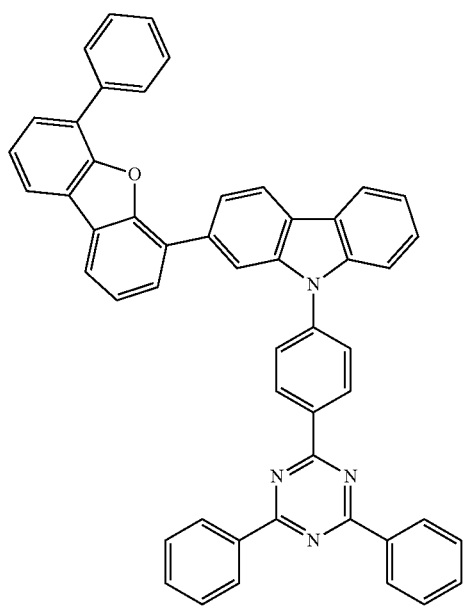
H2-210
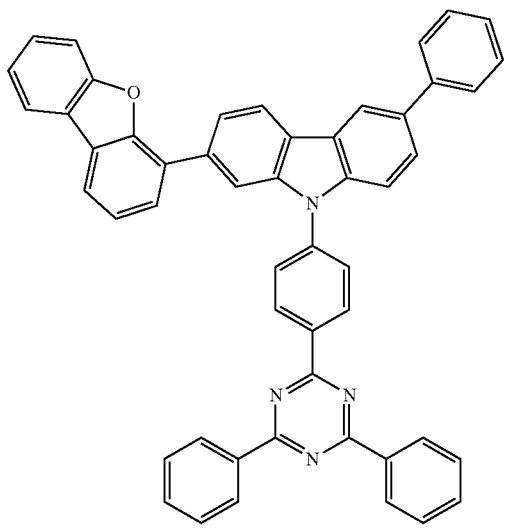
H2-211
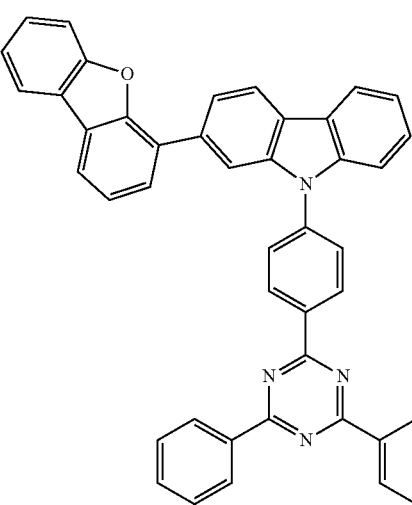
H2-212

H2-213
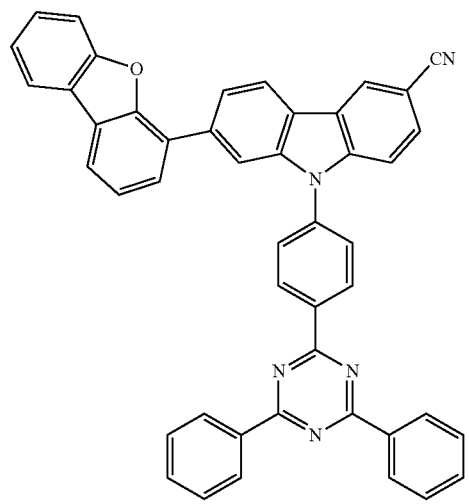
H2-214
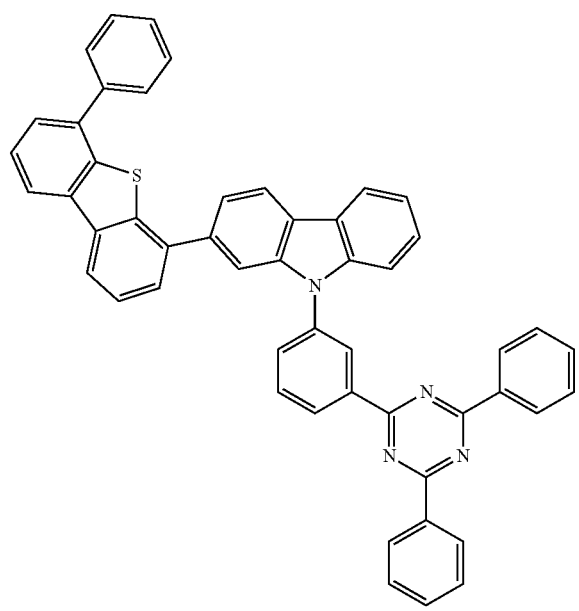
H2-215
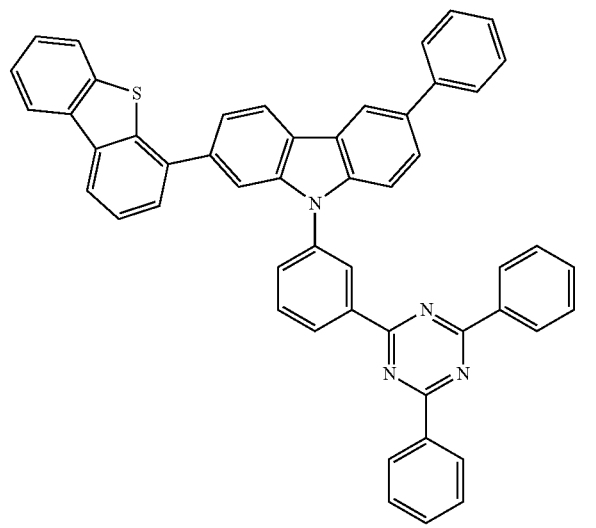
H2-216
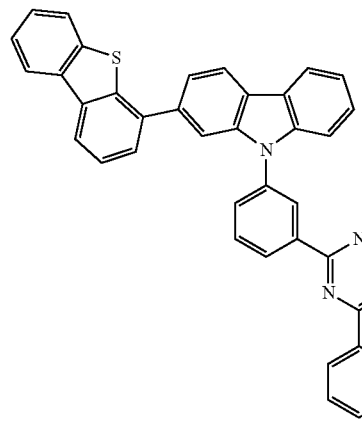
H2-217
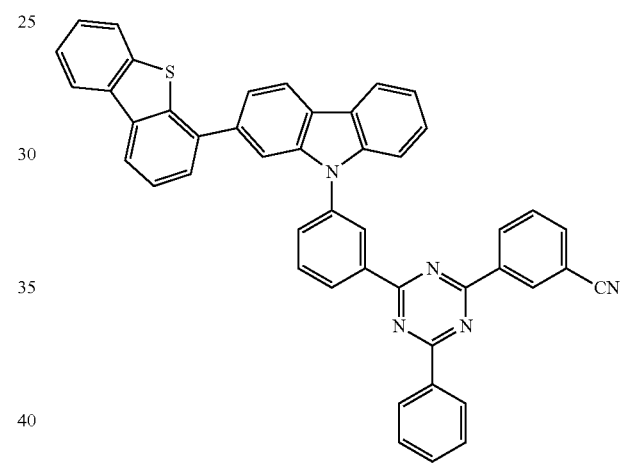
H2-218
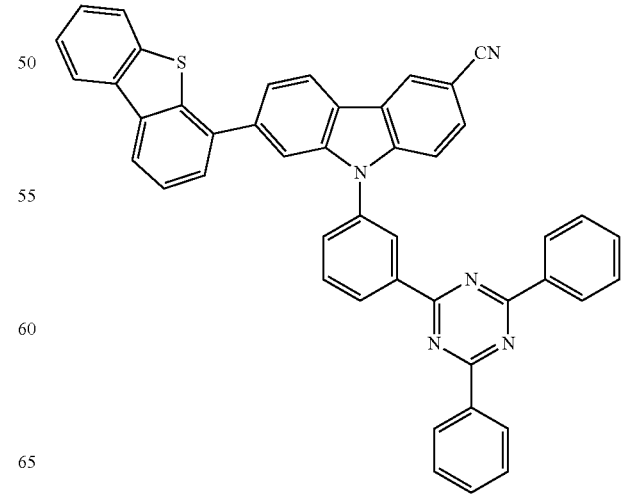

H2-219
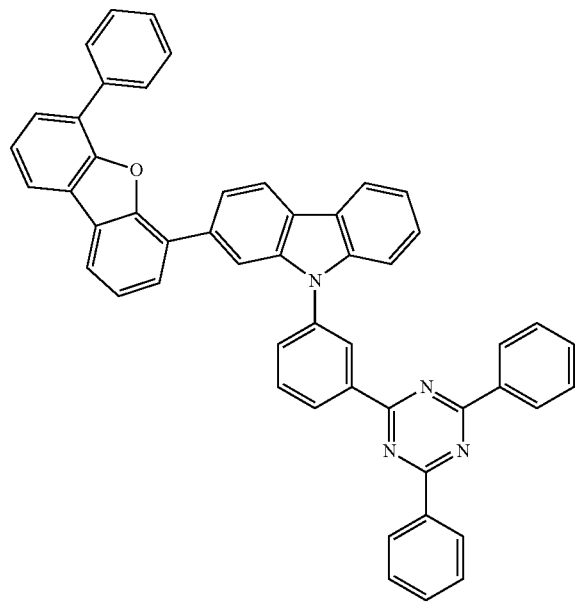
H2-220
H2-221
H2-222
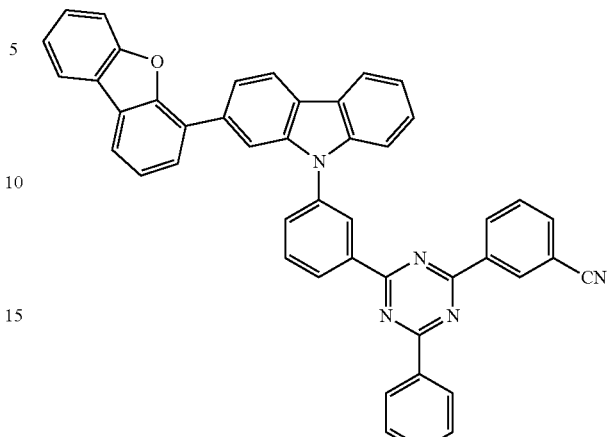
H2-223
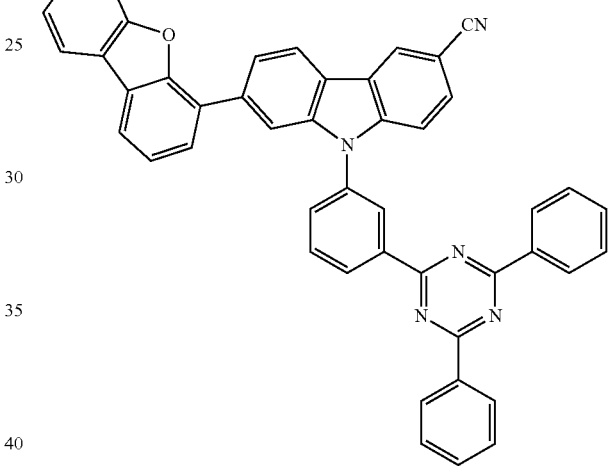
H2-224
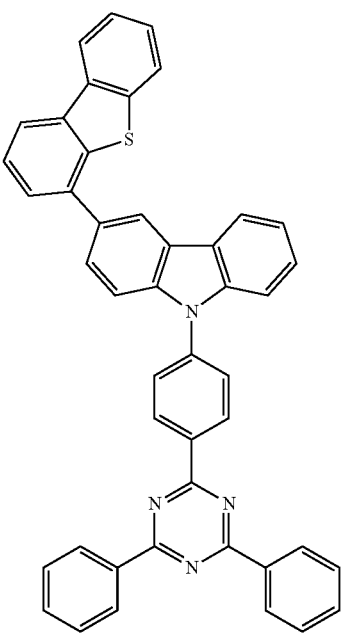

H2-225
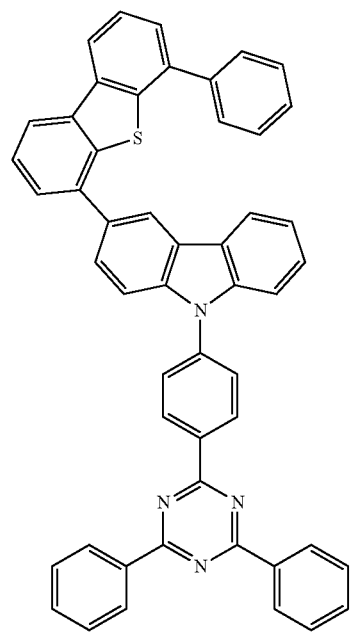
H2-227
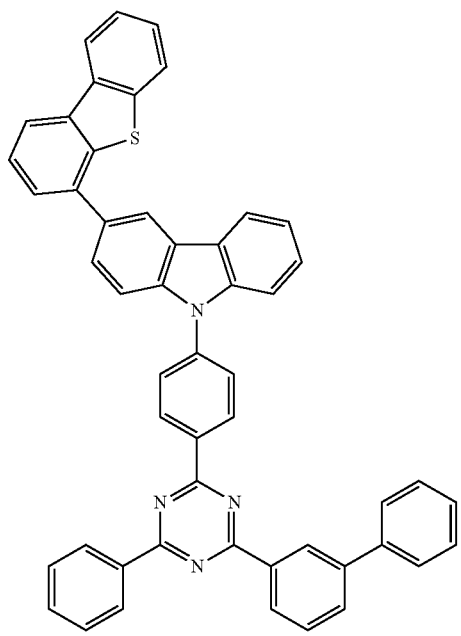
H2-226
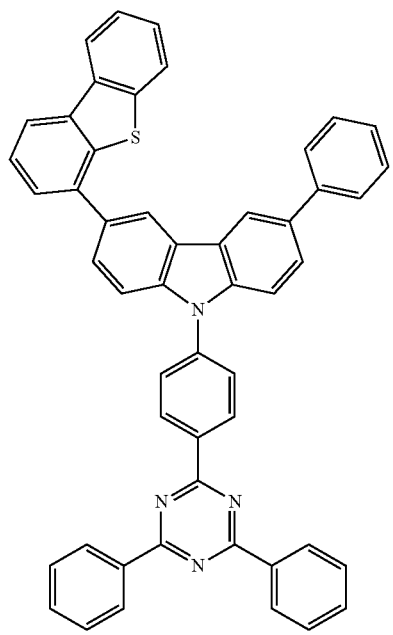
H2-228
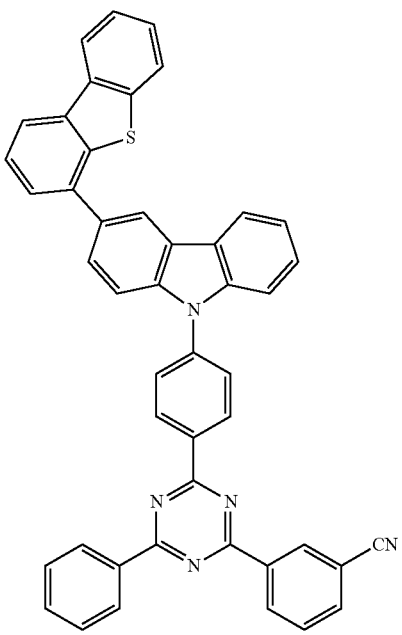

H2-229
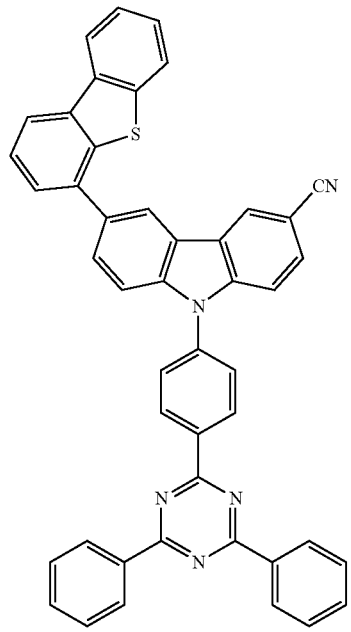
H2-231
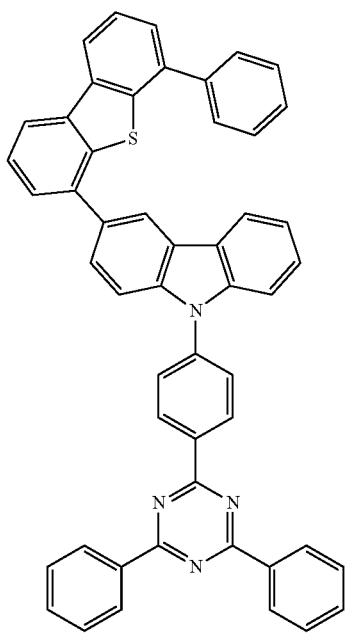
H2-230
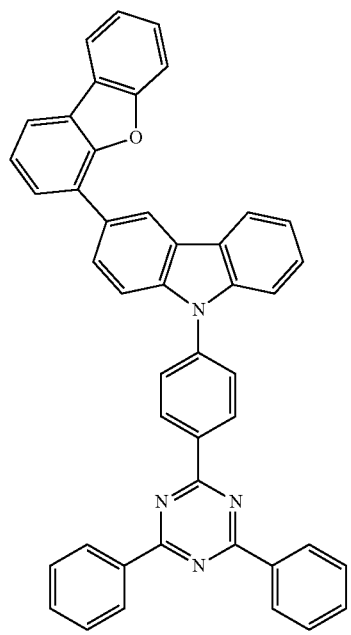
H2-232
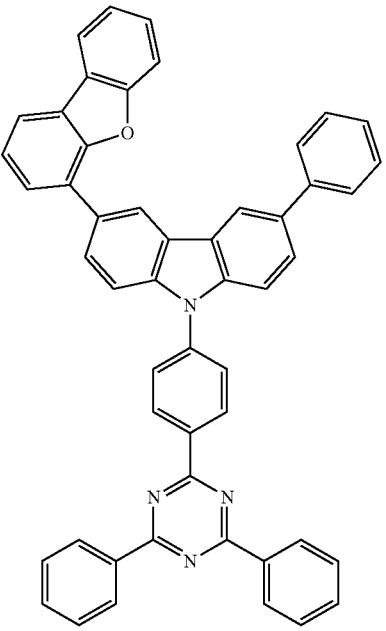

H2-233
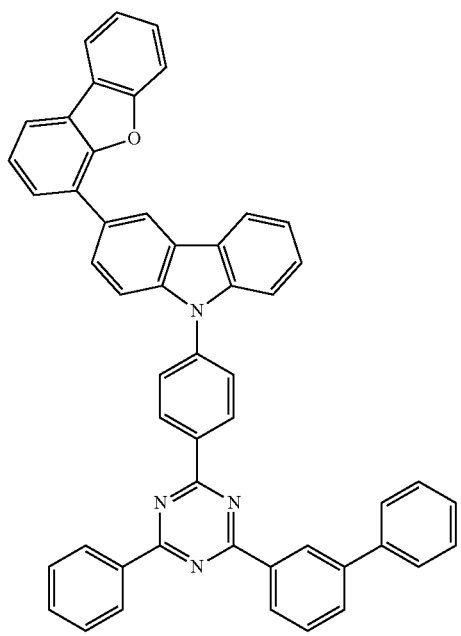
H2-234
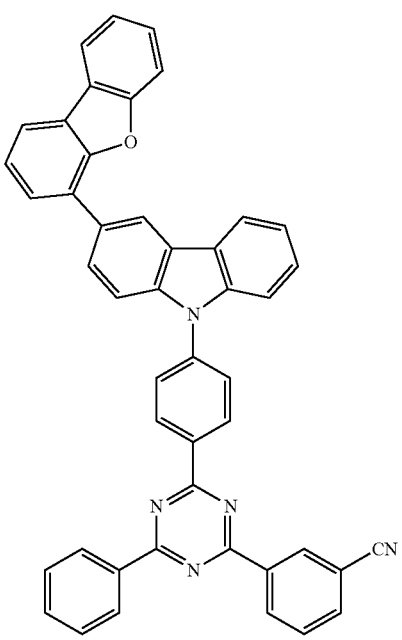
H2-235
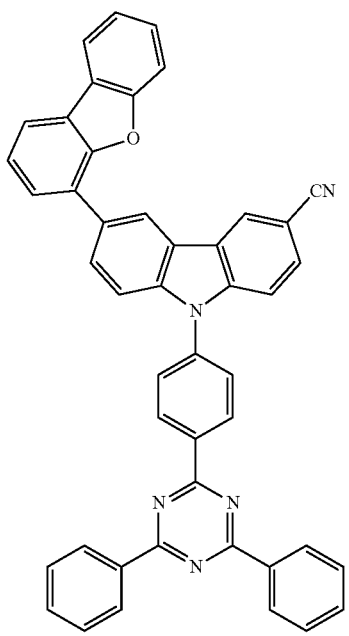
H2-236
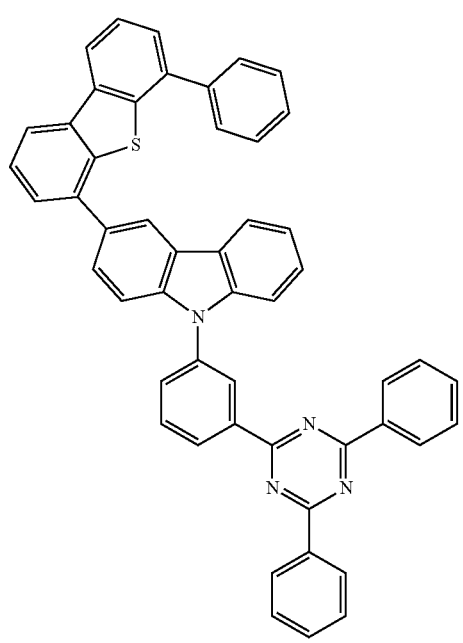

H2-237
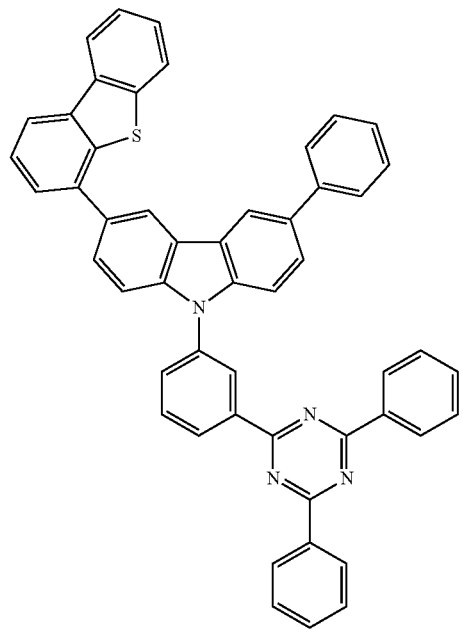
H2-239
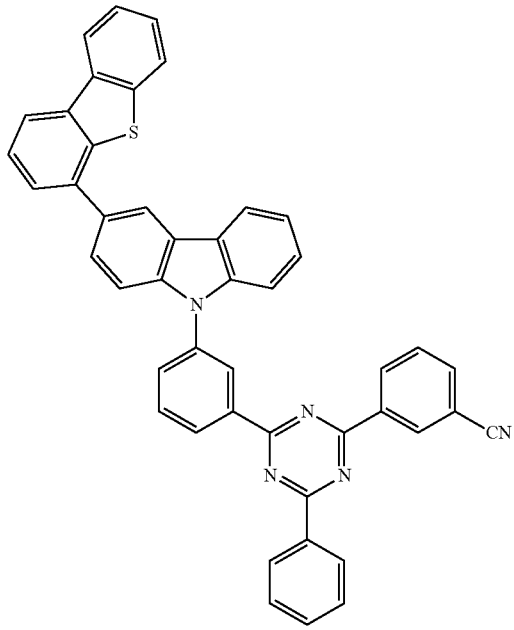
H2-238
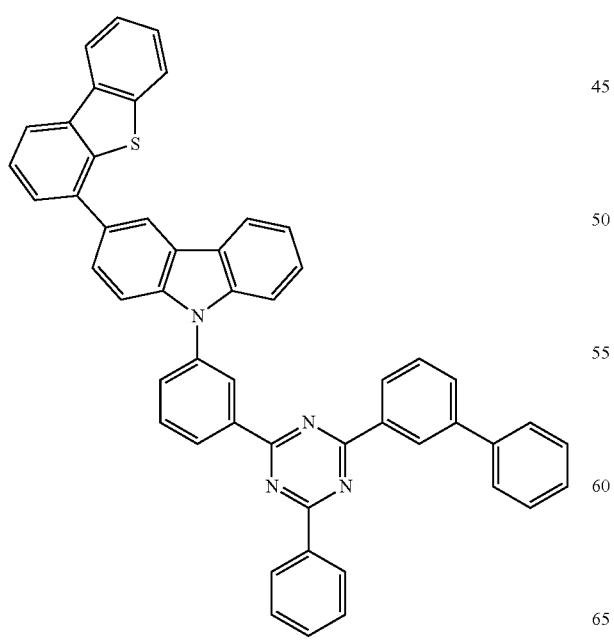
H2-240
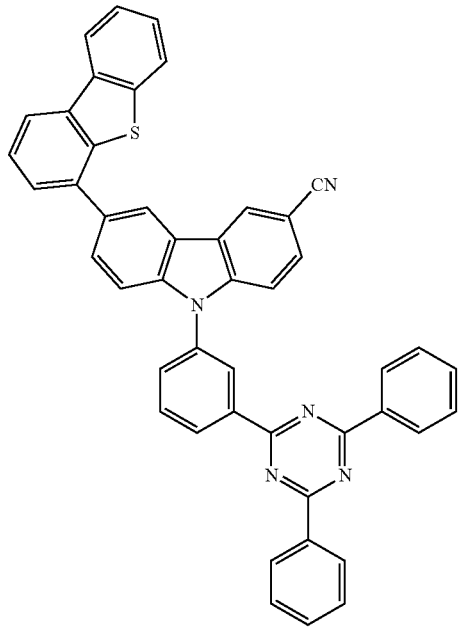

H2-241
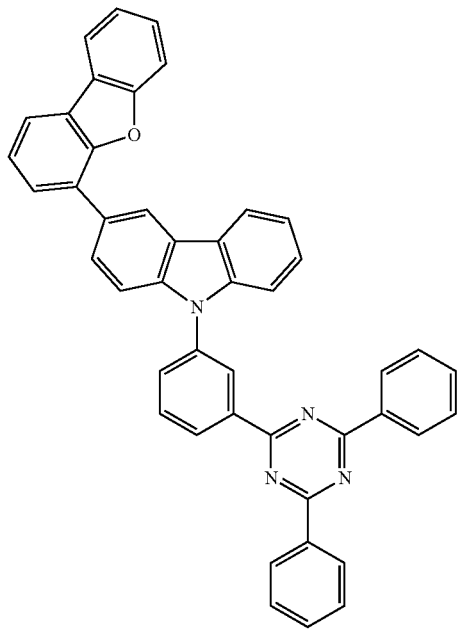
H2-242
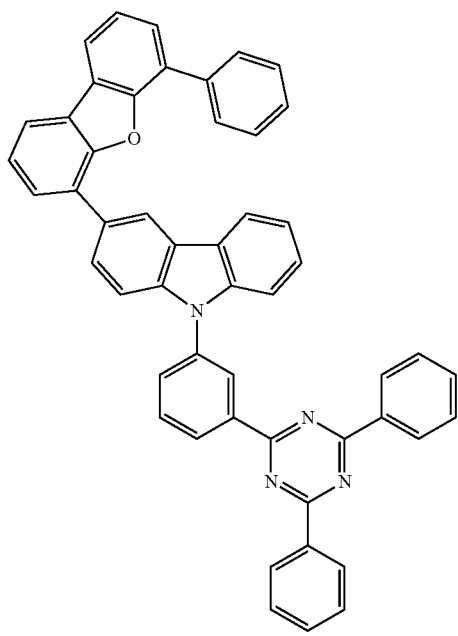
H2-243
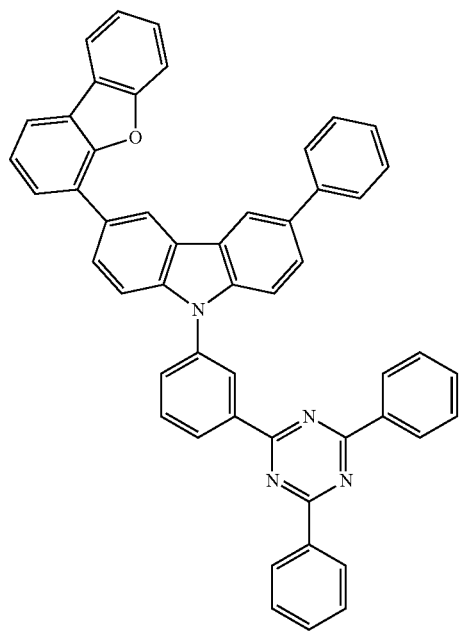
H2-244
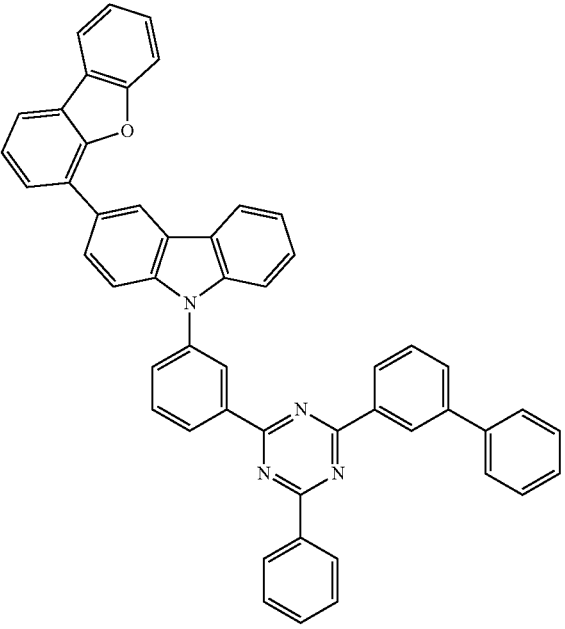

H2-245
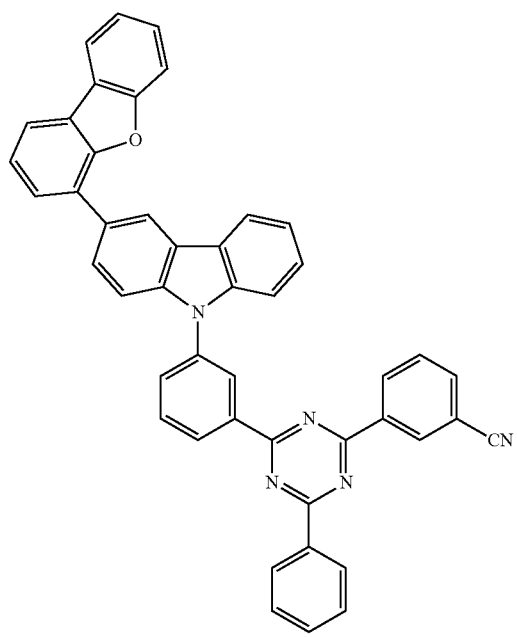
H2-246
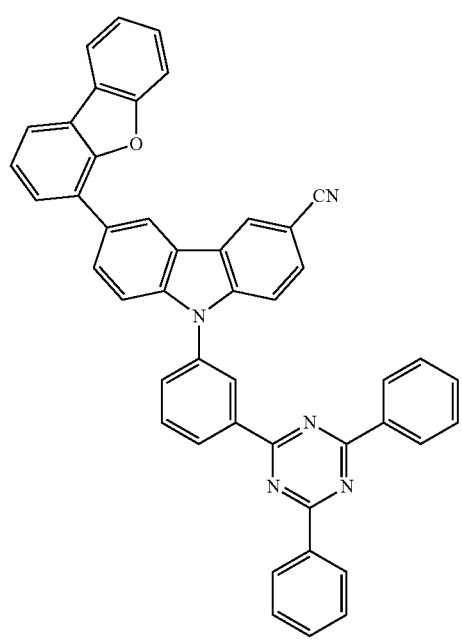
H2-247
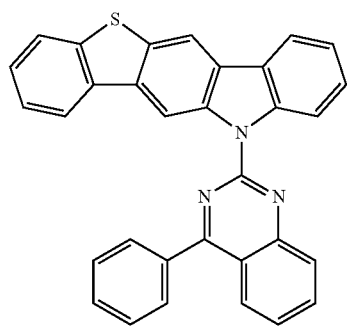
H2-248
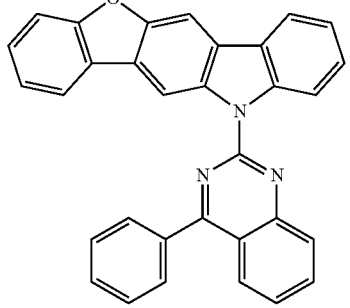
H2-249
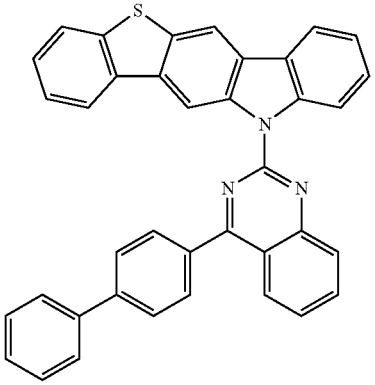
H2-250
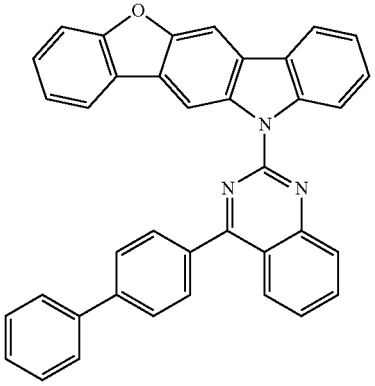
H2-251
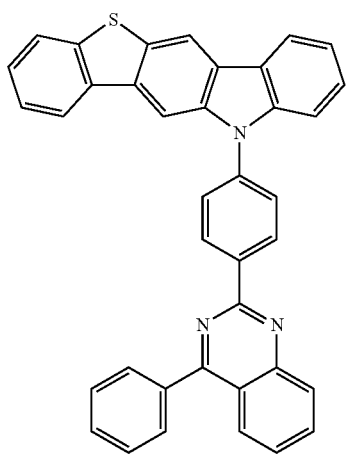

H2-252
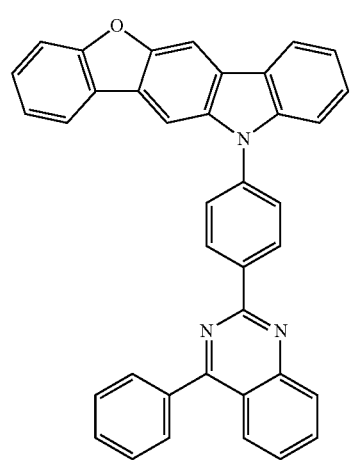
H2-253
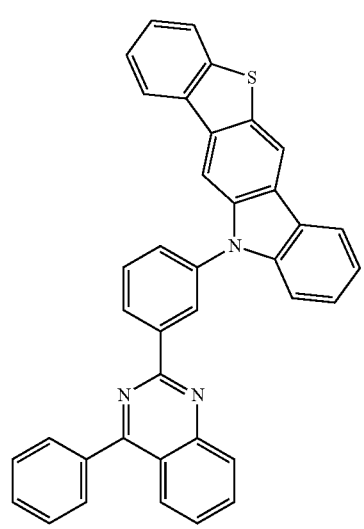
H2-254
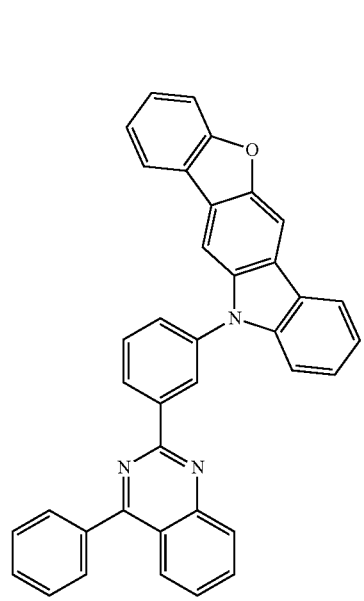
H2-255
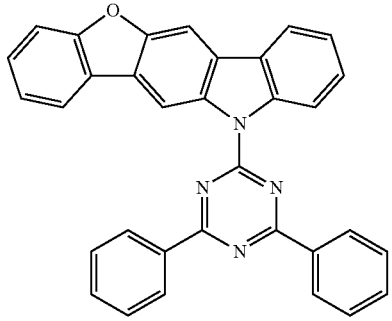
H2-256
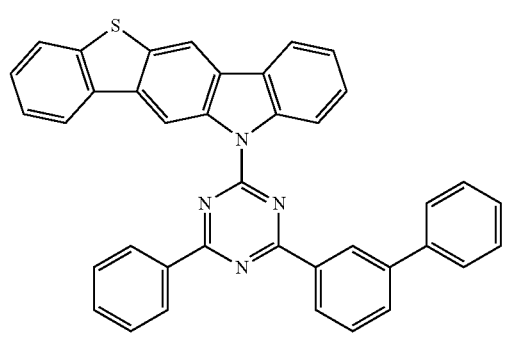
H2-257
H2-258
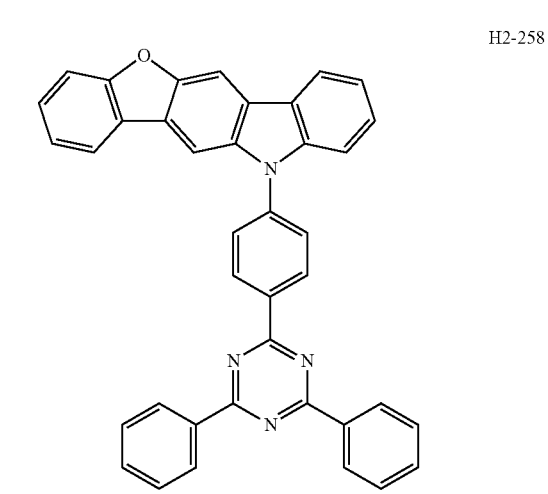

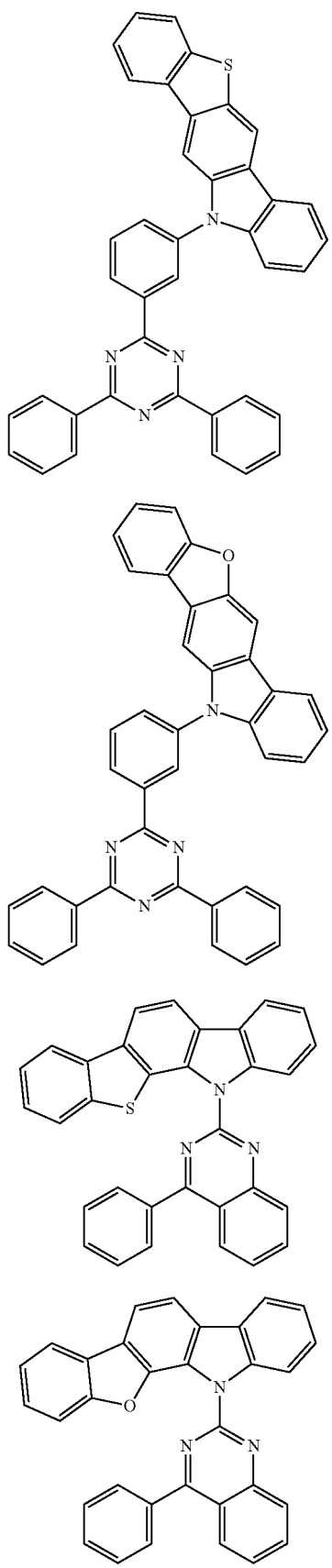
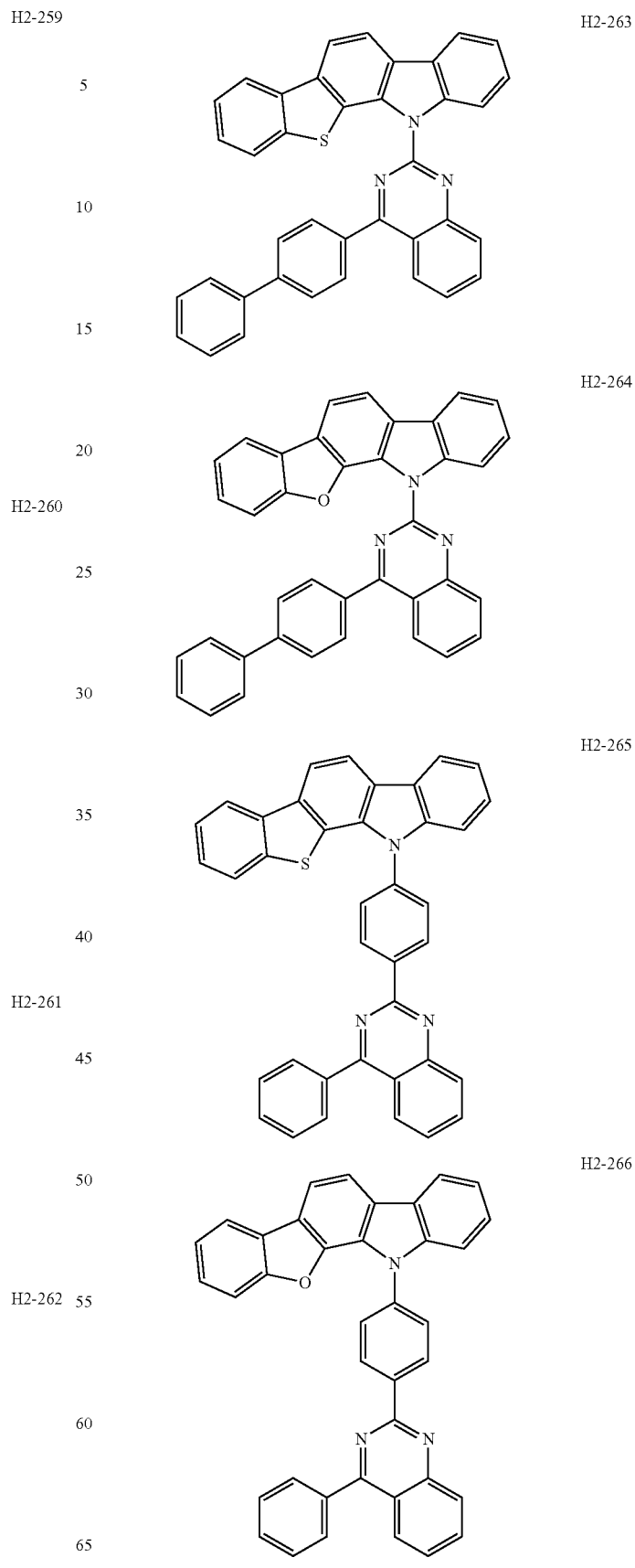

H2-267
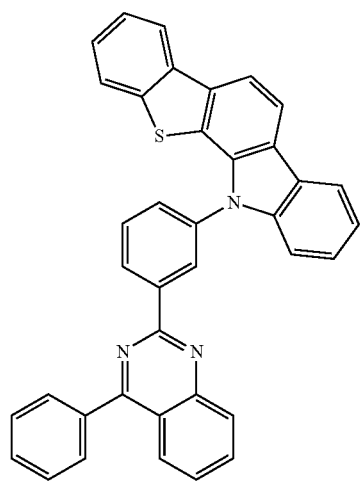
H2-268
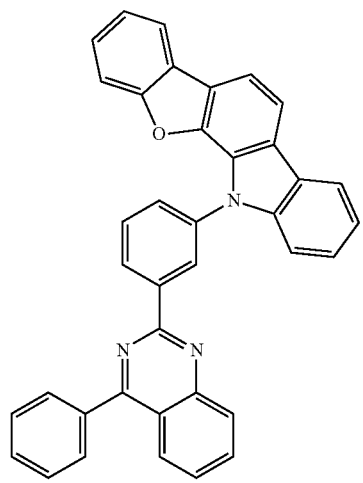
H2-269
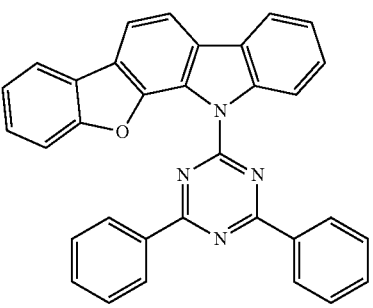
H2-270
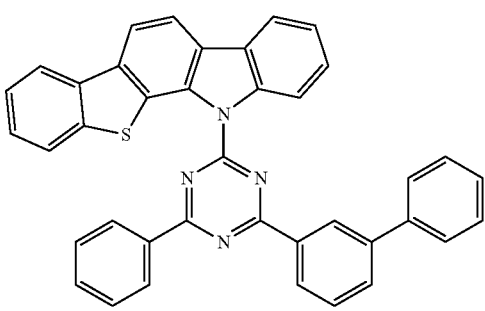
H2-271
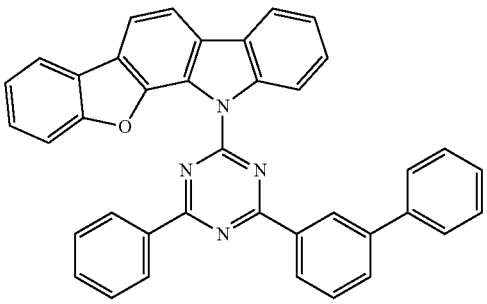
H2-272
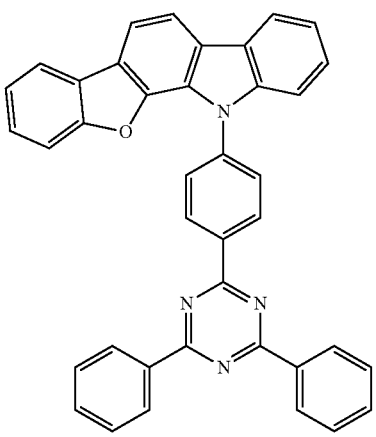
H2-273
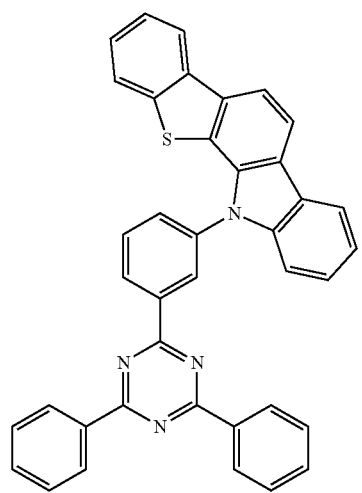

-continued
H2-274
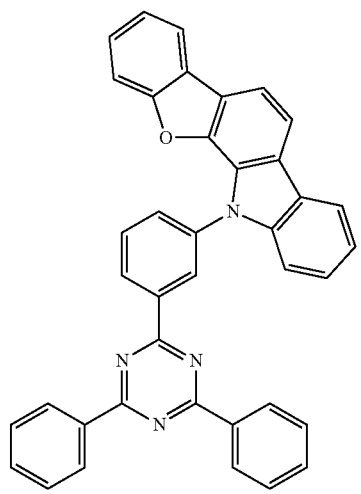
H2-275
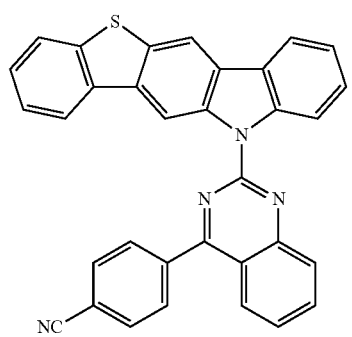
H2-276
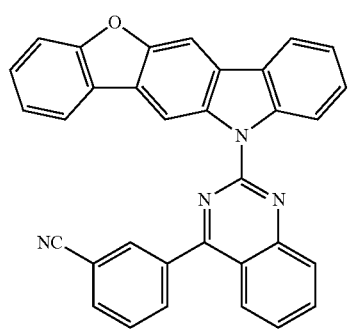
H2-277
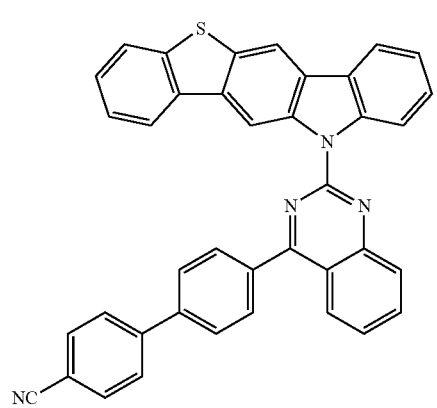
-continued
H2-278
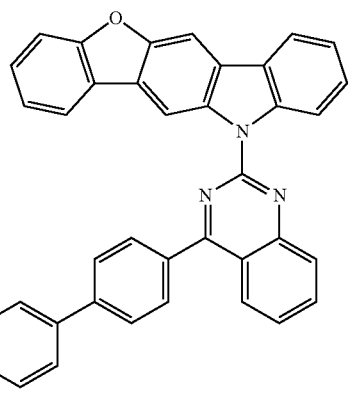
H2-279
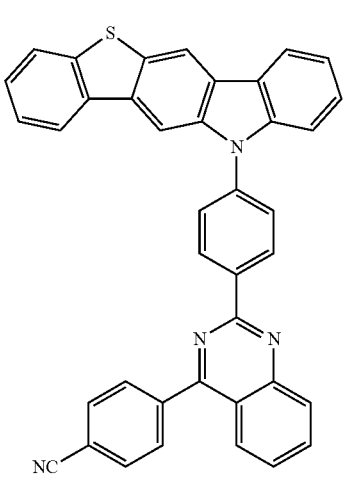
H2-280
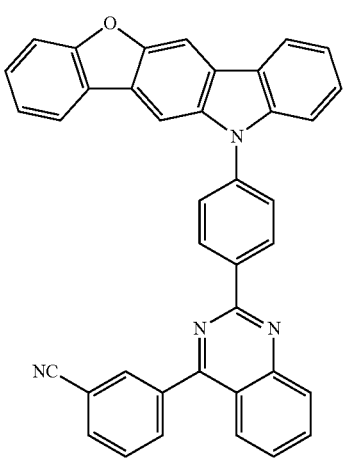

H2-281
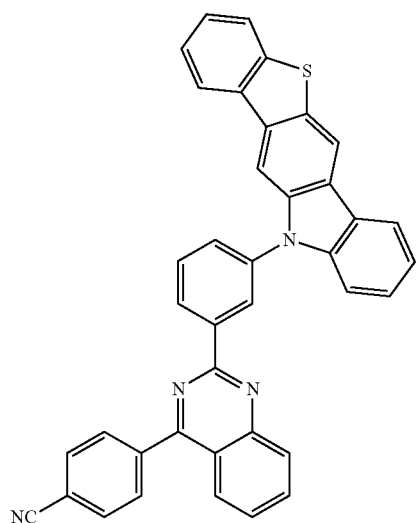
H2-284
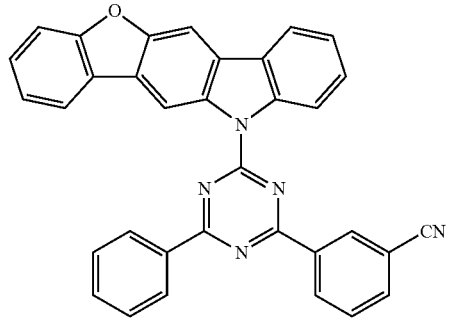
H2-285
H2-282
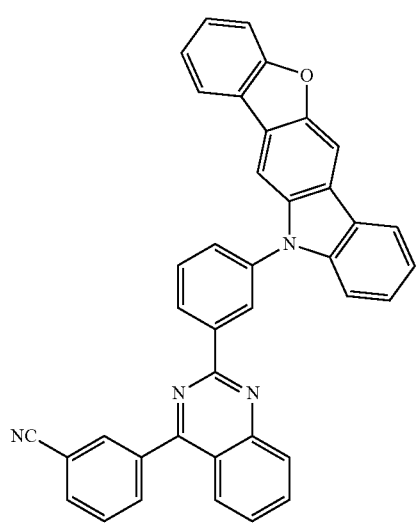
H2-286
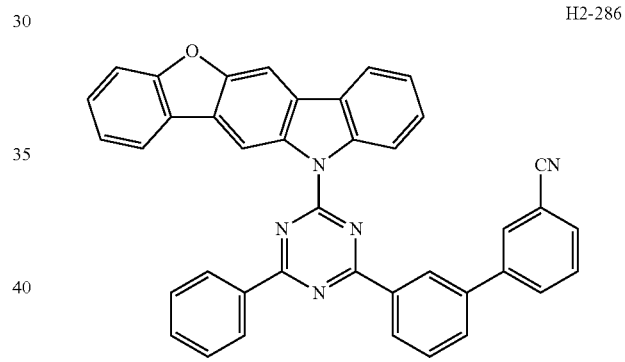
H2-283
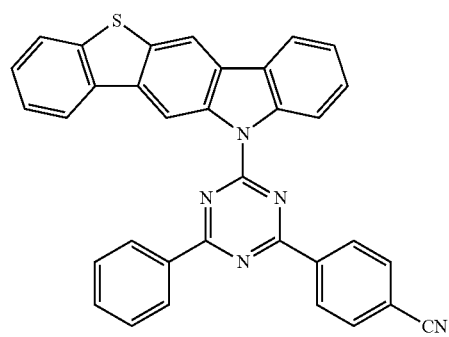
H2-287
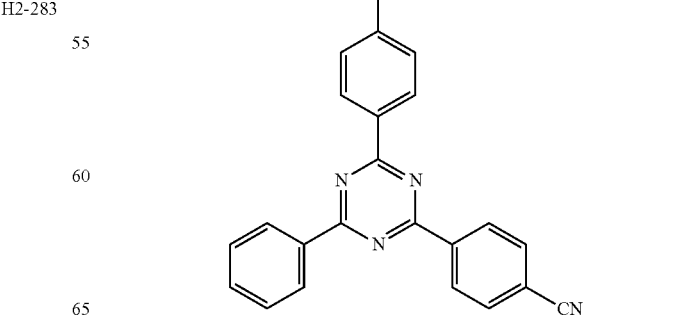

H2-288
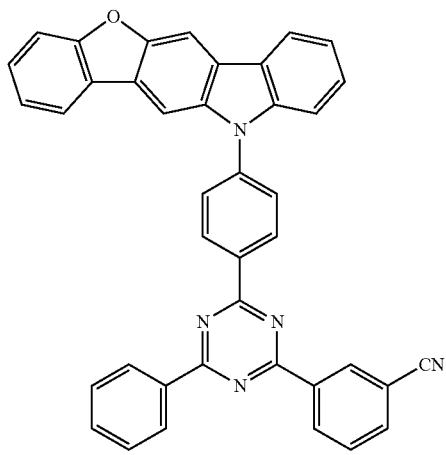
H2-289
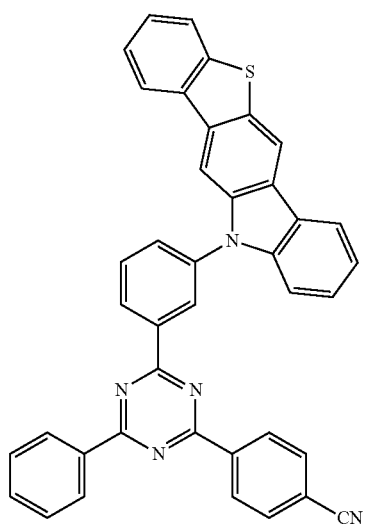
H2-290
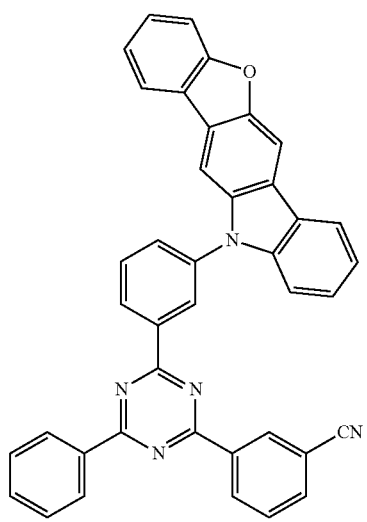
H2-291
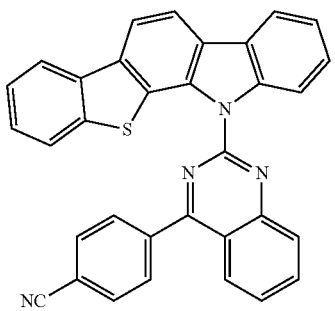
H2-292
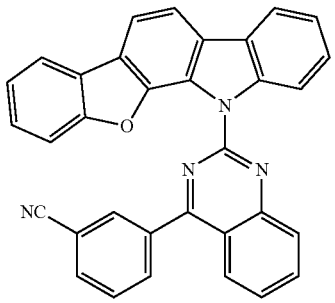
H2-293
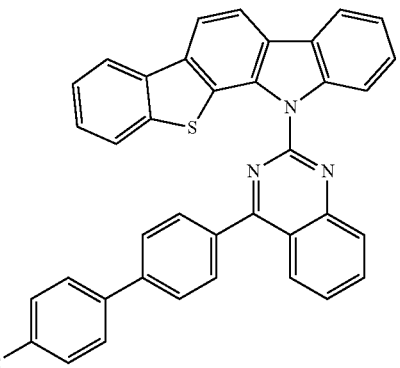
H2-294
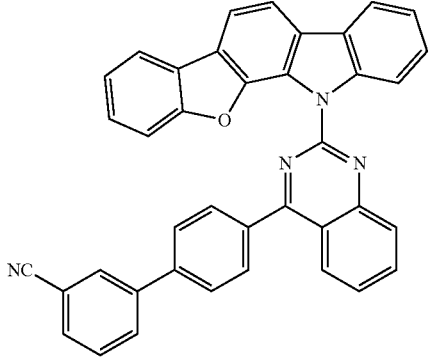

H2-295
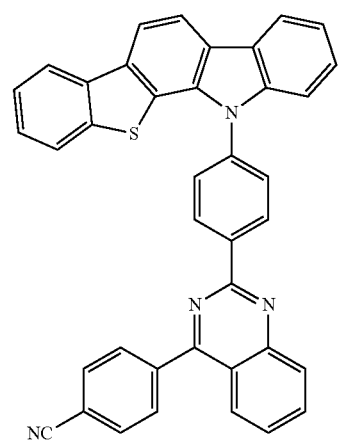
H2-296
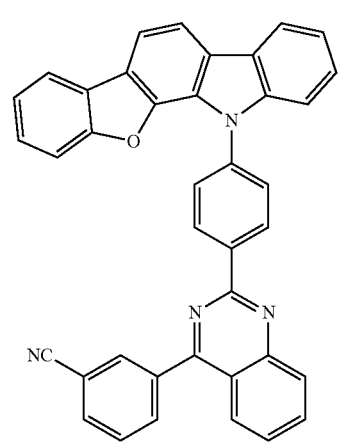
H2-297
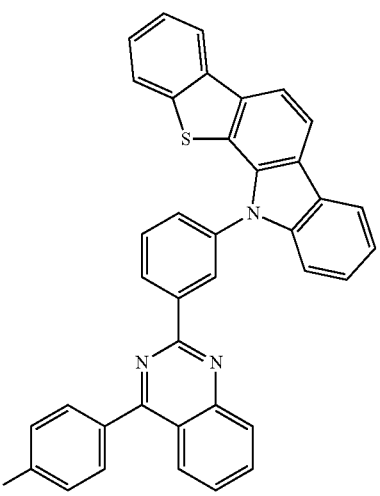
H2-298
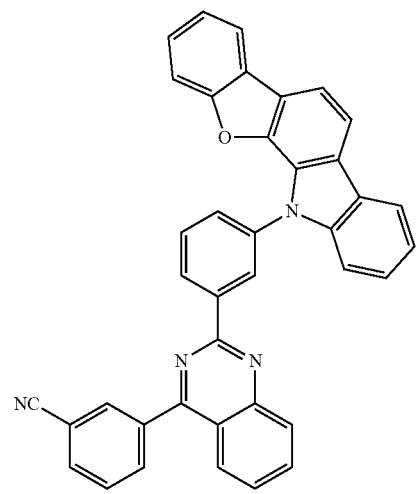
H2-299
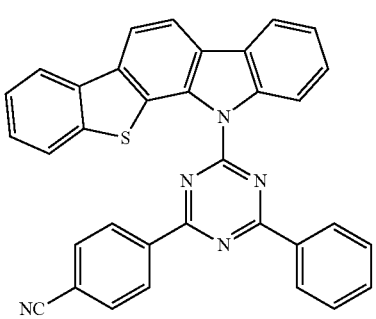
H2-300
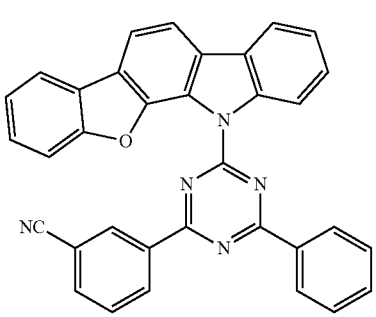
H2-301
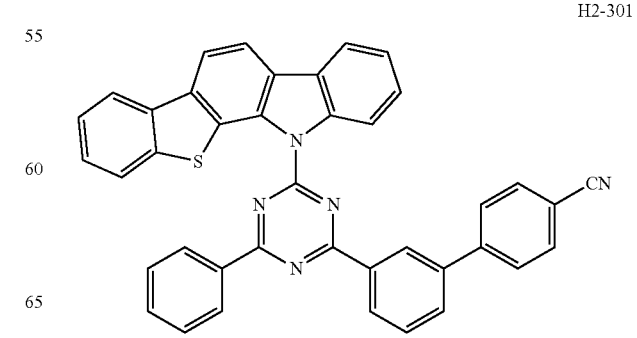

-continued
H2-302
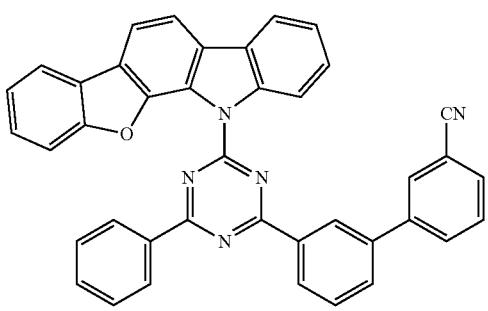
H2-303
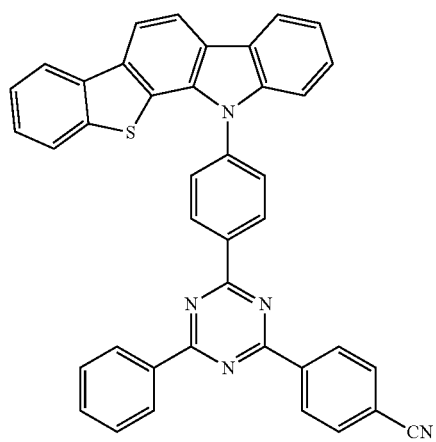
H2-304
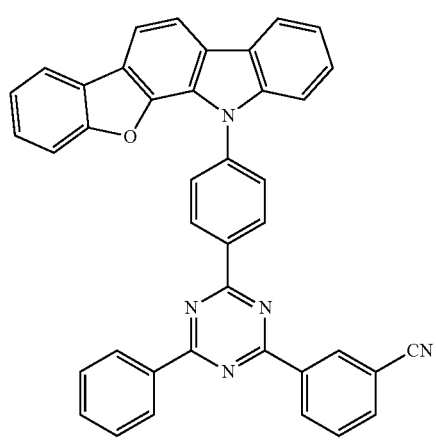
-continued
H2-305
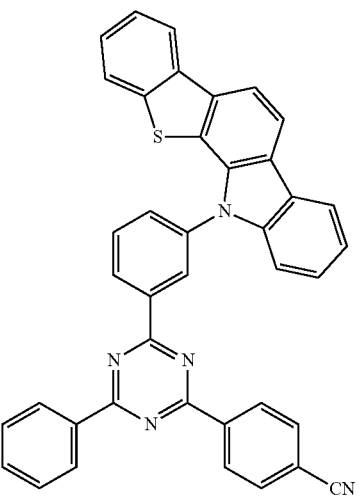
H2-306
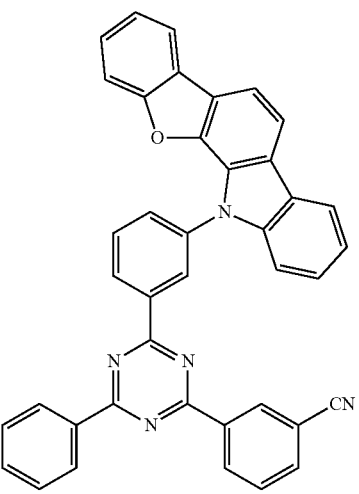
H2-307
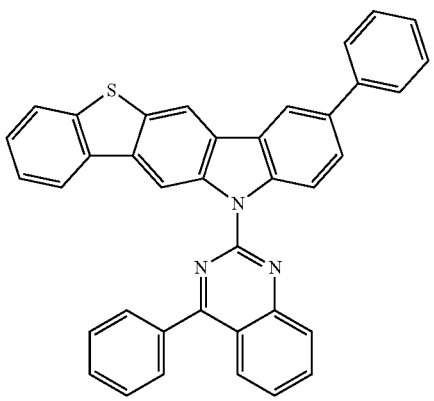

H2-308
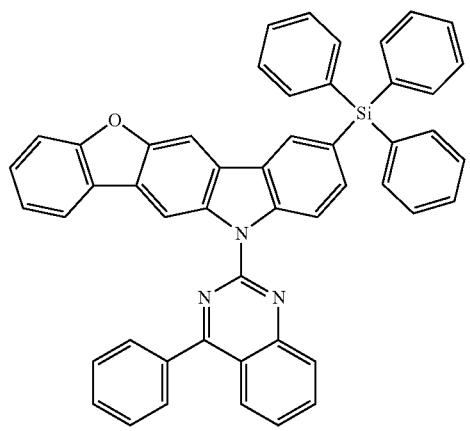
H2-309
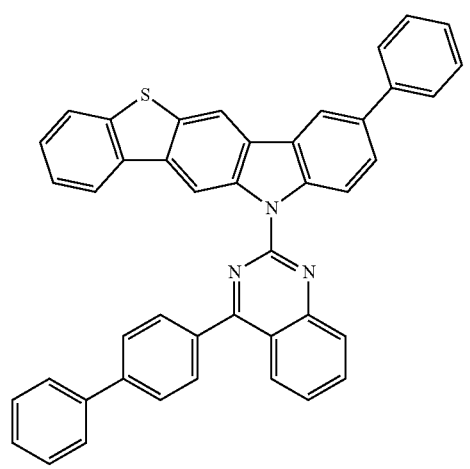
H2-310
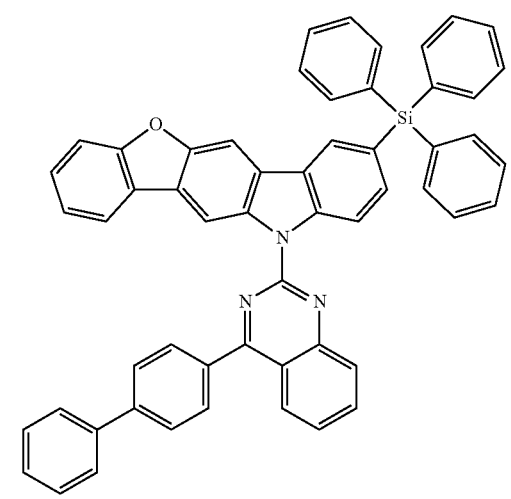
H2-311
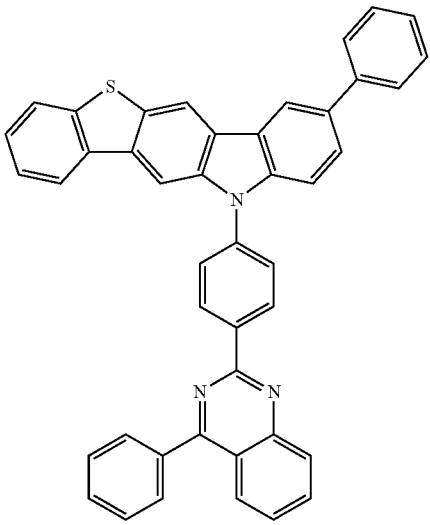
H2-312
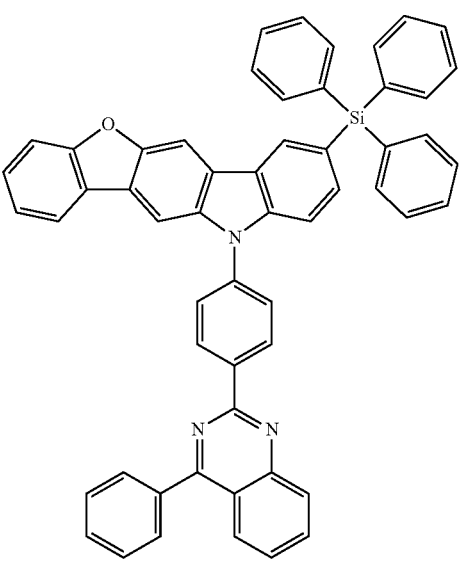
H2-313
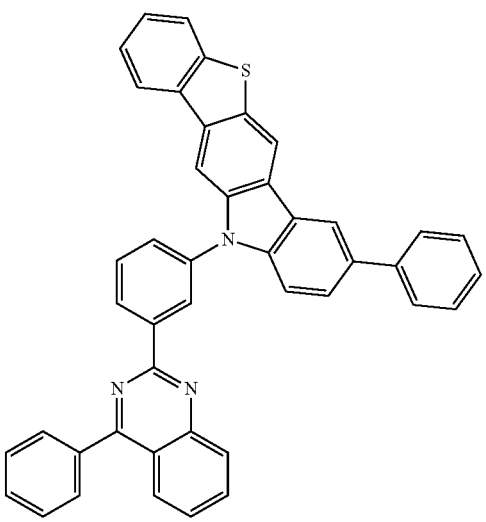

H2-314
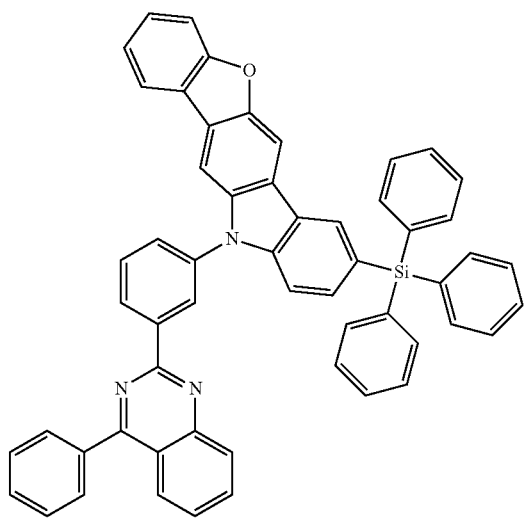
H2-315
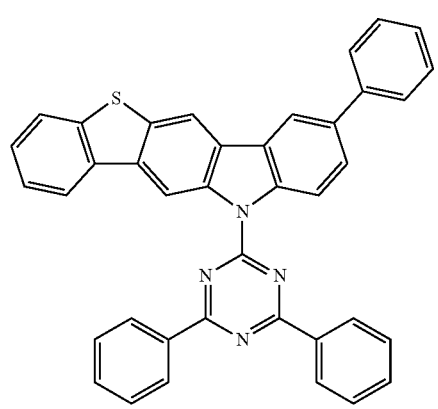
H2-316
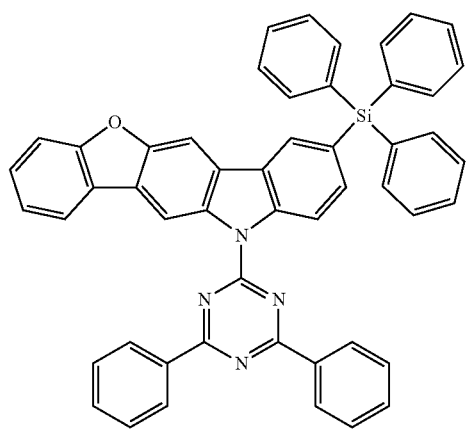
H2-317
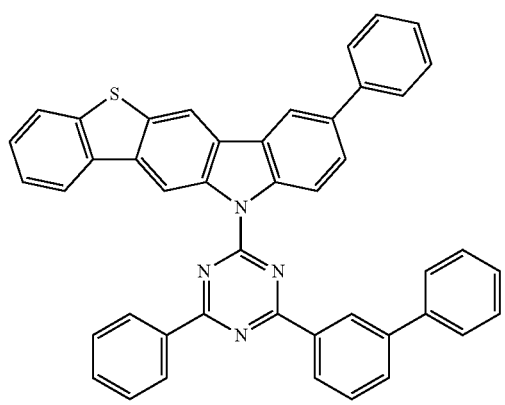
H2-318
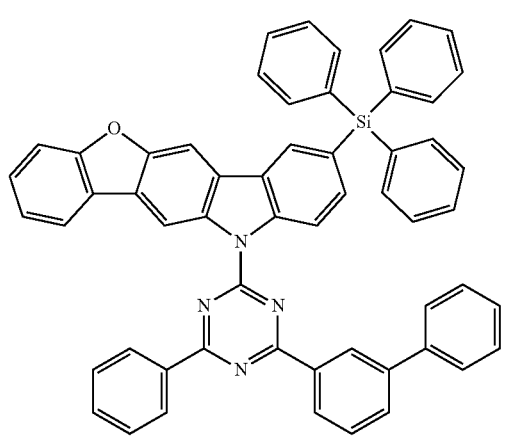
H2-319
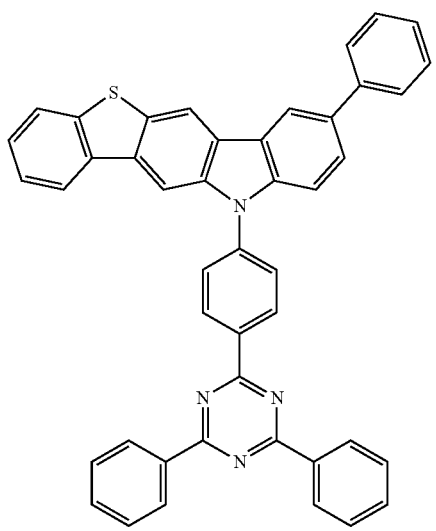

H2-320
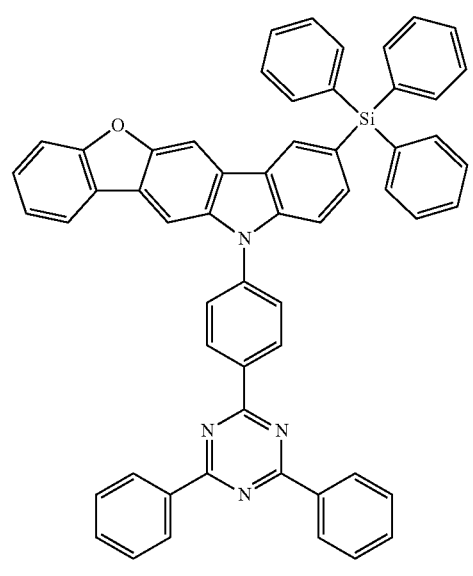
H2-321
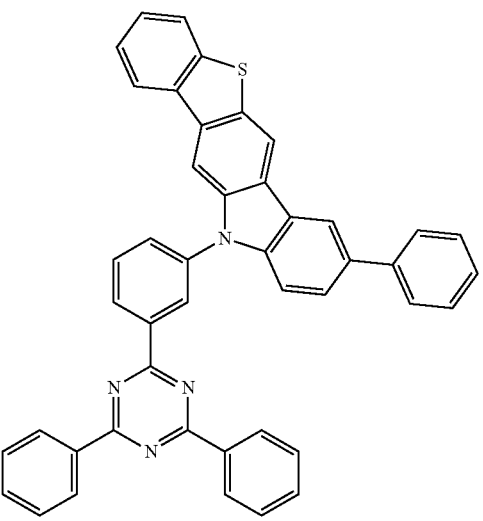
H2-322
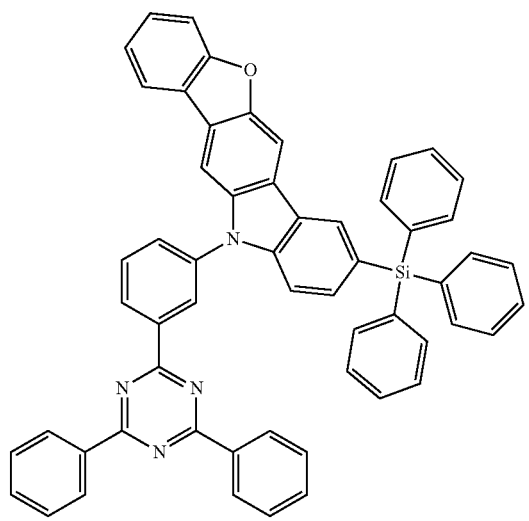
H2-323
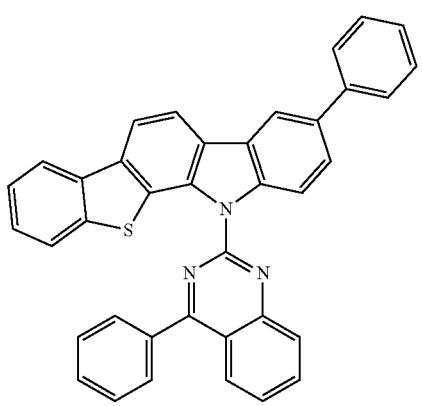
H2-324
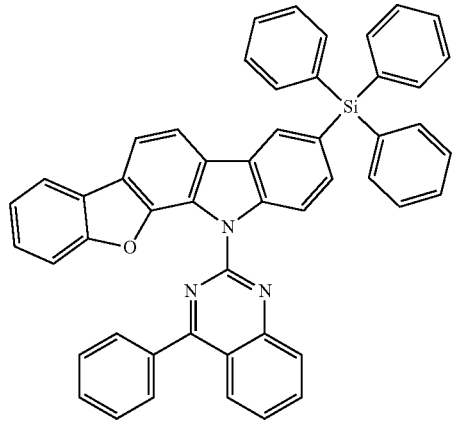
H2-325
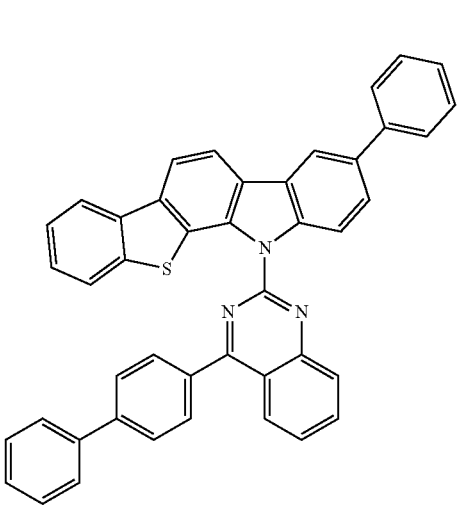

-continued
H2-326
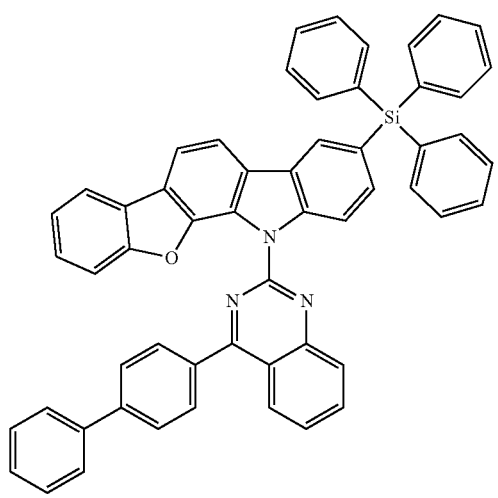
H2-327
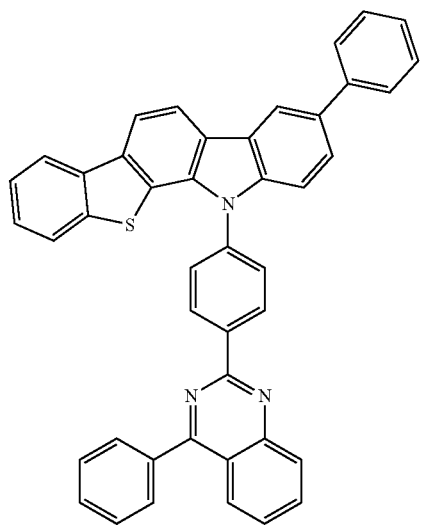
H2-328
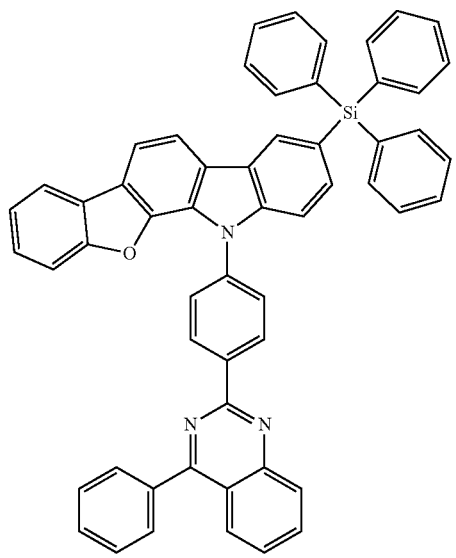
H2-329
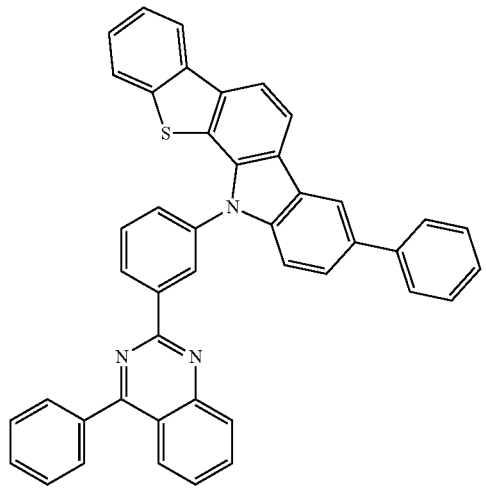
H2-330
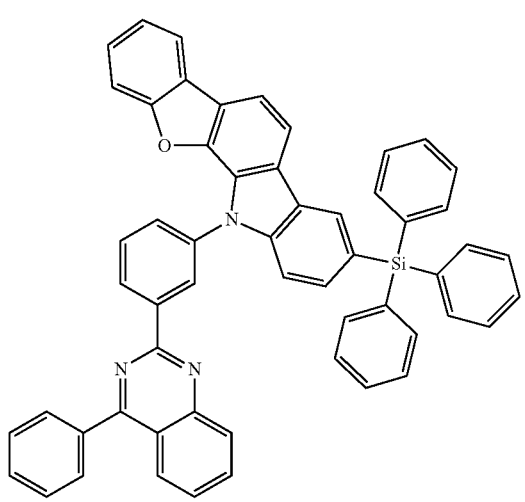
H2-331
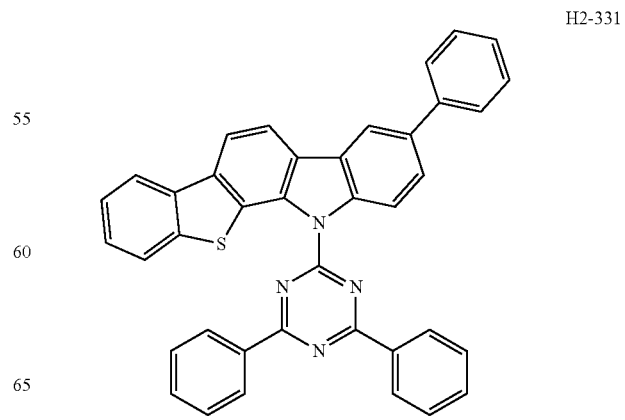

H2-332
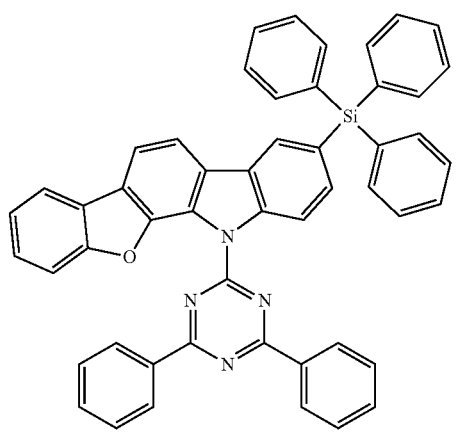
H2-333
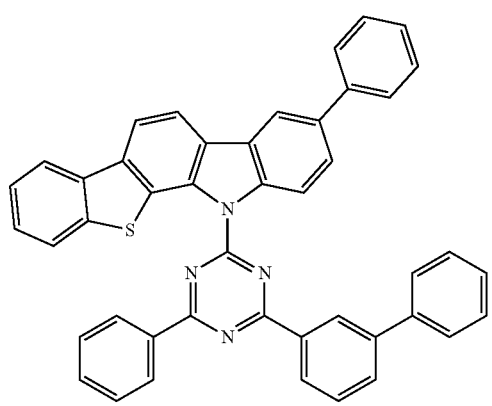
H2-334
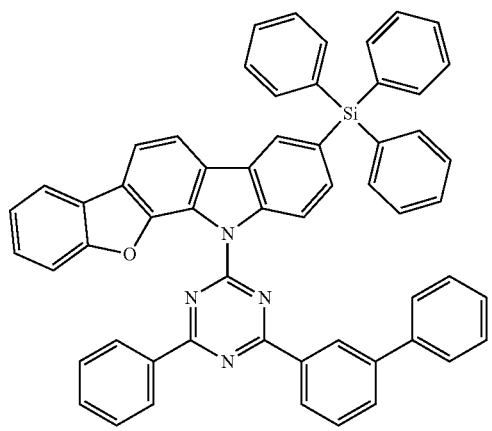
H2-335
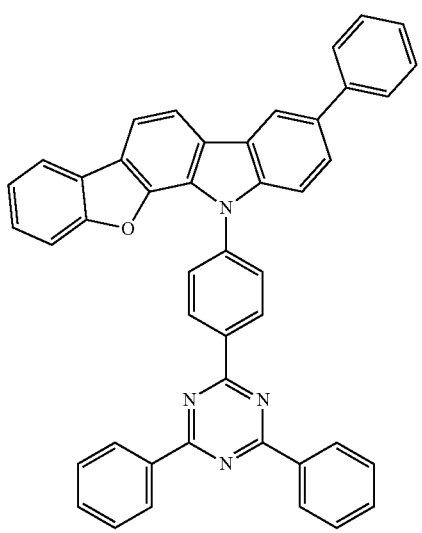
H2-336
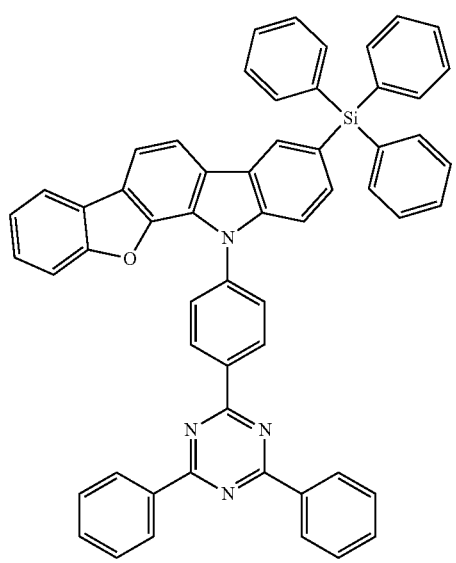
H2-337
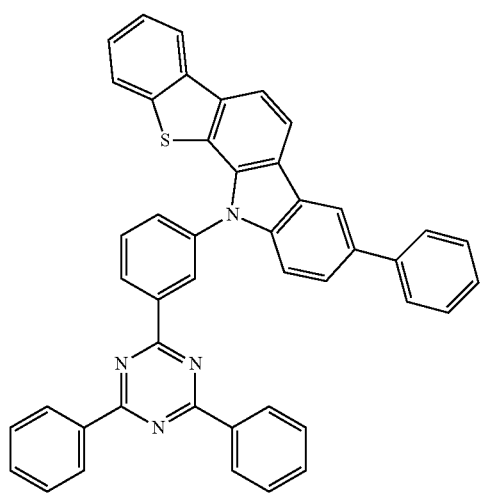

-continued
H2-338
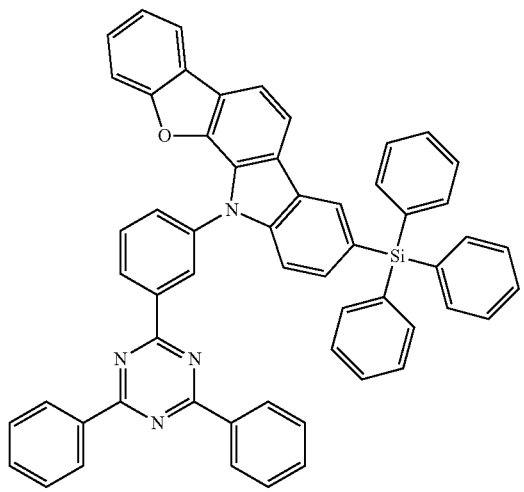
H2-339
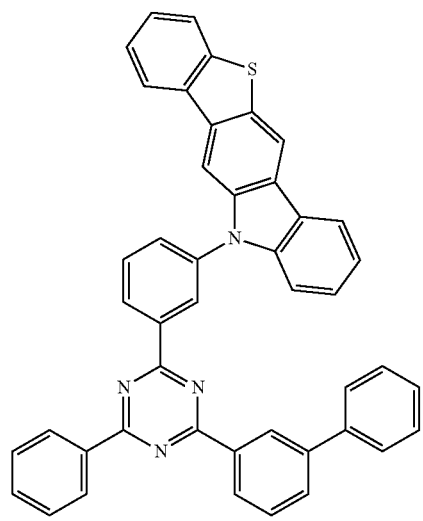
H2-340
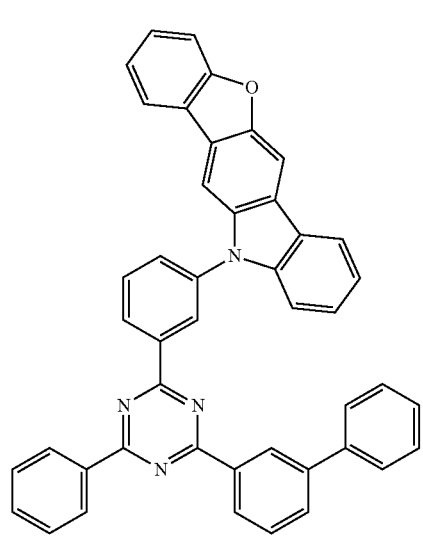
-continued
H2-341
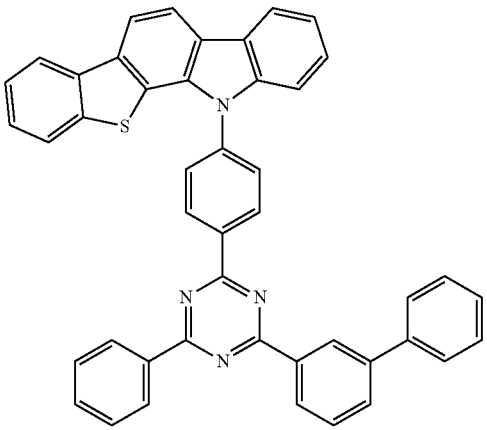
H2-342
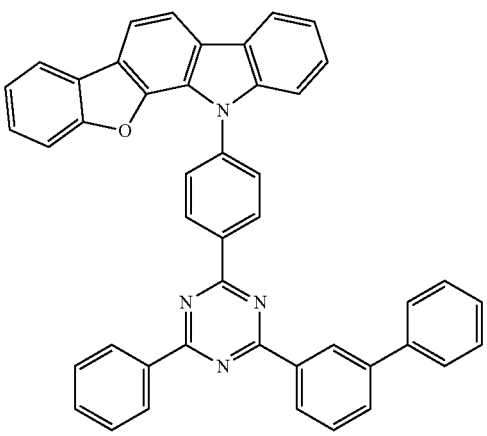
H2-343
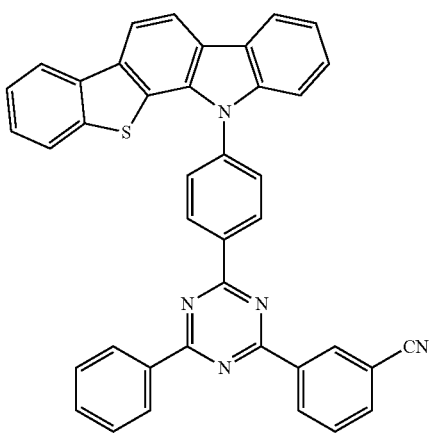

H2-344
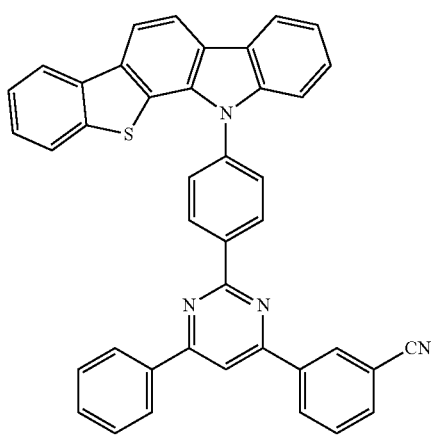
H2-345
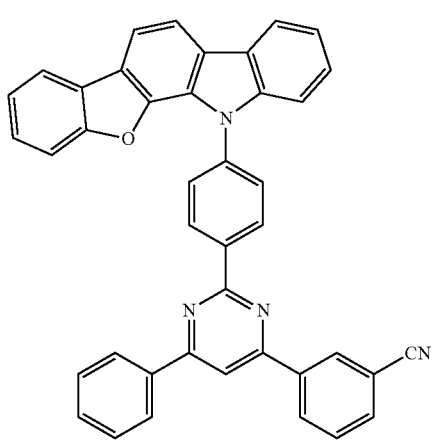
H2-346
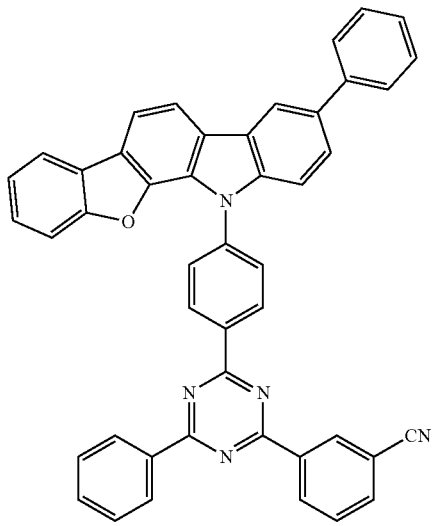
H2-347
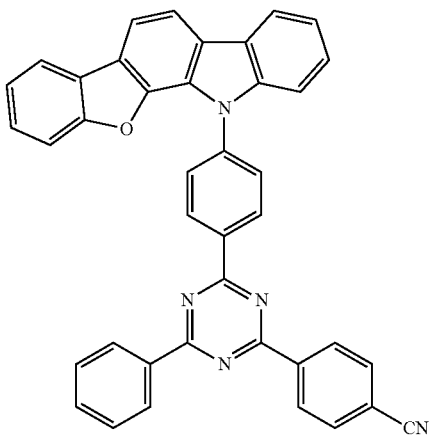
H2-348
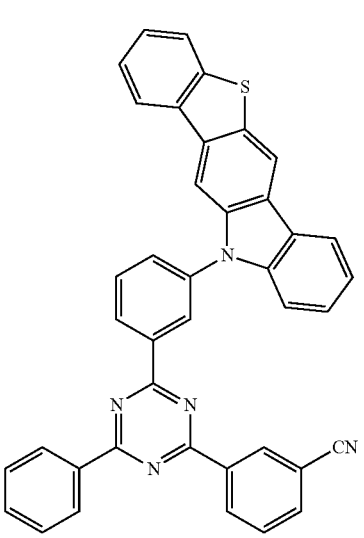
H2-349
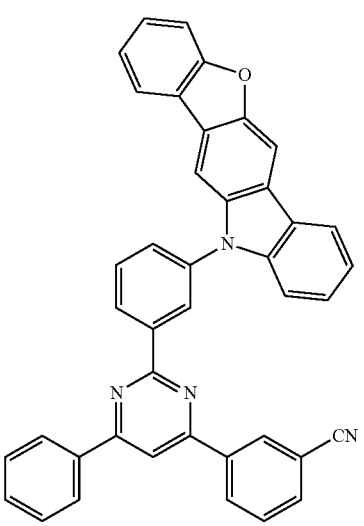

H2-350
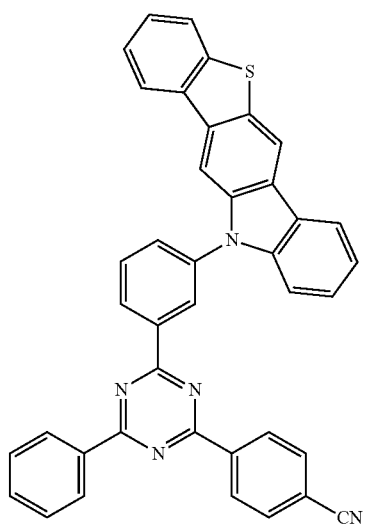
H2-351
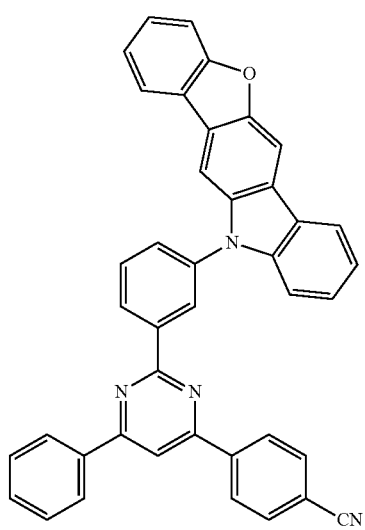
H2-352
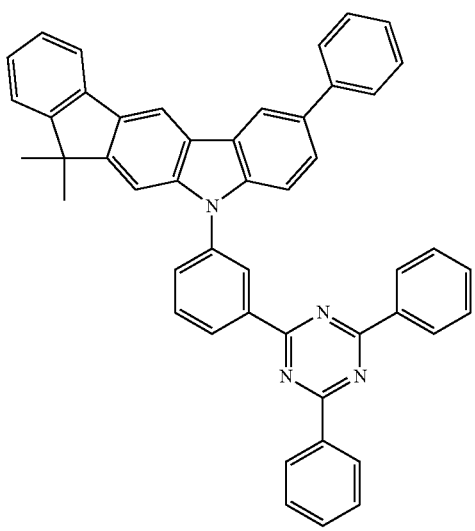
H2-353
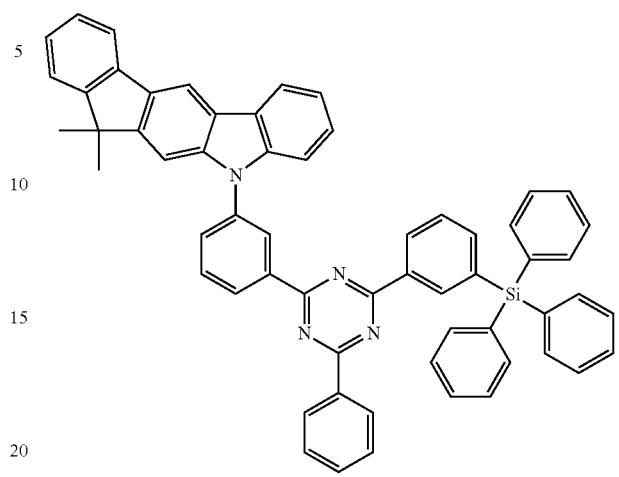
H2-354
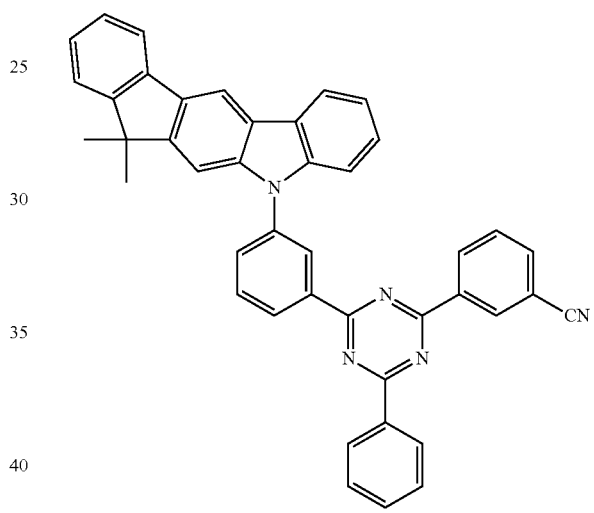
H2-355
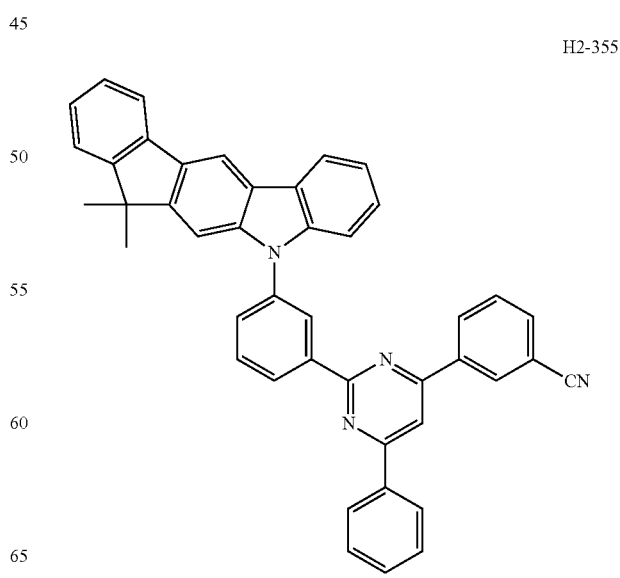

H2-356
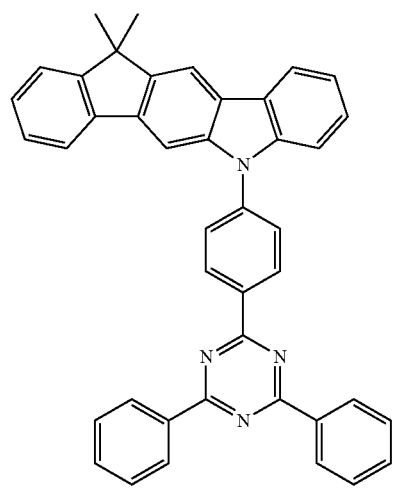
H2-357
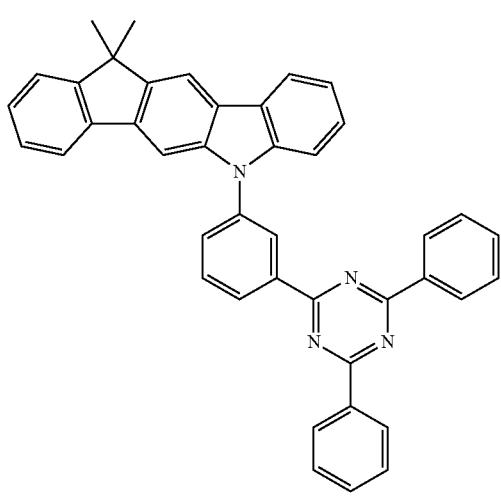
H2-358
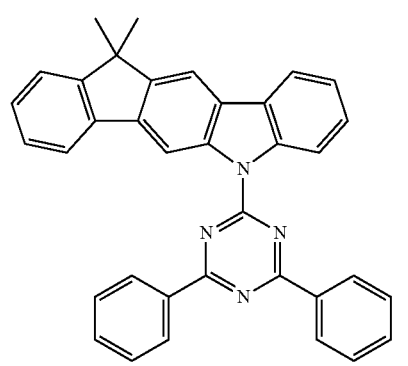
H2-359
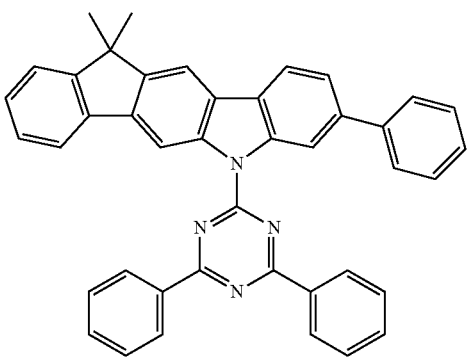
H2-360
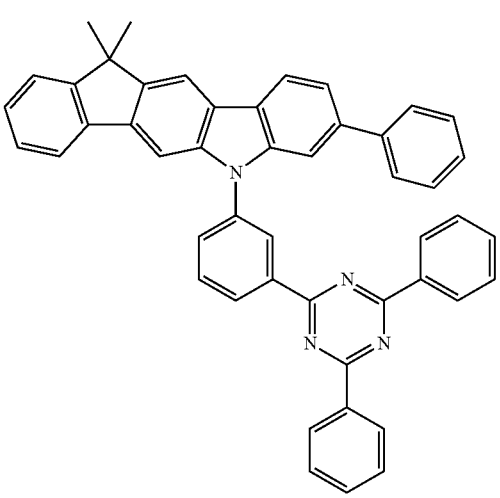
H2-361
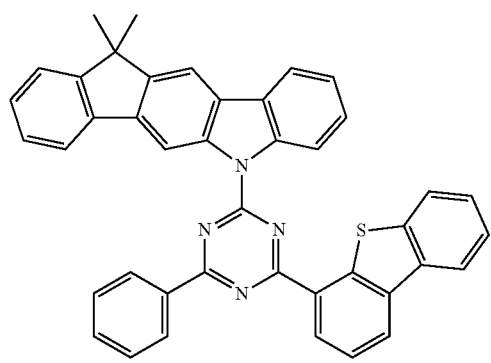
H2-362
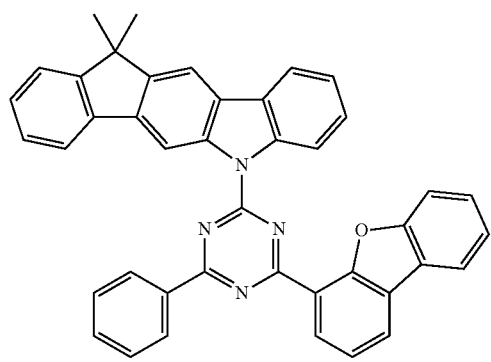

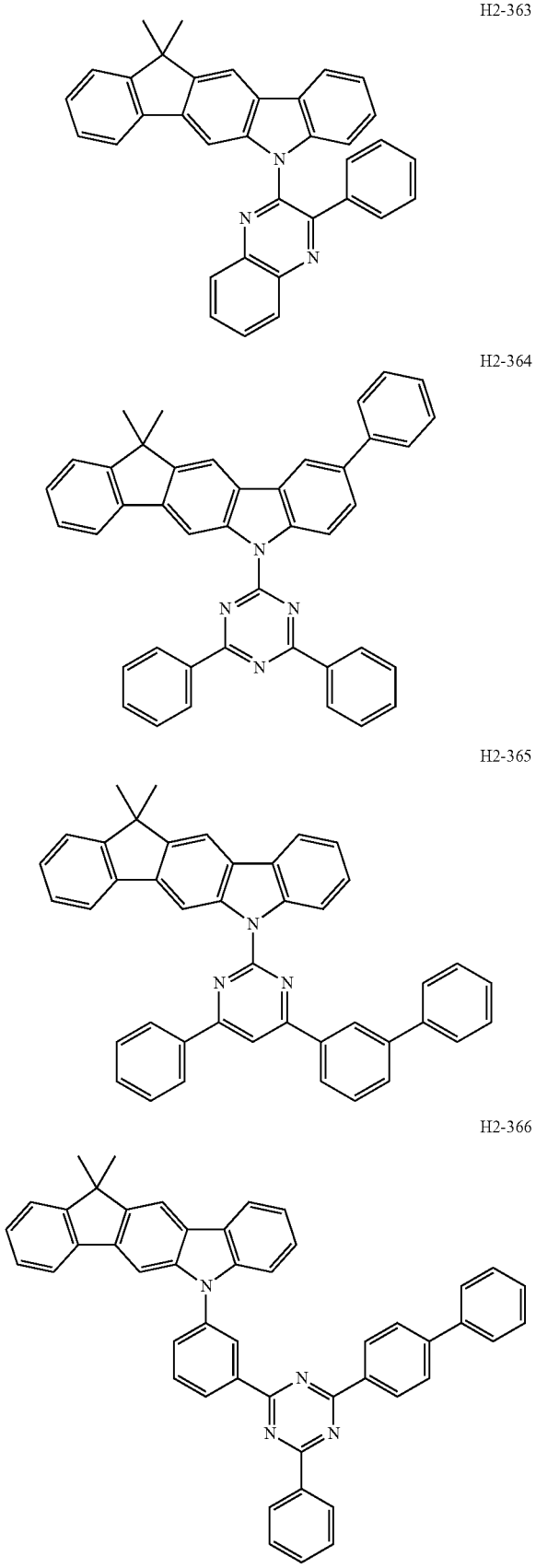
H2-363
H2-364
H2-365
H2-366
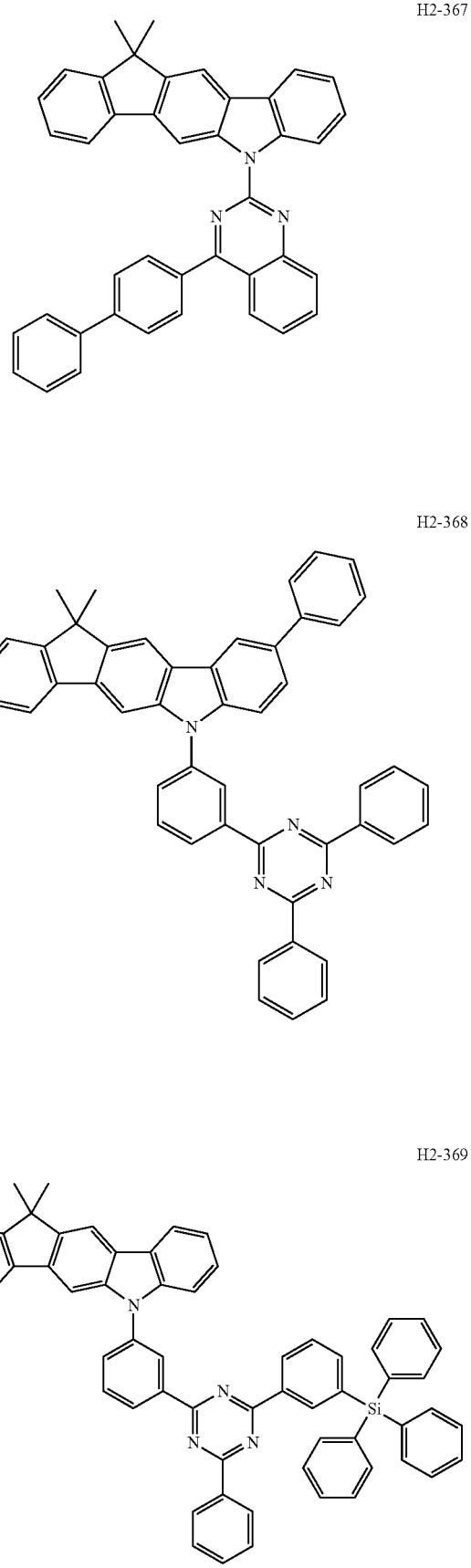
H2-367
H2-368
H2-369

H2-370
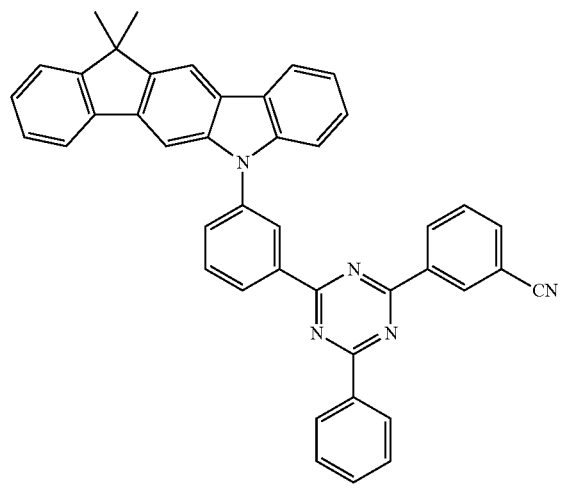
H2-371
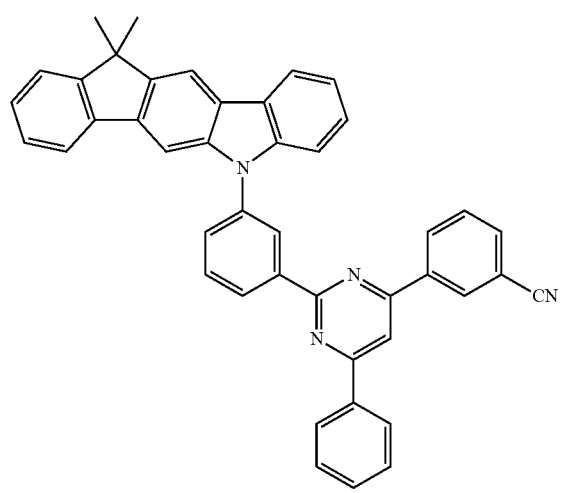
H2-372
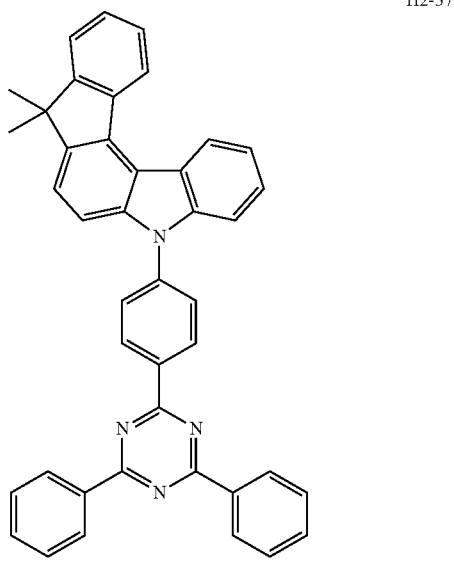
H2-373
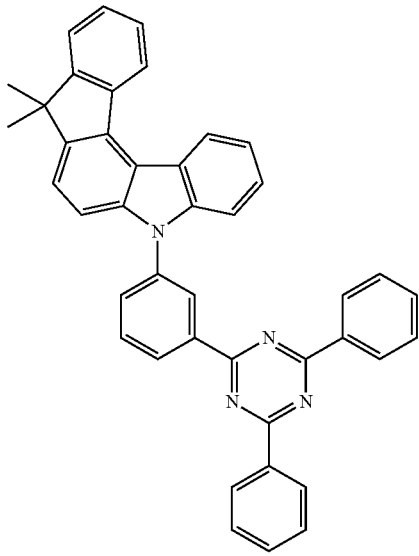
H2-374
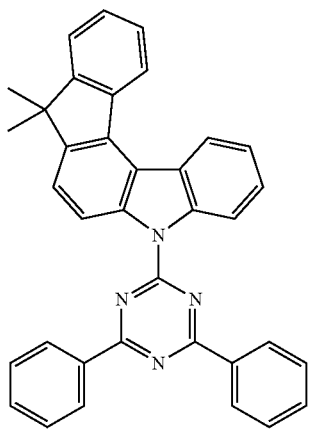
H2-375
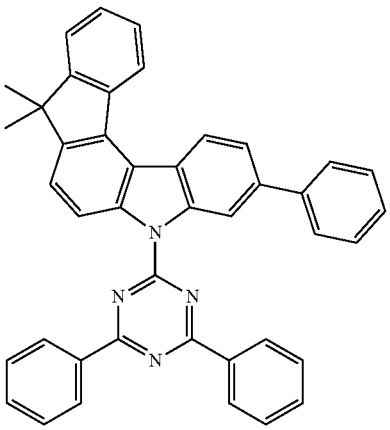

H2-376
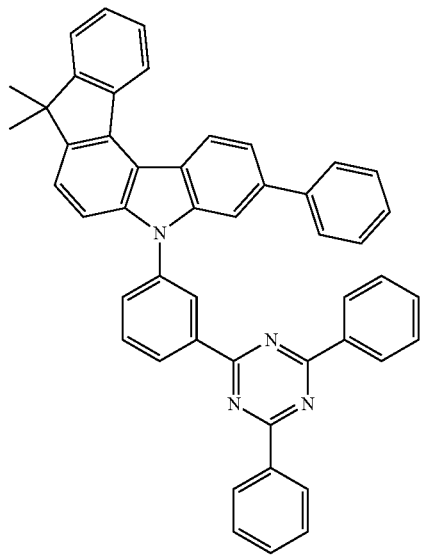
H2-377
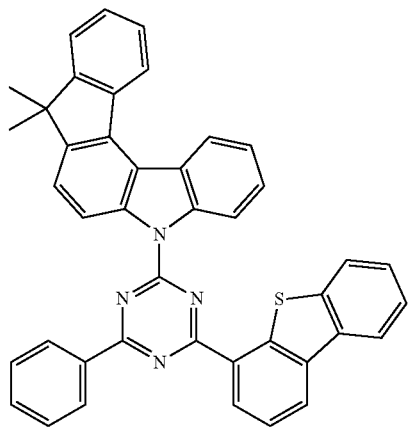
H2-378
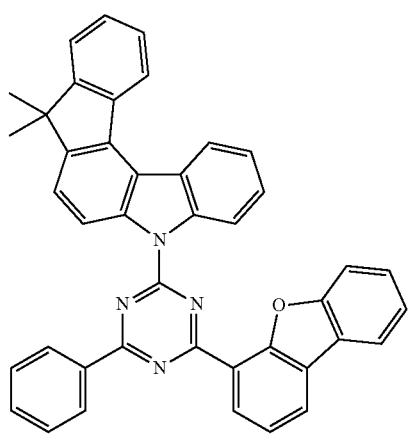
H2-379
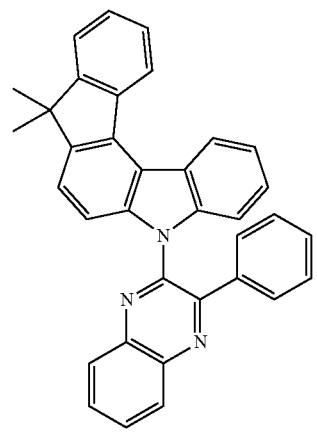
H2-380
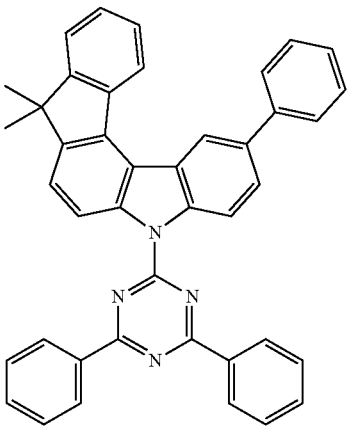
H2-381
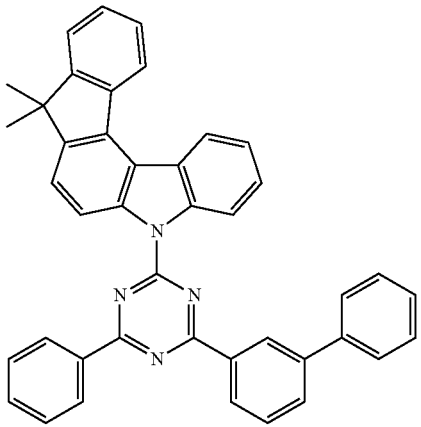

H2-382
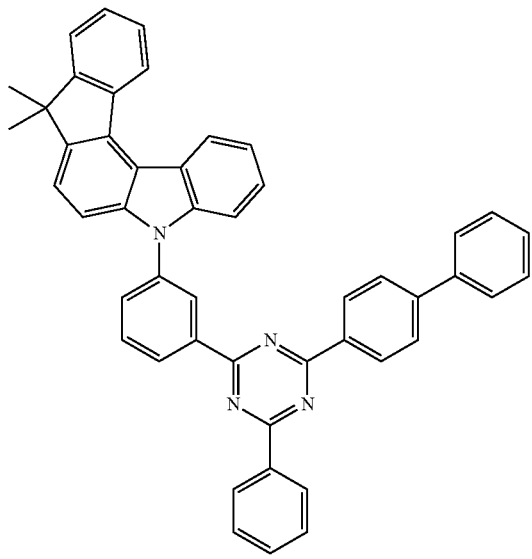
H2-383
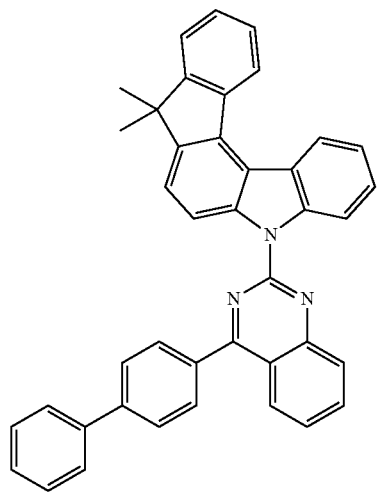
H2-384
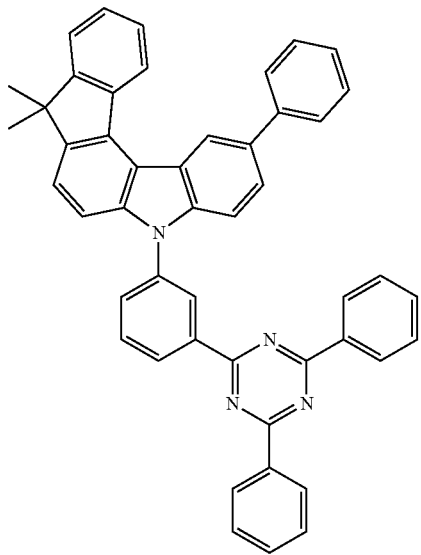
H2-385
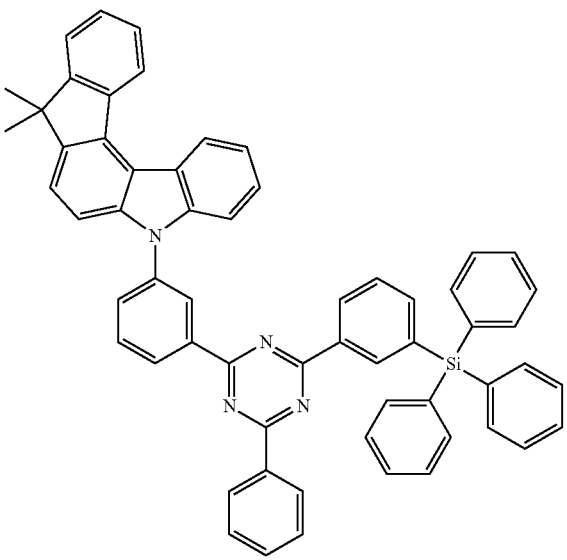
H2-386
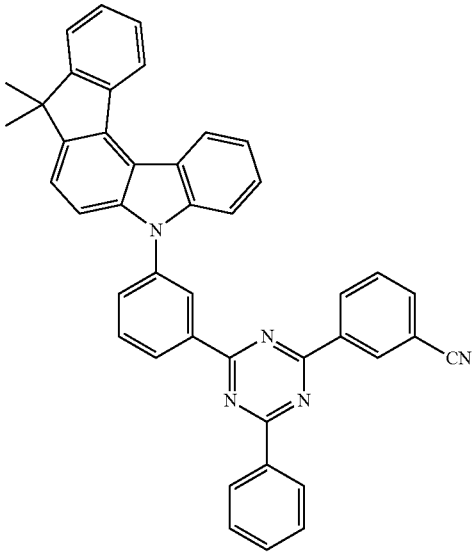

H2-387
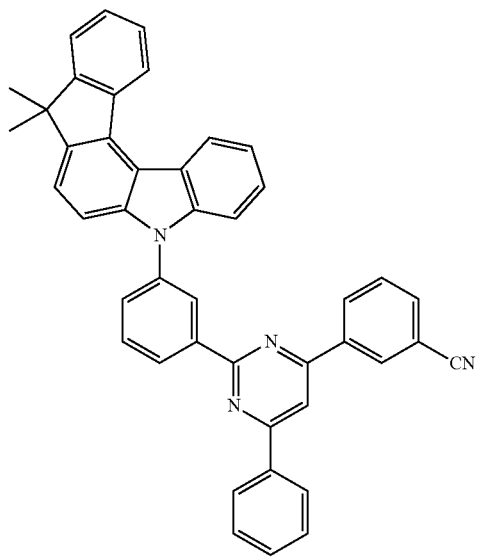
H2-390
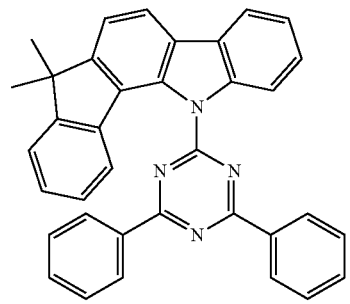
H2-391
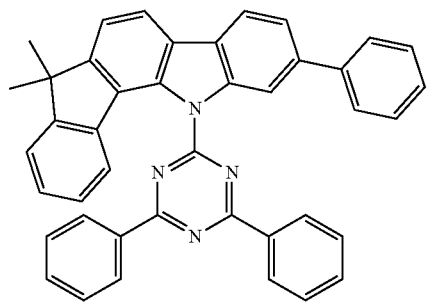
H2-388
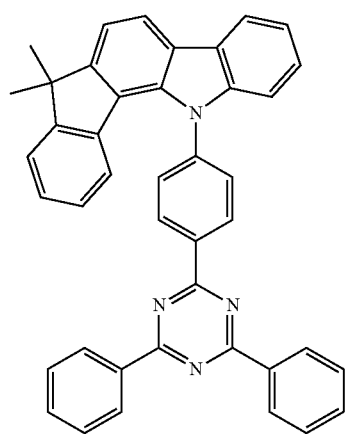
H2-392
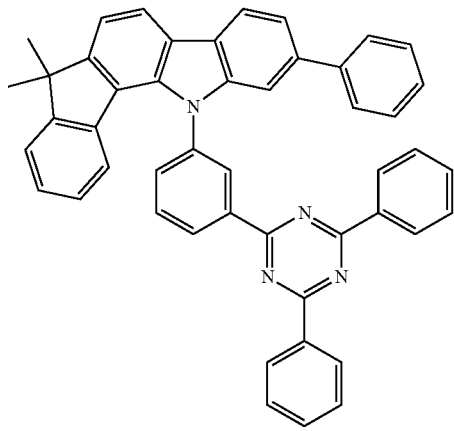
H2-389
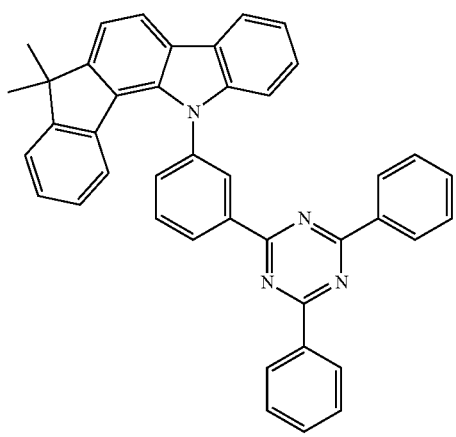
H2-393
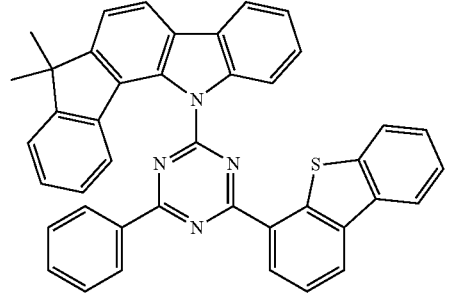

-continued
H2-394
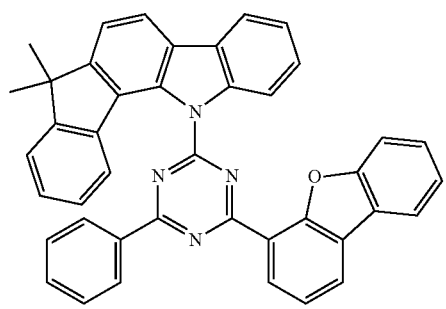
H2-395
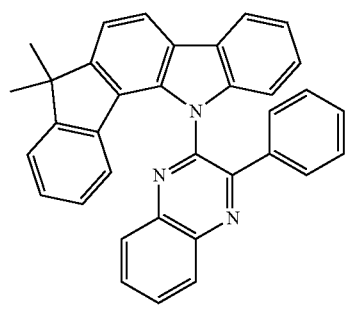
H2-396
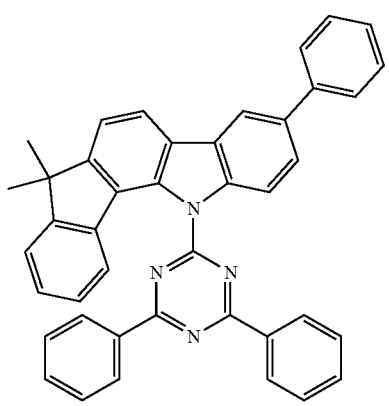
H2-397
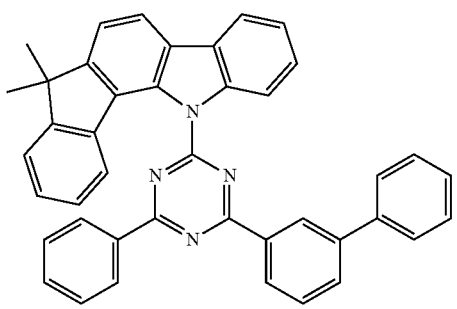
-continued
H2-398
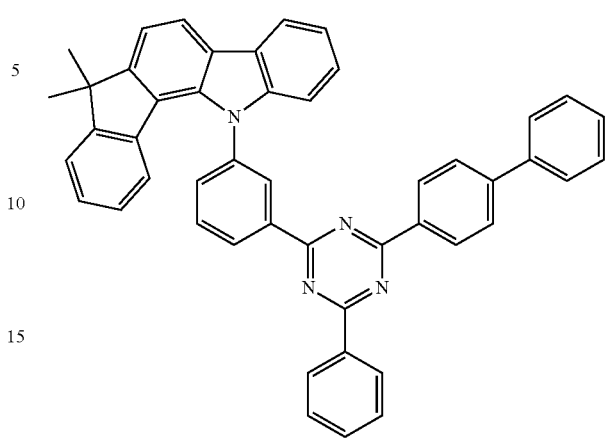
H2-399
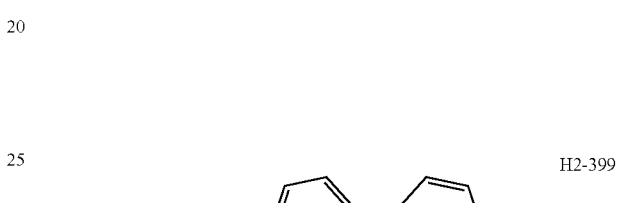
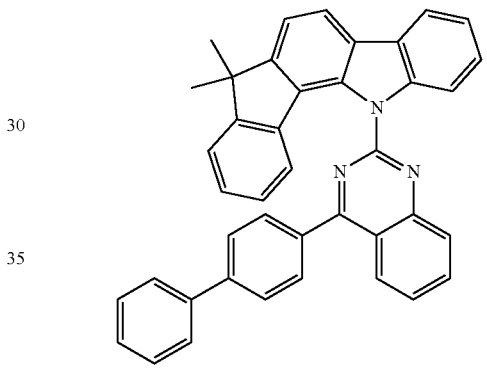
H2-400
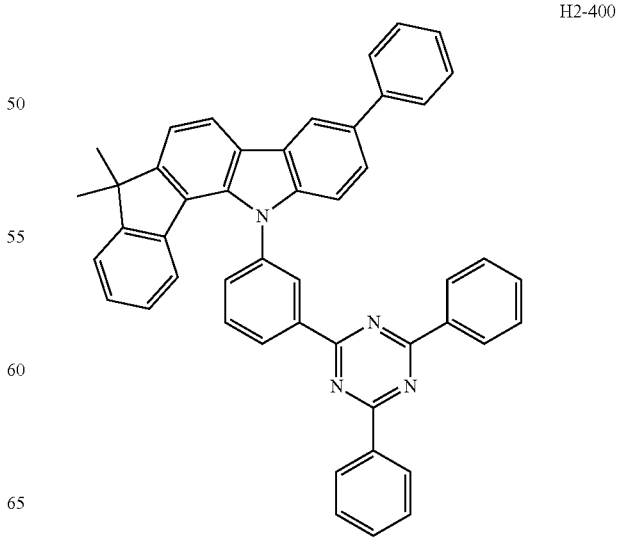

H2-401
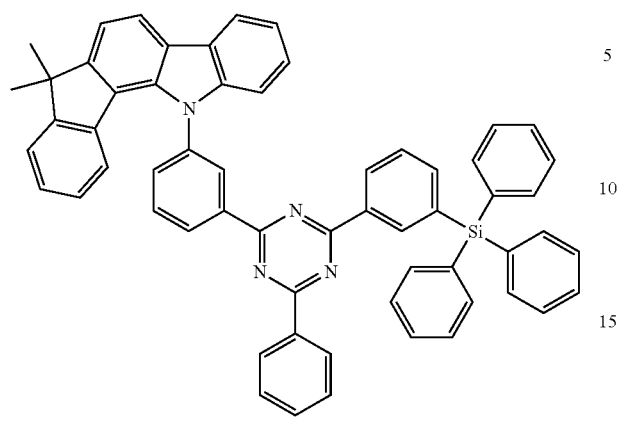
H2-402
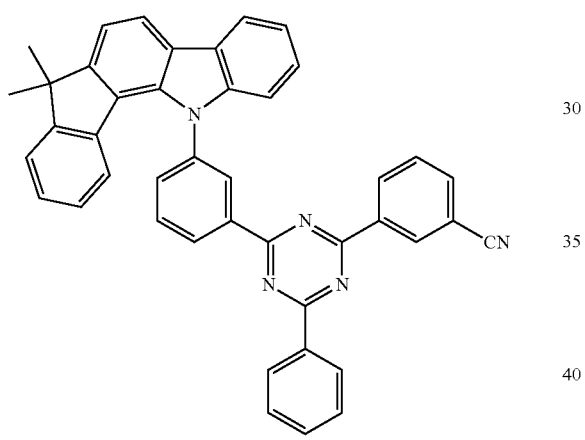
H2-403
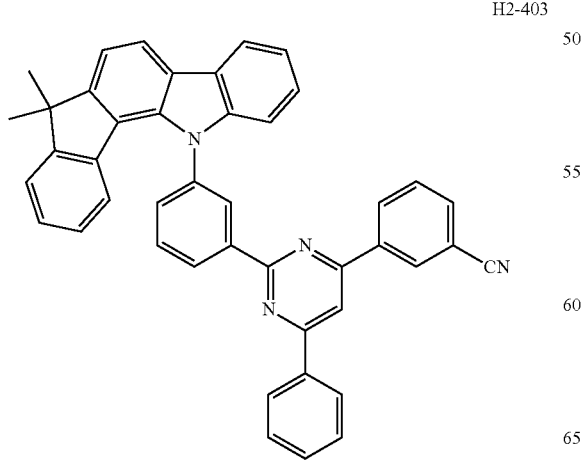
H2-404
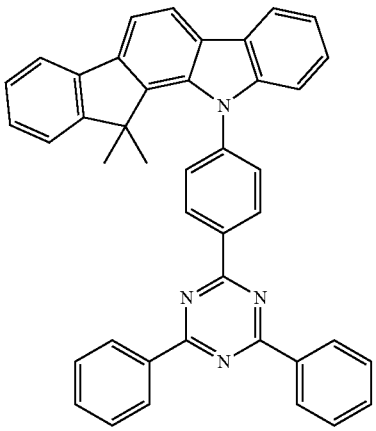
H2-405
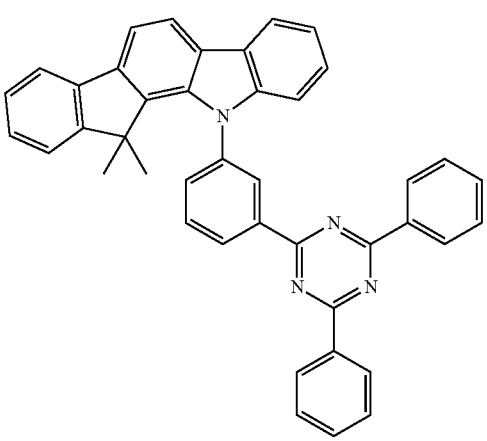
H2-406
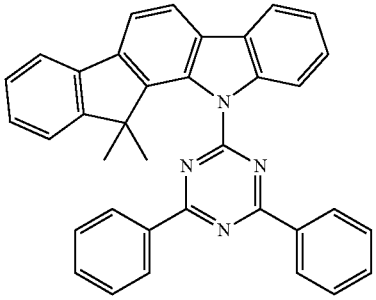
H2-407
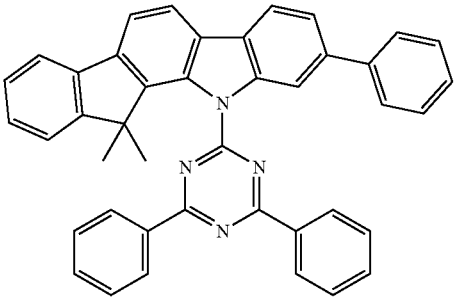

H2-408
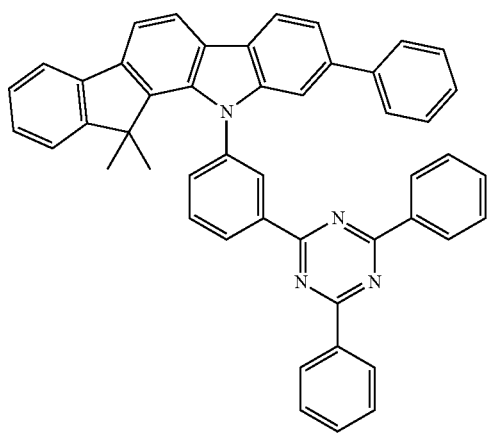
H2-409
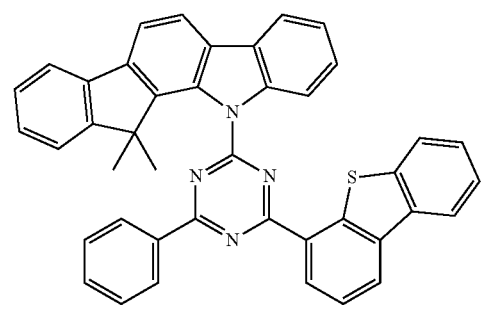
H2-410
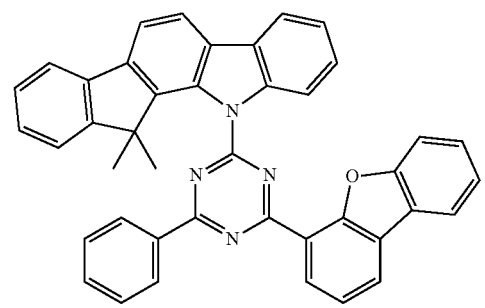
H2-411
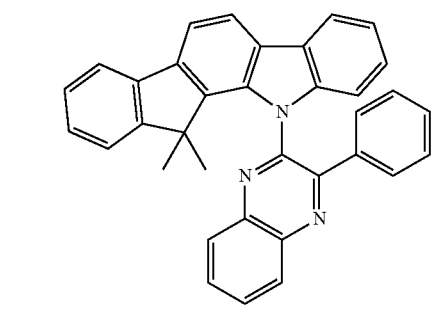
H2-412
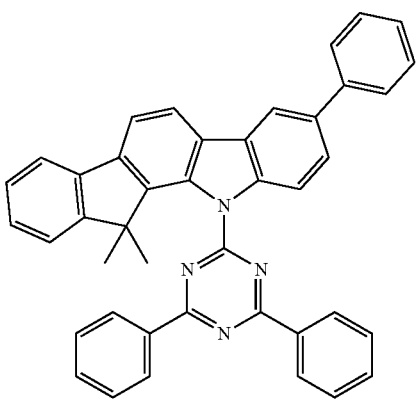
H2-413
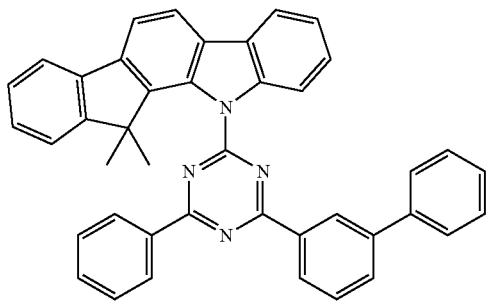
H2-414
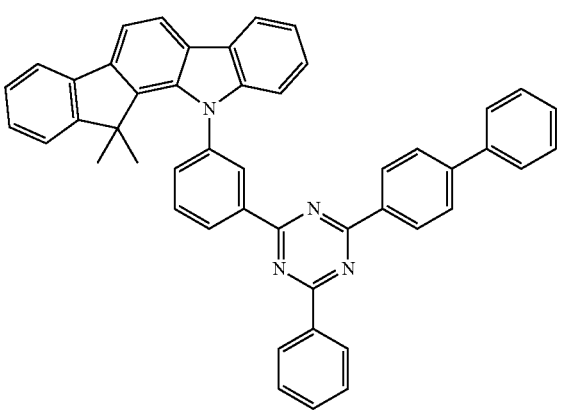
H2-415
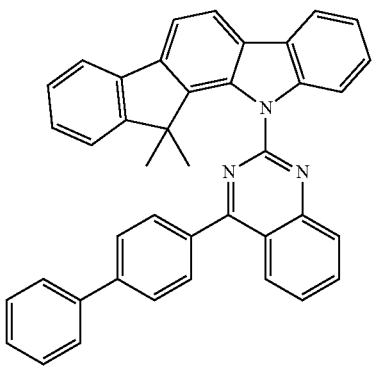

H2-416
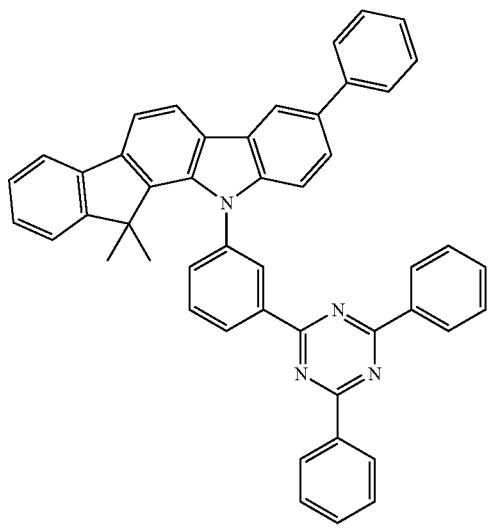
H2-419
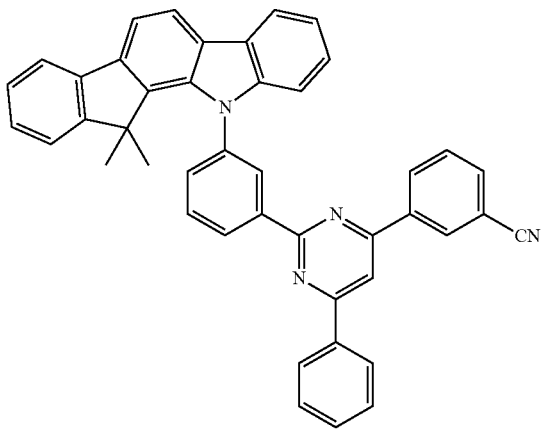
H2-417
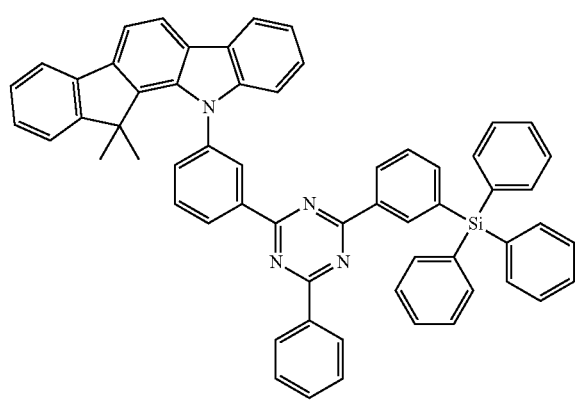
H2-420
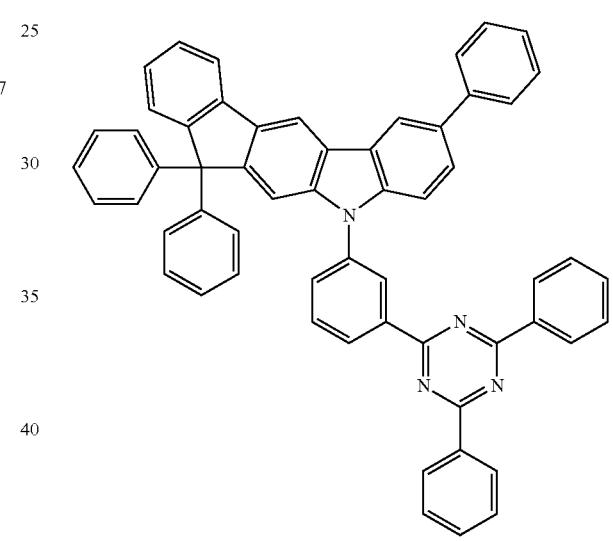
H2-418
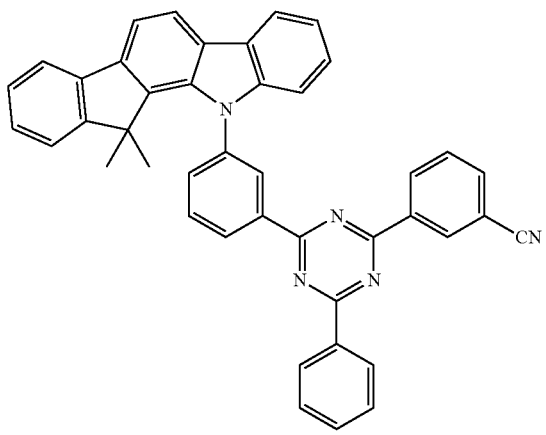
H2-421
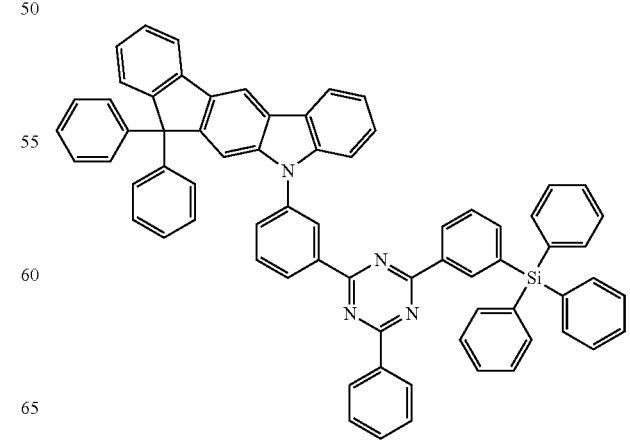

-continued
H2-422
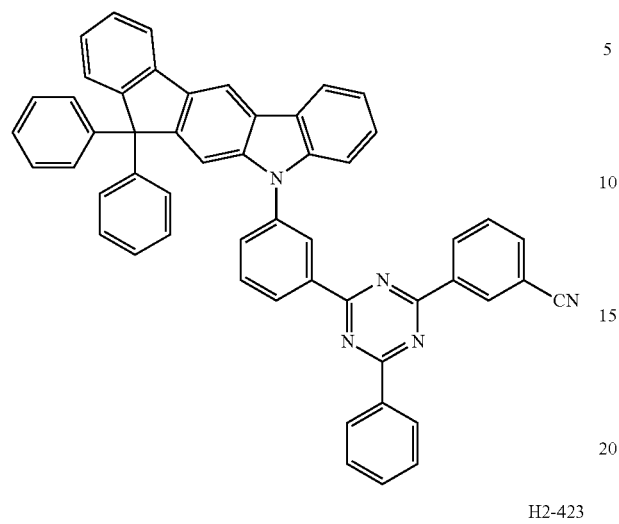
H2-423
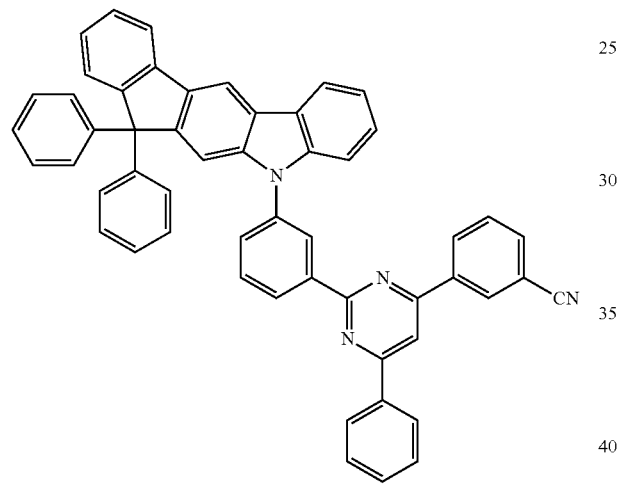
H2-424
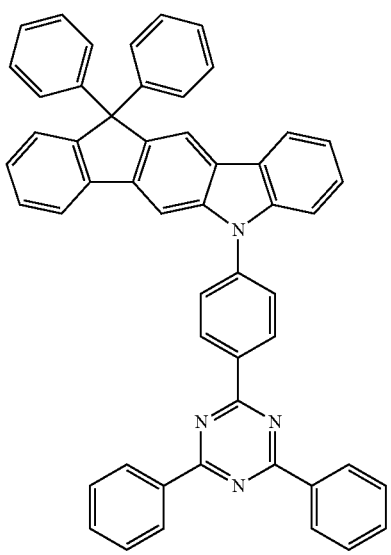
-continued
H2-425
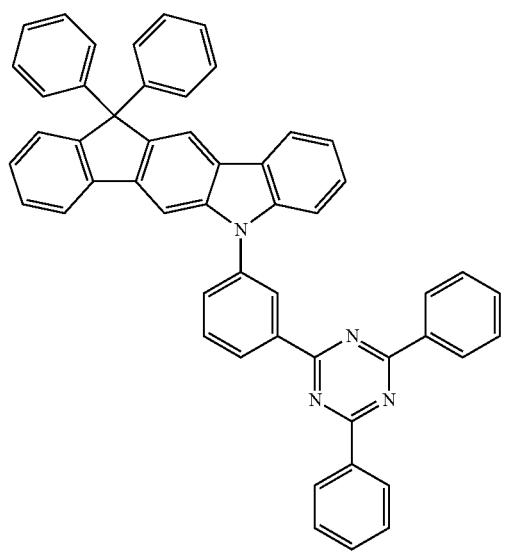
H2-426
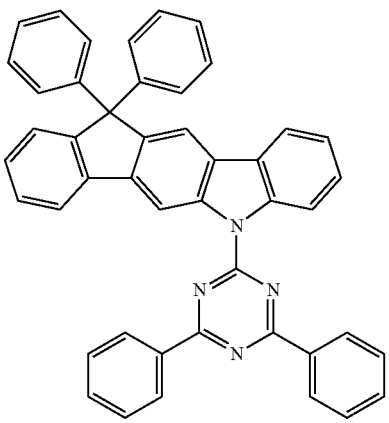
H2-427
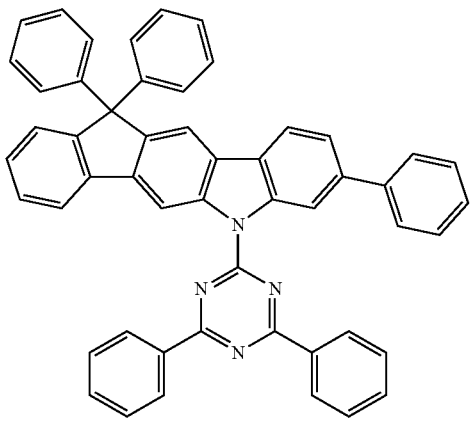

H2-428
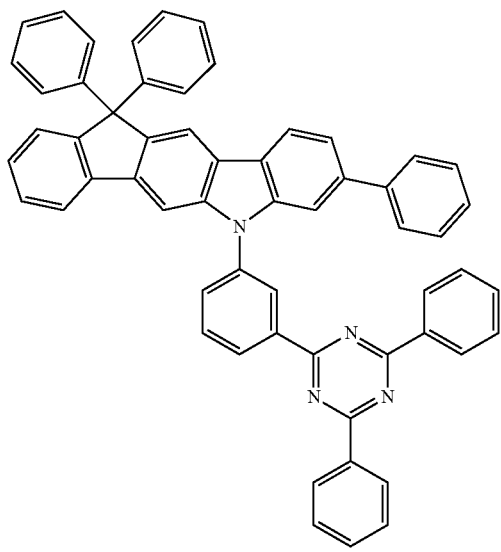
H2-429
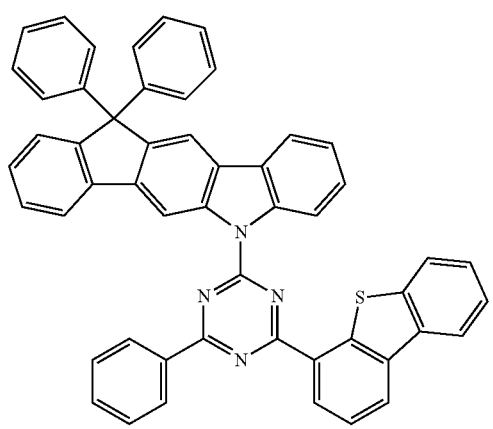
H2-430
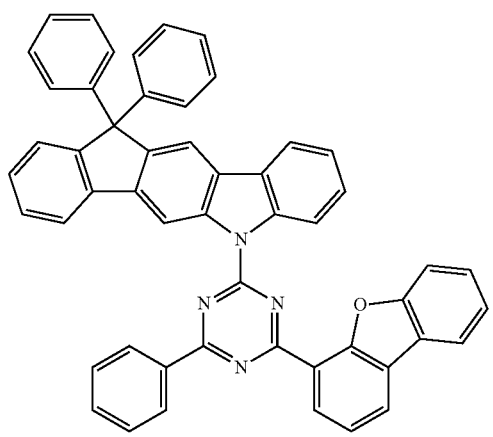
H2-431
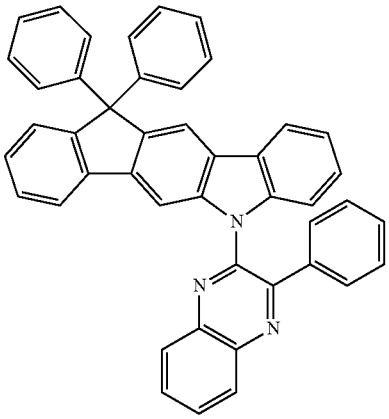
H2-432
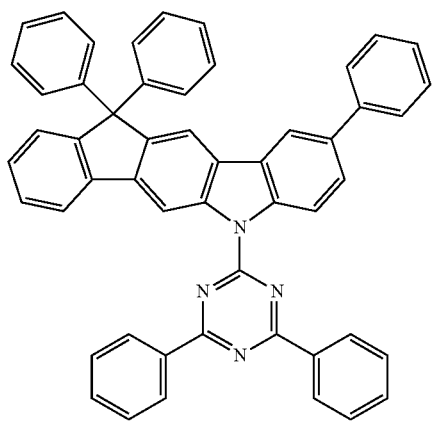
H2-433
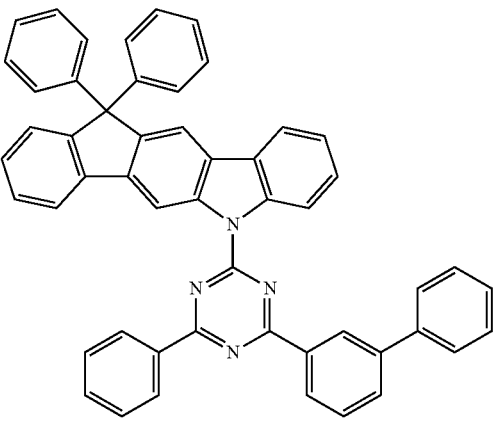

H2-434
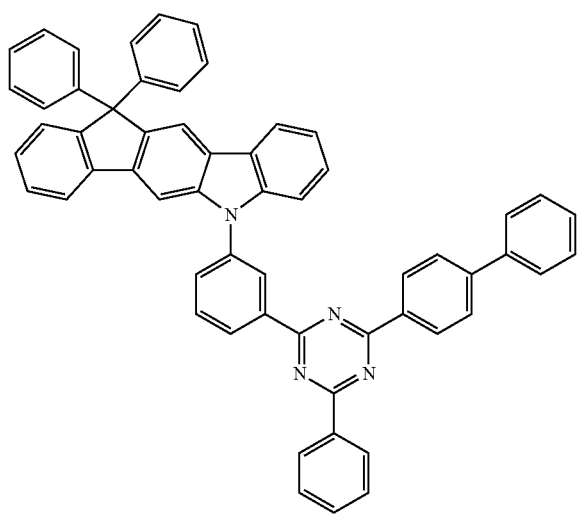
H2-435
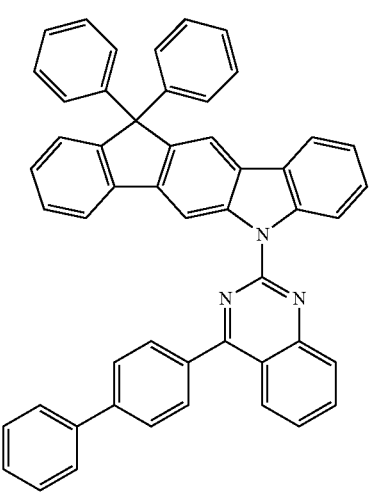
H2-436
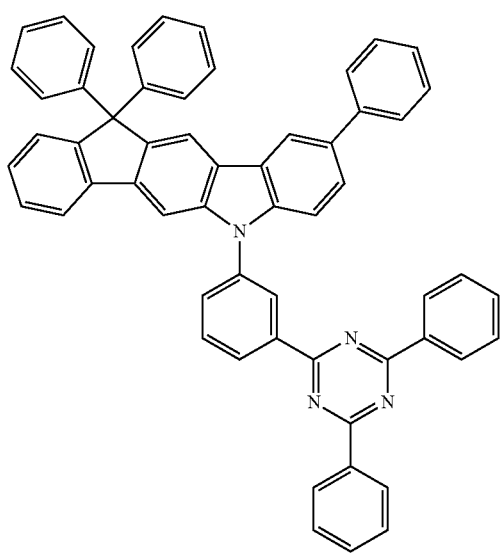
H2-437
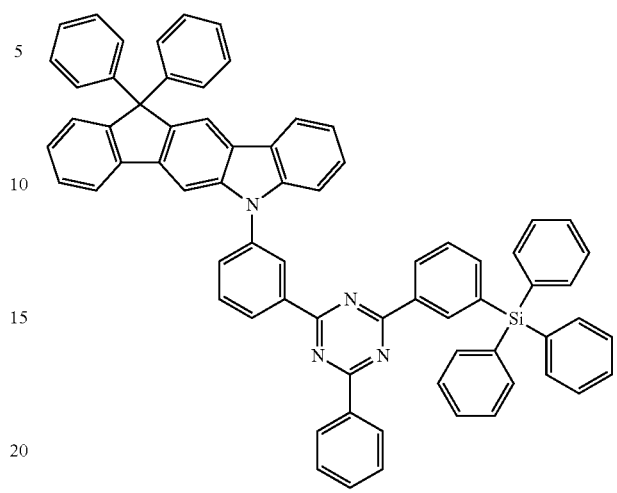
H2-438
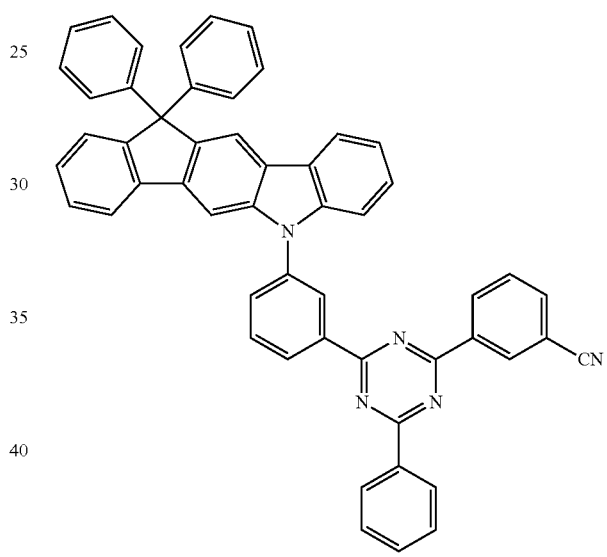
H2-439
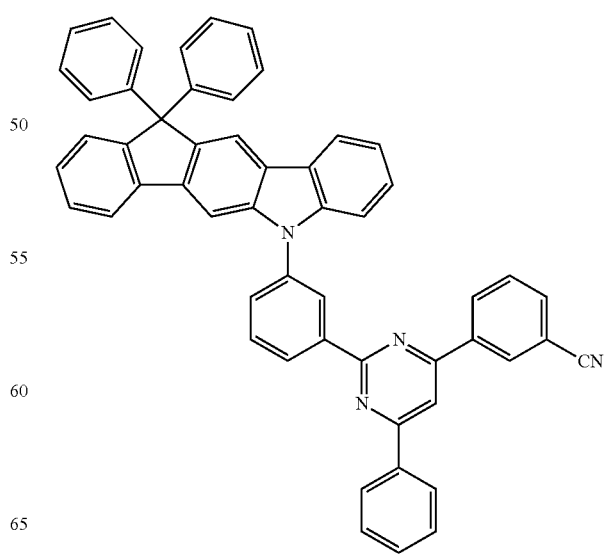

H2-440
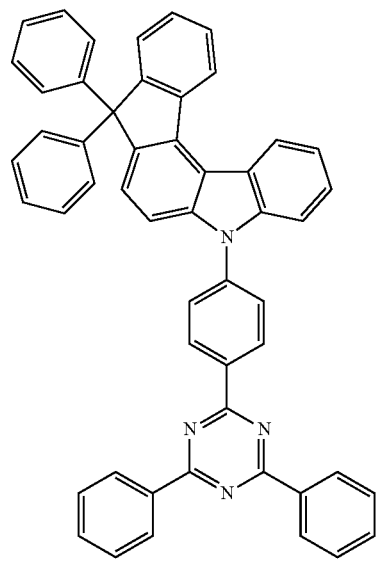
H2-441
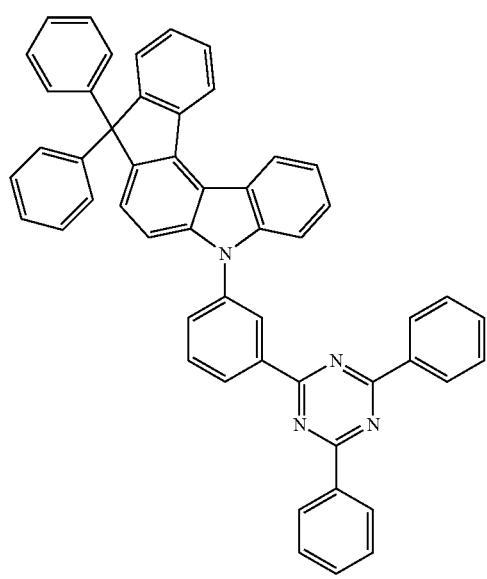
H2-442
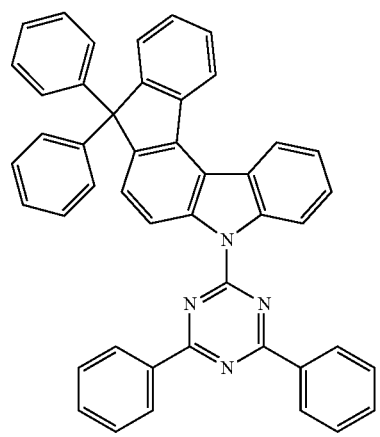
H2-443
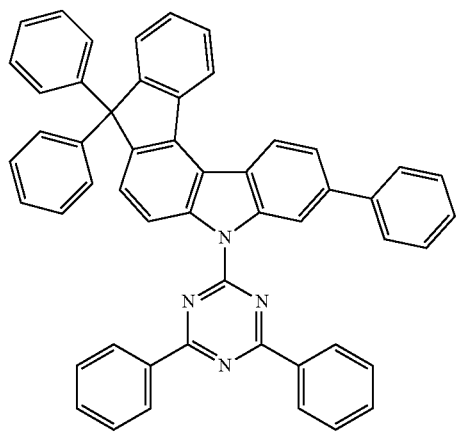
H2-444
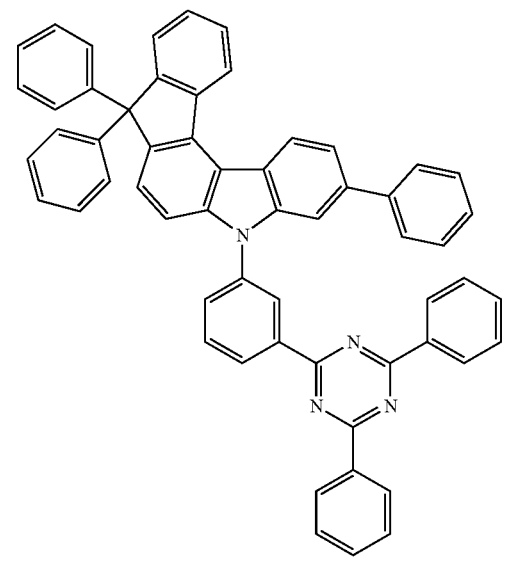
H2-445
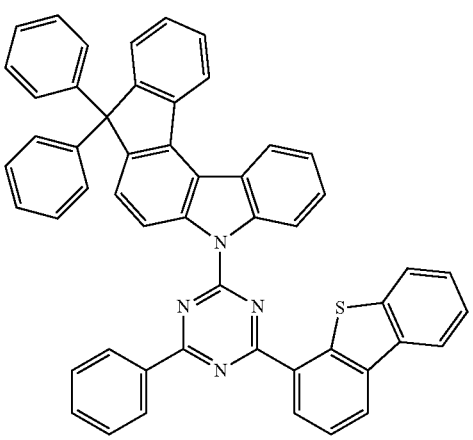

H2-446
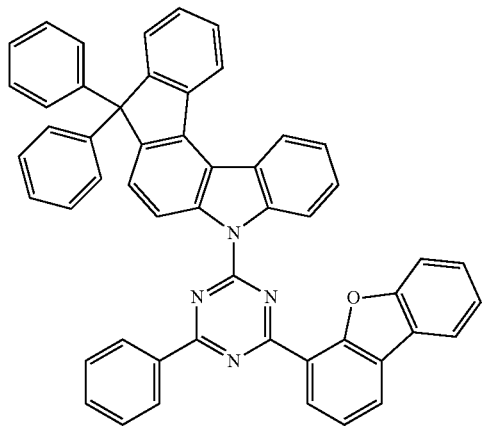
H2-447
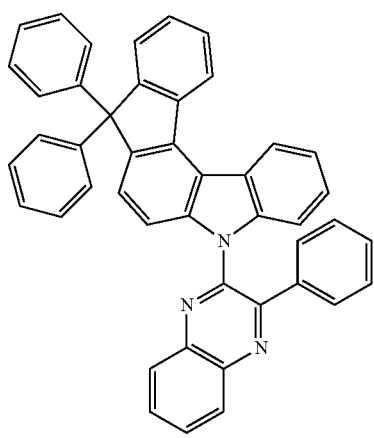
H2-448
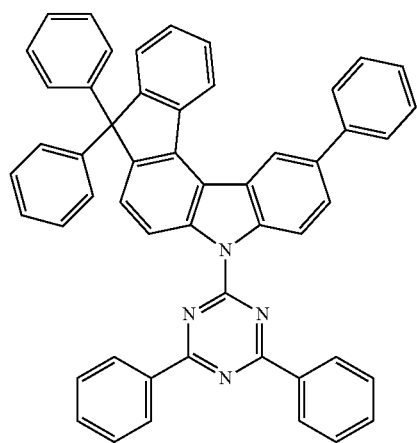
H2-449
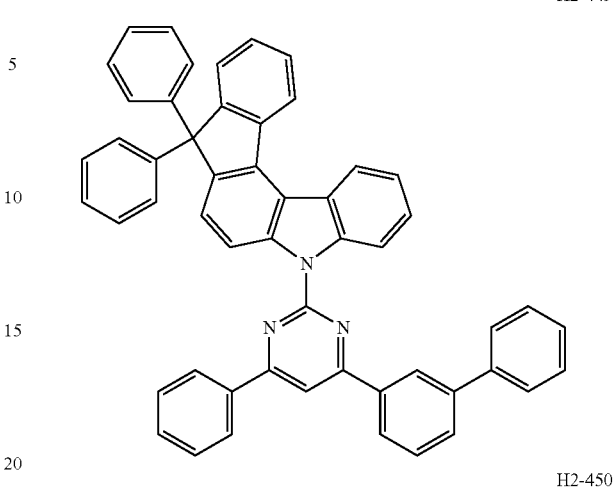
H2-450
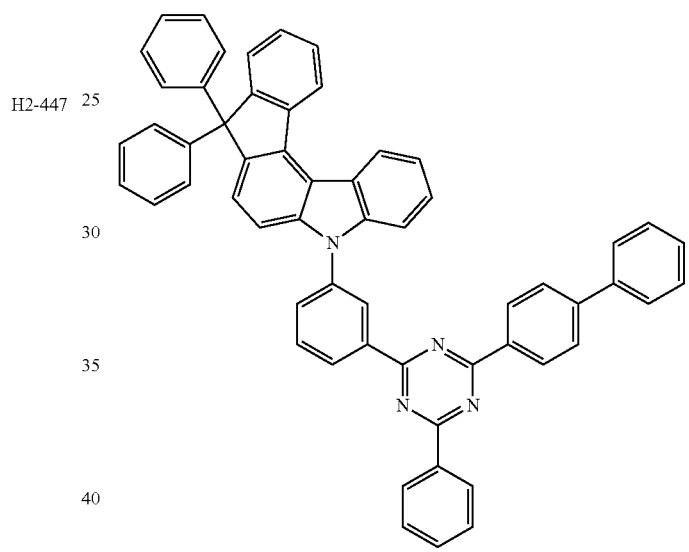
H2-451

167
-continued
H2-452
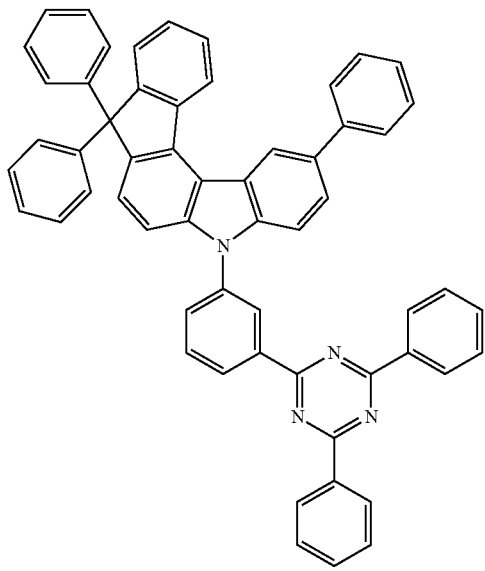
H2-453
H2-454
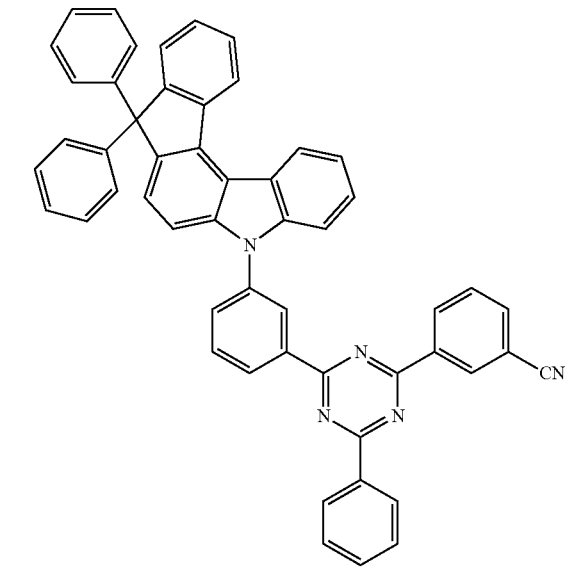
H2-455
168
-continued
H2-456
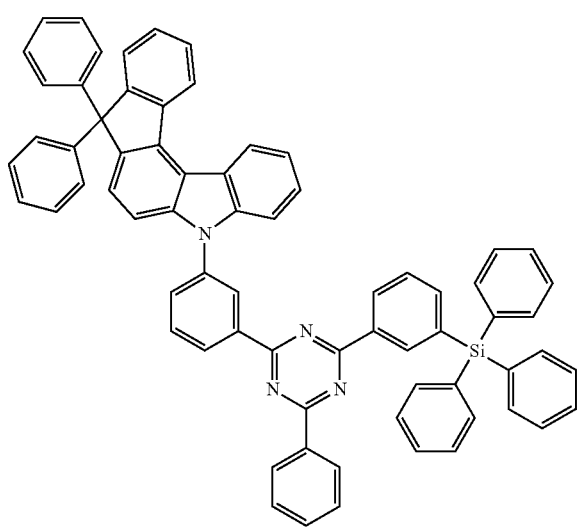

H2-457
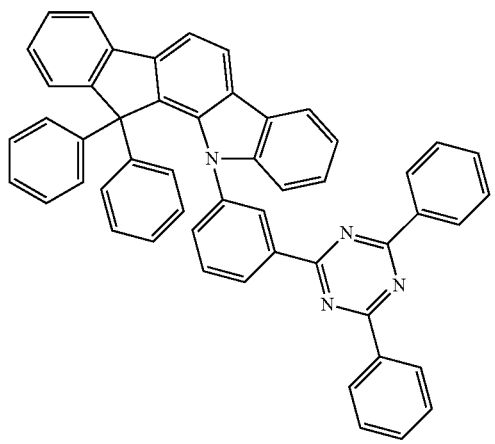
H2-458
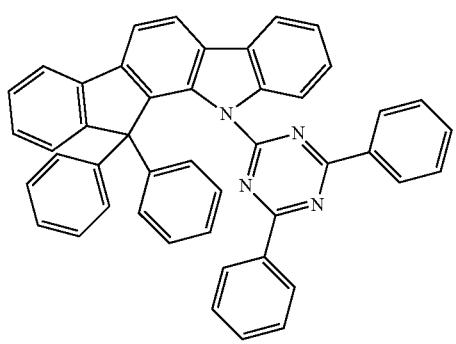
H2-459
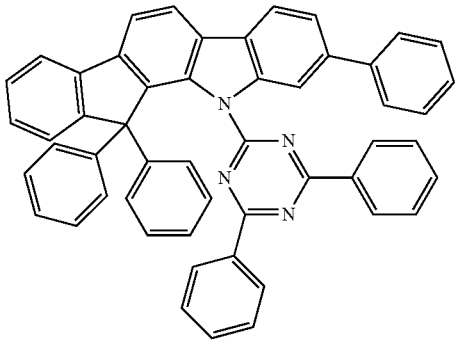
H2-460
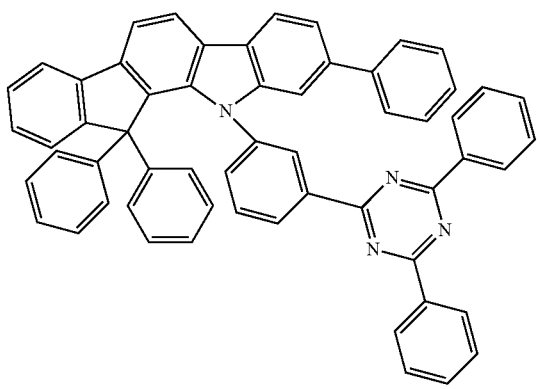
H2-461
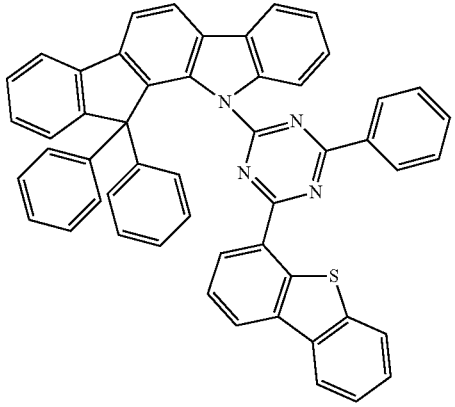
H2-462
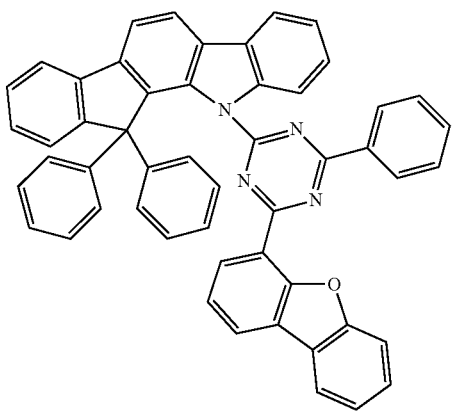
H2-463
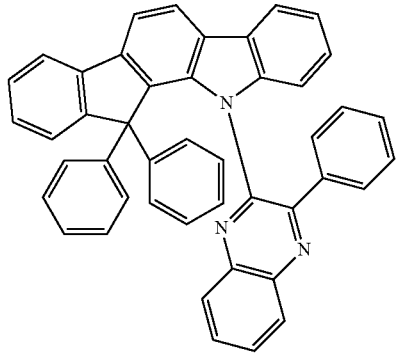
H2-464
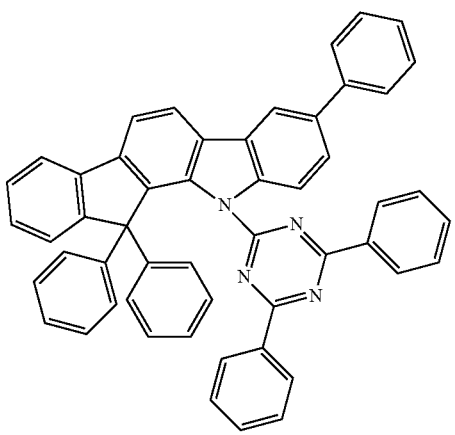

H2-465
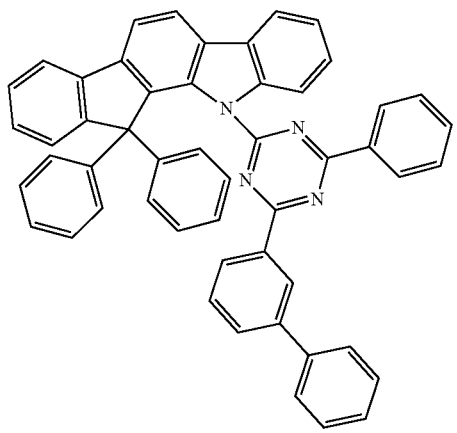
H2-468
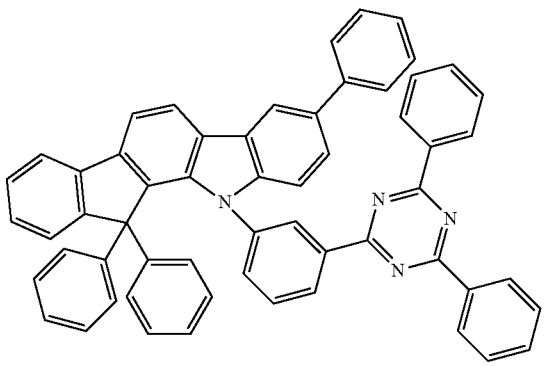
H2-466
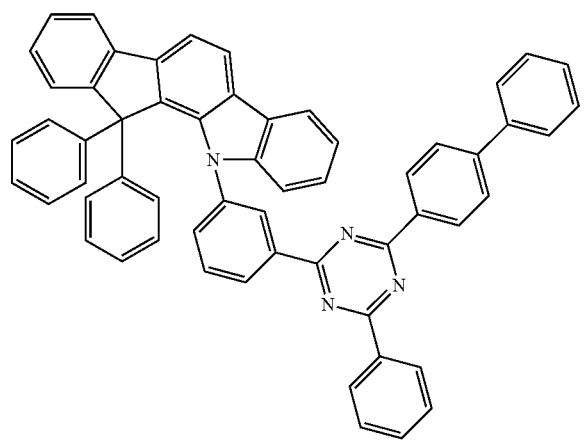
H2-469
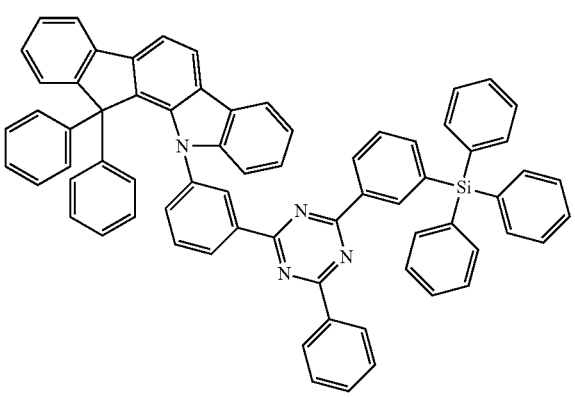
H2-467
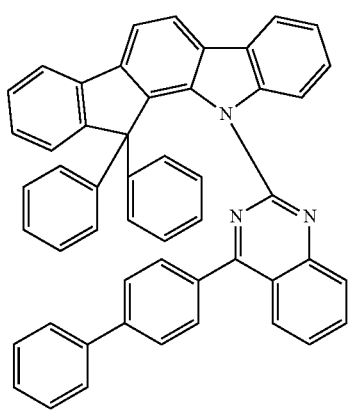
H2-470
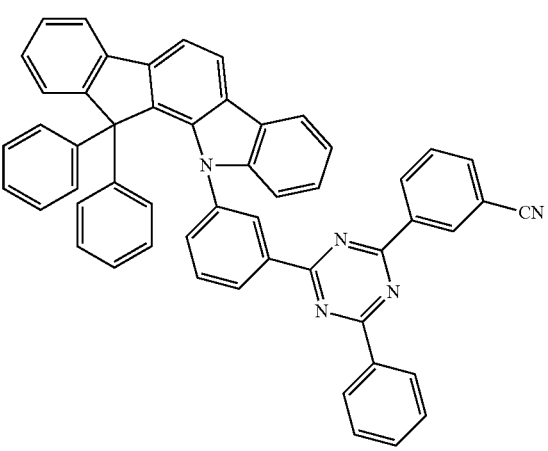

H2-471
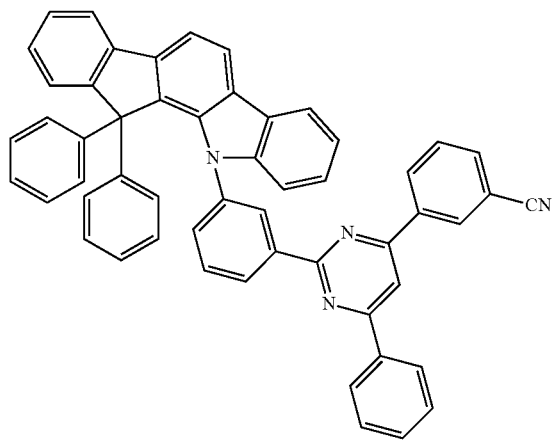
H2-472
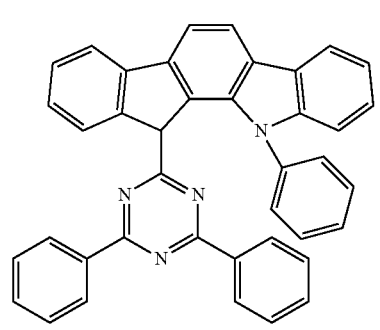
H2-473
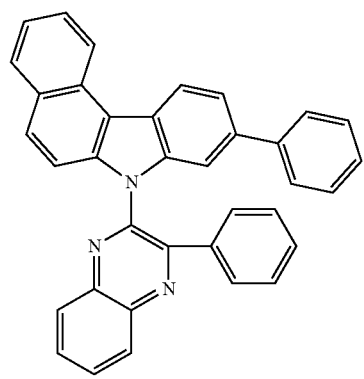
H2-474
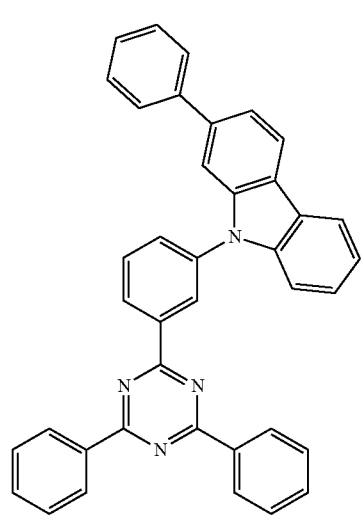
H2-475
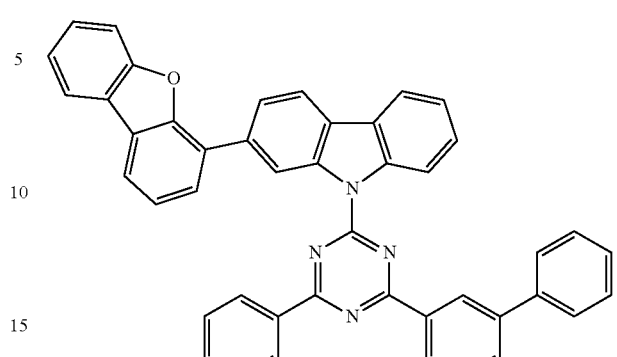
H2-476
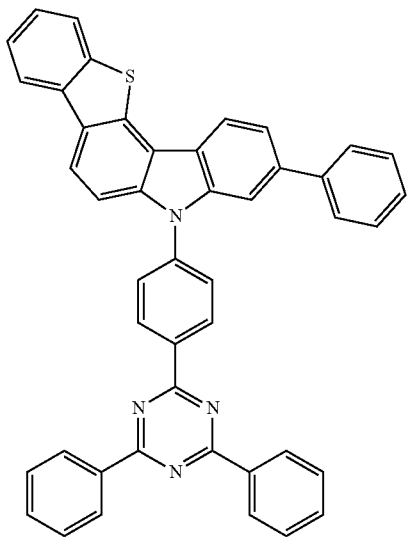
H2-477
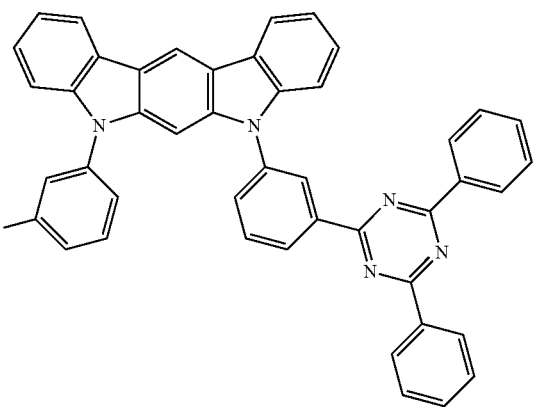

H2-478
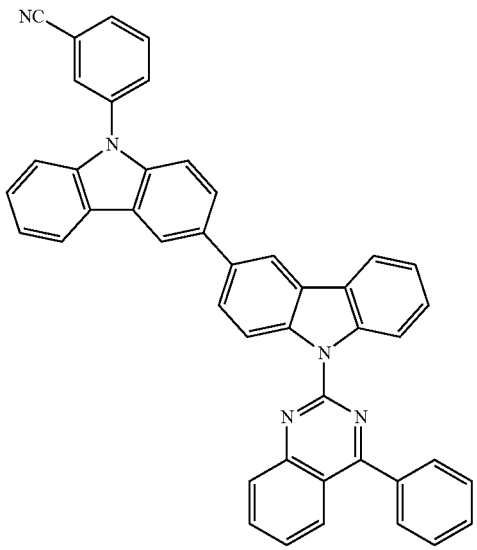
H2-479
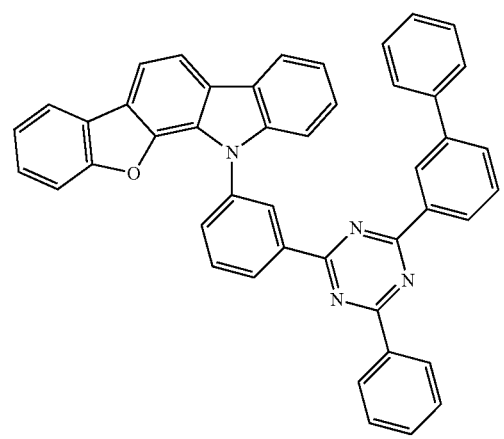
H2-480
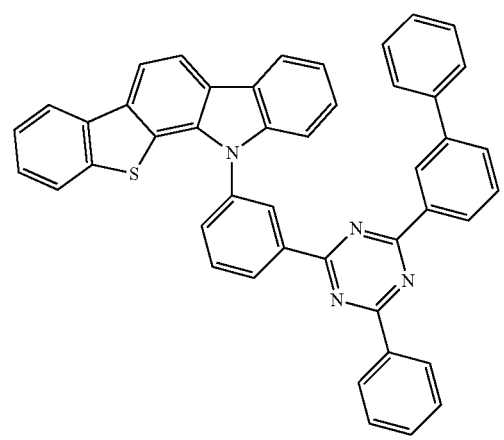
H2-481
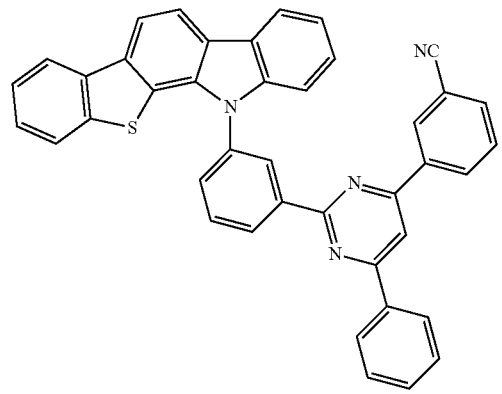
H2-482
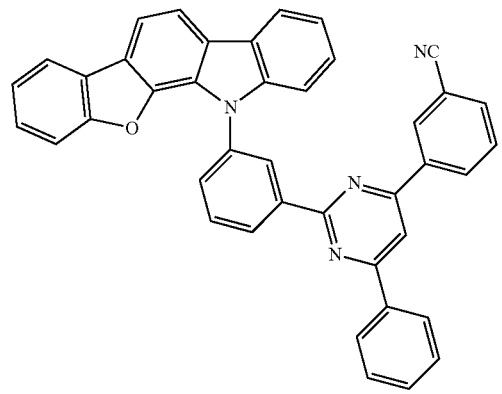
H2-483
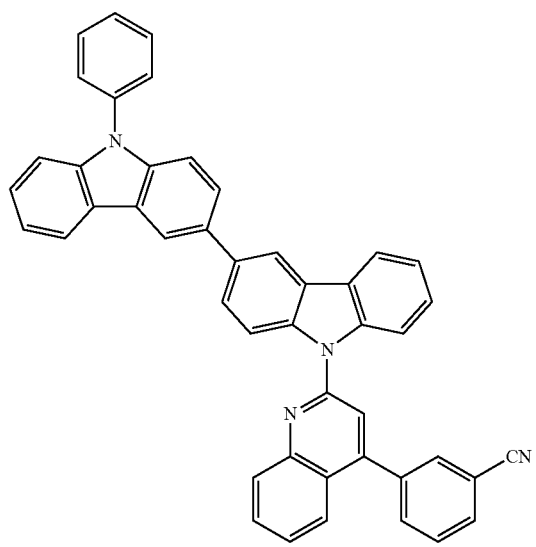

H2-484
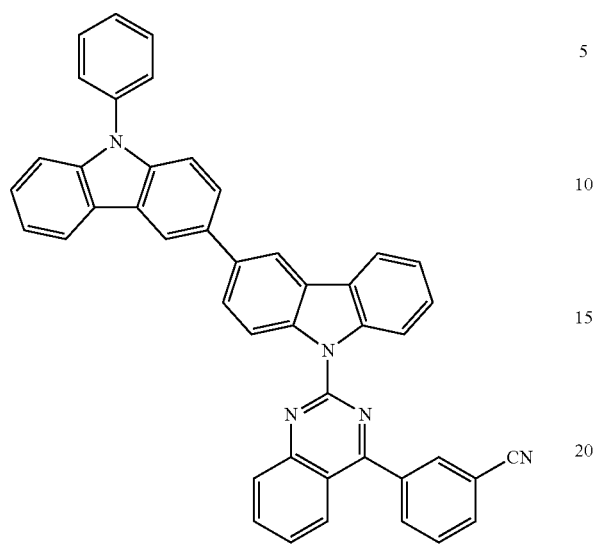
H2-487
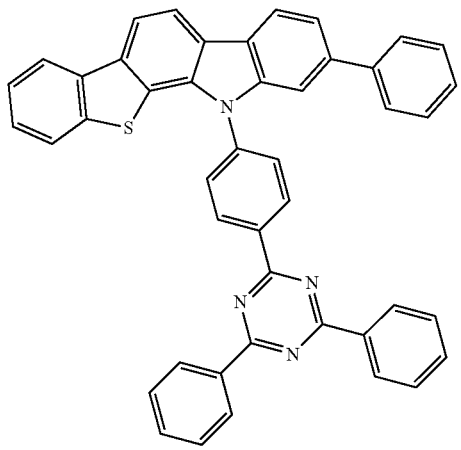
H2-485
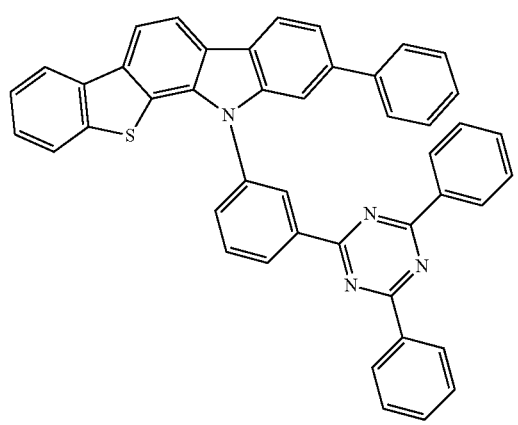
H2-488
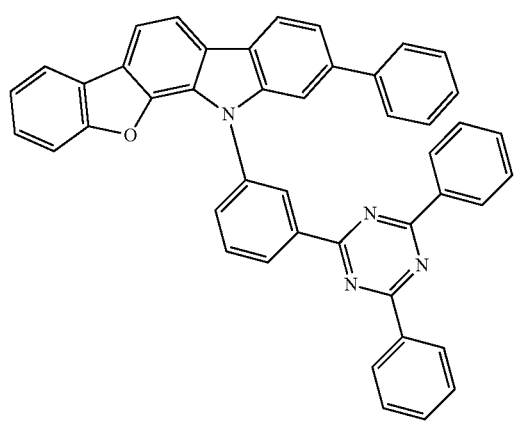
H2-486
H2-489
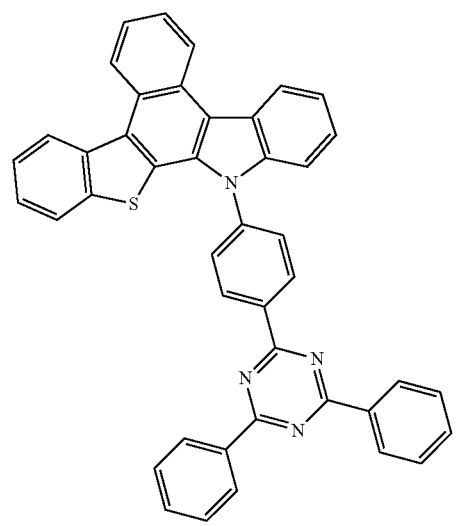

H2-490

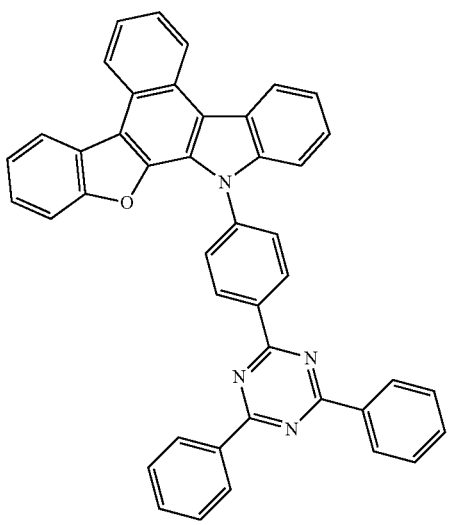

H2-491

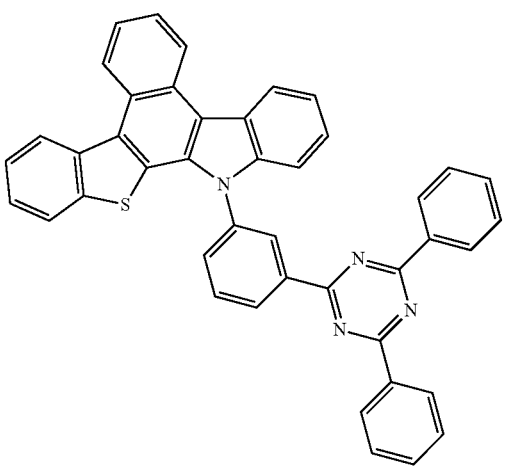

H2-492

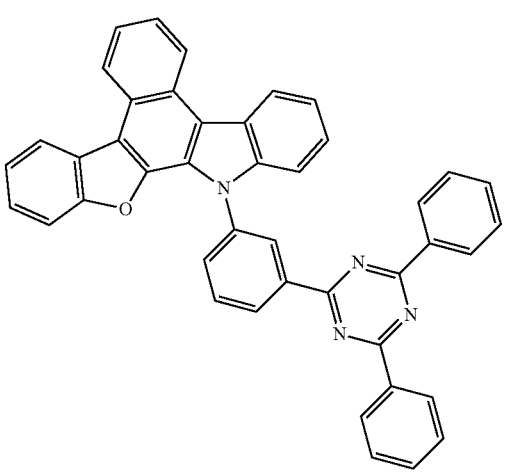

According to an additional aspect of the present disclosure, a combination of the compound of formula 1 and the compound of formula 2, and an organic electroluminescent device comprising the combination are provided.

According to an additional aspect of the present disclosure, a mixture or composition for preparing an organic electroluminescent device is provided. The mixture or composition comprises the compound of formula 1. The mixture or composition may be the one for preparing a light-emitting layer of an organic electroluminescent device. The mixture or composition may further comprise the host compound of formula 2, in addition to a compound of the present disclosure. The mixture or composition may comprise the compound of formula 1 to be combined with the host compound of formula 2. The mixture or composition may further comprise a conventional material which has been used to prepare an organic electroluminescent device.

The organic electroluminescent device of the present disclosure may further comprise, in addition to the compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise a light-emitting layer and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the art, besides the compound of the present disclosure. If necessary, it may further comprise an orange light-emitting layer or a yellow light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer, and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the compound of the present disclosure, the preparation method of the compound, and the luminescent properties of the device will be explained in detail with reference to the following examples.

Example 1: Preparation of Compound D-1

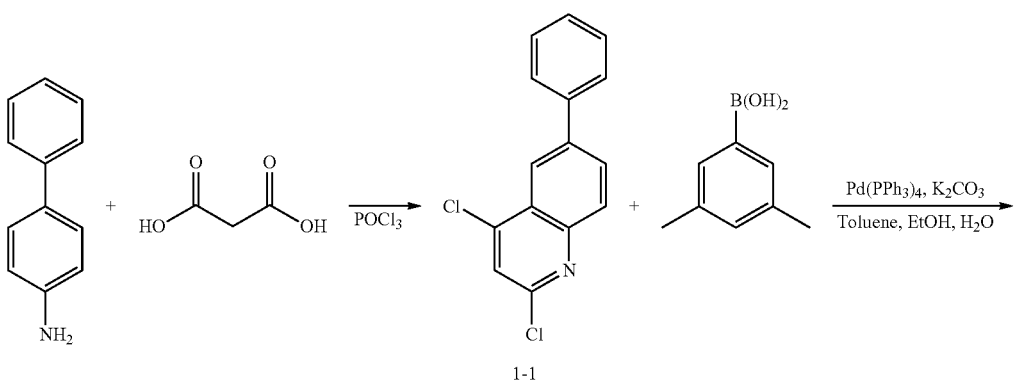

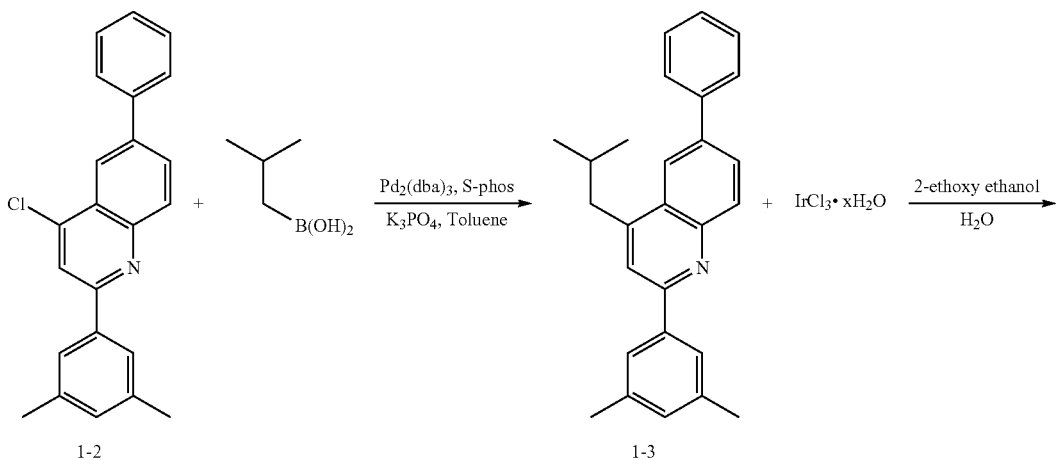

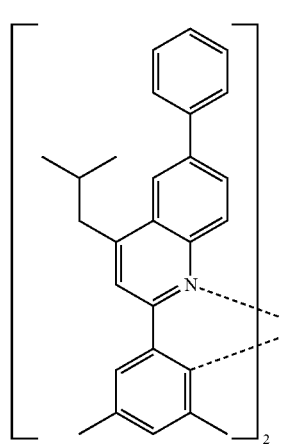

1-4

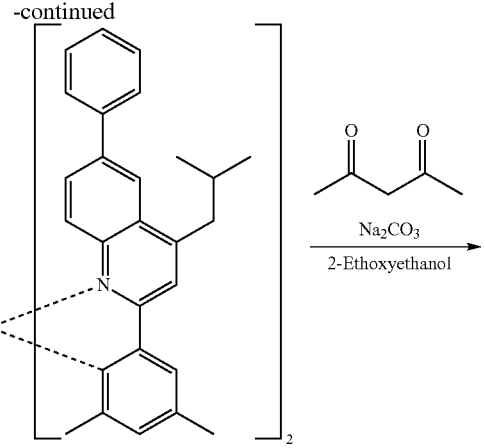

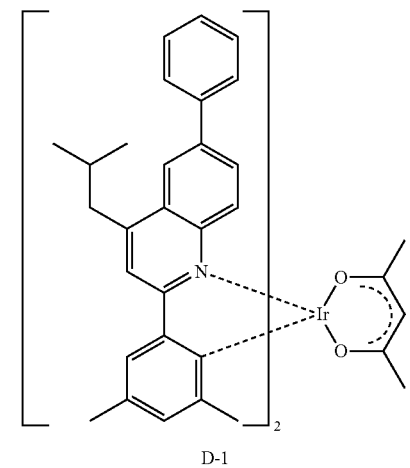

D-1

Preparation of Compound 1-1

After introducing malonic acid (23 g, 222 mmol) and POCl₃ (161 mL, 1729 mmol) into a reaction vessel, the mixture was stirred at room temperature for 10 minutes. [1,1'-biphenyl]-4-amine (25 g, 148 mmol) was slowly added dropwise to the mixture. Afterward, the mixture was stirred at 150° C. After slowly adding H₂O dropwise to the mixture, the mixture was extracted with methylene chloride (MC), and a solvent was removed therefrom. The obtained substance was subjected to column chromatography to obtain compound 1-1 (20 g, 50%).

Preparation of Compound 1-2

After introducing compound 1-1 (19.5 g, 92 mmol), (3,5-dimethylphenyl)boronic acid (13.8 g, 92 mmol), Pd(PPh₃)₄ (3.2 g, 3 mmol), K₂CO₃ (38 g, 276 mmol), toluene (383 mL), and H₂O (128 mL) into a reaction vessel, the mixture was under reflux at 120° C., cooled to room temperature, and then extracted with ethyl acetate and H₂O. The extracted organic layer was subjected to column chromatography to obtain compound 1-2 (15 g, 47%).

Preparation of Compound 1-3

After introducing compound 1-2 (14.5 g, 42 mmol), isobutyl boronic acid (8.6 g, 84 mmol), S-Phos (1.38 g, 3.37 mmol), K₃PO₄ (43.86 g, 207 mmol), Pd₂(dba)₃ (1.55 g, 1.7 mmol), and toluene (280 mL), the mixture was stirred for 12 hours. The mixture was cooled to room temperature, and extracted with ethyl acetate and H₂O. The extracted organic layer was subjected to column chromatography to obtain compound 1-3 (6.5 g, 42%).

Preparation of Compound 1-4

After introducing compound 1-3 (6.5 g, 18 mmol), IrCl₃.xH₂O (2.4 g, 8 mmol), 2-ethoxyethanol (136 mL), and H₂O (68 mL) into a reaction vessel, the mixture was under reflux at 130° C. for 24 hours. The mixture was cooled to room temperature, and H₂O was added thereto. The mixture was stirred for 30 minutes, and filtered to obtain a solid, compound 1-4 (4.8 g, 63%).

Preparation of Compound D-1

After introducing compound 1-4 (4.8 g, 2.5 mmol), pentan-2,4-dione (2.6 mL, 25 mmol), Na₂CO₃ (0.83 g, 7.8 mmol), and 2-ethoxyethanol (10 mL) into a reaction vessel, the mixture was reacted at room temperature overnight. The mixture was filtered, and the obtained solid was subjected to column chromatography to obtain compound D-1 (2 g, 39%).

|  | Molecular Weight | UV (nm) | PL (nm) | Melting Point (MP) (° C.) |
| --- | --- | --- | --- | --- |
| D-1 | 1020.33 | 228 | 613 | 322 |

Example 2: Preparation of Compound D-2
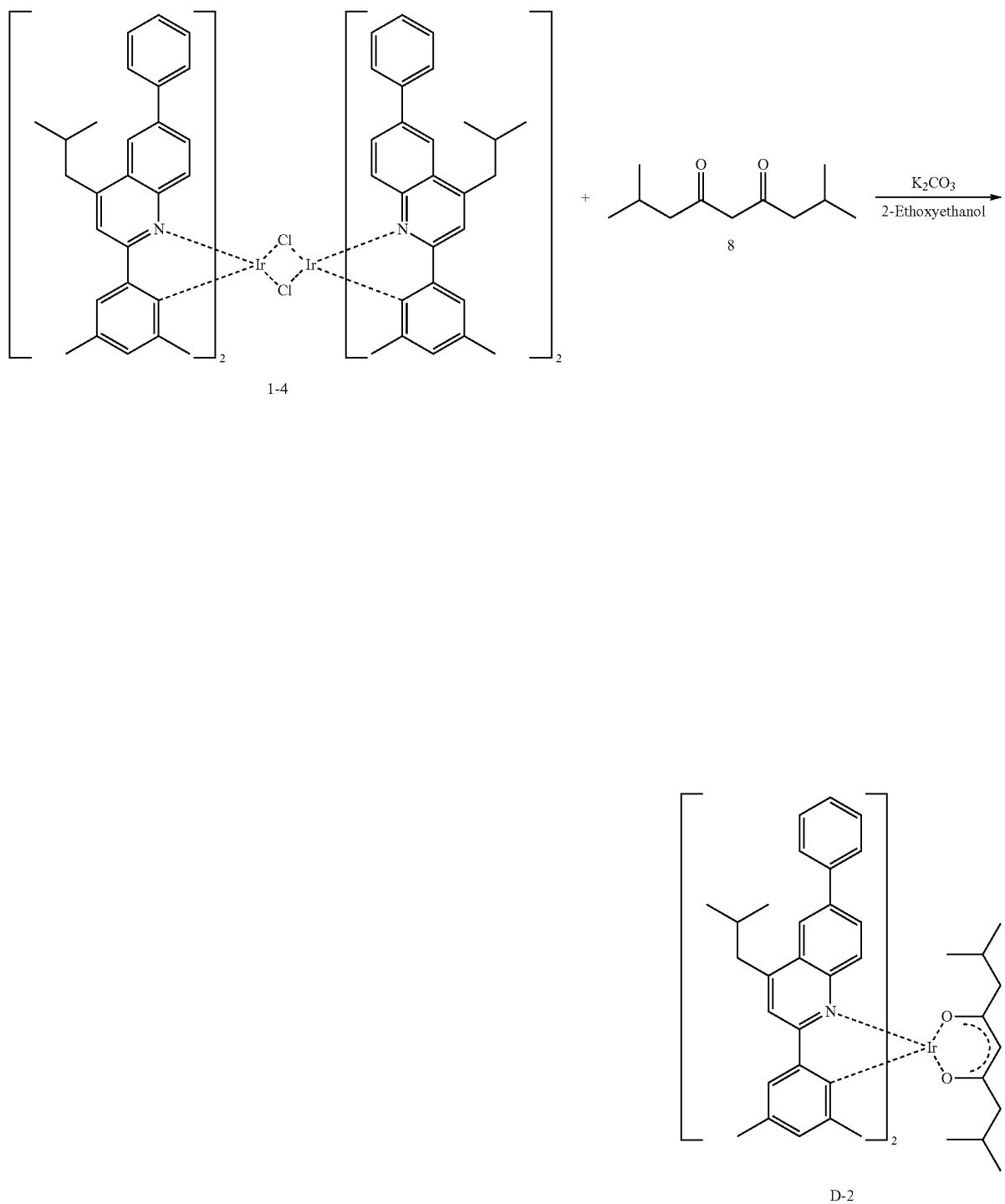
After introducing compound 1-4 (8.0 g, 4.2 mmol), compound 8 (7.9 mL, 41.8 mmol), K$_2$CO$_3$ (5.78 g, 41.8 mmol), and 2-ethoxyethanol (50 mL) into a reaction vessel, the mixture was reacted at room temperature for 24 hours. The mixture was filtered, and the obtained solid was subjected to column chromatography to obtain compound D-2 (1.6 g, 35%).
|     | Molecular weight | UV (nm) | PL (nm) | MP (° C.) |
| --- | --- | --- | --- | --- |
| D-2 | 1104.49 | 258 | 613 | 334 |

Example 3: Preparation of Compound D-7
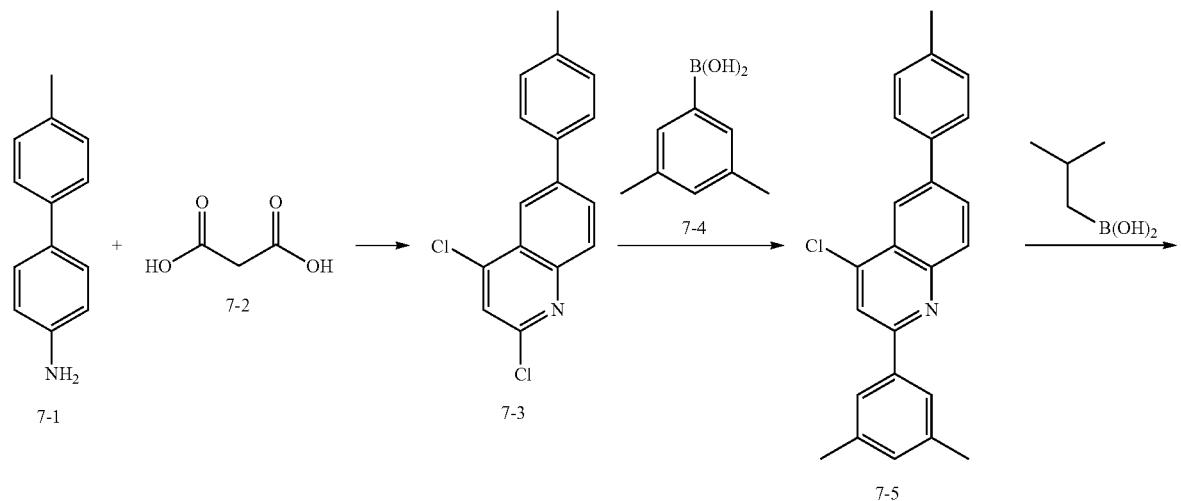
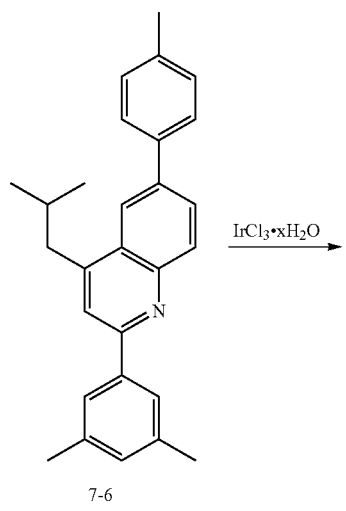

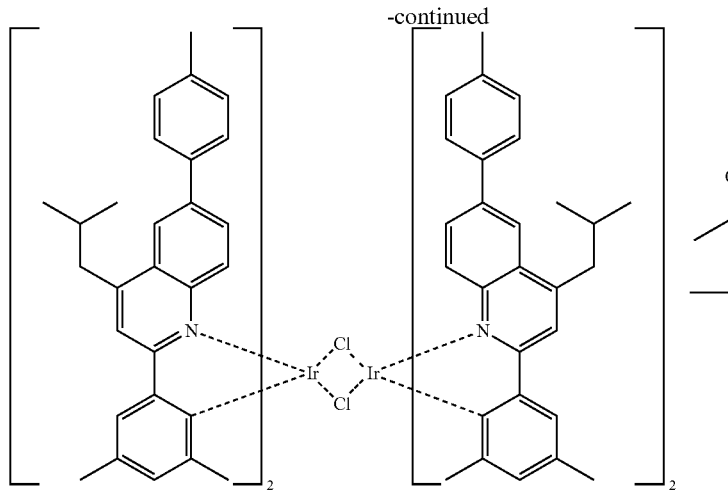
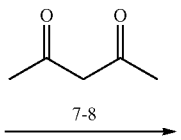
7-7

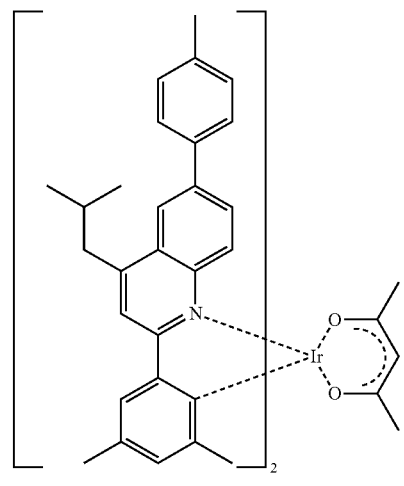
D-7

Preparation of Compound 7-3

After introducing compound 7-2 (34 g, 327 mmol) and POCl$_3$ (218 mL, 2342 mmol) into a reaction vessel, the mixture was stirred at room temperature for 10 minutes. After slowly adding compound 7-1 (40 g, 218 mmol) dropwise to the mixture, the mixture was stirred at 150° C. After slowly adding H$_2$O dropwise, the mixture was extracted with MC, and the solvent was removed therefrom. The remaining substance was subjected to column chromatography to obtain compound 7-3 (34 g, 44%).

Preparation of Compound 7-5

After introducing compound 7-3 (33 g, 116 mmol), compound 7-4 (21 g, 139 mmol), Pd(PPh$_3$)$_4$ (4.01 g, 3.47 mmol), K$_2$CO$_3$ (48 g, 347 mmol), toluene (500 mL), and H$_2$O (173 mL) into a reaction vessel, the mixture was stirred under reflux at 120° C. The mixture was cooled to room temperature, extracted with ethyl acetate and H$_2$O, and subjected to column chromatography to obtain compound 7-5 (28 g, 68%).

Preparation of Compound 7-6

After introducing compound 7-5 (27 g, 75.4 mmol), isobutyl boronic acid (15.4 g, 150.9 mmol), S-Phos (2.5 g, 6 mmol), K$_3$PO$_4$ (78.4 g, 369 mmol), Pd$_2$(dba)$_3$ (2.76 g, 3 mmol), and toluene (300 mL) into a reaction vessel, the mixture was stirred for 5 hours. The mixture was cooled to room temperature, extracted with ethyl acetate and H$_2$O, and subjected to column chromatography to obtain compound 7-6 (20 g, 69%).

Preparation of Compound 7-7

After introducing compound 7-6 (20 g, 52.7 mmol), IrCl$_3$.xH$_2$O (7.2 g, 23.9 mmol), 2-ethoxyethanol (210 mL), and H$_2$O (70 mL) into a reaction vessel, the mixture was stirred under reflux at 130° C. for 24 hours. The mixture was cooled to room temperature, and H$_2$O was added thereto. The mixture was stirred for 30 minutes, and filtered to obtain a solid, compound 7-7 (12 g, 51%).

Preparation of Compound D-7

After introducing compound 7-7 (6 g, 3 mmol), compound 7-8 (3.1 mL, 30 mmol), K$_2$CO$_3$ (4.1 g, 30 mmol), and 2-ethoxyethanol (50 mL) into a reaction vessel, the mixture was reacted at room temperature for 24 hours. The mixture was filtered, and the obtained solid was subjected to column chromatography to obtain compound D-7 (1.5 g, 23.8%).

|  | Molecular Weight | MP (° C.) | UV (nm) | PL (nm) |
| --- | --- | --- | --- | --- |
| D-7 | 1048.38 | 270 | 344 | 616 |

Example 4: Preparation of Compound D-10
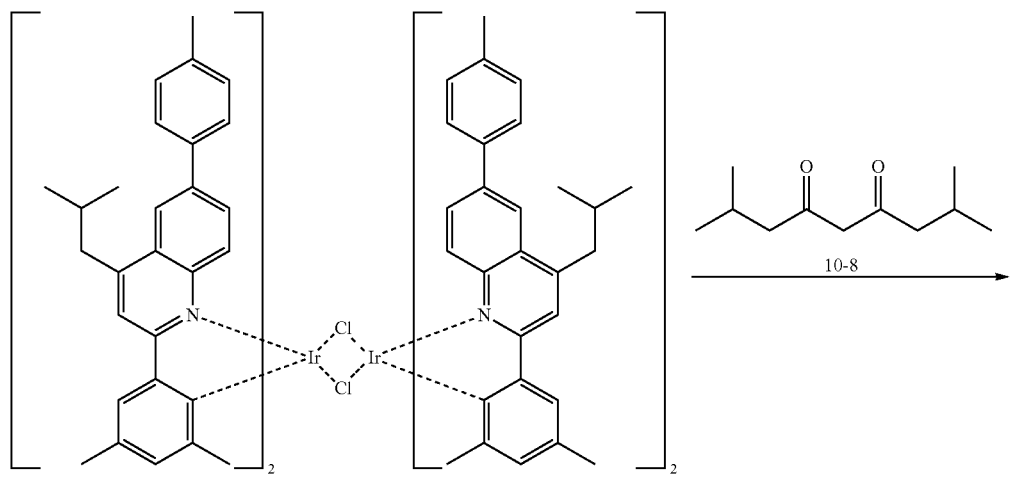
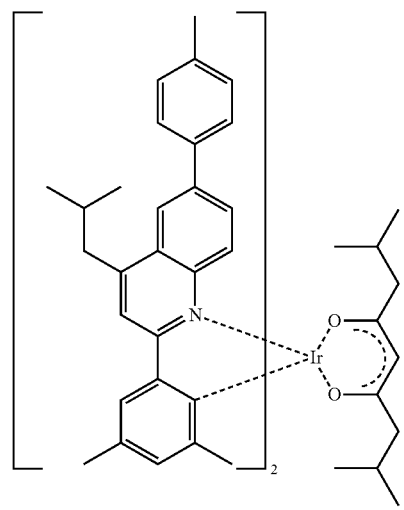
After introducing compound 7-7 (6 g, 3 mmol), compound 10-8 (4 mL, 17.3 mmol), $K_2CO_3$ (4.8 g, 30 mmol), and 2-ethoxyethanol (60 mL) into a reaction vessel, the mixture was reacted at room temperature for 24 hours. The mixture was filtered and subjected to column chromatography to obtain compound D-10 (1.8 g, 23%).
| | Molecular weight | MP (° C.) | UV (nm) | PL (nm) |
|---|---|---|---|---|
| D-10 | 1132.54 | 293 | 344 | 615 |

Example 5: Preparation of Compound D-13
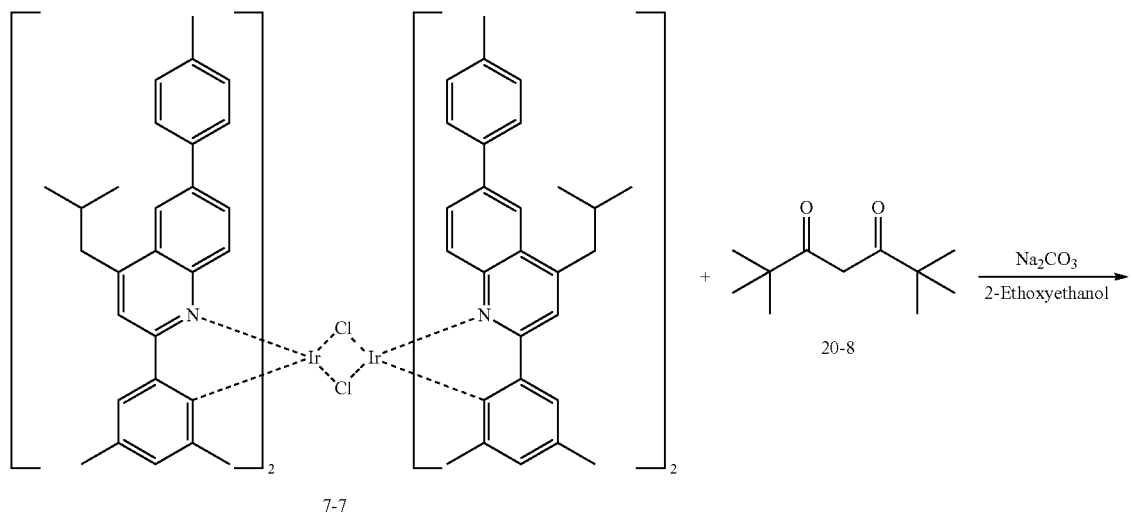
7-7
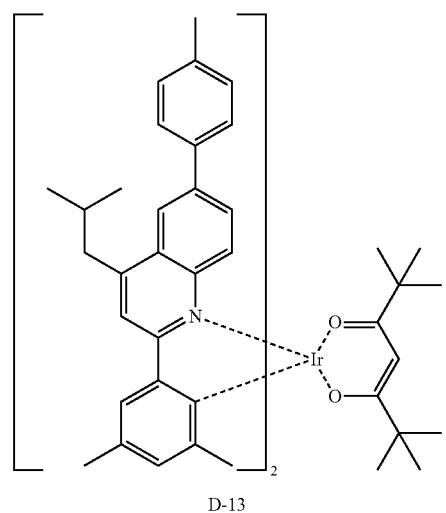
D-13
After introducing compound 7-7 (9 g, 4.6 mmol), compound 20-8 (8.4 g, 46 mmol), Na$_2$CO$_3$ (4.9 g, 46 mmol), and 2-ethoxyethanol (57 mL) into a reaction vessel, the mixture was reacted at room temperature overnight. The mixture was filtered, and the obtained solid was subjected to column chromatography to obtain compound D-13 (1 g, 10%).
| | Molecular Weight | MP (° C.) | UV (nm) | PL (nm) |
|---|---|---|---|---|
| D-13 | 1132.54 | 306 | 278 | 615 |

Example 6: Preparation of Compound D-20
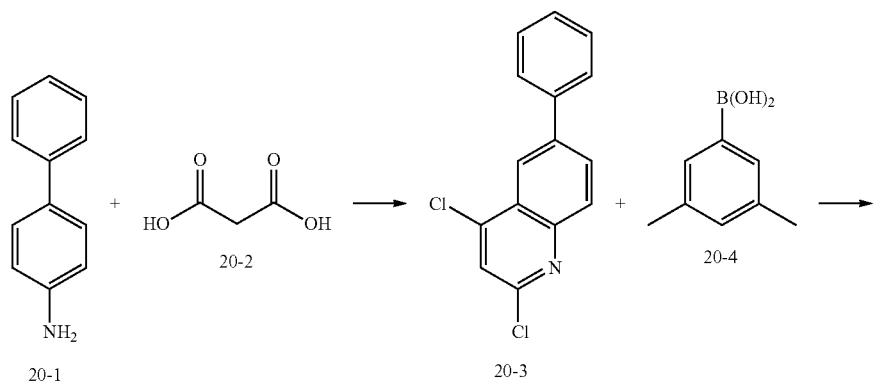
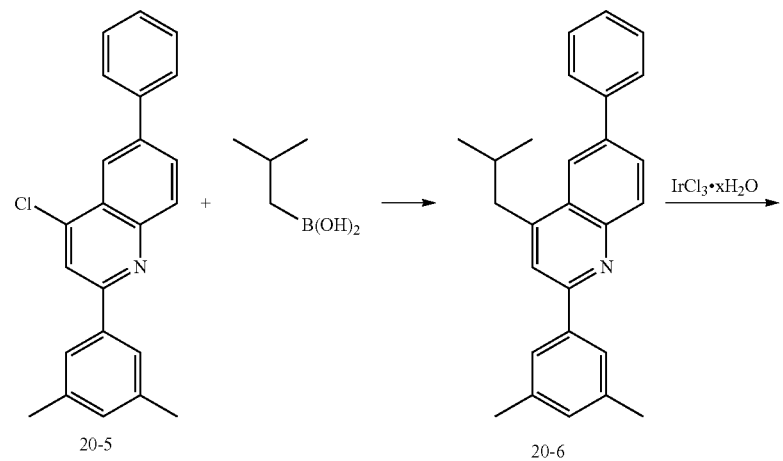
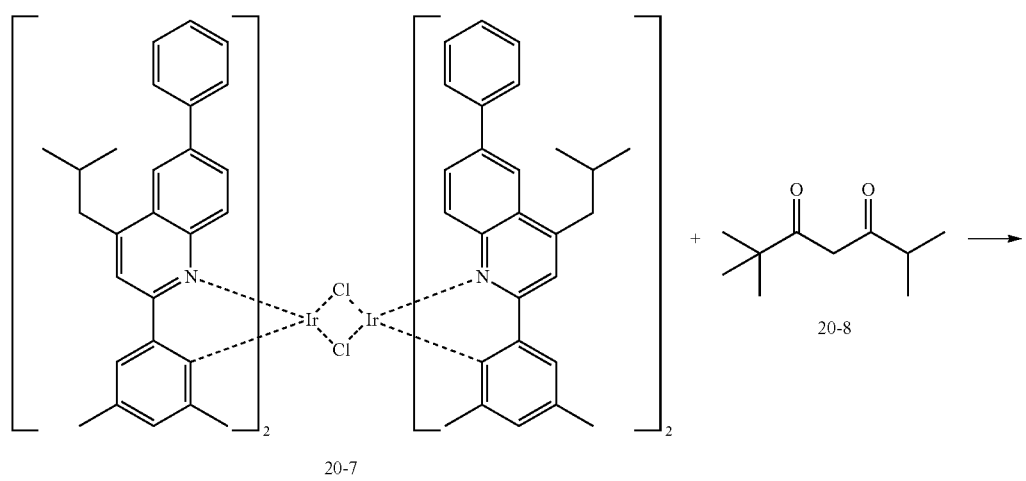

-continued

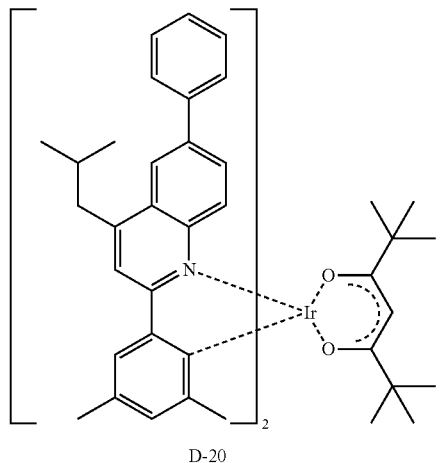

D-20

Preparation of Compound 20-3

After introducing compound 20-2 (23 g, 222 mmol) and POCl$_3$ (161 mL, 1729 mmol) into a reaction vessel, the mixture was stirred at room temperature for 10 minutes. After slowly adding compound 20-1 (25 g, 148 mmol) dropwise, the mixture was stirred at 150° C. After slowly adding H$_2$O dropwise, the mixture was extracted with MC, and the solvent was removed therefrom. The remaining substance was subjected to column chromatography to obtain compound 20-3 (20 g, 50%).

Preparation of Compound 20-5

After introducing compound 20-3 (19.5 g, 92 mmol), compound 20-4 (13.8 g, 92 mmol), Pd(PPh$_3$)$_4$ (3.2 g, 3 mmol), K$_2$CO$_3$ (38 g, 276 mmol), toluene (383 mL), and H$_2$O (128 mL) into a reaction vessel, the mixture was under reflux at 120° C. The mixture was cooled to room temperature, extracted with ethyl acetate and H$_2$O, and subjected to column chromatography to obtain compound 20-5 (15 g, 47%).

Preparation of Compound 20-6

After introducing compound 20-5 (15 g, 43 mmol), isobutylboronic acid (8.9 g, 87 mmol), S-Phos (1.4 g, 3.49 mmol), K$_3$PO$_4$ (45 g, 213 mmol), Pd$_2$(dba)$_3$ (1.6 g, 1.7 mmol), and toluene (290 mL) into a reaction vessel, the mixture was stirred for 12 hours. The mixture was cooled to room temperature, extracted with ethyl acetate and H$_2$O, and subjected to column chromatography to obtain compound 20-6 (12.2 g, 77%).

Preparation of Compound 20-7

After introducing compound 20-6 (12 g, 33 mmol), IrCl$_3$.xH$_2$O (4.5 g, 15 mmol), 2-ethoxyethanol (115 mL), and H$_2$O (55 mL) into a reaction vessel, the mixture was under reflux at 130° C. for 24 hours. The mixture was cooled to room temperature, and H$_2$O was added thereto. The mixture was stirred for 30 minutes, and filtered to obtain a solid, compound 20-7 (8 g, 57%).

Preparation of Compound D-20

After introducing compound 20-7 (8 g, 4.2 mmol), compound 20-8 (7.7 g, 42 mmol), Na$_2$CO$_3$ (4.4 g, 42 mmol), and 2-ethoxyethanol (50 mL) into a reaction vessel, the mixture was reacted at room temperature overnight. The mixture was filtered, and the obtained solid was subjected to column chromatography to obtain compound D-20 (2.2 g, 24%).

| | Molecular Weight | MP (° C.) | UV (nm) | PL (nm) |
|---|---|---|---|---|
| D-20 | 1104.49 | 365 | 246 | 619 |

[Examples 1-1 to 1-5] OLED Comprising the Dopant of the Present Disclosure

An organic electroluminescent device (OLED) was produced using the light-emitting compound of the present disclosure as follows. A transparent electrode indium tin oxide (ITO) thin film (10 Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. HI-1 was introduced into a cell of the vacuum vapor depositing apparatus, and then the pressure in the chamber of the apparatus was controlled to $10^{-6}$ torr. Thereafter, an electric current was applied to the cell to evaporate the above introduced material, thereby forming a first hole injection layer having a thickness of 80 nm on the ITO substrate. HI-2 was then introduced into another cell of said vacuum vapor depositing apparatus, and evaporated by applying electric current to the cell, thereby forming a second hole injection layer having a thickness of 5 nm on the first hole injection layer. HT-1 was introduced into one cell of the vacuum vapor depositing apparatus, and evaporated by applying electric current to the cell, thereby forming a first hole transport layer having a thickness of 10 nm on the second hole injection layer. HT-2 was introduced into another cell of the vacuum vapor depositing apparatus, and evaporated by applying electric current to the cell, thereby forming a second hole transport layer having a thickness of 60 nm on the first hole transport layer. Thereafter, compound H2-16 was introduced into one cell of the vacuum vapor depositing apparatus as a host, and a dopant material shown in Table 1 below was introduced into another cell as a dopant. The two materials were evaporated at different rates, so that the dopant was deposited in a doping amount of 3 wt % based on the total amount of the host and dopant to form a light-emitting layer having a thickness of 40 nm on the second hole transport layer. ET-1 and EI-1 were introduced into two cells of the vacuum vapor depositing apparatus, respectively, and evaporated at a 1:1 rate to form an electron transport layer having a thickness of 30 nm on the light-emitting layer. After depositing EI-1 as an electron injection layer having a thickness of 2 nm, an Al cathode having a thickness of 80 nm was then deposited by another vacuum vapor deposition apparatus on the electron injection layer to produce OLED.

HI-1

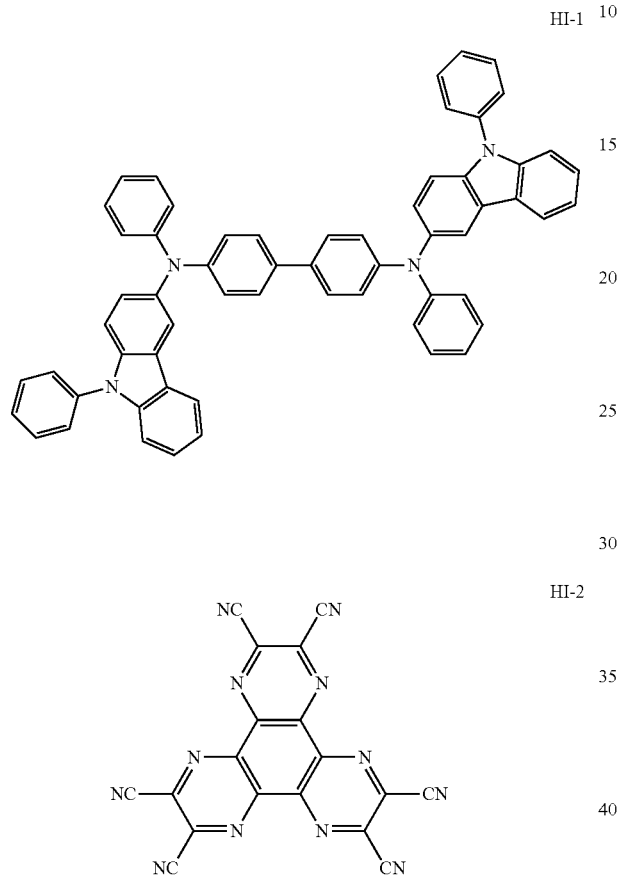

HI-2

HT-1

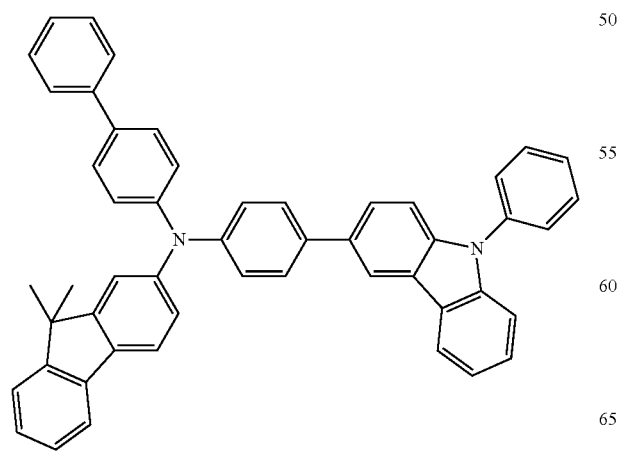

HT-2

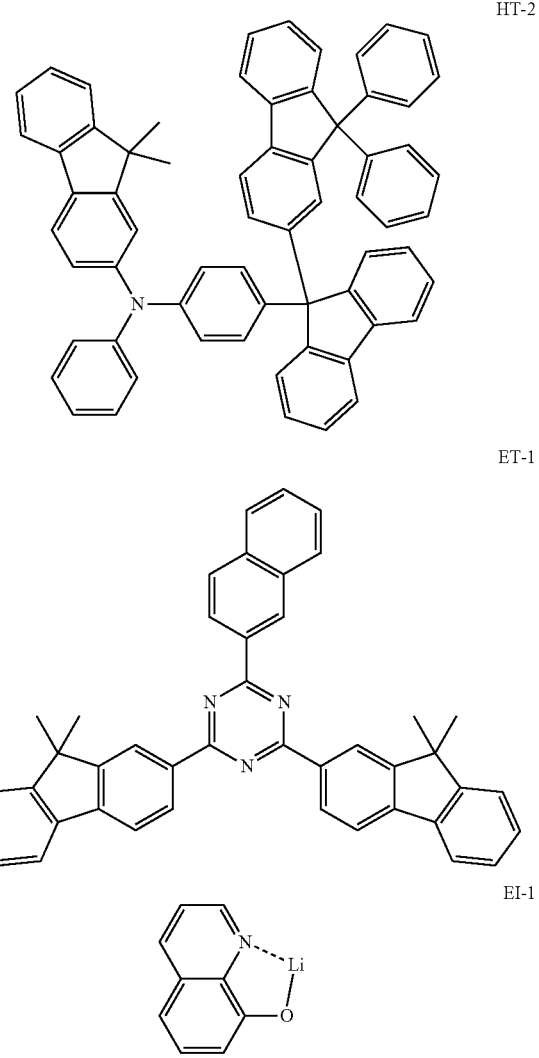

ET-1

EI-1

[Comparative Examples 1-1 to 1-4] OLED Using a Conventional Organic Electroluminescent Compound OLED was produced in the same manner as in Device Examples 1-1 to 1-5, except that a dopant shown in Table 1 below was used as a dopant for a light-emitting layer.

RD-1

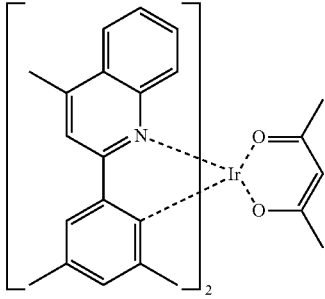

RD-2

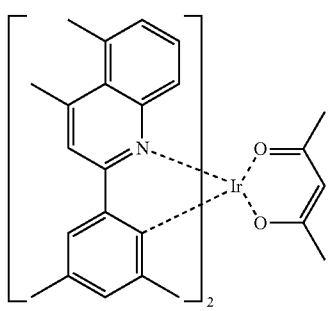

RD-3

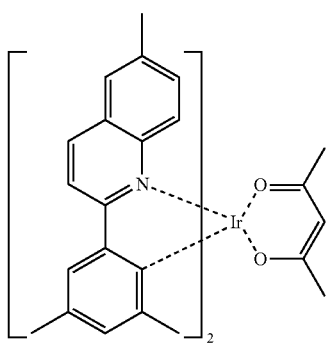

RD-4

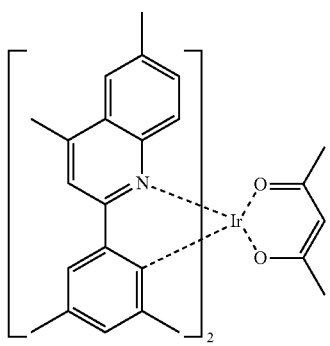

Organic electroluminescent devices produced in Device Examples 1-1 to 1-5 and Comparative Examples 1-1 to 1-4 were characterized as shown in Table 1 below.

The data (voltage and color coordinates) of Device Examples 1-1 to 1-5 and Comparative Examples 1-1 to 1-4 shown in Table 1 were measured at a luminance of 1000 cd/m$^2$, except lifespan. Said lifespan is the time taken to be 97% of the luminance when the early luminance at 5000 cd/m$^2$ and a constant current is taken as 100% of the luminance.

The color gamut is calculated based on a color space which was made by US National Television System Committee (NTSC) in view of the color coordinate system defined by the CIE of the International Commission on Illumination. An area ($t_0$) of triangle made by three points of red (0.67, 0.33), green (0.21, 0.71), and blue (0.14, 0.08) defined by the NTSC was determined, and then, an area ($t_1$) of triangle made by blue and green points defined by the NTSC and a red point described in Table 1 above was determined. Thereafter, color gamut (%) was calculated as follows: Color gamut (%)=[$t_1$ (the area of color coordinate made by the present disclosure)/$t_0$ (an area of color coordinate based on NTSC standards)]*100. Where the numerical value of the color gamut is larger and larger, the device can display a larger and larger number of colors. Therefore, the color gamut is better when it has a larger numerical value.

By using the organic electroluminescent compound of the present disclosure, an organic electroluminescent device showing better color purity and lifespan is provided, compared with conventional organic electroluminescent compounds.

The invention claimed is:
1. A compound represented by the following formula 1:

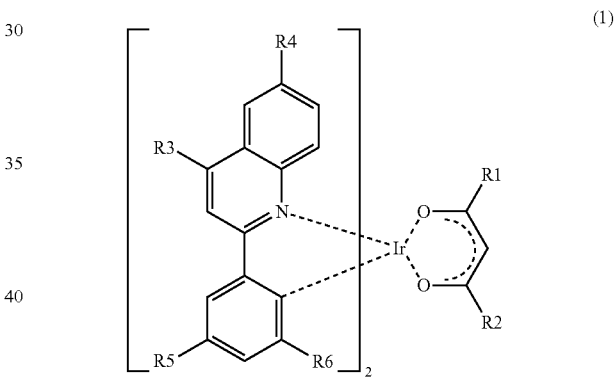

(1)

TABLE 1

|  | Dopant | Voltage (V) | Color Coordinates (x, y) | | Color Gamut of NTSC Standards (%) | Lifespan (T97) |
| --- | --- | --- | --- | --- | --- | --- |
| Device Example 1-1 | D-1 | 3.9 | 668 | 331 | 100 | 188 |
| Device Example 1-2 | D-2 | 3.9 | 667 | 331 | 99 | 194 |
| Device Example 1-3 | D-7 | 4.0 | 665 | 333 | 99 | 165 |
| Device Example 1-4 | D-10 | 3.9 | 667 | 332 | 99 | 220 |
| Device Example 1-5 | D-20 | 4.0 | 670 | 329 | 100 | 118 |
| Comparative Example 1-1 | RD-1 | 4.0 | 635 | 364 | 92 | 60 |
| Comparative Example 1-2 | RD-2 | 4.0 | 612 | 318 | 89 | 97 |
| Comparative Example 1-3 | RD-3 | 4.2 | 648 | 351 | 95 | 4 |
| Comparative Example 1-4 | RD-4 | 4.0 | 624 | 375 | 90 | 73 | wherein

R₁ and R₂, each independently, represent a (C1-C5)alkyl,

R₃ represents a (C3-C5)alkyl unsubstituted or substituted with deuterium,

R₄ represents phenyl unsubstituted or substituted with a (C1-C5)alkyl unsubstituted or substituted with deuterium, and R₅ and R₆, each independently, represent methyl unsubstituted or substituted with deuterium.

2. The compound according to claim 1, wherein R₄ is phenyl unsubstituted or substituted with a (C1-C4)alkyl.

3. The compound according to claim 1, wherein R₃ is a branched (C3-C5)alkyl unsubstituted or substituted with deuterium, and R₄ is phenyl unsubstituted or substituted with methyl unsubstituted or substituted with deuterium.

4. The compound according to claim 1, wherein R₁ and R₂, each independently, are selected from methyl, ethyl, and a branched (C3-C5)alkyl.

5. The compound according to claim 1, wherein the compound of formula 1 is selected from the group consisting of:

D-1

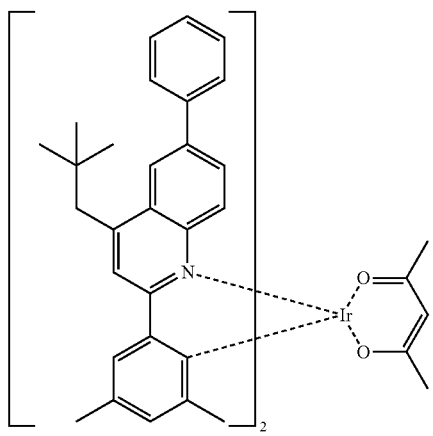

D-2

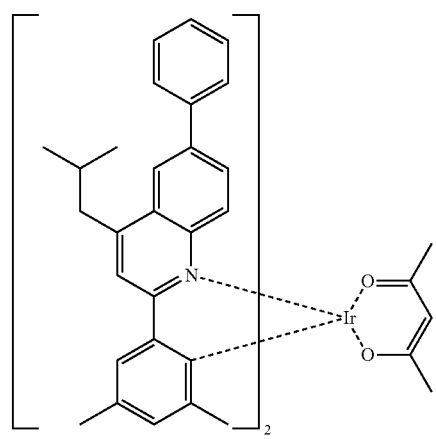

D-3

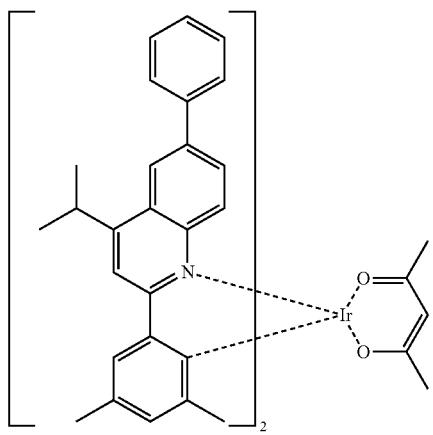

D-4

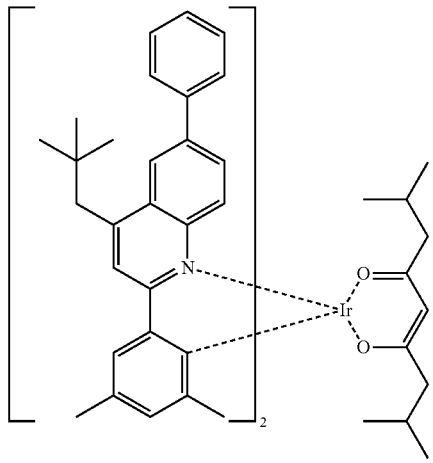

D-5

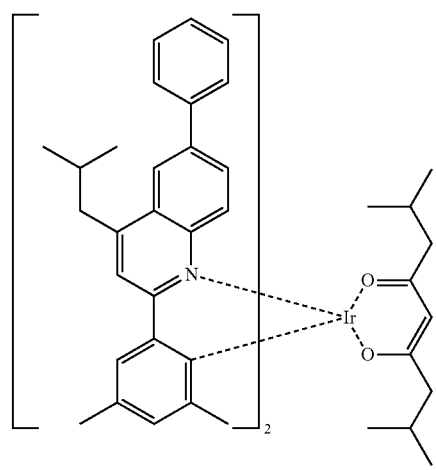

D-6
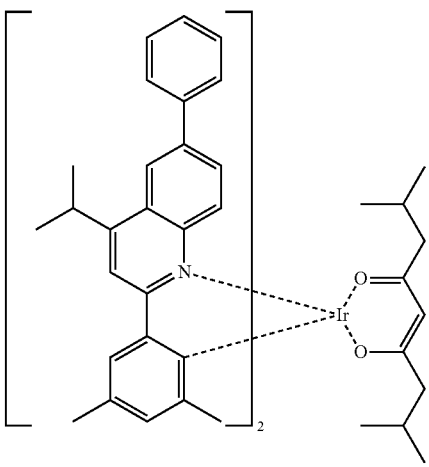
D-7
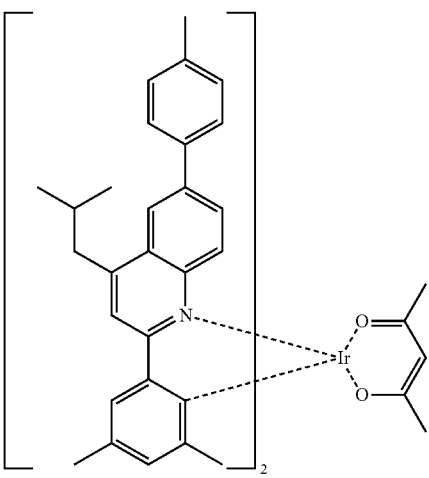
D-8
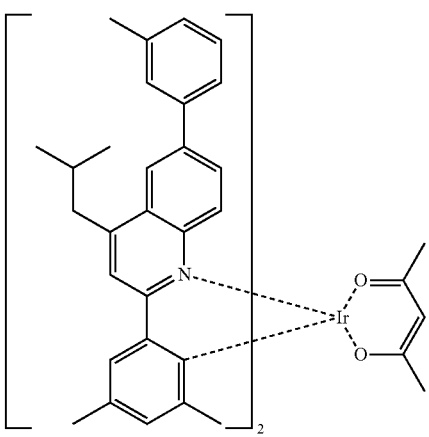
D-9
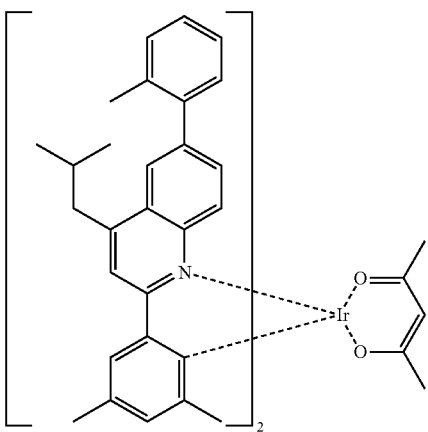
D-10
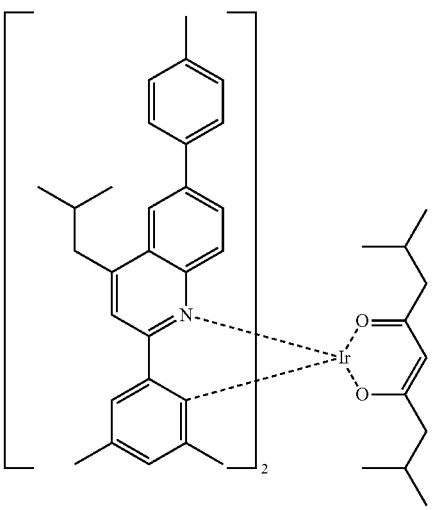
D-11
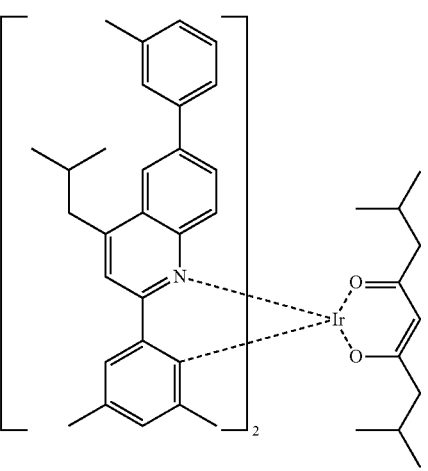

D-12
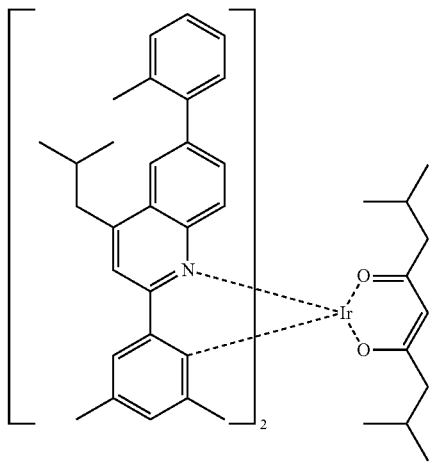
D-13
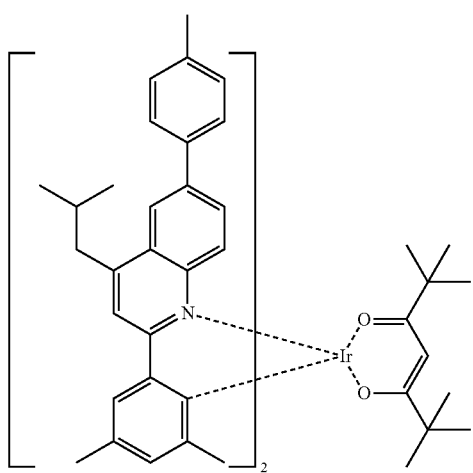
D-15
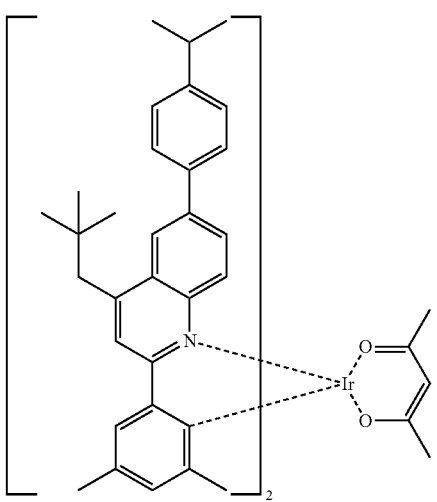
D-16
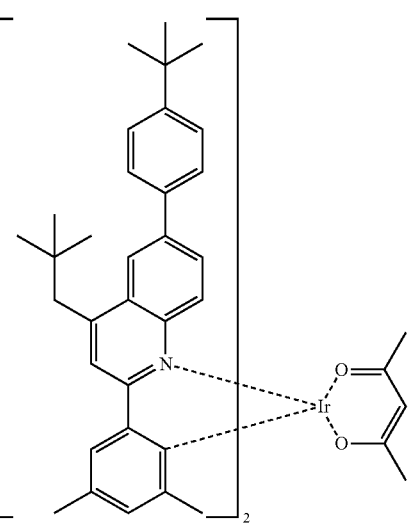
D-17
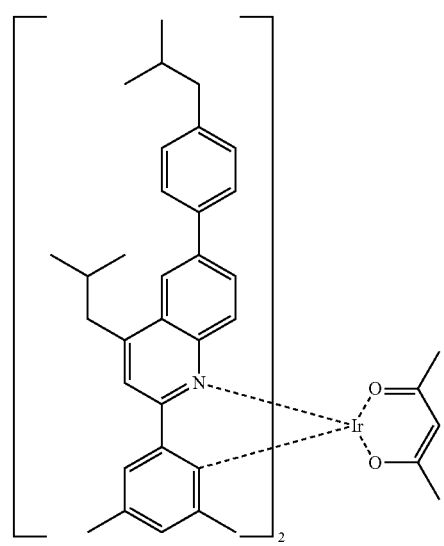
D-18
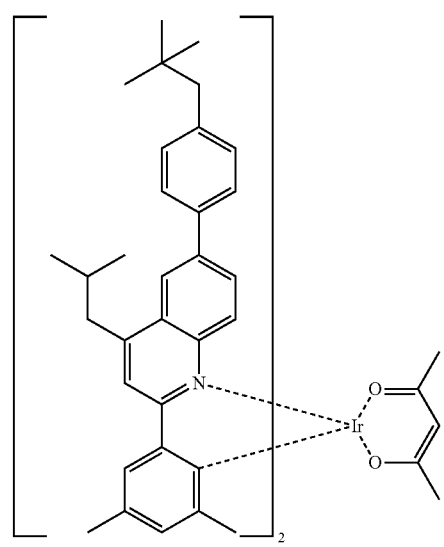

D-19
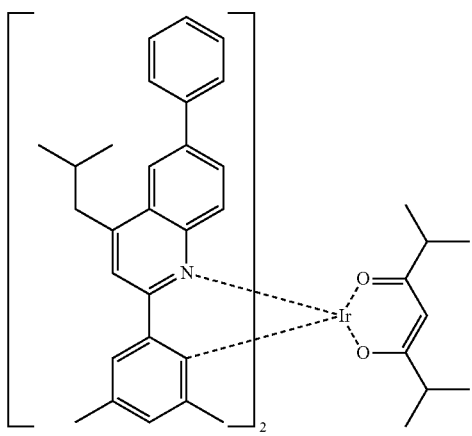
D-20
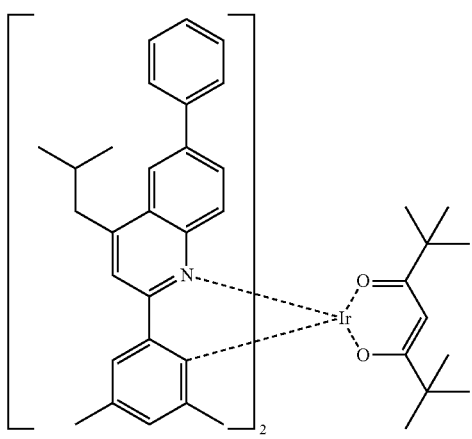
D-21
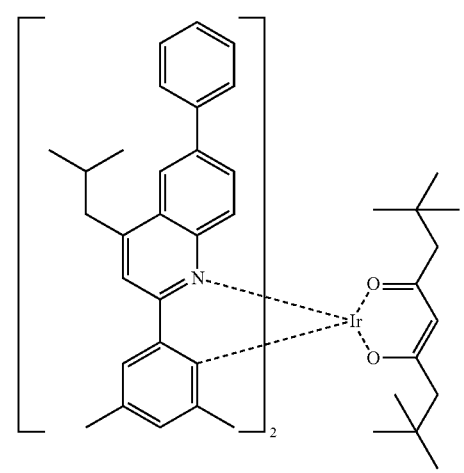
D-22
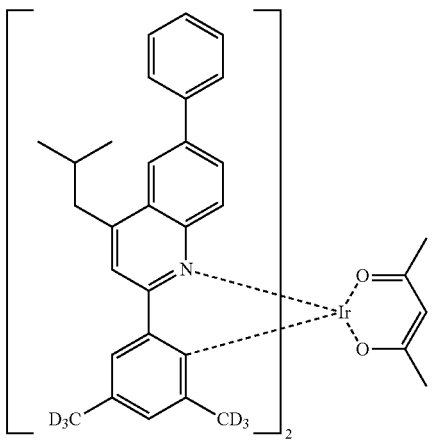
D-23
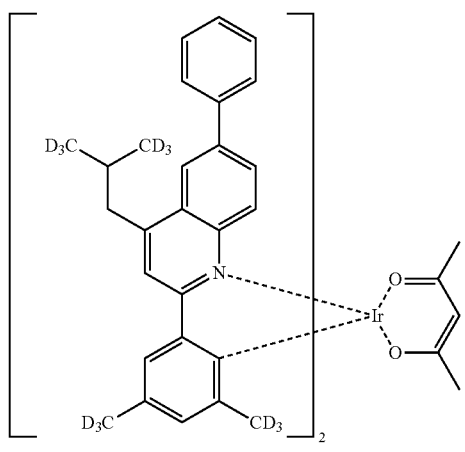
D-24
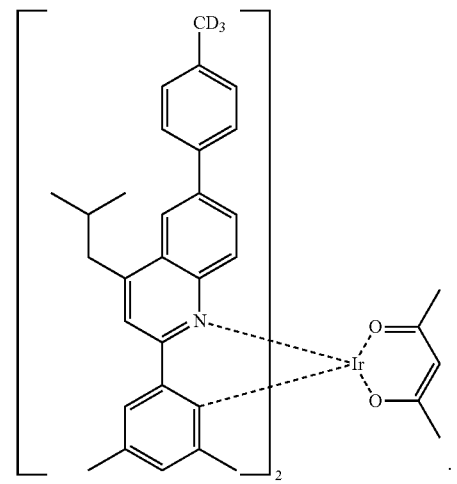
6. An organic electroluminescent device comprising the compound according to claim 1.
* * * * *